US009598466B2

(12) United States Patent
Danishefsky et al.

(10) Patent No.: US 9,598,466 B2
(45) Date of Patent: Mar. 21, 2017

(54) GLYCOPEPTIDE CONSTRUCTS AND USES THEREOF

(75) Inventors: Samuel J. Danishefsky, Englewood, NJ (US); Jianglong Zhu, New York, NY (US); Dongjoo Lee, New York, NY (US); Philip Livingston, New York, NY (US); Govind Ragupathi, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 1766 days.

(21) Appl. No.: 13/003,739

(22) PCT Filed: Jul. 13, 2009

(86) PCT No.: PCT/US2009/050434
§ 371 (c)(1),
(2), (4) Date: Jun. 7, 2011

(87) PCT Pub. No.: WO2010/006343
PCT Pub. Date: Jan. 14, 2010

(65) Prior Publication Data
US 2011/0229510 A1 Sep. 22, 2011

Related U.S. Application Data

(60) Provisional application No. 61/079,919, filed on Jul. 11, 2008.

(51) Int. Cl.
*A61K 38/00* (2006.01)
*C07K 9/00* (2006.01)
*A61K 39/00* (2006.01)

(52) U.S. Cl.
CPC .......... *C07K 9/001* (2013.01); *A61K 39/0011* (2013.01); *C07K 9/006* (2013.01); *A61K 38/00* (2013.01); *A61K 2039/6081* (2013.01); *A61K 2039/6093* (2013.01)

(58) Field of Classification Search
None
See application file for complete search history.

(56) References Cited

U.S. PATENT DOCUMENTS

| | | |
|---|---|---|
| 5,977,081 A | 11/1999 | Marciani |
| 6,080,725 A | 6/2000 | Marciani |
| 6,184,344 B1 | 2/2001 | Kent et al. |
| 6,645,935 B2 | 11/2003 | Danishefsky et al. |
| 6,660,714 B1 | 12/2003 | Danishefsky et al. |
| 7,160,856 B2 | 1/2007 | Danishefsky et al. |
| 7,531,181 B2 | 5/2009 | Danishefsky et al. |
| 7,550,146 B2 | 6/2009 | Danishefsky et al. |
| 7,645,454 B2 | 1/2010 | Danishefsky et al. |
| 7,824,687 B2 | 11/2010 | Danishefsky et al. |
| 7,854,934 B2 | 12/2010 | Danishefsky et al. |
| 7,879,335 B1 | 2/2011 | Danishefsky et al. |
| 8,623,378 B2 | 1/2014 | Danishefsky et al. |
| 8,754,192 B2 | 6/2014 | Danishefsky et al. |
| 2002/0038017 A1 | 3/2002 | Danishefsky et al. |
| 2003/0153492 A1 | 8/2003 | Danishefsky et al. |
| 2004/0102607 A1 | 5/2004 | Danishefsky et al. |
| 2006/0229432 A1* | 10/2006 | Danishefsky et al. ........ 530/300 |
| 2006/0233747 A1 | 10/2006 | Kochendoerfer et al. |
| 2009/0060938 A1 | 3/2009 | Danishefsky et al. |
| 2011/0229510 A1 | 9/2011 | Danishefsky et al. |
| 2013/0095173 A1 | 4/2013 | Danishefsky et al. |
| 2013/0323774 A1 | 12/2013 | Danishefsky et al. |
| 2013/0324520 A1 | 12/2013 | Xu et al. |
| 2014/0271817 A1 | 9/2014 | Danishefsky et al. |

FOREIGN PATENT DOCUMENTS

| | | |
|---|---|---|
| WO | WO-9846246 | 10/1998 |
| WO | WO-9948515 | 9/1999 |
| WO | WO-9961916 A1 | 12/1999 |
| WO | WO-0114395 A2 | 3/2001 |
| WO | WO-0165261 A1 | 9/2001 |
| WO | WO-03003985 A2 | 1/2003 |
| WO | WO-2004011476 A1 | 2/2004 |
| WO | WO-2004050711 A2 | 6/2004 |
| WO | WO-2004060915 A2 | 7/2004 |
| WO | WO-2005044841 A1 | 5/2005 |
| WO | WO-2005056572 A2 | 6/2005 |
| WO | WO-2007079448 A2 | 7/2007 |
| WO | WO-2007146070 A2 | 12/2007 |
| WO | WO-2010006343 A2 | 1/2010 |

OTHER PUBLICATIONS

Fontenot et al. Structure-based design of peptides that recognize the CD4 binding domain of HIV-1 gp120. AIDS 1998, 12:1413-1418.*
Adluri et al., "Immunogenicity of Synthetic TF-KLH (Keyhole Limpet Hemocyanin) and sTn-KLH Conjugates in Colorectal Carcinoma Patients," *Cancer Immunol. Immunother*. 1995, 41, 185-192.
Allen et al., "A Second Generation Synthesis of the MBr1 (Globo-H) Breast Tumor Antigen: New Application of the *n*-Pentenyl Glycoside Method for Achieving Complex Carbohydrate Protein Linkages, " *Chem. Eur. J.* 2000, 6(8), 1366-1375.
Allen et al., "New Applications of the *n*-Pentenyl Glycoside Method in the Synthesis and Immunoconjugation of Fucosyl $GM_1$: A Highly Tumor-Specific Antigen Associated with Small Cell Lung Carcinoma, " *J. Am. Chem. Soc.* 1999, 121, 10875-10882.
Allen et al., "Pursuit of Optimal Carbohydrate-Based Anticancer Vaccines: Preparation of a Multiantigenic Unimolecular Glycopeptide Containing the Tn, MBr1, and $Lewis^y$ Antigens," *J. Am. Chem. Soc.* 2001, 123, 1890-1897.

(Continued)

*Primary Examiner* — Jeanette Lieb
(74) *Attorney, Agent, or Firm* — Choate, Hall & Stewart, LLP; Brenda Herschbach Jarrell, JD; John P. Rearick, JD

(57) ABSTRACT

Glycopeptide conjugates, and methods of making and using such conjugates are disclosed. Certain glycopeptide conjugates comprise tumor associated carbohydrate antigens and peptide epitopes. Certain glycopeptide conjugates comprise cyclic peptide scaffolds that display carbohydrate antigens in a clustered fashion. The immunogenicity of select glycopeptide conjugates is demonstrated.

4 Claims, 109 Drawing Sheets

(56) References Cited

OTHER PUBLICATIONS

Arab et al., "Expression of the Verotoxin Receptor Glycolipid, Globotriaosylceramide, in Ovarian Hyperplasias," *Oncology Research* 1997, 9, 553-563.

Arklie et al., "Differentiation Antigens Expressed by Epithelial Cells in the Lactating Breast are also Detectable in Breast Cancers," *Int. J. Cancer* 1981, 28, 23-29.

Barratt-Boyes et al., "Immunization of Chimpanzees with Tumor Antigen MUC1 Mucin Tandem Repeat Peptide Elicits Both Helper and Cytotoxic T-Cell Responses," *Clin. Cancer Res.* 1999, 5, 1918-1924.

Bean et al., "Conformational Analysis of Cyclic Hexapeptides Containing the D-PRO-L-Pro Sequence to Fix β-Turn Positions," *J. Am. Chem. Soc.* 1992, 114, 5328-5334.

Biswas et al., "Construction of Carbohydrate-Based Antitumor Vaccines: Synthesis of Glycosyl Amino Acids by Olefin Cross-Metathesis." *Tetrahedron Lett.* 2002, 43, 6107-6110.

Bodanszky et al., "Side Reactions in Peptide Synthesis, VII. Sequence Dependence in the Formation of Aminosuccinyl Derivatives from β-Benzyl-Aspartyl Peptides," *Int. J. Peptide Protein Res.* 1978, 12, 69-74.

Bodanszky et al., "Side Reactions in Peptide Synthesis. II. Formation of Succinimide Derivatives from Aspartyl Residues," *J. Org. Chem.* 1975, 40, 2495-2499.

Bon et al., "Clinical and Technical Evaluation of ACS™ BR Serum Assay of *MUC1* Gene-Derived Glycoprotein in Breast Cancer, and Comparison With CA 15-3 Assays," *Clin. Chem.* 1997, 43, 585-593.

Bon et al., "Mucin-Like Carcinoma-Associated Antigen Serum Levels in Patients with Adenocarcinomas Originating from Ovary, Breast and Colon," *Gynecol. Obstet. Inv.* 1996, 42, 58-62.

Bona et al., "Towards Development of T-Cell Vaccines," *Immunology Today* 1998, 19, 126-133.

Bondurant et al., "Definition of an Immunogenic Region Within the Ovarian Tumor Antigen Stratum Corneum Chymotryptic Enzyme, " *Clin. Cancer Res.* 2005, 11, 3446-3454.

Boon, "Tumor Antigens Recognized by Cytolytic T Lymphocytes: Present Perspectives for Specific Immunotherapy," *Int. J. Cancer* 1993, 54, 177-180.

Bradford, "A Rapid and Sensitive Method for the Quantitation of Microgram Quantities of Protein Utilizing the Principle of Protein-Dye Binding," *Anal. Biochem.* 1976, 72, 248-254.

Brockhausen, "3. Biosynthesis of O-glycans of the N-acetylgalactosamine-α-Ser/Thr Linkage Type," in *Glycoproteins*; Elsevier Science: New York, 1995; pp. 201-259.

Burchell et al., "A Short Sequence, Within the Amino Acid Tandem Repeat of a Cancer-Associated Mucin, Contains Immunodominant Epitopes," *Int. J. Cancer* 1989, 44, 691-696.

Buskas et al., "Towards a Fully Synthetic Carbohydrate-Based Anticancer Vaccine: Synthesis and Immunological Evaluation of a Lipidated Glycopeptide Containing the Tumor-Associated Tn Antigen," *Angew. Chem. Int. Ed.* 2005, 44, 5985-5988.

Butts et al., "Randomized Phase IIB Trial of BLP25 Liposome Vaccine in Stage IIIB and IV Non-Small-Cell Lung Cancer," *J. Clin. Oncol.* 2005, 23 (27) 6674-6681.

Cannon et al., "Novel Target Antigens for Dendritic Cell-Based Immunotherapy Against Ovarian Cancer," *Expert Rev. Anticancer Ther.* 2002, 2, 97-105.

Carlstedt et al., "Glycoconjugates Facing the Outside World," *Biochem. Soc. Trans.* 1997, 25, 214-219.

Cho et al., "Organic Synthesis in Pursuit of Immunology: Large-Scale Synthesis of Peracetylated GM2 Glycosylamino Acid for Preparation of a Multiantigenic Prostate Cancer Vaccine," *Bioorg. Med. Chem.* 2005, 13, 5259-5266.

Cohen-Anisfeld et al., "A Practical, Convergent Method for Glycopeptide Synthesis," *J. Am. Chem. Soc.* 1993, 115, 10531-10537.

Danishefsky et al., "From the Laboratory to the Clinic: A Retrospective on Fully Synthetic Carbohydrate-Based Anticancer Vaccines," *Angew. Chem. Int. Ed. Engl.* 2000, 39, 836-863.

Deck et al., "Specificity of Glycopeptide-Specific T Cells," *J. Immunol.* 1995, 155, 1074-1078.

Dickler et al., "Immunogenicity of a Fucosyl-GM1-Keyhole Limpet Hemocyanin Conjugate Vaccine in Patients with Small Cell Lung Cancer," *Clin. Cancer Res.* 1999, 5, 2773-2779.

Doolan et al., "HLA-DR-Promiscuous T Cell Epitopes From *Plasmodium falciparum* Pre-Erythrocytic-Stage Antigens Restricted by Multiple HLA Class II Alleles," *J. Immunol.*, 2000, 165, 1123-1137.

Dranoff et al., "Vaccination with Irradiated Tumor Cells Engineered to Secrete Murine Granulocyte-Macrophage Colony-Stimulating Factor Stimulates Potent, Specific, and Long-Lasting Anti-Tumor Immunity," *Proc. Natl. Acad. Sci, USA* 1993, 90, 3539-3543.

Dumy et al., "A Convenient Synthesis of Cyclic Peptides as Regioselectively Addressable Functionalized Templates (RAFT)," *Tetrahedron Lett.* 1995, 36 (8), 1225-1258.

Dziadek et al., "A Fully Synthetic Vaccine Consisting of a Tumor-Associated Glycopeptide Antigen and a T-Cell Epitope for the Induction of a Highly Specific Humoral Immune Response," *Angew. Chem. Int. Ed.* 2005, 44, 7630-7635.

Dziadek, et al., "Biomimetic Synthesis of the Tumor-Associated (2,3)-Sialyl-T Antigen and Its Incorporation into Glycopeptide Antigens from the Mucins MUC1 and MUC4," *Chem. Eur. J.* 2004, 10, 4150-4162.

Favre et al., "Structural Mimicry of Canonical Conformations in Antibody Hypervariable Loops Using Cyclic Peptides Containing a Heterochiral Diproline Template," *J. Am. Chem. Soc.* 1999, 121, 2679-2685.

Hakomori, "Tumor Malignancy Defined by Aberrant Glycosylation and Sphingo(glyco)lipid Metabolism," *Cancer Res.* 1996, 56, 5309-5318.

Gendler et al., "Structure and Biology of a Carcinoma-associated Mucin, MUC1," *Am. Rev. Respir. Dis.* 1991, 144, S42-S47.

Gendler et al., "Molecular Cloning and Expression of Human Tumor-associated Polymorphic Epithelial Mucin," *J. Biol. Chem.* 1990, 265(25), 15286-15293.

Gilewski et al., "Immunication of Metastatic Breast Cancer Patients With a Fully Synthetic Globo H Conjugate: A Phase I Trial," *Proc. Natl. Acad. Sci. USA* 2001, 98, 3270-3275 and correction (*Proc. Natl. Acad. Sci. USA* 2001, 98, 14186).

Gilewski T. et al., "Vaccination of High-Risk Breast Cancer Patients with Mucin-1 (MUC1) Keyhole Limpet Hemocyanin Conjugate Plus QS-21," *Clin. Cancer Res.* 2000, 6, 1693-1701.

Giuntoli II et al., "Mucin Gene Expression in Ovarian Cancers," *Cancer Res.* 1998, 58, 5546-5550.

Glunz et al., "Design and Synthesis of Le$^y$-Bearing Glycopeptides that Mimic Cell Surface Le$^y$Mucin Glycoprotein Architecture," *J. Am. Chem. Soc.* 2000, 122, 7273-7279.

Grigalevicius et al., "Chemoselective Assembly and Immunological Evaluation of Multiepitopic Glycoconjugates Bearing Clustered Tn Antigen as Synthetic Anticancer Vaccines," *Bioconjugate Chem.* 2005, 16, 1149-1159.

Gum et al., "The Human *MUC2* Intestinal Mucin Has Cysteine-rich Subdomains Located Both Upstream and Downstream of Its Central Repetitive Region," *J. Biol. Chem.* 267(30) 1992, 21375-21383.

Gum et al., "MUC3 Human Intestinal Mucin," *J. Biol. Chem.* 272(42) 1997, 26678-26686.

Hakomori, "Tumor-Associated Carbohydrate Antigens Defining Tumor Malignancy: Basis for Development of Anti-Cancer Vaccines," *Advances in Exp. Med. Biol.* 2001, 491, 369-402.

Hakomori et al., "Glycosphingolipid Antigens and Cancer Therapy," *Chem. Biol.* 1997, 4, 97-104.

Hardy et al., "Separation of Positional Isomers of Oligosaccharides and Glycopeptides by High-Performance Anion-Exchange Chromatography with Pulsed Amperometric Detection," *Proc. Natl. Acad. Sci. USA* 1988, 85, 3289-3293.

Haurum et al., "Recognition of Carbohydrate by Major Histocompatibility Complex Class I-restricted, Glycopeptide-specific Cytotoxic T Lymphocytes," *J. Exp. Med.* 1994, 180, 739-744.

Helling et al, "G$_{D3}$ Vaccines for Melanoma: Superior Immunogenicity of Keyhole Limpet Hemocyanin Conjugate Vaccines," *Cancer Res.* 1994, 54, 197-203.

(56) References Cited

OTHER PUBLICATIONS

Helling et al., "$G_{M2}$-KLH Conjugate Vaccine: Increased Immunogenicity in Melanoma Patients After Administration with Immunological Adjuvant QS-21," Cancer Res. 1995, 55, 2783-2788.

Hermans et al., "NKT Cells Enhance CD4$^+$ and CD8$^+$ T Cell Responses to Soluble Antigen In Vivo Through Direct Interaction with Dendritic Cells," J. Immunol. 2003, 171, 5140-5147.

Hilkens et al., "Monoclonal Antibodies Against Human Milk-Fat Globule Membranes Detecting Differentiation Antigens of the Mammary Glad and Its Tumors," Int. J. Cancer 1984, 34, 197-206.

Hiltbold et al., "Naturally Processed Class II Epitope from the Tumor Antigen MUC1 Primes Human CD4$^+$ T Cells," Cancer Res. 1998, 58, 5066-5070.

Hollingsworth et al., "Expression of MUC1, MUC2, MUC3 and MUC4 Mucin mRNAs in Human Pancreatic and Intestinal Tumor Cell Lines," Int. J. Cancer 1994, 57, 198-203.

Ingale et al., "Robust Immune Responses Elicited by a Fully Synthetic Three-Component Vavccine," Nat. Chem. Biol. 2007, 3 (10), 663-667.

International Search Report for PCT/US2009/050434, mailed Feb. 24, 2010.

Itzkowitz et al., "Expression of Tn, Sialosyl-Tn, and T Antigens in Human Colon Cancer," Cancer Res. 1989, 49, 197-204.

Jiang et al., "Combinatorial Biomimetic Chemistry: Parallel Synthesis of a Small Library of β-Hairpin Mimetics Based on Loop III from Human Platelet-Derived Growth Factor B," Helv. Chim. Acta 2000, 83, 3097-3112.

Joyce et al., "An Oligosaccharide-Based HIV-1 2G12 Mimotope Vaccine Induces Carbohydrate-Specific Antibodies that Fail to Neutralize HIV-1 Virions," Proc. Natl. Acad. Sci. USA 2008, 105, 15684-15689.

Kawakami et al., "Synthesis of Reaper, a Cysteine-Containing Polypeptide, Using a Peptide Thioester in the Presence of Silver Chloride as an Activator," Tetrahedron Lett. 1998, 39, 7901-7904.

Keding et al., "Synthetic Carbohydrate-Based Vaccines," Carbohydrate-Based Drug Discovery 2003, 1, 381-406.

Keding et al., "Prospects for Total Synthesis: A Vision for a Totally Synthetic Vaccine Targeting Epithelial Tumors," Proc. Natl. Acad. Sci. USA 2004, 101 (33), 11937-11942.

Keding et al., "Synthesis of Non-Natural Glycosylamino Acids Containing Tumor-Associated Carbohydrate Antigens," Tetrahedron 2003, 59, 7023-7031.

Keding et al., "Hydroxynorleucine as a Glycosyl Acceptor is an Efficient Means for Introducing Amino Acid Functionality into Complex Carbohydrates," Tetrahedron Lett. 2003, 44, 3413-3416.

Kensil et al., "Separation and Characterization of Saponins with Adjuvant Activity from Quillaja saponaria Molina Cortex," J. Immunol. 1991, 146, 431-437.

Kiguchi et al., "Characteristic Expression of Globotriaosyl Ceramide in Human Ovarian Carcinoma-Derived Cells with Anticancer Drug Resistance," Cancer Science 2006, 97, 1321-1326.

Kim et al., "Mucin Glycoproteins in Neoplasia," Glyconjugate J. 1996, 13, 693-707.

Kim et al., "Comparison of the Effect of Different Immunological Adjuvants on the Antibody and T-Cell Response to Immunization with MUC1-KLH and GD3-KLH Conjugate Cancer Vaccines," Vaccine 2000, 18, 597-603.

Kim et al., "Effect of Immunological Adjuvant Combinations on the Antibody and T-Cell Response to Vaccination with MUC1-KLH and GD3-KLH Conjugates," Vaccine 2001, 19, 530-537.

Kingsbury et al., "A Recyclable Ru-Based Metathesis Catalyst," J. Am. Chem. Soc. 1999, 121, 791-799.

Kocer et al., "Humoral Immune Response to MUC5AC in Patients with Colorectal Polyps and Colorectal Carcinoma," BMC Gastroenterology 2006, 6: 4, doi:10.1186/1471-230X-6-4.

Krauss et al., "Fully Synthetic Carbohydrate HIV Antigens Designed on the Logic of the 2G12 Antibody," J. Am. Chem. Soc. 2007, 129, 11042-11044.

Krug et al., "Vaccination of Patients with Small-Cell Lung Cancer with Synthetic Fucosyl GM-1 Conjugated to Keyhole Limpet Hemocyanin," Clin. Cancer Res. 2004, 10, 6094-6100.

Kudryashov et al., "Toward Optimized Carbohydrate-Based Anticancer Vaccines: Epitope Clustering, Carrier Structure, and Adjuvant All Influence Antibody Responses to Lewis$^y$ Conjugates in Mice," Proc. Natl. Acad. Sci. USA 2001, 98, 3264-3269.

Kuduk et al., "Synthetic and Immunological Studies on Clustered Modes of Mucin-Related Tn and TF O-Linked Antigens: The Preparation of a Glycopeptide-Based Vaccine for Clinical Trials Against Prostate Cancer," J. Am. Chem. Soc. 1998, 120, 12474-12485.

Kunz et al., "Synthetic Glycopeptides for the Construction of Anticancer Vaccines," ACS Symposium Series 2008, 989 (Carbohydrate-Based Vaccines), 293-310.

Kunz, et al., "The Allyl Group as Mildly and Selectively Removable Carboxy-Protecting Group for the Synthesis of Labile O-glycopeptides," Angew. Chem., Int. Ed. 1984, 23, 71-72.

Lanzavechis, "Identifying Strategies for Immune Intervention," Science 1993, 260, 937-944.

Lauer, et al. "Sequence Dependence of Aspartimide Formation During 9-Fluorenylmethoxycarbonyl Solid-Phase Peptide Synthesis," Lett. Peptide Sci. 1994, 1, 197-205.

Le Poole et al., "Emerging Strategies in Tumor Vaccines," Curr. Opin. Oncol. 2002, 14, 641-648.

Lee et al., "'Biologic' Level Structures Through Chemistry: A Total Synthesis of a Unimolecular Pentavalent MUC1 Glycopeptide Construct," Tetrahedron. Lett. 2009, 50, 2167-2170.

Lingwood et al., Globotriaosyl Ceramide (Gb$_3$) Expression in Human Tumour Cells: Intracellular Trafficking Defines a New Retrograde Transport Pathway from the Cell Surface to the Nucleus, Which Correlates with Sensitivity to Verotoxin, Acta Biochimica Polonica 1998, 45, 351-359.

Livingston et al., "Carbohydrate Vaccines That Induce Antibodies Against Cancer. 2. Previous Experience and Future Plans," Cancer Immunol. Immunother. 1997, 45, 10-19.

Livingston et al., "Carbohydrate Vaccines That Induce Antibodies Against Cancer. 1. Rationale," Cancer Immunol. Immunother. 1997, 45, 1-9.

Livingston, "Construction of Cancer Vaccines with Carbohydrate and Protein (Peptide) Tumor Antigens," Curr. Opin. Immunol. 1992, 4, 624-629.

Livingston, "Cancer Vaccines Targeting Carbohydrate Antigens," Human Vaccines 2006, 2, 137-143.

Livingston et al., "Characterization of IgG and IgM Antibodies Induced in Melanoma Patients by Immunization with Purified $G_{M2}$ Ganglioside," Cancer Res. 1989, 49, 7045-7050.

Livingston et al., "Improved Survival in Stage III Melanoma Patients With GM2 Antibodies: A Randomized Trial of Adjuvant Vaccination with GM2 Ganglioside," J. Clin. Oncol., 1994, 12, 1036-1044.

Livingston, "Augmenting the Immunogenicity of Carbohydrate Tumor Antigens," Semin. Cancer Biol. 1995, 6, 357-366.

Lloyd et al., "High Performance Anion Exchange Chromatography of Reduced Oligosaccharides from Sialomucins," Glycoconjugate J. 1991, 8, 493-498.

MacLean et al., "Immunization of Breast Cancer Patients Using a Synthetic Sialyl-Tn Glycoconjugate Plus Detox Adjuvant," Cancer Immunol. Immunother. 1993, 36, 215-222.

MacLean et al., "Active Specific Immunotherapy Against Adenocarcinomas," Cancer Invest 1994, 12, 46-56.

MacLean et al., "Enhancing the Effect of THERATOPE STn-KLH Cancer Vaccine in Patients with Metastatic Breast Cancer by Pretreatment with Low-Dose Intravenous Cyclophosphamide," J. Immunother. 1996, 19, 309-316.

MacLean et al., "Antibodies Against Mucin-Associated Sialyl-Tn Epitopes Correlate with Survival of Metastatic Adenocarcinoma Patients Undergoing Active Specific Immunotherapy with Synthetic STn Vaccine," J. Immunother. 1996, 19, 59-68.

Marcaurelle et al., "Recent Advances in the Chemical Synthesis of Mucin-like Glycoproteins," Glycobiology 2002, 12(6), 69R-77R.

(56) References Cited

OTHER PUBLICATIONS

Marciani et al., "Development of Semisynthetic Triterpenoid Saponin Derivatives with Immune Stimulating Activity," *Vaccine* 2000, 18, 3141-3151.
Mergler et al., "The Aspartimide Problem in Fmoc-Based SPPS. Part I," *J. Peptide Sci.* 2003, 9, 36-46.
Mong et al., "Reactivity-Based One-Pot Total Synthesis of Fucose $GM_1$ Oligosaccharide: A Sialylated Antigenic Epitope of Small-Cell Lung Cancer," *Proc. Natl. Acad. Sci. USA* 2003, 100, 797-802.
Mouritsen et al., "Attachment of Oligosaccharides to Peptide Antigen Profoundly Affects Binding to Major Histocompatibility Complex Class II Molecules and Peptide Immunogenicity," *Eur. J. Immunol.* 1994, 24, 1066-1072.
Musselli et al., "Keyhole Limpet Hemocyanin Conjugate Vaccines Against Cancer: The Memorial Sloan Kettering Experience," *J. Cancer Res. Clin. Oncol.* 2001, 127, R20-R26.
Nagorny et al., "On the Emerging Role of Chemistry in the Fashioning of Biologics: Synthesis of a Bidomainal Fucosyl GM1-Based Vaccine for the Treatment of Small Cell Lung Cancer," *J. Org. Chem.* 2009, 74, 5157-5162.
Nakamori et al., "MUC1 Mucin Expression as a Marker of Progression and Metastasis of Human Colorectal Carcinoma," *Gasteroenterology* 1994, 106, 353-361.
Nicolaou et al., "A Practical and Enantioselective Synthesis of Glycosphingolipids and Related Compounds. Total Synthesis of Globotriaosylceramide ($Gb_3$)," *J. Am.Chem. Soc.* 1988, 110, 7910-7912.
O'Boyle et al., "Specificity Analysis of Murine Monoclonal Antibodies Reactive with Tn, Sialylated Tn, T, and Monosialylated (2→6) T Antigens," *Hybridoma* 1996, 15, 401-408.
Ouerfelli et al., "Synthetic Carbohydrate-Based Antitumor Vaccines: Challenges and Opportunities," *Expert Rev. Vaccines* 2005, 4, 677-685.
Pardoll, "New Strategies for Enhancing the Immunogenicity of Tumors," *Curr. Opin. Immunol.* 1993, 5, 719-725.
Pittelkow et al.,"Selective Synthesis of Carbamate Protected Polyamines Using Alkyl Phenyl Carbonates," *Synthesis* 2002, 15, 2195-2202.
Prakash et al., "Glycotyping of Prostate Specific Antigen," *Glycobiology*, 2000 10(2), 173-176.
Price et al., "Immunological and Structural Features of the Protein Core of Human Polymorphic Epithelial Mucin," *Mol. Immunol.* 1990, 27(8), 795-802.
Ragupathi et al., "Immunization of Mice with a Fully Synthetic Globo H Antigen Results in Antibodies Against Human Cancer Cells: A Combined Chemical—Immunological Approach to the Fashioning of an Anticancer Vaccine," *Angew. Chem., Int. Ed. Engl.* 1997, 36, 125-128.
Ragupathi et al., "Preparation and Evaluation of Unimolecular Pentavalent and Hexavalent Antigenic Constructs Targeting Prostate and Breast Cancer: A Synthetic Route to Anticancer Vaccine Candidates," *J. Am. Chem. Soc.* 2006, 128, 2715-2725.
Ragupathi et al., "On the Power of Chemical Synthesis: Immunological Evaluation of Models for Multiantigenic Carbohydrate-Based Cancer Vaccines," *Proc. Natl. Acad. Sci. USA* 2002, 99, 13699-13704.
Ragupathi et al., "Comparison of Antibody Titers After Immunization with Monovalent or Tetravalent KLH Conjugate Vaccines," *Vaccine* 2002 20, 1030-1038.
Ragupathi, "Carbohydrate Antigens as Targets for Active Specific Immunotherapy," *Cancer Immunol. Immunother.* 1996, 43, 152-157.
Ragupathi et al., "A Preclinical Study Comparing Approaches for Augmenting the Immunogenicity of a Heptavalent KLH-Conjugate Vaccine Against Epithelial Cancers," *Cancer Iummonol. Immunother.* 2003, 52, 608-616.
Reichel et al., "Synthetic Carbohydrate-Based Vaccines: Synthesis of an L-*Glycero*-D-*Manno*-Heptose Antigen-T-Epitope-Lipopeptide Conjugate," *Chem. Commun.* 1997, 2087-2088.
Renaudet et al.,"Chemoselectively Template-Assembled Glycoconjugates as Mimics for Multivalent Presentation of Carbohydrates," *Org. Lett.* 2003, 5(3), 243-246.
Robinson, "The Design, Synthesis and Comformation of Some New β-Hairpin Mimetics: Novel Reagents for Drug and Vaccine Discovery," *Synlett* 1999, 429-441.
Rudensky et al., "Sequence Analysis of Peptides Bound to MHC Class II Molecules," *Nature* 1991, 353, 622-627.
Sabbatini et al., "Immunization of Ovarian Cancer Patients With a Synthetic Lewis$^y$-Protein Conjugate Vaccine: A Phase 1 Trial," *Int. J. Cancer*. 2000, 87, 79-85.
Schmidt et al., "New Aspects of Glycoside Bond Formation," *Pure Appl. Chem.* 1999, 71, 729-744.
Sieling et al., "CD1-Restricted T Cell Recognition of Microbial Lipoglycan Antigens," *Science* 1995, 269, 227-230.
Singh et al., "Synthetic Peptide Templates for Molecular Recognition: Recent Advances and Applications," *ChemBioChem* 2006, 7, 1298-1314.
Slovin et al., "A Bivalent Conjugate Vaccine in the Treatment of Biochemically Relapsed Prostate Cancer: A Study of Glycosylated MUC-2-KLH and Globo H-KLH Conjugate Vaccines Given With the New Semi-Synthetic Saponin Immunological Adjuvant GPI-0100 OR QS-21," *Vaccine* 2005, 23, 3114-3122.
Slovin et al., "Carbohydrate Vaccines in Cancer: Immunogenicity of a Fully Synthetic Globo H Hexasaccharide Conjugate in Man," *Proc. Natl. Acad. Sci. USA*, 1999, 96, 5710-5715.
Slovin et al., "Carbohydrate Vaccines as Immunotherapy for Cancer," *Immunol. Cell Biol.* 2005, 83, 418-428.
Slovin et al., "Fully Synthetic Carbohydrate-Based Vaccines in Biochemically Relapsed Prostate Cancer: Clinical Trial Results with α-*N*-Acetylgalactosamine-*O*-Serine/Threonine Conjugate Vaccine," *J. Clin. Oncol.* 2003, 21, 4292-4298.
Southwood et al., "Several Common HLA-DR Types Share Largely Overlapping Peptide Binding Repertoires," *J. Immun.* 1998, 160, 3363-3373.
Springer, "T and Tn Pancarcinoma Markers: Autoantigenic Adhesion Molecules in Pathogenesis, Prebiopsy Carcinoma-Detection, and Long-Term Breast Carcinoma Immunotherapy," *Crit. Rev. Oncogenesis* 1995, 6, 57-85.
Springer, "Immunoreactive T and Tn Epitopes in Cancer Diagnosis, Prognosis, and Immunotherapy," *J. Mol. Med.* 1997, 75, 594-602.
Springer, "T and Tn, General Carcinoma Autoantigens," *Science* 1984, 224, 1198-1206.
Svennerholm, "Quantitative Estimation of Sialic Acids II. A Colorimetric Resorcinol-Hydrochloric Acid Method, " *Biochim. Biophys. Acta* 1957, 24, 604-611.
Swallow et al., "The Human Tumour-Associated Epithelial Mucins are Coded by an Expressed Hypervariable Gene Locus PUM," *Nature* 1987, 328, 82-84.
Tam et al., "Mechanisms of Aspartimide Formation: The Effects of Protecting Groups, Acid, Base, Temperature and Time," *Pept. Res.* 1988, 1, 6-18.
Tampellini et al., "Relationship Between CA 15-3 Serum Levels and Disease Extent in Predicting Overall Survival of Breast Cancer Patients with Newly Diagnosed Metastatic Disease," *Br. J. Cancer* 1997, 75, 698-702.
Tao et al, "Idiotype/Granulocyte-Macrophage Colony-Stimulating Factor Fusion Protein as a Vaccine for B-Cell Lymphoma," *Nature* 1993, 362, 755-758.
Toyokuni et al., "Synthetic Carbohydrate Vaccines Based on Tumour-Associated Antigens," *Chem. Soc. Rev.* 1995, 231-242.
Van Den Steen et al., "Concepts and Principles of O-Linked Glycosylation," *Crit. Rev. Biochem. Mol. Biol.* 1998, 33, 151-208.
Wan et al., "Olefin Cross-Metathesis: A Powerful Tool for Constructing Vaccines Composed of Multimeric Antigens," *J. Carbohydr. Chem.* 2005, 24, 425-440.
Wang et al., "Novel Template-Assembled Oligosaccharide Clusters as Epitope Mimics for HIV-Neutralizing Antibody 2G12. Deisign, Synthesis, and Antibody Binding Study," *Org. Biomol. Chem.* 2007, 5, 1529-1540.
Wang et al., "A Highly Convergent Synthesis of an N-Linked Glycopeptide Presenting the H-Type 2 Human Blood Group Determinant," *Tetrahedron* 2006, 62, 4954-4978.

(56) References Cited

OTHER PUBLICATIONS

Warren et al., "Synthetic Glycopeptide-Based Vaccines," *Top Curr. Chem.* 2007, 267, 109-141.
Westerlind et al., "Synthetic Vaccines Consisting of Tumor-Associated MUC1 Glycopeptide Antigens and a T-Cell Epitope for the Induction of a Highly Specific Humoral Immune Response," *Angew. Chem., Int. Ed.* 2008, 47, 7551-7556.
Wilson et al., "Synthetic Carbohydrate-Based Antitumor Vaccines," *ACS Symposium Series* 2008, 989 (*Carbohydrate-Based Vaccines*), 258-292.
Wittrock et al., "Synthetic Vaccines of Tumor-Associated Glycopeptide Antigens by Immune-Compatible Thioether Linkage to Bovine Serum Albumin," *Angew. Chem., Int. Ed.* 2007, 46, 5226-5230.
Yin et al., "Molecular Cloning of the CA125 Ovarian Cancer Antigen," *J. Biol. Chem.* 2001, 276, 27371-27375.
Yin et al., "Serological and Immunochemical Analysis of Lewis Y (Le$^y$) Blood Group Antigen Expression in Epithelial Ovarian Cancer," *Int. J. Cancer* 1996, 65, 406-412.
Zegers et al., "Use of T Cell Epitopes in Raising Immune Responses," (ed) *Immunological Recognition of Peptides in Medicine and Biology*, CRC Press, Boca Raton, 1995, 105-123.
Zhang et al., "Immune Sera and Monoclonal Antibodies Define Two Configurations for the Sialyl Tn Tumor Antigen," *Cancer Res.* 1995, 55, 3364-3368.
Zhang et al., "Augmenting the Immunogenicity of Synthetic MUC1 Peptide Vaccines in Mice," *Cancer Res.* 1996, 56, 3315-3319.
Zhang et al., "Selection of Tumor Antigens as Targets for Immune Attack Using Immunohistochemistry: Protein Antigens," *Clin. Cancer Res.* 1998, 4, 2669-2676.
Zhang et al., "Selection of Tumor Antigens as Targets for Immune Attack Using Immunohistochemistry: I. Focus on Gangliosides," *Int. J. Cancer* 1997, 73, 42-49.
Zhang et al., "Selection of Tumor Antigens as Targets for Immune Attack Using Immunohistochemistry: II. Blood Group-Related Antigens," *Int. J. Cancer* 1997, 73, 50-56.
Zhu et al., "Synthesis of Human Cancer Associated Globo-H (MBr1) Glycosylamino Acid: Some Mechanistic and Conformational Reinvestigations," *Heterocycles* 2009, 79(1), 441-449.
Zhu, J. et al., "Biologics Through Chemistry: Total Synthesis of a Proposed Dual-Acting Vaccine Targeting Ovarian Cancer by Orchestration of Oligosaccharide and Polypeptide Domains," *J. Am. Chem. Soc.* 2009, 131, 4151-4158.
Extended European Search Report for EP 09795292.3, dated Jan. 3, 2012.
International Preliminary Report on Patentability for PCT/US2009/050434, issued Jan. 11, 2011.
International Search Report for PCT/US11/40074, mailed Feb. 14, 2012.
Written Opinion of the International Searching Authority for PCT/US11/40074, mailed Feb. 14, 2012.
International Preliminary Report on Patentability for PCT/US11/40074, mailed Dec. 27, 2012.

\* cited by examiner

*Clustered Vaccines:*

*Unimolecular pentavalent Vaccines:*

(a) 5% Et$_2$NH in DMF; (b) 1-17, AgCl, HOOBt, $^i$Pr$_2$NEt, DMSO; (c) 1-15b, AgCl, HOOBt, $^i$Pr$_2$NEt, DMSO; (d) Ac$_2$O, cat. DMAP, pyridine.

(a) TBAF, AcOH, THF; (b) NaOMe, MeOH; (c) NaOH, THF; (d) Na, NH₃, THF; (e) Ac₂O, DMAP, Py; (f) DMAP, NaOMe; (g) Ac₂O, DMAP, Py; 56% (7 steps); (h) 3-A, 3-B, CH₂Cl₂, rt; (i) H₂, Pt/C, MeOH-H₂O; 49%, 2 steps.

(a) Piperidine, DMF; (b) Ac₂O, Py; (c) Pd(PPh₃)₄, PhSiH₃, CH₂Cl₂/DMF (1:1); (d) SAMA-OPfb, TEA, Py; (e) TFA/PhOH/H₂O/TIPS, (71% from 3-9, 5 steps); (f) NaOH in MeOH/H₂O, pH = 10.5, 19%; (g) i) TCEP gel; ii) PBS buffer, pH = 7.2, 0.9 M NaCl, 0.1 M EDTA.

SEQ ID NO: 24

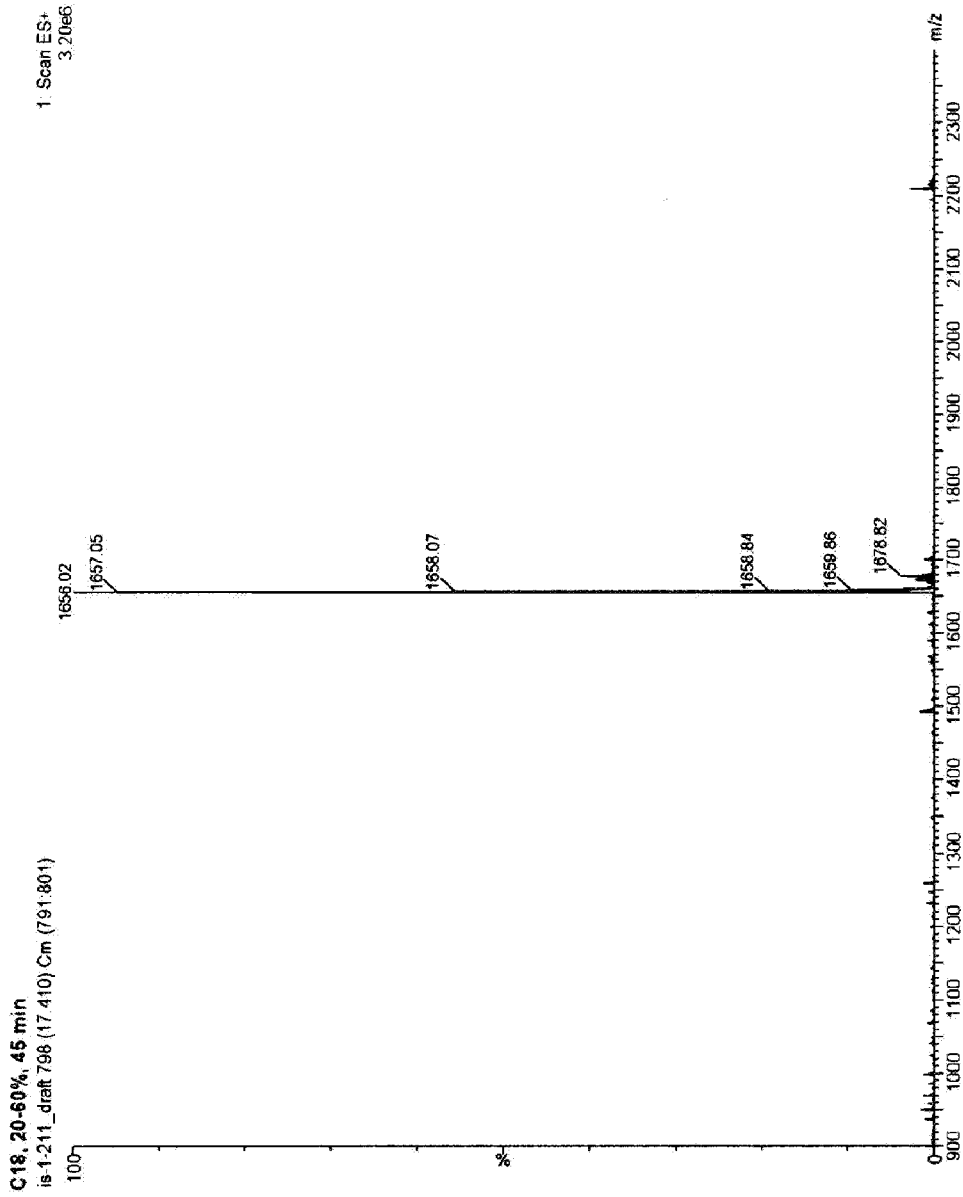

Figure 47 — Compound 3-7

Figure 51 Compound 3-8a

Figure 54 Compound 3-8

Figure 67 Compound 3-11

Figure 68 Compound 3-11

SEQUENCE LISTING

<160> NUMBER OF SEQ ID NOS: 71

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Thr Ser Ala Pro Asp Thr Arg Pro Ala Pro Gly Ser Thr Ala Pro
1               5                   10                  15

Pro Ala His Gly
            20

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Thr Ser Thr Thr Ser Ala Pro
1               5

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Asp Thr Arg Pro Ala Pro Gly Ser Thr Ala Pro Pro Ala His Gly
1               5                   10                  15

Val Thr Ser Ala
            20

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Pro Asp Thr Arg
1               5

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Gly Val Thr Ser Ala Pro Asp Thr Arg Pro Ala Pro Gly Ser Thr
1               5                   10                  15

Ala Pro Pro Ala

```
<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Thr Thr Thr Pro Ile Thr Thr Thr Thr Thr Val Thr Pro Thr Pro
1               5                  10                  15

Thr Pro Thr Gly Thr Gln Thr
            20

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Thr Thr Thr Pro Ile Ser Thr Thr Thr Val Thr Pro Thr Pro
1               5                  10                  15

Thr Pro Thr Gly Thr Gln Thr
            20

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Ser Thr Pro Ser Phe Thr Ser Ser Ile Thr Thr Thr Glu Thr Thr
1               5                  10                  15

Ser

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ser Ser Ala Ser Thr Gly His Ala Thr Pro Leu Pro Val Thr Asp
1               5                  10                  15

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Thr Ala Ala Pro Pro Thr Pro Ser Ala Thr Thr Pro Ala Pro Pro
1               5                  10                  15
```

Ser Ser Ser Ala Pro Pro Glu
            20

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Thr Thr Thr Glu Thr Thr Ser His Ser Thr Pro Ser Phe Thr Ser
1               5                   10                  15

Ser

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ser Val Pro Thr Thr Ser Thr Pro
1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ser Val Ser Thr Thr Ser Thr Ser Thr Pro
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Pro Leu Tyr Ser Cys Arg Leu Thr Leu Leu Arg
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Leu Gly Pro Tyr Thr Leu
1               5

<210> SEQ ID NO 16
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid

<400> SEQUENCE: 16

Phe Thr Leu Asn Phe Thr Ile Xaa Asn Leu
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid

<400> SEQUENCE: 17

Pro Gly Ser Arg Lys Phe Asn Xaa Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Lys Lys Glu Gly Glu Tyr
1               5

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gln Pro Gly Thr Thr Asn Tyr Gln Arg Asn Lys
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Pro Arg Leu Asp Arg
1               5

<210> SEQ ID NO 21
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 21

Lys Ala Gln Pro Gly Thr Thr Asn Tyr Gln Arg Asn
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Thr Pro Asp Thr Ser Thr Met His Leu Ala Thr Ser Arg Thr
1               5                   10                  15

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Val Thr Ser Ala Pro Asp Thr Arg Pro Ala Pro Gly Ser Thr Ala Pro
1               5                   10                  15

Pro Ala His Gly Val Thr Ser Ala Pro Asp Thr Arg Pro Ala
            20                  25                  30

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Thr Ala Pro Pro Ala His Gly Val Thr Ser Ala Pro Asp Thr Arg
1               5                   10                  15

Pro Ala Pro Gly
            20

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Asn Trp Val Asn His Ala Val Pro Leu Ala Met Lys Leu Ile
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 26

Lys Ser Lys Tyr Lys Leu Ala Thr Ser Val Leu Ala Gly Leu Leu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Leu Ala Tyr Lys Phe Val Val Pro Gly Ala Ala Thr Pro Tyr
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Thr Ser Gln Phe Phe Leu Pro Ala Leu Pro Val Phe Thr Trp Leu
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Pro Gln Glu Trp Lys Pro Ala Ile Thr Val Lys Val Leu Pro Ala
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Val Phe Pro Ala Ser Phe Phe Ile Lys Leu Pro Ile Ile Leu Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ser Val Phe Asn Val Val Asn Ser Ser Ile Gly Leu Ile Met
1               5                   10                  15

<210> SEQ ID NO 32

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Lys Asn Val Ile Gly Pro Phe Met Lys Ala Val Cys Val Glu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Ser Ile Ile Phe Gly Ala Phe Pro Ser Leu His Ser Gly Cys Cys
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Arg Lys Leu Ala Ile Leu Ser Val Ser Ser Phe Leu Phe Val
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Val Asn Leu Leu Ile Phe His Ile Asn Gly Lys Ile Ile Lys
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Pro Gln Gly Ser Thr Tyr Ala Ala Ser Ser Ala Thr Ser Val Asp
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Ala Gly Leu Leu Gly Asn Val Ser Thr Val Leu Leu Gly Gly Val
1               5                   10                  15
```

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Phe Ala Thr Cys Phe Leu Ile Pro Leu Thr Ser Gln Phe Phe Leu Pro
1               5                   10                  15
```

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Asn Leu Ser Asn Val Leu Ala Thr Ile Thr Thr Gly Val Leu Asp Ile
1               5                   10                  15
```

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Ile Lys Leu Pro Ile Ile Leu Ala Phe Ala Thr Cys Phe Leu Ile Pro
1               5                   10                  15
```

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Thr His His Tyr Phe Val Asp Leu Ile Gly Gly Ala Met Leu Ser Leu
1               5                   10                  15
```

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Leu Ala Ala Ile Ile Phe Leu Phe Gly Pro Pro Thr Ala Leu Arg Ser
1               5                   10                  15
```

<210> SEQ ID NO 43
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 43

Gln Glu Ile Asp Pro Leu Ser Tyr Asn Tyr Ile Pro Val Asn Ser Asn
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Val Tyr Gln Glu Pro Gln Val Ser Pro Pro Gln Arg Ala Glu Thr
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asn Val Lys Tyr Leu Val Ile Val Phe Leu Ile Phe Phe Asp Leu
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Trp Trp Ser Thr Met Tyr Leu Thr His His Tyr Phe Val Asp Leu
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Ser Ser Ala Val Ala Val
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycosylated residue

<400> SEQUENCE: 48

Xaa Thr Thr Ser Thr Thr Ser Ala Pro
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycosylated residue
<220> FEATURE:
<221> NAME/KEY: MOD_RES
<222> LOCATION: (10)..(10)
<223> OTHER INFORMATION: Glycosylated residue

<400> SEQUENCE: 49

Xaa Thr Thr Ser Thr Thr Ser Ala Pro Xaa
1               5                   10

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glycosylated residue
<220> FEATURE:
<221> NAME/KEY: MOD_RES
<222> LOCATION: (10)..(10)
<223> OTHER INFORMATION: Glycosylated residue
<220> FEATURE:
<221> NAME/KEY: MOD_RES
<222> LOCATION: (19)..(19)
<223> OTHER INFORMATION: Glycosylated residue

<400> SEQUENCE: 50

Xaa Thr Thr Ser Thr Thr Ser Ala Pro Xaa Thr Thr Ser Thr Thr Ser
1               5                   10                  15

Ala Pro Xaa

<210> SEQ ID NO 51
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Glycosylated residue
<220> FEATURE:
<221> NAME/KEY: MOD_RES
<222> LOCATION: (18)..(18)
<223> OTHER INFORMATION: Glycosylated residue
<220> FEATURE:
<221> NAME/KEY: MOD_RES
<222> LOCATION: (27)..(27)
<223> OTHER INFORMATION: Glycosylated residue

<400> SEQUENCE: 51

Thr Thr Ser Thr Thr Ser Ala Pro Xaa Thr Thr Ser Thr Thr Ser Ala
1               5                   10                  15

```
Pro Xaa Thr Thr Ser Thr Thr Ser Ala Pro Xaa
            20                  25
```

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 52

```
Pro Xaa Tyr Xaa Tyr Xaa Pro Xaa Cys Xaa Phe Xaa
1               5                   10
```

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Asp(tBu)
<220> FEATURE:
<221> NAME/KEY: MOD_RES
<222> LOCATION: (6)..(6)
<223> OTHER INFORMATION: Asp(tBu)
<220> FEATURE:
<221> NAME/KEY: MOD_RES
<222> LOCATION: (8)..(8)
<223> OTHER INFORMATION: Asp(tBu)
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Asp(tBu)

<400> SEQUENCE: 53

Pro Asp Tyr Ala Tyr Asp Pro Asp Cys Ala Phe Asp

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Asp(tBu)
<220> FEATURE:
<221> NAME/KEY: MOD_RES
<222> LOCATION: (4)..(4)
<223> OTHER INFORMATION: Asp(tBu)
<220> FEATURE:
<221> NAME/KEY: MOD_RES
<222> LOCATION: (6)..(6)
<223> OTHER INFORMATION: Asp(tBu)
<220> FEATURE:
<221> NAME/KEY: MOD_RES
<222> LOCATION: (8)..(8)
<223> OTHER INFORMATION: Asp(tBu)
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (10)..(10)
<223> OTHER INFORMATION: Asp(tBu)
<220> FEATURE:
<221> NAME/KEY: MOD_RES
<222> LOCATION: (12)..(12)
<223> OTHER INFORMATION: Asp(tBu)

<400> SEQUENCE: 54

Pro Asp Tyr Asp Tyr Asp Pro Asp Cys Asp Phe Asp
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Asp(allyl)
<220> FEATURE:
<221> NAME/KEY: MOD_RES
<222> LOCATION: (6)..(6)
<223> OTHER INFORMATION: Asp(tBu)
<220> FEATURE:
<221> NAME/KEY: MOD_RES
<222> LOCATION: (8)..(8)
<223> OTHER INFORMATION: Asp(allyl)
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Asp(tBu)

<400> SEQUENCE: 55

```
Pro Asp Tyr Ala Tyr Asp Pro Asp Cys Ala Phe Asp
1               5                   10
```

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (9)..(9)
<223> OTHER INFORMATION: Cys(SS-tBu)

<400> SEQUENCE: 56

```
Pro Asp Tyr Ala Tyr Asp Pro Asp Cys Ala Phe Asp
1               5                   10
```

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (9)..(9)
<223> OTHER INFORMATION: Cys(SS-tBu)

<400> SEQUENCE: 57

```
Pro Asp Tyr Asp Tyr Asp Pro Asp Cys Asp Phe Asp
1               5                   10
```

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Asp(allyl)
<220> FEATURE:
<221> NAME/KEY: MOD_RES
<222> LOCATION: (8)..(8)
<223> OTHER INFORMATION: Asp(allyl)
<220> FEATURE:
<221> NAME/KEY: MOD_RES
<222> LOCATION: (9)..(9)
<223> OTHER INFORMATION: Cys(SS-tBu)

<400> SEQUENCE: 58

```
Pro Asp Tyr Ala Tyr Asp Pro Asp Cys Ala Phe Asp
1               5                   10
```

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Glycosylated residue
<220> FEATURE:
<221> NAME/KEY: MOD_RES
<222> LOCATION: (4)..(4)
<223> OTHER INFORMATION: Glycosylated residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (10)..(10)
<223> OTHER INFORMATION: Glycosylated residue
<220> FEATURE:
<221> NAME/KEY: MOD_RES
<222> LOCATION: (12)..(12)
<223> OTHER INFORMATION: Glycosylated residue

<400> SEQUENCE: 59

Pro Asn Tyr Asn Tyr Asn Pro Asn Cys Asn Phe Asn
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Glycosylated residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Glycosylated residue

<400> SEQUENCE: 60

Pro Asn Tyr Ala Tyr Asn Pro Asn Cys Ala Phe Asn
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Glycosylated residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Glycosylated residue

<400> SEQUENCE: 61

Pro Asn Tyr Ala Tyr Asn Pro Asn Cys Ala Phe Asn
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Glycosylated residue
<220> FEATURE:
<221> NAME/KEY: MOD_RES
<222> LOCATION: (4)..(4)
<223> OTHER INFORMATION: Glycosylated residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (10)..(10)
<223> OTHER INFORMATION: Glycosylated residue
<220> FEATURE:
<221> NAME/KEY: MOD_RES
<222> LOCATION: (12)..(12)
<223> OTHER INFORMATION: Glycosylated residue

<400> SEQUENCE: 62

Pro Asn Tyr Asn Tyr Asn Pro Asn Cys Asn Phe Asn
1               5                   10

<210> SEQ ID NO 63
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Glycosylated residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Glycosylated residue

<400> SEQUENCE: 63

Pro Asn Tyr Ala Tyr Asn Pro Asn Cys Ala Phe Asn
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Glycosylated residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Glycosylated residue

<400> SEQUENCE: 64

Pro Asn Tyr Ala Tyr Asn Pro Asn Cys Ala Phe Asn
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
```

```
<223> OTHER INFORMATION: Glycosylated residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Glycosylated residue

<400> SEQUENCE: 65

Pro Asn Tyr Ala Tyr Asn Pro Asn Cys Ala Phe Asn
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Protected residue
<220> FEATURE:
<221> NAME/KEY: MOD_RES
<222> LOCATION: (3)..(3)
<223> OTHER INFORMATION: Tyr(tBu)
<220> FEATURE:
<221> NAME/KEY: MOD_RES
<222> LOCATION: (5)..(5)
<223> OTHER INFORMATION: Tyr(tBu)
<220> FEATURE:
<221> NAME/KEY: MOD_RES
<222> LOCATION: (6)..(6)
<223> OTHER INFORMATION: Protected residue
<220> FEATURE:
<221> NAME/KEY: MOD_RES
<222> LOCATION: (8)..(8)
<223> OTHER INFORMATION: Protected residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Protected residue

<400> SEQUENCE: 66

Pro Asp Tyr Ala Tyr Asp Pro Asp Cys Ala Phe Asp
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
```

```
<222> LOCATION: (2)..(2)
<223> OTHER INFORMATION: Protected residue
<220> FEATURE:
<221> NAME/KEY: MOD_RES
<222> LOCATION: (3)..(3)
<223> OTHER INFORMATION: Tyr(tBu)
<220> FEATURE:
<221> NAME/KEY: MOD_RES
<222> LOCATION: (5)..(5)
<223> OTHER INFORMATION: Tyr(tBu)
<220> FEATURE:
<221> NAME/KEY: MOD_RES
<222> LOCATION: (6)..(6)
<223> OTHER INFORMATION: Protected residue
<220> FEATURE:
<221> NAME/KEY: MOD_RES
<222> LOCATION: (8)..(8)
<223> OTHER INFORMATION: Protected residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Protected residue

<400> SEQUENCE: 67

Pro Asp Tyr Ala Tyr Asp Pro Asp Cys Ala Phe Asp
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Protected residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Protected residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Glycosylated residue

<400> SEQUENCE: 68

Pro Asn Tyr Ala Tyr Asn Pro Asn Cys Ala Phe Asn
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
```

<221> NAME/KEY: MOD_RES
<222> LOCATION: (2)..(2)
<223> OTHER INFORMATION: Protected residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Protected residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Glycosylated residue

<400> SEQUENCE: 69

Pro Asn Tyr Ala Tyr Asn Pro Asn Cys Ala Phe Asn
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Glycosylated residue
<220> FEATURE:
<221> NAME/KEY: MOD_RES
<222> LOCATION: (6)..(6)
<223> OTHER INFORMATION: Glycosylated residue
<220> FEATURE:
<221> NAME/KEY: MOD_RES
<222> LOCATION: (8)..(8)
<223> OTHER INFORMATION: Glycosylated residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Glycosylated residue

<400> SEQUENCE: 70

Pro Asn Tyr Ala Tyr Asn Pro Asn Cys Ala Phe Asn
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: cyclic peptide
<220> FEATURE:
<221> NAME/KEY: MOD_RES
<222> LOCATION: (2)..(2)
<223> OTHER INFORMATION: Protected residue
<220> FEATURE:
<221> NAME/KEY: MOD_RES
<222> LOCATION: (6)..(6)
<223> OTHER INFORMATION: Protected residue
<220> FEATURE:
<221> NAME/KEY: MOD_RES
<222> LOCATION: (8)..(8)
<223> OTHER INFORMATION: Protected residue
<220> FEATURE:
<221> NAME/KEY: MOD_RES
<222> LOCATION: (9)..(9)
<223> OTHER INFORMATION: Cys(SS-tBu)
<220> FEATURE:
<221> NAME/KEY: MOD_RES
<222> LOCATION: (12)..(12)
<223> OTHER INFORMATION: Protected residue

<400> SEQUENCE: 71

Pro Asp Tyr Ala Tyr Asp Pro Asp Cys Ala Phe Asp
1               5                  10
```

GLYCOPEPTIDE CONSTRUCTS AND USES THEREOF

CROSS REFERENCE TO RELATED APPLICATIONS

The present application is a U.S. national phase application under 35 U.S.C. §371 of international PCT application no. PCT/US09/50434, filed Jul. 13, 2009, which claims priority under 35 U.S.C. §119(e) to U.S. provisional application U.S. Ser. No. 61/079,919, filed Jul. 11, 2008, the entire contents of each of which are hereby incorporated by reference.

GOVERNMENT SUPPORT

The invention was made with government support under grant No. CA028824 awarded by National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Mar. 9, 2015, is named 2003080-0397_SL.txt and is 27,465 bytes in size.

BACKGROUND OF THE INVENTION

The improvement of existing therapeutics and the development of novel therapeutics to treat and/or prolong survival of cancer patients has been the subject of continuing research in the scientific community. Although certain of these efforts have been directed to "traditional" chemotherapeutics (e.g., Paclitaxel and other small molecule and/or natural product based therapies) that act by killing malignant cancer cells, it has also been a long-standing goal (Lanzavechis, *Science,* 260, 937-944; Pardoll et al., *Curr. Opin. Immunol.* 1993, 5, 719-725; Livingston et al., *Curr. Opin. Immunol.* 1992, 4, 2; Dranoff et al., *Proc. Natl. Acad. Sci, USA* 1993, 90, 3539; M. H. Taoet et al., *Nature,* 1993, 362, 755; T. Boon, *Int. J. Cancer* 1993, 54, 177) to develop an anticancer vaccine that will induce an anticancer immune response. Although cancer vaccines have thus far been perceived as a mode of treatment subsequent to the detection of the disease (for example, by providing an enhanced immunological response), it would be most desirable to develop a selective vaccine that would be able to provide enhanced protection against tumor recurrence and metastasis, for example when the tumor burden has been addressed through surgery, radiation or other chemotherapeutic treatment.

In general, tumor immunotherapy is based on the theory that tumors possess specific antigens that can be recognized when presented to or processed by a properly trained immune system. The goal for the development of an effective anticancer vaccine is to break the tolerance which the immune system has for these antigens expressed mainly or exclusively by the tumor. One approach researchers have taken has been to present glycoconjugate versions of the antigens, to induce an effective immune response. In an effort to achieve this goal, identified cancer carbohydrate antigens such as TF, Tn, sTN, KH-1, Le$^y$ and Globo-H have been carefully characterized as being over-expressed at the surface of malignant cells in a variety of cancers (breast, colon, prostate, ovarian, liver, small cell lung and adenocarcinomas). In addition, they have been immunocharacterized by monoclonal antibodies and therefore have relevant serological markers available for immunological studies. Such studies have suggested that patients immunized in an adjuvant setting with carbohydrate-based vaccines produce antibodies reactive with human cancer cells, and that the production of such antibodies prohibits tumor recurrence and correlates with a more favorable diagnosis (see, Livingston et al., *J. Cancer Res.* 1989, 49, 7045; Ragupathi, G. *Cancer Immunol. Immunother.* 1996, 43, 152). Additionally, the isolation and careful structural identification of specific carbohydrate antigens overexpressed in cancer cells has provided a framework for an attack using carbohydrate-based tumor immunotherapy (For reviews see (a) Hakomori, S.; Zhang, Y. *Chem. Biol.* 1997, 4, 97; (b) Toyokuni, T.; Singhal, A. K. *Chem. Soc. Rev.* 1995, 24, 23 and references therein).

Although several synthetic constructs have been developed in recent years, as described above, and in other references described herein, there remains a need for the further investigation to develop novel constructs capable of eliciting a more sustained or effective (and preferably selective) immune response. Clearly, in an effort to achieve this goal, it would be useful to develop new strategies for inducing an immunogenic response as well as improved and/or novel synthetic methods to access heretofore synthetically unavailable antigenic components (e.g., more complex antigenic components) for further immunologic and therapeutic studies.

SUMMARY OF THE INVENTION

The present disclosure encompasses the recognition that additional glycopeptide vaccines would be useful in the treatment of and prevention of cancer. In some embodiments, the present disclosure provides cyclic peptides that display carbohydrate antigens in a clustered fashion. In certain embodiments, the present disclosure provides constructs comprising tumor associated carbohydrate antigens and peptide epitopes. In certain embodiments, the peptide epitopes are MHC-II binding peptides. In certain embodiments, the peptide epitopes are mucin tandem repeat sequences.

DEFINITIONS

Certain compounds of the present disclosure, and definitions of specific functional groups are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl," used alone or a part of a larger moiety, refers to groups formed by removing a hydroxy group from a carboxylic acid.

The term "halogen" means F, Cl, Br, or I.

The terms "aralkyl" and "arylalkyl" are used interchangeably and refer to alkyl groups in which a hydrogen atom has been replaced with an aryl group. Such groups include, without limitation, benzyl, cinnamyl, and dihydrocinnamyl.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or $14\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present disclosure provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

Provided compounds may comprise one or more saccharide moieties. Unless otherwise specified, both D- and L-configurations, and mixtures thereof, are within the scope of the disclosure. Unless otherwise specified, both α- and β-linked embodiments, and mixtures thereof, are contemplated by the present disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present disclosure is not intended to be limited to these protecting groups; rather, a variety of additional equivalent protecting groups can be readily identified using the above criteria and utilized in the method of the present disclosure. Additionally, a variety of protecting groups are described by Greene and Wuts (supra).

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH=CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR-$, $SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ})_2$; $SiR^{\circ}_3$; $-(C_{1-4}$ straight or branched alkylene)O—$N(R^{\circ})_2$; or $-(C_{1-4}$ straight or branched alkylene)C(O)O—$N(R^{\circ})_2$, wherein each $R^{\circ}$ may be substituted as defined below and is independently hydrogen, $C_{1-6}$ aliphatic, $-CH_2Ph$, $-O(CH_2)_{0-1}Ph$, $-CH_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^○$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^○$ (or the ring formed by taking two independent occurrences of $R^○$ together with their intervening atoms), are independently halogen, $-(CH_2)_{0-2}R^●$, $-(haloR^●)$, $-(CH_2)_{0-2}OH$, $-(CH_2)_{0-2}OR^●$, $-(CH_2)_{0-2}CH(OR^●)_2$; $-O(haloR^●)$, $-CN$, $-N_3$, $-(CH_2)_{0-2}C(O)R^●$, $-(CH_2)_{0-2}C(O)OH$, $-(CH_2)_{0-2}C(O)OR^●$, $-(CH_2)_{0-2}SR^●$, $-(CH_2)_{0-2}SH$, $-(CH_2)_{0-2}NH_2$, $-(CH_2)_{0-2}NHR^●$, $-(CH_2)_{0-2}NR^●_2$, $-NO_2$, $-SiR^●_3$, $-OSiR^●_3$, $-C(O)SR^●$, $-(C_{1-4}$ straight or branched alkylene)$C(O)OR^●$, or $-SSR^●$ wherein each $R^●$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^○$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^●$, $-(haloR^●)$, $-OH$, $-OR^●$, $-O(haloR^●)$, $-CN$, $-C(O)OH$, $-C(O)OR^●$, $-NH_2$, $-NHR^●$, $-NR^●_2$, or $-NO_2$, wherein each $R^●$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^†$, $-NR^†_2$, $-C(O)R^†$, $-C(O)OR^†$, $-C(O)C(O)R^†$, $-C(O)CH_2C(O)R^†$, $-S(O)_2R^†$, $-S(O)_2NR^†_2$, $-C(S)NR^†_2$, $-C(NH)NR^†_2$, or $-N(R^†)S(O)_2R^†$; wherein each $R^†$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, $-R^●$, $-(haloR^●)$, $-OH$, $-OR^●$, $-O(haloR^●)$, $-CN$, $-C(O)OH$, $-C(O)OR^●$, $-NH_2$, $-NHR^●$, $-NR^●_2$, or $-NO_2$, wherein each $R^●$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

When used as a chemical bond, " ~~~ " shall be understood to depict a single carbon-carbon bond with undefined stereochemistry at a carbon center. Thus, a substituent attached to a carbon atom with a " ~~~ " bond refers to embodiments where the substituent is coming out of the plane of the paper, embodiments where the substituent is going behind the plane of the paper, and combinations (i.e., stereochemical mixtures) thereof.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

The term "natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid" as used herein refers to all amino acids which are not natural amino acids. Such amino acids include the D-isomer of any of the 20 naturally occurring amino acids Unnatural amino acids also include homoserine, ornithine, norleucine, and thyroxine. Additional unnatural amino acids are well known to one of ordinary skill in the art and include unnatural aliphatic side chains. In certain embodiments, unnatural amino acids are N-alkylated, cyclized, phosphorylated, acetylated, amidated, azidylated, labelled, and the like. In some embodiments, an unnatural amino acid is a D-isomer. In some embodiments, an unnatural amino acid is a L-isomer. In certain embodiments, an unnatural amino acid is an alpha amino acid. In other embodiments, an unnatural amino acid is a beta amino acid.

More generally, the term "amino acid", as used herein, encompasses natural amino acids and unnatural amino acids.

As used herein and in the claims, the singular forms "a", "an", and "the" include the plural reference unless the context clearly indicates otherwise. Thus, for example, a reference to "a compound" includes a plurality of such compounds.

The terms "compound" and "construct" are used interchangeably in the present disclosure. Thus, a construct as described herein is considered a compound, and vice versa.

The term "peptide epitope", as used herein, refers to a polypeptide including a sequence that is recognized or capable of recognition by the immune system. In some embodiments, a peptide epitope is recognized by antibodies, B cells, T cells, or a combination thereof. In certain embodiments, a peptide epitope functions to stimulate B cells or T cells. In some embodiments, such stimulation has an additive and/or synergistic effect on the overall immune response when compared to immune response in the absence of a peptide epitope. In some embodiments, a peptide epitope comprises or is found in a mucin peptide sequence. In some embodiments, a peptide epitope comprises or is found in a mucin tandem repeat peptide sequence. In some embodiments, a peptide epitope comprises or is found in a mucin peptide sequence present on tumor cells. In certain embodiments, a peptide epitope comprises or is found in a MHC-II binding peptide. In some embodiments, a peptide epitope as described herein is a polypeptide that comprises about 50, 45, 40, 35, 30, 25, 24, 23, 22, 21, 20, 19, 18, 17, 16, 15, 14, 13, 12, 11, 10, 9, 8, 7, 6, or 5 amino acids or fewer. In some embodiments, a peptide epitope as described herein is a polypeptide that comprises about 5-15 amino acids. In some embodiments, a peptide epitope as described herein is a polypeptide that comprises about 5-25 amino acids. In some embodiments, a peptide epitope as described herein is a polypeptide that comprises about 5-35 amino acids. Other exemplary lengths of peptide epitopes are described herein.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "palliative" refers to treatment that is focused on the relief of symptoms of a disease and/or side effects of a therapeutic regimen, but is not curative.

BRIEF DESCRIPTION OF THE DRAWINGS

FIG. 26 discloses '5-4' as SEQ ID NO: 62 and '5-5' as SEQ ID NO: 63. FIG. 27 discloses '5-6' as SEQ ID NO: 64 and '5-7' as SEQ ID NO: 65.

FIG. 28 discloses the linear '$P\rho X_1 Y X_2 Y X_3 P\rho X_4 C X_5 F X_6$' as SEQ ID NO: 52 and constructs 5-9, 5-10, 5-11, 5-1, 5-12 and 5-13 as SEQ ID NOS 53-58, respectively.

FIG. 29a discloses '5-12', '5-14', 5-4' as SEQ ID NOS 57, 59 and 62, respectively. FIG. 29b discloses '5-1', '5-15', 5-16' as SEQ ID NOS 56, 60 and 61, respectively. FIG. 29c discloses '5-5' and '5-6' as SEQ ID NOS 63 and 64, respectively.

FIG. 30a discloses '5-17' and '5-18' as SEQ ID NOS 66 and 67, respectively.

FIG. 31a discloses '5-13', '5-19', 5-20' as SEQ ID NOS 58, 68 and 69, respectively. FIG. 31b discloses '5-21' and '5-7' as SEQ ID NOS 70 and 65, respectively.

FIGS. 32a-b depict LCMS characterization data for purified peptide 5-1.

FIG. 50 depicts a $^1$H-NMR spectrum of compound 3-8a.
FIGS. 51-52 depict LCMS characterization data for compound 3-8a.
FIG. 63 depicts a $^1$H-NMR spectrum of compound 3-11a.
FIGS. 64-65 depict LCMS characterization data for compound 3-11a.

DETAILED DESCRIPTION OF CERTAIN EMBODIMENTS

Figure 1:
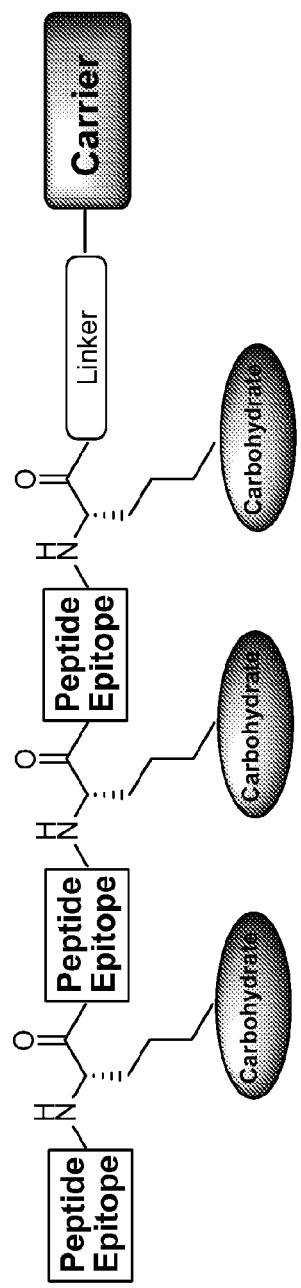
FIG. 1 depicts a novel carbohydrate-peptide based vaccine.

In certain embodiments, the present disclosure provides a construct having the structure:

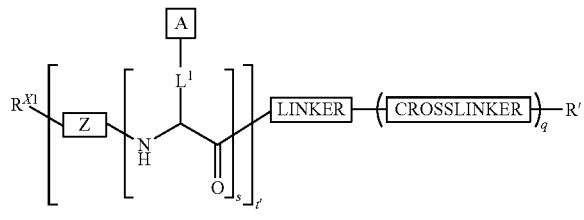

wherein,
q is 0 or 1;
each occurrence of s is independently an integer from 0-20;
t' is an integer from 1-20;
$R^{X1}$ is hydrogen, alkyl, acyl, aryl, heteroaryl, -alkyl(aryl), -alkyl(heteroaryl), a nitrogen protecting group, an amino acid or a protected amino acid;
R' is hydrogen or an immunogenic carrier;
the cross linker is a moiety suitable for conjugation to an immunogenic carrier;
each occurrence of Z is independently a covalent bond or comprises a peptide epitope and optionally comprises a linker, wherein at least one occurrence of Z comprises a peptide epitope, wherein each occurrence of the peptide epitope independently comprises a sequence found in a MHC-II binding peptide or a mucin peptide sequence;
each occurrence of the linker is either a covalent bond, an ester, —O—, (carboxamido)alkyl carboxamide, MBS, primary carboxamide, mono- or dialkyl carboxamide, mono- or diarylcarboxamide, linear or branched chain (carboxy)alkyl carboxamide, linear or branched chain (alkoxycarbonyl)alkyl-carboxamide, linear or branched chain (carboxy)arylalkylcarboxamide, linear or branched chain (alkoxycarbonyl)alkylcarboxamide, an oligoester fragment comprising from 2 to about 20 hydroxy acyl residues, a peptidic fragment comprising from 2 to about 20 amino acyl residues, a linear or branched chain alkyl or aryl carboxylic ester, or a $C_{1-20}$ saturated or unsaturated, straight or branched, hydrocarbon chain, wherein one or more methylene units of the linker are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—;
each occurrence of $L^1$ is independently a substituted or unsubstituted aliphatic or heteroaliphatic moiety;
each occurrence of A is independently a carbohydrate determinant having the structure:

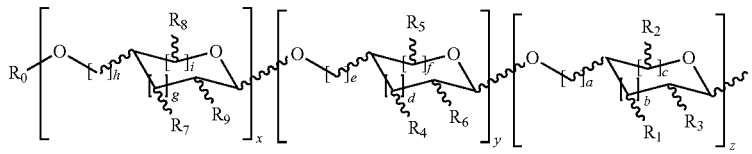

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0;

$R_0$ is hydrogen, or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R_1$, $R_2$, $R_3$, $R_4$, $R_5$, $R_6$, $R_7$, $R_8$ and $R_9$ is independently hydrogen, OH, OR, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur; or a saccharide moiety having the structure:

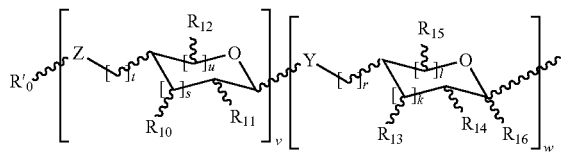

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0;

$R'_0$ is hydrogen, or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R_{10}$, $R_{11}$, $R_{12}$, $R_{13}$, $R_{14}$ and $R_{15}$ is independently hydrogen, OH, OR, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur;

each occurrence of $R_{16}$ is hydrogen, COOH, COOR, CONHR, a substituted or unsubstituted linear or branched chain alkyl or aryl group;

each R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur; or: two R on the same nitrogen atom are taken with the nitrogen to form a 4-7-membered heterocyclic ring having 1-2 heteroatoms independently selected from the group consisting of nitrogen, oxygen, and sulfur.

In some embodiments, q is 0. In some embodiments, q is 1.

In some embodiments, Z is a covalent bond. In some embodiments, Z is a peptide epitope as described herein. In certain embodiments, Z comprises a linker.

In some embodiments, s is an integer from 2-20. In some embodiments, s is an integer from 3-20. In some embodiments, s is an integer from 0-10. In some embodiments, s is an integer from 0-6. In some embodiments, s is an integer from 1-3. In some embodiments, s is 0. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 11. In some embodiments, s is 12. In some embodiments, s is 13. In some embodiments, s is 14. In some embodiments, s is 15. In some embodiments, s is 16. In some embodiments, s is 17. In some embodiments, s is 18. In some embodiments, s is 19. In some embodiments, s is 20.

In some embodiments, t' is an integer from 2-20. In some embodiments, t' is an integer from 3-20. In some embodiments, t' is an integer from 1-10. In some embodiments, t' is an integer from 1-6. In some embodiments, t' is 1. In some embodiments, t' is 2. In some embodiments, t' is 3. In some embodiments, t' is 4. In some embodiments, t' is 5. In some embodiments, t' is 6. In some embodiments, t' is 7. In some embodiments, t' is 8. In some embodiments, t' is 9. In some embodiments, t' is 10. In some embodiments, t' is 11. In some embodiments, t' is 12. In some embodiments, t' is 13. In some embodiments, t' is 14. In some embodiments, t' is 15. In some embodiments, t' is 16. In some embodiments, t' is 17. In some embodiments, t' is 18. In some embodiments, t' is 19. In some embodiments, t' is 20.

In certain embodiments, $R^{X1}$ is hydrogen. In certain embodiments, $R^{X1}$ is alkyl. In certain embodiments, $R^{X1}$ is acyl. In certain embodiments, $R^{X1}$ is aryl. In certain embodiments, $R^{X1}$ is heteroaryl. In certain embodiments, $R^{X1}$ is -alkyl(aryl). In certain embodiments, $R^{X1}$ is -alkyl(heteroaryl). In certain embodiments, $R^{X1}$ is a nitrogen protecting group. In certain embodiments, $R^{X1}$ is an amino acid. In certain embodiments, $R^{X1}$ is a protected amino acid. In certain embodiments, $R^{X1}$ is -Fmoc. In some embodiments, $R^{X1}$ is —Ac. In some embodiments, $R^{X1}$ is hydrogen.

In some embodiments, R' is hydrogen. In other embodiments, R' is an immunogenic carrier. In some embodiments, the immunogenic carrier is a protein, peptide, or lipid. In certain embodiments, the carrier is Keyhole Limpet Hemocyanin (KLH). In certain embodiments, the carrier is outer membrane protein complex (OMPC). In certain embodiments, the carrier is bovine serum albumin (BSA). In some embodiments, the carrier is cationized bovine serum albumin. In some embodiments, the carrier is polylysine. In certain embodiments, the carrier is a lipid having the structure:

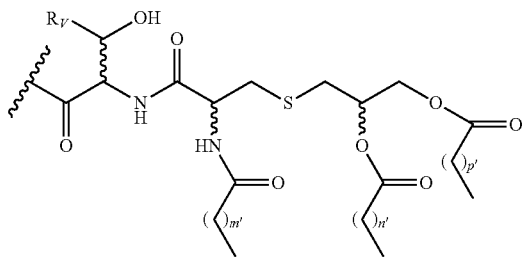

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys).

Crosslinkers suited to the invention are widely known in the art, including bromoacetic NHS ester, 6-(iodoacetamido) caproic acid NHS ester, maleimidoacetic acid NHS ester, maleimidobenzoic acide NHS ester, to name but a few. In certain embodiments, the crosslinker is MMCCH (4-(maleimidomethyl)cyclohexane-1-carboxyl hydrazide). In certain preferred embodiments, the crosslinker is MBS (m-maleimidobenzoyl acid N-Hydroxysuccinimidyl ester).

In certain embodiments, the crosslinker is a fragment having the structure:

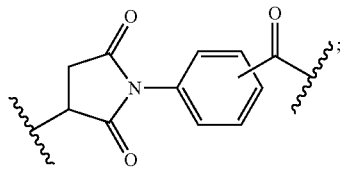

whereby said structure is generated upon conjugation of a maleimidobenzoic acid N-hydroxy succinimide ester with a linker.

In some embodiments, the linker is a covalent bond. In some embodiments, the linker is an ester. In some embodiments, the linker is —O—. In some embodiments, the linker is (carboxamido)alkyl carboxamide. In some embodiments, the linker is maleimidobenzoyl N-hydroxysuccinimide ester (MBS). In some embodiments, the linker is a primary carboxamide. In some embodiments, the linker is a mono- or dialkyl carboxamide. In some embodiments, the linker is a mono- or diarylcarboxamide. In some embodiments, the linker is a linear or branched chain (carboxy)alkyl carboxamide. In some embodiments, the linker is a linear or branched chain (alkoxycarbonyl)alkyl-carboxamide. In some embodiments, the linker is a linear or branched chain (carboxy)arylalkylcarboxamide. In some embodiments, the linker is an oligoester fragment comprising from 2 to about 20 hydroxy acyl residues. In some embodiments, the linker is a linear or branched chain alkyl or aryl carboxylic ester. In some embodiments, the linker is selected from the group consisting of

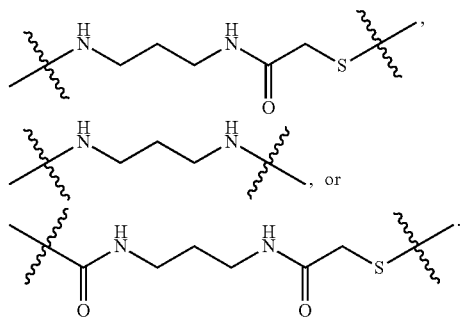

In certain embodiments, the linker is a $C_{1-20}$ saturated or unsaturated, straight or branched, hydrocarbon chain, wherein one or more methylene units of the linker are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—.

In some embodiments, the linker is a peptidic fragment comprising from 2 to about 20 amino acyl residues. In some embodiments, the linker is a peptidic fragment comprising from 2 to about 10 amino acyl residues. In certain embodiments, the linker is a peptidic fragment comprising 2 amino acyl residues. In certain embodiments, the linker is a peptidic fragment comprising 3 amino acyl residues. In certain embodiments, the linker is a peptidic fragment comprising 4 amino acyl residues. In certain embodiments, the linker is a peptidic fragment comprising 5 amino acyl residues. In certain embodiments, the linker is a peptidic fragment comprising 6 amino acyl residues. In certain embodiments, the linker is a peptidic fragment comprising 7 amino acyl residues. In certain embodiments, the linker is a peptidic fragment comprising 8 amino acyl residues. In certain embodiments, the linker is a peptidic fragment comprising 9 amino acyl residues. In certain embodiments, the linker is a peptidic fragment comprising 10 amino acyl residues.

In some embodiments, $L^1$ is an optionally substituted aliphatic moiety. In some embodiments, $L^1$ is a substituted aliphatic moiety. In some embodiments, $L^1$ is an unsubstituted aliphatic moiety. In some embodiments, $L^1$ is an optionally substituted heteroaliphatic moiety. In some embodiments, $L^1$ is a substituted heteroaliphatic moiety. In some embodiments, $L^1$ is an unsubstituted heteroaliphatic moiety. In some embodiments, $L^1$ is a bivalent saturated or unsaturated, straight or branched, hydrocarbon chain. In some embodiments, $L^1$ is an optionally substituted, straight or branched $C_{1-20}$ hydrocarbon chain wherein one or more methylene units is optionally substituted with —O—. In some embodiments, $L^1$ is an optionally substituted, straight or branched $C_{1-12}$ hydrocarbon chain wherein one or more methylene units is optionally substituted with —O—. In some embodiments, $L^1$ is an optionally substituted, straight or branched $C_{1-6}$ hydrocarbon chain wherein one or more methylene units is optionally substituted with —O—. In certain embodiments, $L^1$ is optionally substituted hexyl. In some embodiments, $L^1$ is —(CH$_2$)$_6$—. In some embodiments, $L^1$ is —$(CH_2)_5$—. In some embodiments, $L^1$ is —$(CH_2)_4$—. In some embodiments, $L^1$ is —$(CH_2)_3$—. In some embodiments, $L^1$ is —$(CH_2)_2$—. In some embodiments, $L^1$ is —$(CH_2)$—. In certain embodiments, $L^1$ is other than —$(CH_2)$—. In certain embodiments, $L^1$ is other than —CH(Me)-.

In some embodiments, $L^1$ is —$O(CH_2)_n$—, wherein n is an integer from 0 to 12. In some embodiments, n is an integer from 1 to 12. In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, $L^1$ is other than —$O(CH_2)$—. In some embodiments, $L^1$ is other than —OCH(Me)-.

In some embodiments, each "s" bracketed structure is independently an amino acid substituted with a moiety having the structure:

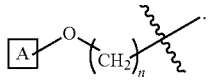

In certain embodiments, an amino acid is substituted with such a moiety at an alpha carbon. In some embodiments, an amino acid has the structure:

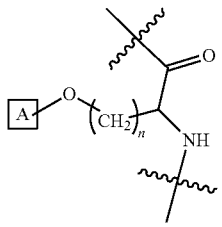

It will be appreciated that the point of attachment to a carbohydrate determinant A can be either α or β stereochemistry, or a mixture thereof.

In some embodiments, a peptide epitope comprises or is found in a mucin sequence expressed on a tumor cell. In some embodiments, a peptide epitope comprises or is found in a mucin tandem repeat peptide sequence. In some embodiments, a peptide epitope comprises or is found in a single occurrence of a mucin tandem repeat peptide sequence. In other embodiments, a peptide epitope comprises or is found in more than one occurrence of a mucin tandem repeat peptide sequence. In some embodiments, a peptide epitope comprises or is found in an unglycosylated mucin sequence. In some embodiments, a mucin sequence is as described by Zhang, et al., *Clin. Cancer Res.* 1998, 4, 2669-2676, the contents of which are hereby incorporated by reference.

In some embodiments, a mucin sequence is a highly clustered glycodomain on adjacent serine and threonine residues. In some embodiments, a mucin sequence is expressed on the surface of a tumor cell. In some embodiments, a mucin sequence is characterized in that it is a T cell epitope. In some embodiments, a mucin sequence is characterized in that it is a B cell epitope.

In certain embodiments, a peptide epitope comprises or is found in a MUC1 sequence. In certain embodiments, a peptide epitope comprises or is found in a MUC2 sequence. In certain embodiments, a peptide epitope comprises or is found in a MUC3 sequence. In certain embodiments, a peptide epitope comprises or is found in a MUC4 sequence. In certain embodiments, a peptide epitope comprises or is found in a MUC5B sequence. In certain embodiments, a peptide epitope comprises or is found in a MUC5AC sequence. In certain embodiments, a peptide epitope comprises or is found in a MUC7 sequence. In certain embodiments, a peptide epitope comprises or is found in a MUC16 sequence. It will be appreciated that where the present disclosure names mucin sequences that are glycosylated in their natural form, the disclosure contemplates both glycosylated and unglycosylated versions of such mucin sequences.

Suitable mucin polypeptides (e.g., comprising peptide epitopes) are known in the art and include those disclosed by Gendler, S. J., et al. Am. Rev. Respir. Dis., 144: S42-S47, 1991; Swallow, D. M.; Gendler, S. J.; Griffith, B.; Corney, G.; Taylor-Papadimitriou, J. Nature 1987, 328, 82-84; Gum, J. R. et al. J. Biol. Chem. 267(30) 1992, 21375-21383; Gum, J. R. et al. J. Biol. Chem. 272(42) 1997, 26678-26686; Yin, B, W. T. and Lloyd, K. O. J. Biol. Chem. 2001, 276(29) 27371-27375; Gilewski, T. et al., *Clin. Cancer Res.* 2000, 6, 1693-1701; Yin, B. W.; Lloyd, K. O. *J. Biol. Chem.* 2001, 276, 27371-27375; and Zhang, S.; Zhang, H. S.; Cordon-Cardo, C.; Ragupathi, G.; Livingston, P. O. *Clin. Cancer Res.* 1998, 4, 2669-2676), the entire contents of each of which is hereby incorporated by reference.

In some embodiments, a mucin polypeptide (e.g., comprising a peptide epitope) comprises a sequence selected from the following list:

| | |
|---|---|
| VTSAPDTRPAPGSTAPPAHG | SEQ ID NO: 1 |
| TTSTTSAP | SEQ ID NO: 2 |
| PDTRPAPGSTAPPAHGVTSA | SEQ ID NO: 3 |
| APDTR | SEQ ID NO: 4 |
| HGVTSAPDTRPAPGSTAPPA | SEQ ID NO: 5 |
| PTTTPITTTTVTPTPTPTGTQT | SEQ ID NO: 6 |
| PTTTPISTTTVTPTPTPTGTQT | SEQ ID NO: 7 |
| HSTPSFTSSITTTETTS | SEQ ID NO: 8 |
| TSSASTGHATPLPVTD | SEQ ID NO: 9 |
| TTAAPPTPSATTPAPPSSSAPPE | SEQ ID NO: 10 |
| ITTTETTSHSTPSFTSS | SEQ ID NO: 11 |
| SSVPTTSTP | SEQ ID NO: 12 |
| SSVSTTSTTSTP | SEQ ID NO: 13 |
| GPLYSCRLTLLR | SEQ ID NO: 14 |
| ELGPYTL | SEQ ID NO: 15 |
| FTLNFTIXNL | SEQ ID NO: 16 |
| PGSRKFNXT | SEQ ID NO: 17 |
| RRKKEGEY | SEQ ID NO: 18 |
| AQPGTTNYQRNK | SEQ ID NO: 19 |

| | |
|---|---|
| SPRLDR | SEQ ID NO: 20 |
| KAQPGTTNYQRN | SEQ ID NO: 21 |
| RTPDTSTMHLATSRT | SEQ ID NO: 22 |
| VTSAPDTRPAPGSTAPPAHGVTSAPDTRPA | SEQ ID NO: 23 |
| STAPPAHGVTSAPDTRPAPG | SEQ ID NO: 24 | or a combination thereof.

In certain embodiments, a peptide epitope comprises or is found in a MHC-II binding peptide. In some embodiments, a MHC-II binding peptide is of the formula:

$$XX(X)_{1-10}Y^1XXXXY^2(X)_{0-7}$$

wherein the total number of amino acids is from 13 to 17, X is any amino acid residue, $Y^1$ is a negatively charged amino acid residue, and $Y^2$ is a hydrophobic residue. In certain embodiments, $Y^1$ is aspartic acid or glutamic acid. In certain embodiments, $Y^2$ is selected from the group consisting of tyrosine, leucine, proline, and phenylalanine.

In some embodiments, a MHC-II binding peptide is selected from the following list:

| | |
|---|---|
| HNWVNHAVPLAMKLI | SEQ ID NO: 25 |
| KSKYKLATSVLAGLL | SEQ ID NO: 26 |
| GLAYKFVVPGAATPY | SEQ ID NO: 27 |
| LTSQFFLPALPVFTWL | SEQ ID NO: 28 |
| IPQEWKPAITVKVLPA | SEQ ID NO: 29 |
| VVFPASFFIKLPIILA | SEQ ID NO: 30 |
| SSVFNVVNSSIGLIM | SEQ ID NO: 31 |
| VKNVIGPFMKAVCVE | SEQ ID NO: 32 |
| SSIIFGAFPSLHSGCC | SEQ ID NO: 33 |
| MRKLAILSVSSFLFV | SEQ ID NO: 34 |
| LVNLLIFHINGKIIK | SEQ ID NO: 35 |
| EPQGSTYAASSATSVD | SEQ ID NO: 36 |
| AGLLGNVSTVLLGGV | SEQ ID NO: 37 |
| FATCFLIPLTSQFFLP | SEQ ID NO: 38 |

| -continued | |
|---|---|
| NLSNVLATITTGVLDI | SEQ ID NO: 39 |
| IKLPIILAFATCFLIP | SEQ ID NO: 40 |
| THHYFVDLIGGAMLSL | SEQ ID NO: 41 |
| LAAIIFLFGPPTALRS | SEQ ID NO: 42 |
| QEIDPLSYNYIPVNSN | SEQ ID NO: 43 |
| RVYQEPQVSPPQRAET | SEQ ID NO: 44 |
| NVKYLVIVFLIFFDL | SEQ ID NO: 45 |
| LWWSTMYLTHHYFVDL | SEQ ID NO: 46 | or a combination thereof.

In certain embodiments, a provided construct comprises one or more "spacer units." In some embodiments, Z comprises a spacer unit. In some embodiments, a spacer unit is a linker as defined herein. In some embodiments, a spacer unit comprises amino acids that are neither considered part of a peptide epitope sequence nor substituted with a carbohydrate determinant. Such amino acid residues may function as "spacer" residues between adjacent peptide epitopes, between a peptide epitope and an amino acid substituted with a carbohydrate determinant, between adjacent amino acids substituted with a carbohydrate determinant, or combinations thereof.

In some embodiments, one or more occurrences of A is a carbohydrate determinant expressed on a tumor cell. In certain embodiments, one or more occurrences of A is a carbohydrate determinant selected from the group consisting of Globo-H, fucosyl GM1, GM2, KH-1, glycophorin, N3, Tn, TF, STn, (2,3)ST, 2,6-ST, $Gb_3$, $Le^y$, and $Le^x$. In some embodiments, one or more occurrences of A is $Gb_3$. In some embodiments, one or more occurrences of A is fucosyl GM1. In some embodiments, one or more occurrences of A is Globo-H.

As described above, in certain embodiments, Z is a peptide epitope. In certain embodiments, provided constructs are of the structure:

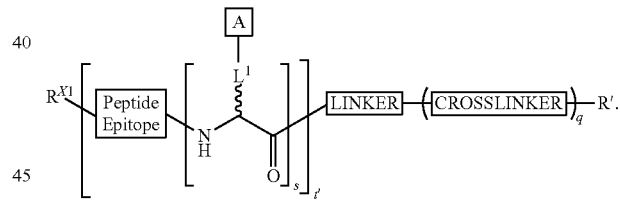

In some embodiments, a provided construct has the structure:

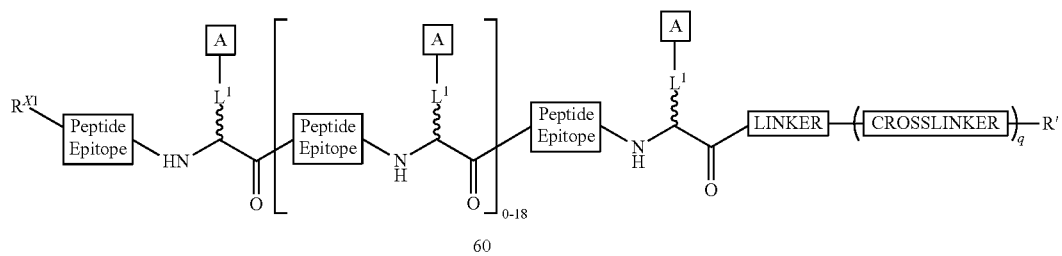

wherein each of $R^{X1}$, $L^1$, A, R', q, the peptide epitope, the linker, and the crosslinker is as defined above and in classes and subclasses herein.

In some embodiments, s is 1, and each occurrence of a peptide epitope is a MUC5AC tandem repeat sequence, thereby providing a construct having the structure:

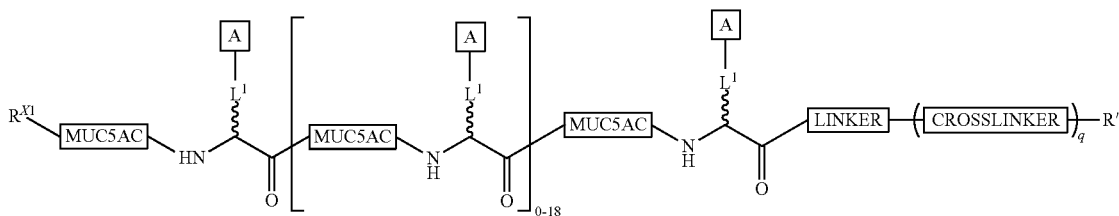

wherein each of $R^{X1}$, $L^1$, A, R', q, the linker, and the crosslinker is as defined above and in classes and subclasses herein.

In some embodiments, a provided construct has the structure:

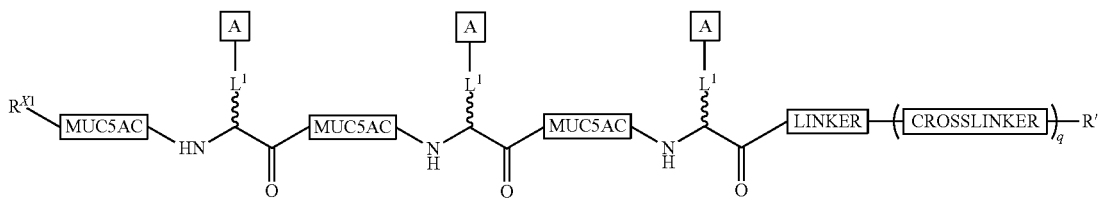

wherein each of $R^{X1}$, $L^1$, A, R', q, the linker, and the crosslinker is as defined above and in classes and subclasses herein.

In some embodiments, a provided construct has the structure:

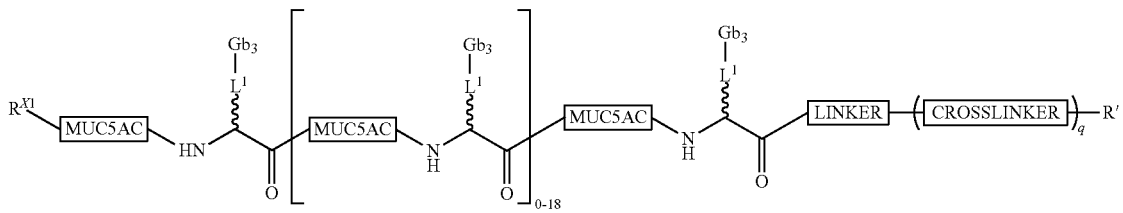

wherein each of $R^{X1}$, $L^1$, R', q, the linker, and the crosslinker is as defined above and in classes and subclasses herein.

In some embodiments, a provided construct has the structure:

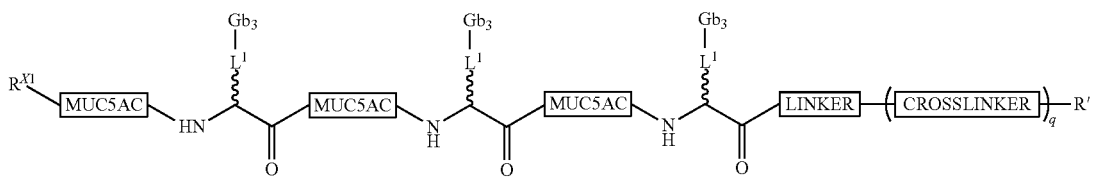

wherein each of $R^{X1}$, $L^1$, R', q, the linker, and the crosslinker is as defined above and in classes and subclasses herein.

In some embodiments, a provided construct has the structure:

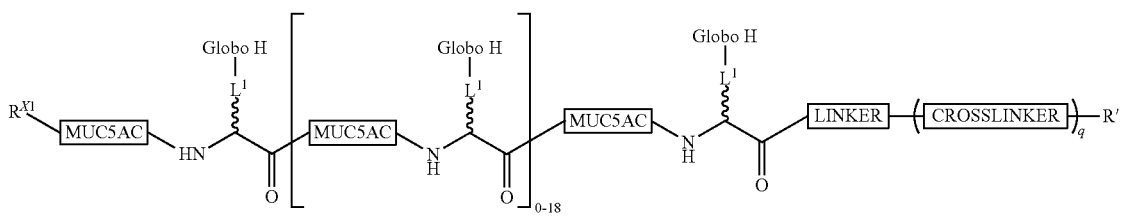

wherein each of $R^{X1}$, $L^1$, R', q, the linker, and the crosslinker is as defined above and in classes and subclasses herein.

In some embodiments, a provided construct has the structure:

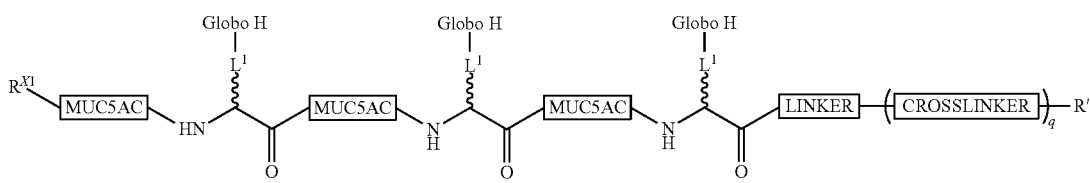

wherein each of $R^{X1}$, $L^1$, R', q, the linker, and the crosslinker is as defined above and in classes and subclasses herein.

In some embodiments, a provided construct has the structure:

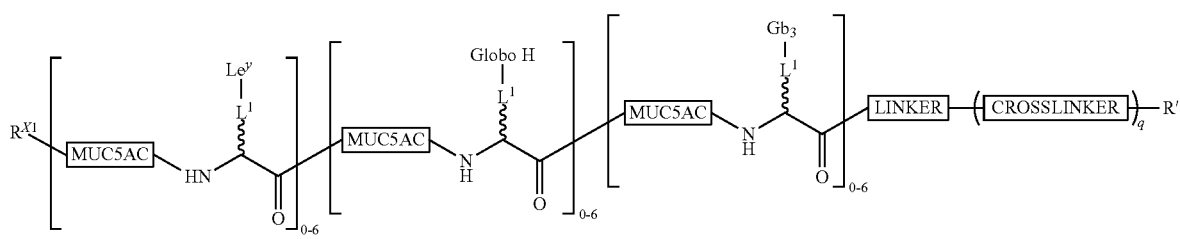

wherein each of $R^{X1}$, $L^1$, R', q, the linker, and the crosslinker is as defined above and in classes and subclasses herein.

In some embodiments, a provided construct has the structure:

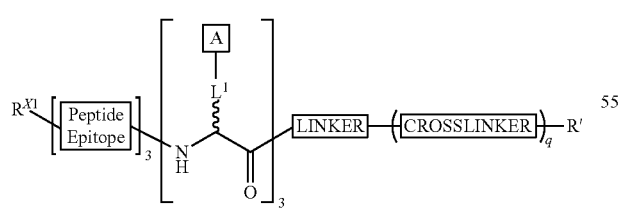

wherein each of $R^{X1}$, $L^1$, A, R', q, the linker, the peptide epitope, and the crosslinker is as defined above and in classes and subclasses herein.

In some embodiments, one or more occurrences of S is zero and Z can be directly attached to the linker. In some embodiments, a provided construct has the structure:

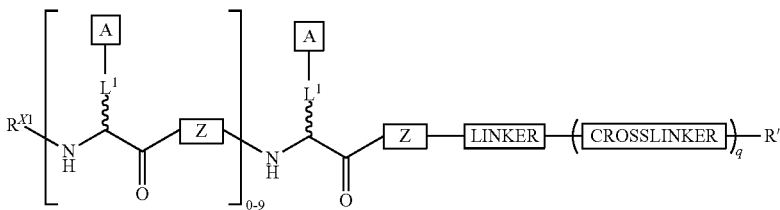

wherein each of $R^{X1}$, $L^1$, A, R', q, Z, the linker, and the crosslinker is as defined above and in classes and subclasses herein.

In some embodiments, a provided construct has the structure:

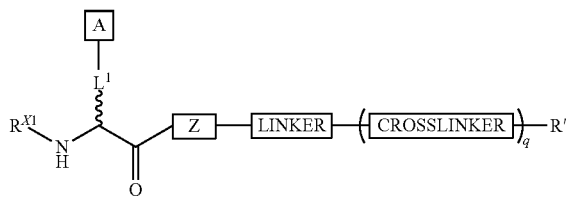

wherein each of $R^{X1}$, $L^1$, A, R', Z, q, the linker, and the crosslinker is as defined above and in classes and subclasses herein.

In some embodiments, a provided construct has the structure:

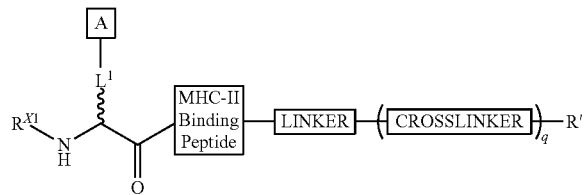

wherein each of $R^{X1}$, $L^1$, A, R', q, the linker, and the crosslinker is as defined above and in classes and subclasses herein.

In some embodiments, a provided construct has the structure:

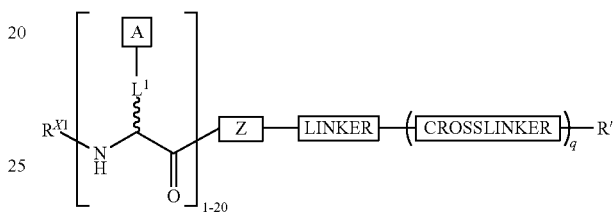

wherein each of $R^{X1}$, $L^1$, A, R', Z, q, the linker, and the crosslinker is as defined above and in classes and subclasses herein.

In some embodiments, a provided construct has the structure:

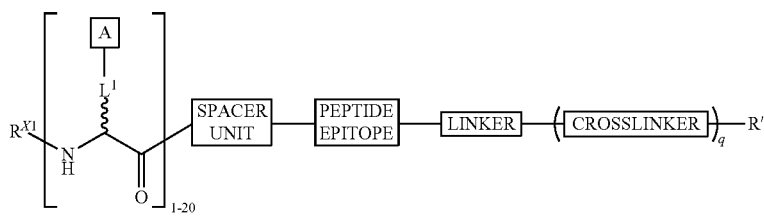

wherein each of $R^{X1}$, $L^1$, A, R', q, the spacer unit, the linker, and the crosslinker is as defined above and in classes and subclasses herein.

In some embodiments, a provided construct has the structure:

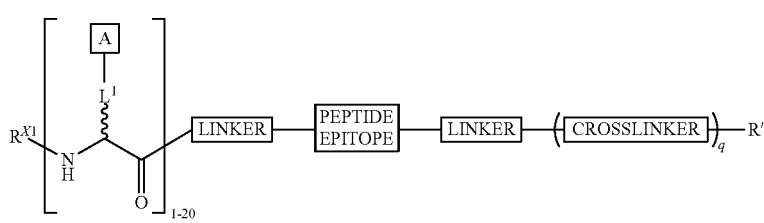

wherein each of $R^{X1}$, $L^1$, A, R', q, the linker, and the crosslinker is as defined above and in classes and subclasses herein.

In some embodiments, a provided construct has the structure:

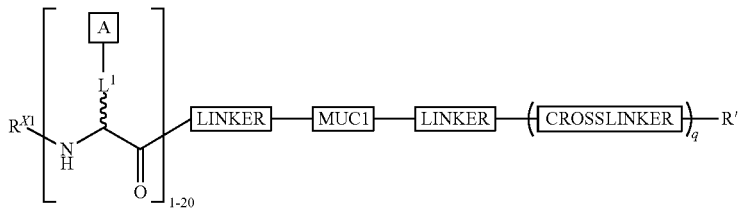

wherein each of $R^{X1}$, $L^1$, A, R', q, the linker, and the crosslinker is as defined above and in classes and subclasses herein.

In some embodiments, a provided construct has the structure:

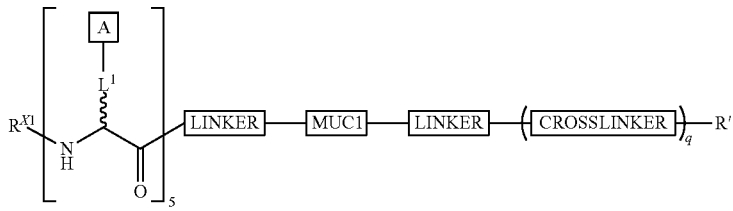

wherein each of $R^{X1}$, $L^1$, A, R', q, the linker, and the crosslinker is as defined above and in classes and subclasses herein.

General Synthesis of Constructs

As described above, the present disclosure contemplates a variety of different markers and carbohydrate antigens that may be used. It will be appreciated by the skilled artisan, having read the present disclosure and the ensuing Examples, that a "cassette" assembly method facilitates the assembly of constructs with relative ease. Scheme A sets forth an example of the cassette assembly of constructs of the present disclosure.

Scheme A

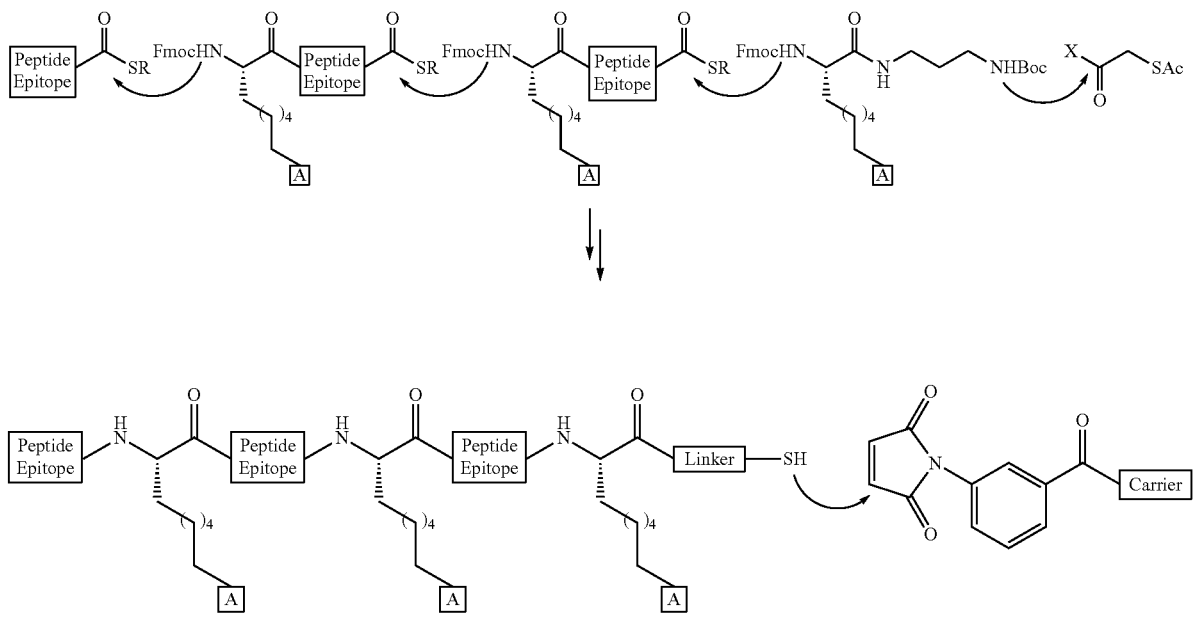

-continued

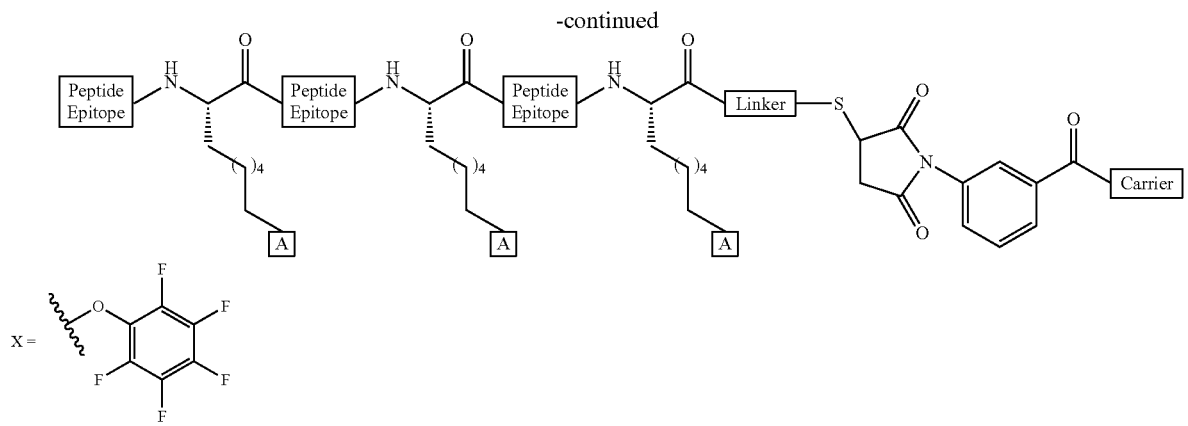

Assembly of various carbohydrate antigen cassettes are described herein and in U.S. Pat. Nos. 6,660,714, 7,160,856, 7,550,146, and U.S. patent application Ser. Nos. 09/641,742, 10/209,618, 10/728,041, and 11/145,002.

I. Mucin-Based Glycopeptide Conjugates

In the quest to develop effective vaccines to combat cancer, tumor immunologists seek to identify the characteristic phenotypes which differentiate tumor cells from normal cells. In this vein, it has been noted that malignantly transformed cells often display aberrant levels and patterns of cell surface glycosylation (Le Poole, I. C.; Gerberi, M. A. T.; Kast, W. M. *Curr. Opin. Oncol.* 2002, 14, 641-648). It may be possible to exploit these distinguishing features by designing vaccine constructs which incorporate these tumor-associated carbohydrate domains. It is believed that such constructs, if properly presented to the immune system, may stimulate the formation of antibodies which would selectively bind and eradicate tumor cells overexpressing the carbohydrate epitopes at issue. Progress in this area of anticancer vaccines has been achieved by Boons (Ingale, S.; Wolfert, M. A.; Gaekwad, J.; Buskas, T.; Boons, G.-J. *Nat. Chem. Biol.* 2007, 3, 663-667; Buskas, T.; Ingale, S.; Boons, G.-J. *Angew. Chem., Int. Ed.* 2005, 44, 5985-5988), Kunz (Kunz, H.; Dziadek, S.; Wittrock, S.; Becker, T. *ACS Symposium Series* 2008, 989 (*Carbohydrate-Based Vaccines*), 293-310; Westerlind, U.; Hobel, A.; Gaidzik, N.; Schmitt, E.; Kunz, H. *Angew. Chem., Int. Ed.* 2008, 47, 7551-7556; Wittrock, S.; Becker, T.; Kunz, H. *Angew. Chem., Int. Ed.* 2007, 46, 5226-5230; Dziadek, S.; Brocke, C.; Kunz, H. *Chem. Eur. J.* 2004, 10, 4150-4162), Schmidt (Hermans, I. F.; Silk, J. D.; Gileadi, U.; Salio, M.; Mathew, B.; Ritter, G.; Schmidt, R.; Harris, Adrian L.; Old, L.; Cerundolo, V. *J. Immunol.* 2003, 171, 5140-5147; Schmidt, R. R.; Castro-Palomino, J. C.; Retz, O. *Pure Appl. Chem.* 1999, 71, 729-744) and their associates.

Over the past two decades, Applicants have engaged in the design and de novo synthesis of complex oligosaccharides and glycoconjugates, with an eye toward developing increasingly potent and versatile vaccines (Danishefsky, S. J.; Allen, J. R. *Angew. Chem., Int. Ed.* 2000, 39, 836-863; Keding, S. J.; Danishefsky, S. J. *Carbohydrate-Based Drug Discovery* 2003, 1, 381-406; Ouerfelli, O.; Warren, J. D.; Wilson, R. M.; Danishefsky, S. J. *Expert Rev. Vaccines* 2005, 4, 677-685; Warren, J. D.; Geng, X.; Danishefsky, S. J. *Top Curr. Chem.* 2007, 267, 109-141; Wilson, R. M.; Warren, J. D.; Ouerfelli, O.; Danishefsky, S. J. *ACS Symposium Series* 2008, 989 (*Carbohydrate-Based Vaccines*), 258-292). Our emphasis has been on the development of immunostimulating strategies allowing for enhanced protection against tumor recurrence and metastasis following resection of tumor burden through surgery, radiation, or chemotherapeutic treatment.

Our initial studies focused on the preparation of constructs, in which a single carbohydrate antigen is attached to an immunogenic carrier molecule, such as KLH (Keyhole Limpet Hemocyanin) (Ragupathi, G.; Park, T. K.; Zhang, S. L.; Kim, I. J.; Graber, L.; Adluri, S.; Lloyd, K. O.; Danishefsky, S. J.; Livingston, P. O. *Angew. Chem., Int. Ed. Engl.* 1997, 36, 125-128; Slovin, S. F.; Ragupathi, G.; Adluri, S.; Ungers, G.; Terry, K.; Kim, S.; Spassova, M.; Bornmann, W. G.; Fazzari, M.; Dantis, L.; Olkiewicz, K.; Lloyd, K. O.; Livingston, P. O.; Danishefsky, S. J.; Scher, H. I. *Proc. Natl. Acad. Sci. U.S.A.* 1999, 96, 5710-5715; Gilewski, T.; Ragupathi, G.; Bhuta, S.; Williams, L. J.; Musselli, C.; Zhang, X.-F.; Bencsath, K. P.; Panageas, K. S.; Chin, J.; Hudis, C. A.; Norton, L.; Houghton, A. N.; Livingston, P. O.; Danishefsky, S. J. *Proc. Natl. Acad. Sci. U.S.A.* 2001, 98, 3270-3275; Krug, L. M.; Ragupathi, G.; Hood, C.; Kris, M. G.; Miller, V. A.; Allen, J. R.; Keding, S. J.; Danishefsky, S. J.; Gomez, J.; Tyson, L.; Pizzo, B.; Baez, V.; Livingston, P. O. *Clin. Cancer Res.* 2004, 10, 6094-6100; Sabbatini, P. J.; Kudryashov, V.; Ragupathi, G.; Danishefsky, S. J.; Livingston, P. O.; Bornmann, W.; Spassova, M.; Zatorski, A.; Spriggs, D.; Aghajanian, C.; Soignet, S.; Peyton, M.; O'Flaherty, C.; Curtin, J.; Lloyd, K. O. *Int. J. Cancer.* 2000, 87, 79-85; Keding, S. J.; Danishefsky, S. J. *Proc. Natl. Acad. Sci. USA.* 2004, 101, 11937-11942). —These monovalent vaccines—which include Globo-H, fucosyl $GM_1$, and Lewis$^y$ ($Le^y$)—have shown varying degrees of promise in early clinical settings. The present disclosure describes the preparation and evaluation of more elaborate constructs, for example in which multiple repeats, or "clusters," of a carbohydrate epitope are presented on a peptide backbone. The design of these constructs is inspired partly by findings from the field of glycohistology which demonstrate that mucins—a family of glycoproteins overexpressed on tumor cell surfaces—often present clusters of two to five adjacent carbohydrates domains (Caristedt, Davies, J. R. *Biochem. Soc. Trans.* 1997, 25, 214). While not wishing to be bound by any particular theory, it is believed that vaccines designed on the basis of such "clustered" antigens will better mimic the surfaces of targeted tumor cells. Previously, Applicants prepared a number of clustered vaccine constructs, such as Tn(c), TF(c) and STn(c), each of which performed as hoped in preclinical studies. For instance, in a Phase I clinical trial against prostate cancer, the Tn(c)-KLH conjugate has produced positive serological results (Kuduk, S. D.; Schwarz, J. B.; Chen, X.-T.; Glunz, P. W.; Sames, D.; Ragupathi, G.; Livingston, P. O.; Danishefsky, S. J. *J. Am. Chem. Soc.* 1998, 120, 12474-12485). These earlier vaccine constructs did not take full account of the multiplicity of carbohydrate epitopes overexpressed within a particular cancer type. For example, even within the lifetime of a single tumor cell, there is a significant amount of heterogeneity of tumor cell surface carbohydrate expression (Zhang, S.; Cordon-Cardo, C.; Zhang, H. S.; Reuter, V. E.; Adluri, S.; Hamilton, W. B.; Lloyd, K. O.; Livingston, P. O. *Int. J. Cancer* 1997, 73, 42-49; Zhang, S.; Zhang, H. S.; Cordon-Cardo, C.; Reuter, V. E.; Singhal, A. K.; Lloyd, K. O.; Livingston, P. O. *Int. J. Cancer* 1997, 73, 50-56). Thus, the present disclosure provides, among other things, carbohydrate-based antitumor vaccines that incorporate multiple antigenic components (Ragupathi, G.; Koide, F.; Livingston, P. O.; Cho, Y. S.; Atsushi, E.; Wan, Q.; Spassova, M. K.; Keding, S. J.; Allen, J.; Ouerfelli, O.; Wilson, R. M.; Danishefsky, S. J. *J. Am. Chem. Soc.* 2006, 128, 2715-2725; Livingston, P. O.; Ragupathi, G. *Human Vaccines* 2006, 2, 137-143).

The present disclosure encompasses the recognition that a peptide backbone, in addition to its role as a linker to a carrier protein, might also provide additional antigenic markers. One class of markers that are noteworthy is the mucin family of O-linked glycoproteins (Van den Steen, P.; Rudd, P. M.; Dwek, R. A.; Opdenakker, G. *Crit. Rev. Biochem. Mol. Biol.* 1998, 33, 151-208; Brockhausen, I. In *Glycoproteins*; Montreuil, J., Vliegenthart, J. F. G., Schachter, H., Eds.; Elsevier Science New York, 1995; pp 201-259). Mucins, which carry highly clustered glycodomains on adjacent serine and threonine residues, are overexpressed on a variety of tumor cell surfaces. Numerous mucin types have been identified, and correlated with tumor types (Zhang, S.; Zhang, H. S.; Cordon-Cardo, C.; Ragupathi, G.; Livingston, P. O. *Clin. Cancer Res.* 1998, 4, 2669-2676). For example, MUC1 expression is most intense in cancers of breast, lung, ovarian, and endometrial origin; MUC2 is overexpressed in cancers of colon and prostate origin; MUC5AC is associated with breast and gastric cancers; MUC4 was found to be highly expressed in 50% of cancers of colon and pancreas origin; and MUC3, MUC5B, and MUC7 are overexpressed in a variety of epithelial cancers, though not intensely so. It has been theorized that these mucins may potentially serve as CD8+ cytotoxic T cell and CD4+ helper T cell epitopes (Barratt-Boyes, S. M.; Vlad, A.; Finn, O. J. *Clin. Cancer Res.* 1999, 5, 1918-1924; Hiltbold, E. M.; Ciborowski, P.; Finn, O. J. *Cancer Res.* 1998, 58, 5066-5070; Kocer, B.; McKolanis, J.; Soran, A. *BMC gastroenterology* 2006, 6, 4; Bondurant, K. L.; Crew, M. D.; Santin, A. D.; O'Brien, T. J.; Cannon, M. J. *Clin. Cancer Res.* 2005, 11, 3446-3454; Cannon, M. J.; O'Brien, T. J.; Underwood, L. J.; Crew, M. D.; Bondurant, K L.; Santin, A. D. *Expert Rev. Anticancer Ther.* 2002, 2, 97-105). MUC1 has also previously been used as a B-cell epitope for generating anti-MUC1 antibodies (Zhang, S.; Graeber, L. A.; Helling, F.; Ragupathi, G.; Adluri, S.; Lloyd, K. O.; Livingston, P. O. *Cancer Res.* 1996, 56, 3315-3319).

Among other things, the present disclosure exemplifies novel glycopeptide constructs that, as described in U.S. Ser. No. 61/079,919, feature both a carbohydrate-based antigen and a mucin derived peptide-based epitope (e.g., FIG. 1). This design seeks to mimic the molecular architecture on tumor cell surfaces, thus provoking a more robust immune response. In these clustered carbohydrate-peptide antigenic constructs, either repeats of the same carbohydrate antigen or a combination of diverse carbohydrate antigens associated with a particular carcinoma can be incorporated. It is believed that this type of vaccine structure has at least two potential advantages. First, a mucin derived peptide fragment is incorporated as both a linker and a marker, which may behave not only as a B-cell epitope for the production of antibodies against mucins, but also as a helper T-cell epitope to activate T-cells. Furthermore, the tandem repeats of both the carbohydrate-based antigen and the peptide-based epitope are expected to expose these B-cell and helper T-cell epitopes to the maximum extent on the surface of the carrier protein (KLH). It is expected that this feature will prove to be useful in stimulating a strong immune response. Finally, vaccines composed of numerous carbohydrate antigens associated with a specific cancer type may provide for heightened and more varied responses, thereby increasing the efficiency of binding to the target cells.

Ovarian cancer is the fifth leading cause of cancer deaths in women and the leading cause of death from gynecological malignancies (Merck Manual of Diagnosis and Therapy Section 18. Gynecology And Obstetrics Chapter 241. Gynecologic Neoplasms). A number of carbohydrates have been found to be overexpressed on ovarian tumor cell surfaces, including Le$^y$ (Yin, B. W.; Finstad, C. L.; Kitamura, K.; Federici, M. G.; Welshinger, M.; Kudryashov, V.; Hoskins, W. J.; Welt, S.; Lloyd, K. O. *Int. J. Cancer* 1996, 65, 406), STn (Zhang, S.; Zhang, H. S.; Cordon-Cardo, C.; Reuter, V. E.; Singhal, A.1 K.; Lloyd, K. O.; Livingston, P. O. *Int. J. Cancer* 1997, 73, 50-56), Globo-H (Livingston, P. O, *Semin. Cancer Biol.* 1995, 6, 357-366) and Gb$_3$ (globotriaosyl ceramide, cf. 1-2, FIG. 5) (Kiguchi, K.; Iwamori, Y.; Suzuki, N.; Kobayashi, Y.; Ishizuka, B.; Ishiwata, I.; Kita, T.; Kikuchi, Y.; Iwamori, M. *Cancer Science* 2006, 97, 1321-1326; Lingwood, C. A.; Khine, A. A.; Arab, S. *Acta Biochimica Polonica* 1998, 45, 351-359; Arab, S.; Russel, E.; Chapman, W. B.; Rosen, B.; Lingwood, C. A. *Oncology Research* 1997, 9, 553-563). Also found on ovarian cancer cell surfaces are the mucin antigens, MUC1 (vide supra), MUC5AC (cf. 1-3) (Giuntoli, R. L. II; Rodriguez, G. C.; Whitaker, R. S.; Dodge, R.; Voynow, J. A. *Cancer Res.* 1998, 58, 5546-5550) and MUC16 (CA125 antigen) (Yin, B. W.; Lloyd, K. O. *J. Biol. Chem.* 2001, 276, 27371-27375). Structurally, MUC1 and MUC5AC consist of tandem repeats of a 20-amino acid sequence VTSAPDTRPAPG-STAPPAHG (SEQ ID NO: 1) and an 8-amino acid sequence TTSTTSAP (SEQ ID NO: 2), which are potentially responsible for the activation of T cells. The present disclosure provides chimeric vaccine constructs, composed of alternating immunogenic carbohydrate and peptide domains. In some embodiments, such constructs incorporate alternating repeats of the Gb$_3$ antigen and the MUC5AC-based peptide marker (1-1, FIG. 5).

It will be appreciated that, in accordance with the present disclosure, provided multi-antigenic constructs may comprise any mucin sequence. Furthermore, provided multi-antigenic constructs may comprise any carbohydrate epitope. One of ordinary skill, having read the present disclosure, will be capable of selecting a desired mucin sequence and carbohydrate epitope according to the desired biological and/or therapeutic use. Additional guidance and experimental details are provided by Zhu, J. et al., *J. Am. Chem. Soc.,* 2009, 131, 4151-4158 (and supporting information), the entire contents of which are hereby incorporated by reference.

II. MHC-II Binding Peptide-Based Glycopeptide Conjugates

Among the large number of emerging anticancer strategies, the prospect of mobilizing the immune system against the disease is especially attractive. One can imagine employing a vaccine-based therapeutic approach against a number of different primary tumors, as well as against metastatic cells, in an adjuvant mode (Khleif, S. N. (ed.) *Tumor Immunology and Cancer Vaccines*, Springer-Verlag, New York, 2005). The present disclosure recognizes the potential benefit of targeting as immune system markers complex carbohydrate epitopes, which are overexpressed on cancer cell surfaces. We have made a particularly strong commitment to accessing these structures by total synthesis (Danishefsky, S. J.; Allen, J. R. *Angew. Chem. Int. Ed. Engl.* 2000, 39, 836-863; Keding, S. J.; Danishefsky, S. J. *Proc. Natl. Acad. Sci. USA* 2004, 101, 11937-11942).

Figure 2:
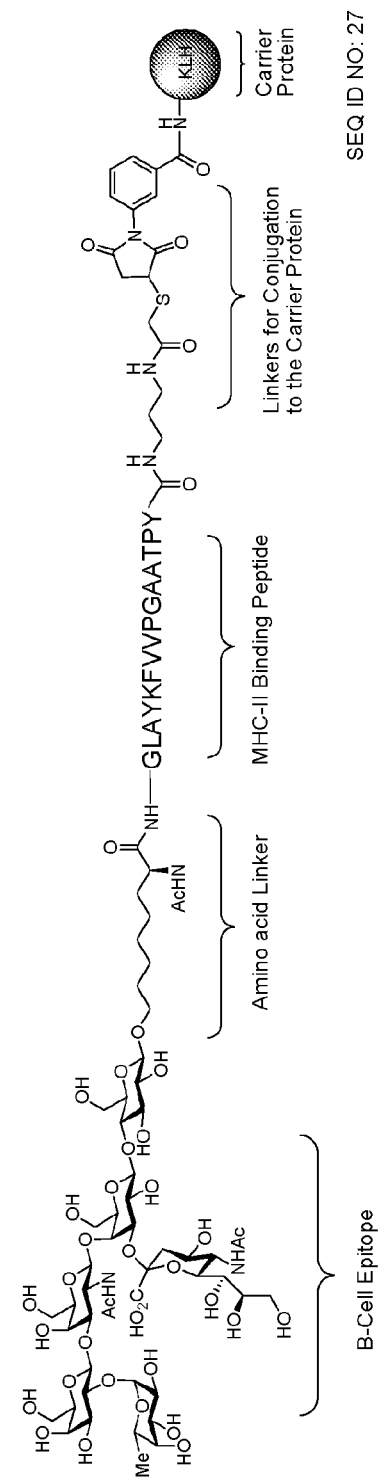
FIG. 2 depicts a new generation bidomainal fucosyl GM1-based vaccine for the treatment of SSLC.

In certain embodiments, a carbohydrate-based anticancer vaccine comprises a complex carbohydrate epitope, overexpressed on the cancer cell, a carrier protein, and a linker attaching the carbohydrate to the protein (FIG. 2). Besides being a potent immunogen, a carrier protein is known to provide the MHC-II binding peptides bound to the epitope, thus helping to present the carbohydrate to the T-cells for T-cell activation and initiation of the cellular response (Zegers, N. D.; Boersma, W. J. A.; Claassen, E. (ed) *Immunological Recognition of Peptides in Medicine and Biology*, CRC Press, Boca Raton, 1995, 105; Rudensky, A. Y.; Preston-Hurlbort, P.; Hong, S.-Ch.; Barlow, A.; Janeway, C. A., Jr. *Nature*, 1991, 353, 622-627; Bona, C. A.; Casares, S.; Brumeanu T. D. *Immunology Today* 1998, 19, 126-133; Musselli, C.; Livingston, P. O.; Ragupathi, G. *J. Cancer Res. Clin. Oncol.* 2001, 127, 20-26). The present disclosure encompasses the recognition that immunogenicity of a vaccine might well be enhanced by providing MHC-II binding peptides in the environs of the epitope, thereby serving to increase the number of epitopes presented to the CD4+ T cell. In a sense, this rationale is related to the idea of conjugating epitopes to carrier protein to create vaccines. However, this approach of placing an MHC-II binding sequence in a fixed relation to the antigen has been pursued mostly for vaccines unconjugated to carrier protein (Dziadek, S.; Hobel, A.; Shmitt, E.; Kunz, H. *Angew. Chem. Int. Ed.* 2005, 44, 7630-7635; Buskas, T.; Ingale, S.; Boons, G.-J. *Angew. Chem. Int. Ed.* 2005, 44, 5985-5988; Ingale, S.; Wolfert, M. A.; Gaekwad, J.; Buskas, T.; Boons, G.-J. *Nature, Chem. Biol.* 2007, 3, 663-667). It is believed that provided conjugates will demonstrate that the introduction of an MHC-II binding sequence improves the immunogenicity of vaccines incorporating standard carriers such as Keyhole Limpet Hemocyanin (KLH).

Among other things, the present disclosure exemplifies novel glycopeptide constructs that, as described in U.S. Ser. No. 61/079,919, featurine both a carbohydrate-based antigen and a MHC-II binding peptide. To test the notion of upgrading the immunogenicity of a candidate carbohydrate based vaccine in this way, we pursued the synthesis of the construct illustrated in FIG. 2. Fucosyl GM1 is a carbohydrate epitope that is expressed on the surface of Small-Cell Lung Cancer (SCLC) cells (Zhang, S.; Cordon-Cardo, C.; Zhang, H. S.; Reuter, V. E.; Adluri, S.; Hamilton, Wm. B.; Lloyd, K. O.; Livingston, P. O. *Int. J. Cancer* 1997, 73, 42-49). This carbohydrate has been synthesized by our group as well as by others (Allen, J. R.; Danishefsky, S. J. *J. Am. Chem. Soc.* 1999, 121, 10875-10882; Mong, T. K.-K.; Lee, H.-K.; Duron, S. G.; Wong, C.-H. *Proc. Natl. Acad. Sci. USA* 2003, 100, 797-802) and it was selected based on the promising results demonstrated by its KLH conjugate in our recent clinical trials (Dickler, M. N.; Ragupathi, G.; Liu, N. X.; Musselli, C.; Martino, D. J.; Miller, V. A.; Kris, M. G.; Brezicka, F.-T.; Livingston, P. O.; Grant, S. C. *Clin. Cancer Res.* 1999, 5, 2773-2779).

HLA-DR is a major histocompatibility complex, MHC class II, cell surface receptor. The complex of HLA-DR and its ligand, a peptide of 9 amino acids in length or longer, constitutes a ligand for the T-cell receptor (TCR). It has been established that many peptides binding to certain HLA-DR molecules bear a motif characterized by a large aromatic or hydrophobic residue in position 1 and a small, noncharged residue in position 6. While peptides binding to MHC-II molecules are usually between 10 to 20 residues long, sizes between 13 and 16 amino acids are frequently observed. It has been shown through the use of algorithms that peptides capable of degenerate binding to multiple DR alleles can be identified (Southwood, S., et al., infra).

While not wishing to be bound by any particular theory, it is believed that, due to the high degree of polymorphism of MHC molecules expressed in the human population, it may be advantageous to develop vaccine constructs comprising MHC-II binding peptides that are capable of binding multiple HLA-DR types. In certain embodiments, a MHC-II binding peptide is any peptide sequence that binds one or more HLA-DR molecules.

As illustrated in Example 3, a fifteen amino acid peptide sequence derived from *Plasmodium Falciparum* and illustrated in FIG. 2 was chosen as an exemplary T-cell epitope. This sequence has been shown to be general for binding up to 9 different alleles of human HLA-DR with binding capacity prevalently in the nanomolar range. See Southwood, S.; Sidney, J.; Kondo, A.; del Guercio, M. S.; Appella, E.; Hoffman, S.; Kubbo, R. T.; Chesnut, R. W.; Grey, H. M.; Sette, A. *J. Immun.* 1998, 160, 3363-3373, the contents of which are hereby incorporated by reference.

In some embodiments, appendage of a fucosyl GM1 epitope to a peptide portion is done using a norleucine linker (Keding, S. J.; Atsushi, E.; Biswas, K.; Zatorski, A.; Coltart, D. M.; Danishefsky, S. J. *Tetrahedron Lett.* 2003, 44, 3413-3416; Wan, Q.; Cho, Y. S.; Lambert, T. H.; Danishefsky, S. J. *J. Carb. Chem.* 2005, 24, 425-440; Ragupathi, G.; Koide, F.; Livingston, P. O.; Cho, Y. S.; Endo, A.; Wan, Q.; Spassova, M. K.; Keding, S. J.; Allen, J.; Ouerfelli, O.; Wilson, R. M.; Danishefsky, S. J. *J. Am. Chem. Soc.* 2006, 128, 2715-2725). While not wishing to be bound by any particular theory, it is believed that the long aliphatic chain of this linker is useful in preventing potentially adverse interactions between the epitope and the peptide backbone. The amino acid functionality makes this linker a useful handle for conjugation.

III. Pentavalent/MUC1 Glycopeptide Conjugates

As discussed above, the development of carbohydrate-based anticancer vaccines elaborated through chemical synthesis has been the focus of extensive research (Fung, P. Y.; Madej, M.; Koganty, R. R. *Cancer Res.* 1996, 56, 5309-5318; Ouerfelli, O.; Warren, J. D.; Wilson, R. M.; Danishefsky, S. J. *Expert Rev. Vaccines* 2005, 4, 677-685). Such research efforts are based on the observation that tumor cells display abnormal levels and types of cell surface carbohydrates, anchored to the cancer cell either through a lipid tail or a protein domain (Slovin, S. F.; Keding, S. J.; Ragupathi, G. *Immunol. Cell Biol.* 2005, 83, 418-428). This distinguishing feature of malignantly transformed cells can be exploited to induce the immune system to selectively recognize and eradicate circulating cancer cells and micrometastases.

In this context, Applicants have developed a range of fully synthetic, carbohydrate-based anticancer vaccine conjugates (Ragupathi, G.; Park, T. K.; Zhang, S. L.; Kim, I. J.; Graber, L.; Adluri, S.; Lloyd, K. O.; Danishefsky, S. J.; Livingston, P. O. *Angew. Chem. Int. Ed.* 1997, 36, 125-128; Slovin, S. F.; Ragupathi, G.; Adluri, S.; Ungers, G.; Terry, K.; Kim, S.; Spassova, M.; Bornmann, W. G.; Fazzari, M.; Dantis, L.; Olkiewicz, K.; Lloyd, K. O.; Livingston, P. O.; Danishefsky, S. J.; Scher, H. I. *Proc. Natl. Acad. Sci. U.S.A.* 1999, 96, 5710-5715; Gilewski, T.; Ragupathi, G.; Bhuta, S.; Williams, L. J.; Musselli, C.; Zhang, X.-F.; Bencsath, K. P.; Panageas, K. S.; Chin, J.; Hudis, C. A.; Norton, L.; Houghton, A. N.; Livingston, P. O.; Danishefsky, S. J. *Proc. Natl. Acad. Sci. U.S.A.* 2001, 98, 3270-3275; Krug, L. M.; Ragupathi, G.; Hood, C.; Kris, M. G.; Miller, V. A.; Allen, J. R.; Keding, S. J.; Danishefsky, S. J.; Gomez, J.; Tyson, L.; Pizzo, B.; Baez, V.; Livingston, P. O. *Clin. Cancer Res.* 2004, 10, 6094-6100; Sabbatini, P. J.; Kudryashov, V.; Ragupathi, G.; Danishefsky, S. J.; Livingston, P. O.; Bornmann, W. G.; Spassova, M.; Zatorski, A.; Spriggs, D.; Aghajanian, C.; Soignet, S.; Peyton, M.; O'Flaherty, C.; Curtin, J.; Lloyd, K. O. *Int. J. Cancer.* 2000, 87, 79-85; Kuduk, S. D.; Schwarz, J. B.; Chen, X.-T.; Glunz, P. W.; Sames, D.; Ragupathi, G.; Livingston, P. O.; Danishefsky, S. J. *J. Am. Chem. Soc.* 1998, 120, 12474-12485). These synthetic constructs are typically attached through a linker domain to an immunogenic carrier protein, such as Keyhole Limpet Hemocyanin (KLH). Preclinical and clinical trials have confirmed the capacity of such constructs to induce antibodies which selectively bind to the carbohydrate-bearing tumor cells in question.

The present disclosure realizes the development of multiantigenic vaccines, in which several different cancer-associated carbohydrates are presented on a single peptide backbone and conjugated to a carrier protein. While not wishing to be bound by any particular theory, it is believed that combining multiple carbohydrate antigens associated with a single cancer type will generate a diverse range antibodies, increasing the percentage of tumor cells targeted by the immune system (Zhang, S. L.; Cordon-Cardo, C.; Zhang, H. S.; Reuter, V. E.; Adluri, S.; Hamilton, W. B.; Lloyd, K. O.; Livingston, P. O. *Int. J. Cancer* 1997, 73, 42-49; Zhang, S. L.; Zhang, H. S.; Cordon-Cardo, C.; Reuter, V. E.; Singhal, A. K.; Lloyd, K. O.; Livingston, P. O. *Int. J. Cancer* 1997, 73, 50-56). Previously, several unimolecular multiantigenic vaccines have now been synthesized and evaluated in preclinical settings (Allen, J. R.; Harris, C. R.; Danishefsky, S. J. *J. Am. Chem. Soc.* 2001, 123, 1890-1897; Ragupathi, G.; Coltart, D. M.; Williams, L. J.; Koide, F.; Kagan, E.; Allen, J.; Harris, C.; Glunz, P. W.; Livingston, P. O.; Danishefsky, S. J. *Proc. Natl. Acad. Sci. U.S.A.* 2002, 99, 13699-13704; Keding, S. J.; Danishefsky, S. J. *Proc. Natl. Acad. Sci. U.S.A.* 2004, 101, 11937-11942; Ragupathi, G.; Koide, F.; Livingston, P. O.; Cho, Y. S.; Endo, A.; Wan, Q.; Spassova, M. K.; Keding, S. J.; Allen, J.; Ouerfelli, O.; Wilson, R. M.; Danishefsky, S. J. *J. Am. Chem. Soc.* 2006, 128, 2715-2725). Of particular interest is a KLH-conjugated pentavalent construct, which incorporates five breast and prostate cancer related antigens (Globo-H, GM2, sTn, TF, and Tn). This conjugate has shown very promising results in preclinical studies.

The present disclosure encompasses the recognition that most carbohydrate epitopes are able to induce only weak T-cell independent B-cell responses. In contrast, peptide domains may be much more immunogenic, as they have the capacity to bind to major histocompatibility complex (MHC) molecules, and, in favorable cases, to trigger the desired T-cell mediated reaction (Deck, B.; Elofsson, K.; Kihlberg, J.; Unanue, E. E. *J. Immunol.* 1995, 155, 1074-1078; Haurum, J. S.; Arsequell, G.; Lellouch, A. C.; Wong, S. Y. C.; Dwek, R. A.; McMichael, A. J.; Elliot, T. *J. Exp. Med.* 1994, 180, 739-744; Mouritsen, S.; Meldal, M.; Christiansen-Brams, I; Elsner, H.; Werdelin, O. *Eur. J. Immunol.* 1994, 24, 1066-1072; Sieling, P. A.; Chatterjee, D.; Porcelli, S. A.; Prigozy, T. L.; Mazzaccaro, R. J.; Soriano, T.; Bloom, B. R.; Brenner, M. B.; Kronenberg, M.; Brennan, P. J. *Science* 1995, 269, 227-230). In certain embodiments, such peptide domains are mucin tandem repeat sequences as described above.

In some embodiments, a peptide domain is the human-tumor associated epithelial mucin, MUC1 (Gendler, S. J.; Lancaster, C. A.; Taylor-Papadimitriou, T.; Duhig, N.; Peat, N.; Burchell, J.; Pemberton, E.-N.; Lalani, N.; Wilson, D. *J. Biol. Chem.* 1990, 265, 15286-15293). Over-expressed on the tumor cell surface as a high molecular weight glycoprotein, MUC1 contains numerous repeating units of a 20-amino acid sequence HGVTSAPDTRPAPGSTAPPA (SEQ ID NO: 5) in the extracellular portion of the molecule. Monoclonal antibody studies focused on tumor MUC1-induced antibodies reveal the PDTRP (Burchell, J.; Taylor-Papadimitriou, J.; Boshell, M.; Gendler, S.; Duhig, T. *Int. J. Cancer* 1989, 44, 691-696; Price, M. R.; Hudecz, F.; O'Sullivan, C.; Baldwin, R. W.; Edwards, P. M.; Tendler, S. J. B. *J. Mol. Immunol.* 1990, 62, 795-802) amino acid segment within the repeating units to be the most antigenic epitope. Expression of MUC1 on normal tissues is largely restricted to the apical surface of secretory cells, a site with minimal access to the immune system (Arklie, J.; Taylor-Papadimitriou, J.; Bodmer, W.; Egan, M.; Millis, R. *Int. J. Cancer* 1981, 28, 23-29; Hollingsworth, M. A.; Strawhecker, J. M.; Caffrey, T. C.; Mack, D. R. *Int. J. Cancer* 1994, 57, 198-203). The over-expression of MUC1 is correlated with the progression of breast (Tampellini, M.; Berruti, A.; Gerbino, A.; Buniva, T.; Torta, M.; Gorzegno, G.; Faggiuolo, R.; Cannoner, R.; Farris, A.; Destefanis, M.; Moro, G.; Deltetto, F.; Dogliotti, L. *Br. J. Cancer* 1997, 75, 698-702), ovarian (Bon, G. G.; Verheijen, R. H. M.; Zuetenhorst, J. M.; Van Kamp, G. J.; Verstraeten, A. A.; Kenemans, P. *Gynecol. Obstet. Inv.* 1996, 42, 58-62), and colon (Nakamori, S.; Ota, D. M.; Cleary, K. R.; Shirotani, K.; Irimura, T. *Gastroenterology* 1994, 106, 353-361) carcinoma, and MUC1 has long been used as a marker for monitoring recurrence of breast cancer (Hilkens, J.; Buijs, F.; Hilgers, J.; Hageman, P.; Calafat, J.; Sonnenberg, A; Der VanVlak, M. *Int. J. Cancer* 1984, 34, 197-206; Bon, G. G.; Von Mensdorff-Pouilly, S.; Kenemans, P.; Van Kamp, G. J.; Verstraeten, R. A.; Hilgers, J.; Meijer, S.; Vermorken, J. B. *Clin. Chem.* 1997, 43, 585-593). Animal studies and clinical trials show that the MUC1 antigen is capable of inducing a T-helper type I response (Butts, C.; Murray, N.; Maksymiuk, A.; Goss, G.; Marshall, E.; Soulières, D.; Cormier, Y.; Ellis, P.; Price, A.; Sawhney, R.; Davis, M.; Mansi, J.; Smith, C.; Vergidis, D.; Ellis, P.; MacNeil, M.; Palmer, M. *J. Clin. Oncol.* 2005, 23, 6674-6681). It is therefore thought that MUC1 could presumably serve as a synergic component in the development of carbohydrate vaccines, in that the robust formation of antibodies depends on the cooperative interactions between T- and B-cells.

Figure 3:
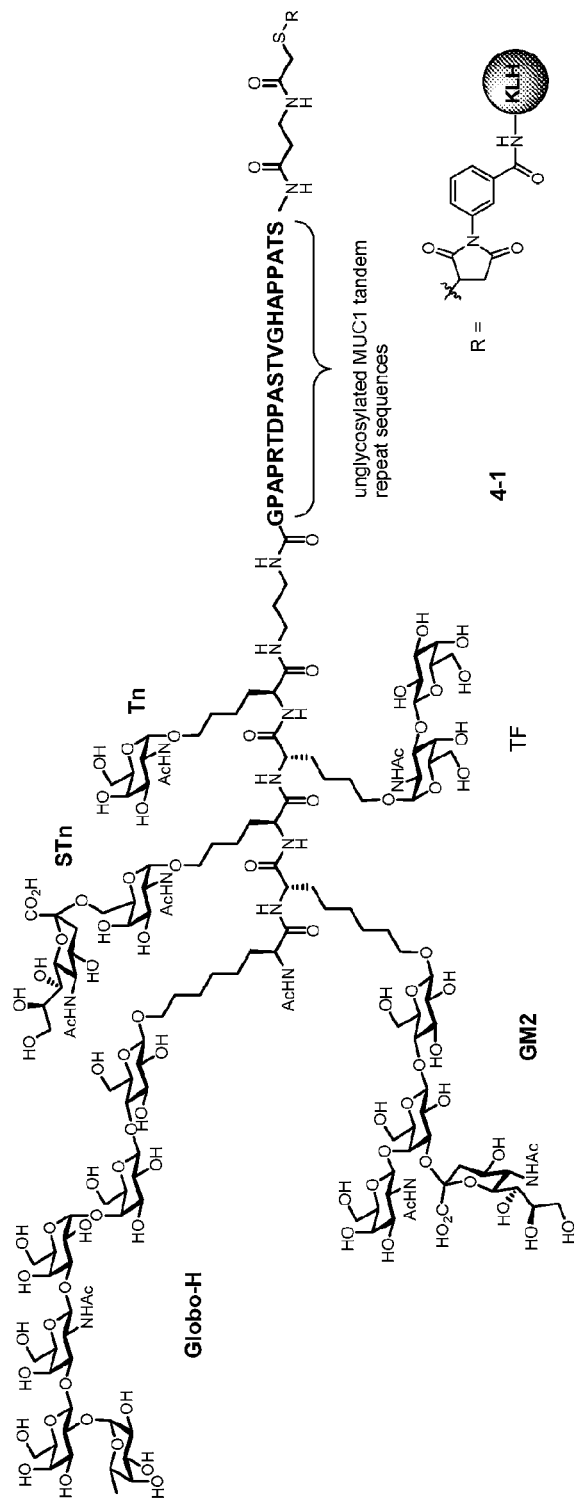
FIG. 3 depicts unimolecular KLH-conjugated pentavalent-MUC1 construct 4-1.

Among other things, the present disclosure describes novel glycopeptide constructs that, as described in U.S. Ser. No. 61/079,919, feature both a multivalent carbohydrate-based antigen moiety and a mucin derived peptide-based epitope. In some embodiments, a provided a construct is a hybrid vaccine (4-1) incorporating the previously synthesized unimolecular pentavalent carbohydrate domain as well as the MUC1 peptide (see FIG. 3). The strategy for the synthesis of the KLH-conjugated unimolecular pentavalent-MUC1 construct (4-1) is highly convergent. In some embodiments, the synthetic methods employed are compatible with both the carbohydrate and peptide domains. In some embodiments, the synthetic components comprise: (1) the fully protected unimolecular pentavalent glycopeptide, equipped with a C-terminal diaminopropyl spacer; (2) the fully protected unglycosylated MUC1 tandem sequence, possessing a β-alanine spacer and a terminal thiol functionality as a handle for late-stage conjugation; and (3) the KLH carrier protein. The protected glycopeptide and MUC1 peptide domains are assembled through direct amide coupling or chemical ligation. Subsequent global deprotection and, finally, conjugation to the carrier protein yields construct (4-1). Additional guidance and experimental details are provided by Lee, D., Danishefsky, S. J., *Tet. Lett.*, 2009, 50, 2167-2170 (and supplementary data), the entire contents of which are hereby incorporated by reference.

IV. Cyclic Peptide Scaffold-Based Glycopeptides

Our laboratory is engaged in efforts toward the development of novel, fully synthetic carbohydrate-based vaccines for the treatment of cancer. This research program is based, among other things, on the finding that malignantly transformed cells often exhibit significant alteration in the nature and quantity of carbohydrates presented on their cell surfaces, either as glycosphingolipids or as glycoproteins (Danishefsky, S. J.; Allen, J. R. *Angew. Chem., Int. Ed.* 2000, 39, 836-863; Livingston, P. O.; Zhang, S. *Cancer Immunol. Immunother.* 1997, 45, 1-9; Livingston, P. O.; Ragupathi, G. *Cancer Immunol. Immunother.* 1997, 45, 10-19.; Toyokuni, T.; Singhal, A. K. *Chem. Soc. Rev.* 1995, 231-242; Hakomori, S. I. *Advances in Exp. Med. Biol.* 2001, 491, 369-402). Presumably, when introduced properly to the immune system, a tumor-associated carbohydrate-based antigen may set into motion an exploitable immune response, leading to the generation of antibodies that selectively bind to and eliminate those tumor cells which over-express the carbohydrates in question. The viability of this carbohydrate vaccine concept has been confirmed experimentally in our laboratory. Thus, when these tumor-associated antigens are presented to the immune system as glycoconjugates appended to immunogenic carrier molecules (such as KLH carrier protein) (Helling, F.; Shang, A.; Calves, M.; Zhang, S. L.; Ren, S. L.; Yu, R. K.; Oettgen, H. F.; Livingston, P. O.; *Cancer Res.* 1994, 54, 197-203; Helling, F.; Zhang, S.; Shang, A.; Adluri, S.; Calves, M.; Koganty, R.; Longenecker, B. M.; Yao, T. J.; Oettgen, H. F.; Livingston, P. O. *Cancer Res.* 1995, 55, 2783-2788) and co-administered with an immunological adjuvant (such as QS21) (Kensil, C. R.; Patel, U.; Lennick, M.; Marciani, D. *J. Immunol.* 1991, 146, 431-437; Marciani, D. J.; Press, J. B.; Reynolds, R. C.; Pathak, A. K.; Pathak, V. L.; Gundy, E.; Farmer, J. T.; Koratich, M. S.; May, R. D. *Vaccine* 2000, 18, 3141-3151; Kim, S.-K.; Ragupathi, G.; Musselli, C.; Choi, S. J.; Park, Y. S.; Livingston, P. O. *Vaccine* 1999, 18, 597-603; Kim, S.-K.; Ragupathi, G.; Cappello, S.; Kagan, E. P.; Livingston, O. *Vaccine* 2000, 19, 530-537), a carbohydrate-specific antibody response may be observed. A number of complex, fully synthetic carbohydrate-based constructs, synthesized in our laboratories, have shown significant promise in preclinical, and even clinical, settings (Ragupathi, G.; Park, T. K.; Zhang, S. L.; Kim, I. J.; Graber, L.; Adluri, S.; Lloyd, K. O.; Danishefsky, S. J.; Livingston, P. O. *Angew. Chem., Int. Ed. Engl.* 1997, 36, 125-128; Slovin, S. F.; Ragupathi, G.; Adluri, S.; Ungers, G.; Terry, K.; Kim, S.; Spassova, M.; Bornmann, W. G.; Fazzari, M.; Dantis, L.; Olkiewicz, K.; Lloyd, K. O.; Livingston, P. O.; Danishefsky, S. J.; Scher, H. I. *Proc. Natl. Acad. Sci. U.S.A.* 1999, 96, 5710-5715; Gilewski, T.; Ragupathi, G.; Bhuta, S.; Williams, L. J.; Musselli, C.; Zhang, X. F.; Bencsath, K. P.; Panageas, K. S.; Chin, J.; Hudis, C. A.; Norton, L.; Houghton, A. N.; Livingston, P. O.; Danishefsky, S. *J. Proc. Natl. Acad. Sci. U.S.A.* 2001, 98, 3270-3275; Krug, L. M.; Ragupathi, G.; Hood, C.; Kris, M. G.; Miller, V. A.; Allen, J. R.; Keding, S. J.; Danishefsky, S. J.; Gomez, J.; Tyson, L.; Pizzo, B.; Baez, V.; Livingston, P. O. *Clin. Cancer Res.* 2004, 10, 6094-6100; Sabbatini, P. J.; Kudryashov, V; Ragupathi, G.; Danishefsky, S. J.; Livingston, P. O.; Bornmann, W.; Spassova, M.; Zatorski, A.; Spriggs, D.; Aghajanian, C.; Soignet, S.; Peyton, M.; O'Flaherty, C.; Curtin, J.; Lloyd, K. O. *Int. J. Cancer.* 2000, 87, 79-85).

Exemplary Cyclic Peptide Displaying STn and Tn Carbohydrate Epitopes (Top Sequence Disclosed as SEQ ID NO: 71; Bottom Sequence Disclosed as SEQ ID NO: 65)

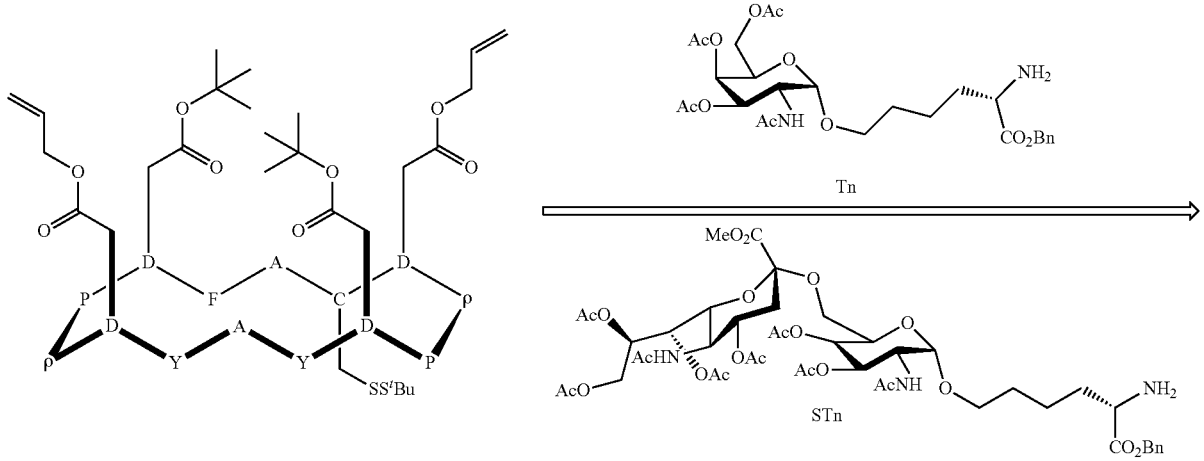

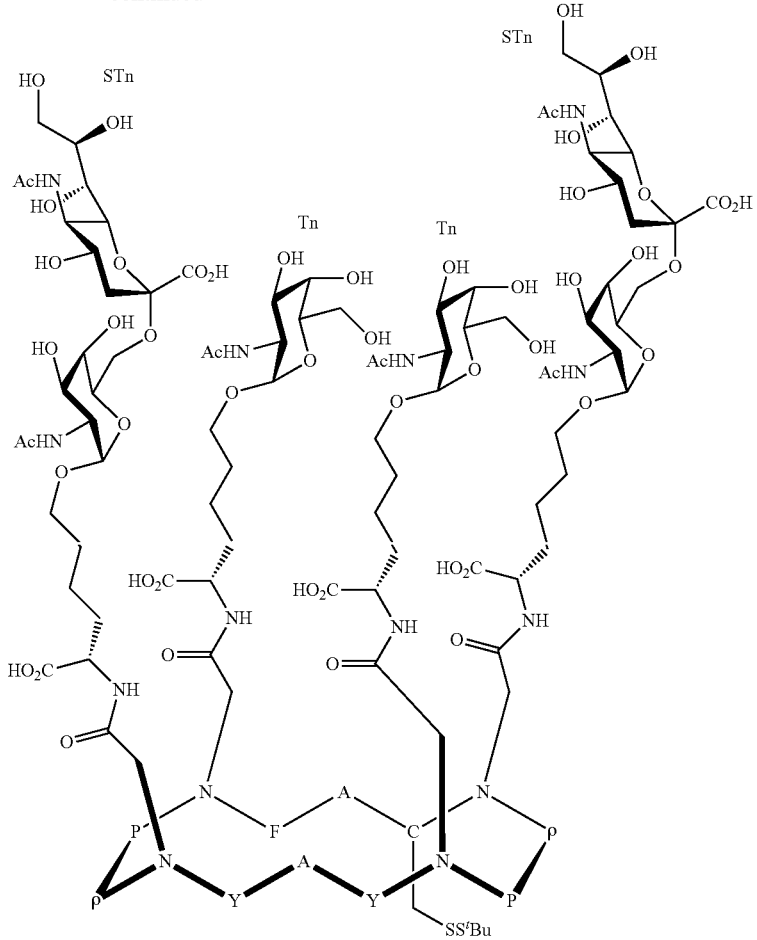

When designing a carbohydrate-based vaccine construct, it may be useful to consider the way in which the antigen is displayed in its natural environment, i.e. on the surface of the transformed cell, and to attempt to mimic this natural setting in the context of the vaccine. Along these lines, we have taken note of the mucin-bound carbohydrate antigens, Tn and STn, which are over-expressed on the surfaces of a variety of epithelial cancers, such as prostate, breast, colon, and ovarian (Springer, G. F. *Science* 1984, 224, 1198-1206; Itzkowitz, S. H.; Yuan, M.; Montgomery, C. K.; Kjeldsen, T.; Takahashi, H. K.; Bigbee, W. L.; Kim, Y. S. *Cancer Res.* 1989, 49, 197-204; Kim, Y. S.; Gum, J.; Brockhausen, I. *Glycoconjugate J.* 1996, 13, 693-707; Springer, G. F. *J. Mol. Med.* 1997, 75, 594-602; Springer, G. F. *Crit. Rev. Oncogenesis* 1995, 6, 57-85). On the tumor cell surface, Tn and STn are presented in broadly conserved "clusters" of 2-4 carbohydrate units, O-linked to the mucin peptide through serine or threonine residues.

Figure 4A:
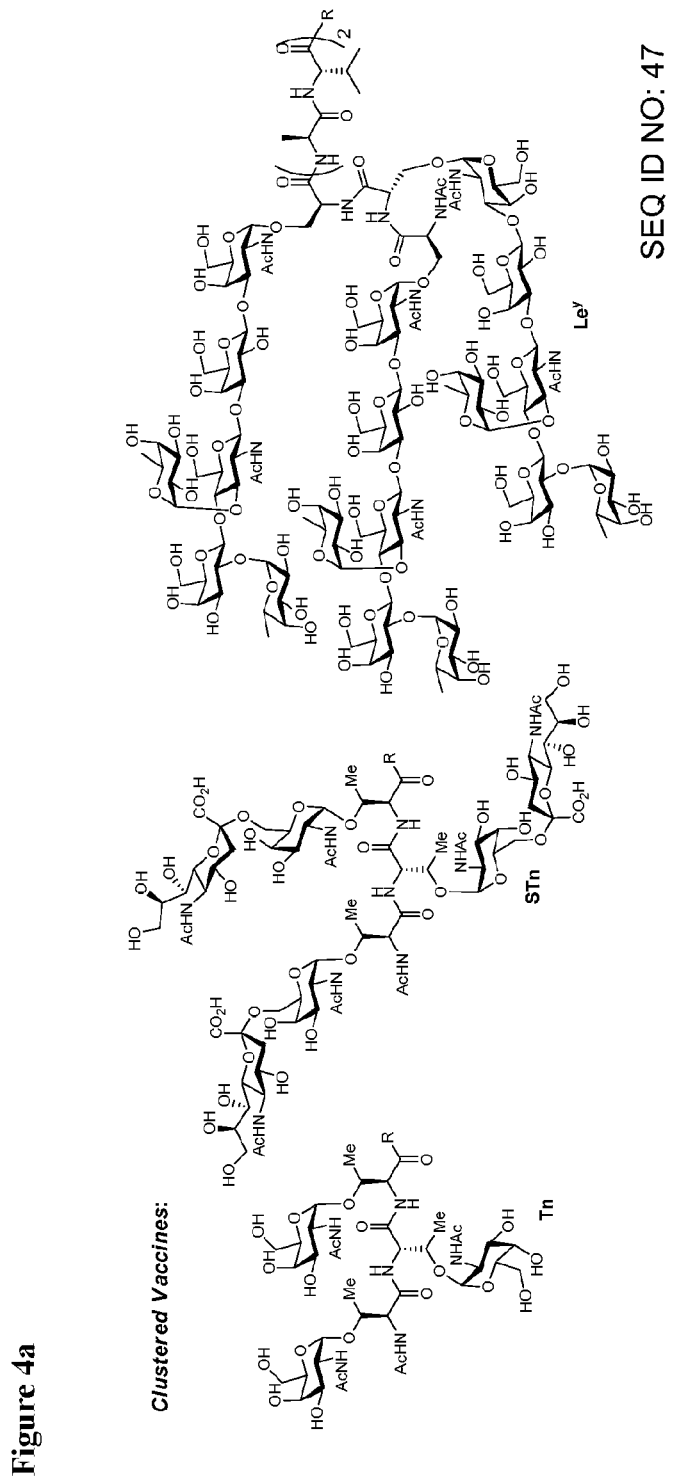
FIGS. 4a-b depict representative anticancer vaccine constructs.
Figure 4B:
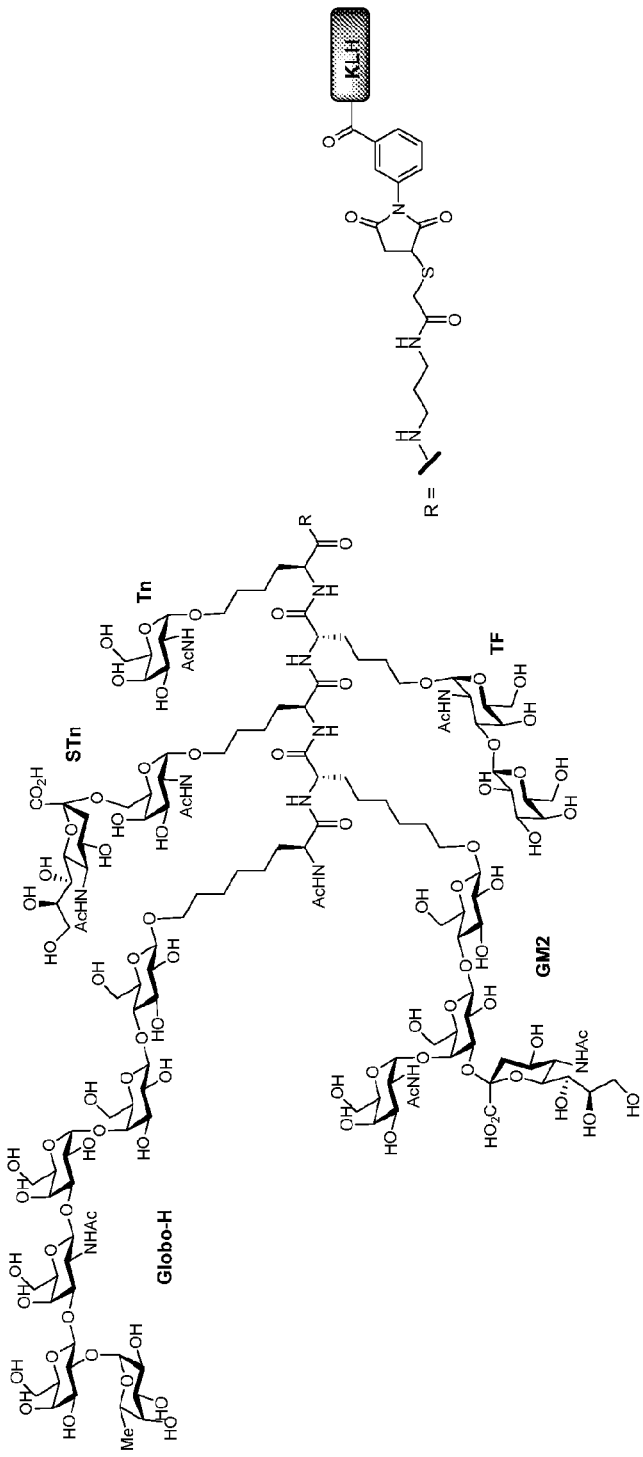

Approaches using monomeric Tn or STn antigen, in which one glycan unit is covalently appended to an immunogenic carrier protein, have proven beneficial (Adluri, S; Helling, F; Ogata, S; Zhang, S.; Itzkowitz, S. H.; Lloyd, K. O.; Livingston, P. O. *Cancer Immunol. Immunother.* 1995, 41, 185-192; MacLean, G. D.; Reddish, M.; Koganty, R. R.; Wong, T.; Gandhi, S.; Smolenski, M.; Samuel, J.; Nabholtz, J. M.; Longenecker, B. M. *Cancer Immunol. Immunother.* 1993, 36, 215-222; MacLean, G. D.; Reddish, M. A.; Bowen-Yacyshyn, M. B.; Poppema, S.; Longenecker, B. M. *Cancer Invest* 1994, 12, 46-56; MacLean, G. D.; Miles, D. W.; Rubens, R. D.; Reddish, M. A.; Longenecker, B. M. *J. Immunother.* 1996, 19, 309-316; MacLean, G. D.; Reddish, M. A.; Koganty, R. R.; Longenecker, B. M. *J. Immunother.* 1996, 19, 59-68; O'Boyle, K. P.; Markowitz, A. L.; Khorshidi, M.; Lalezari, P.; Longenecker, B. M.; Lloyd, K. O.; Welt, S.; Wright, K. E. *Hybridoma.* 1996, 15, 401-408). However, it has been shown that clustered vaccines—wherein multiple copies of the carbohydrate are incorporated on a peptide backbone (FIGS. 4a-b)—induce higher titers against some carbohydrate epitopes (Kudryashov, V.; Glunz, P. W.; Williams, L. J.; Hintermann, S.; Danishefsky, S. J.; Lloyd, K. O. *Proc. Natl. Acad. Sci. U.S.A.* 2001, 98, 3264-3269). Indeed, recent studies with the antitumor monoclonal antibody (MAb) B72.3 revealed that it preferentially recognized clustered STn rather than monovalent STn (Slovin, S. F.; Ragupathi, G.; Musselli, C.; Olkiewicz, K.; Verbel, D.; Kuduk, S. D.; Schwarz, J. B.; Sames, D.; Danishefsky, S. J.; Livingston, P. O.; Scher, H. I. *J. Clin. Oncol.* 2003, 21, 4292-4298; Zhang, S.; Walberg, L. A.; Ogata, S.; Itzkowitz, S. H.; Koganty, R. R.; Reddish, M.; Gandhi, S. S.; Longenecker, B. M.; Lloyd, K. O.; Livingston, P. O. *Cancer Res.* 1995, 55, 3364-3368).

Figure 25:
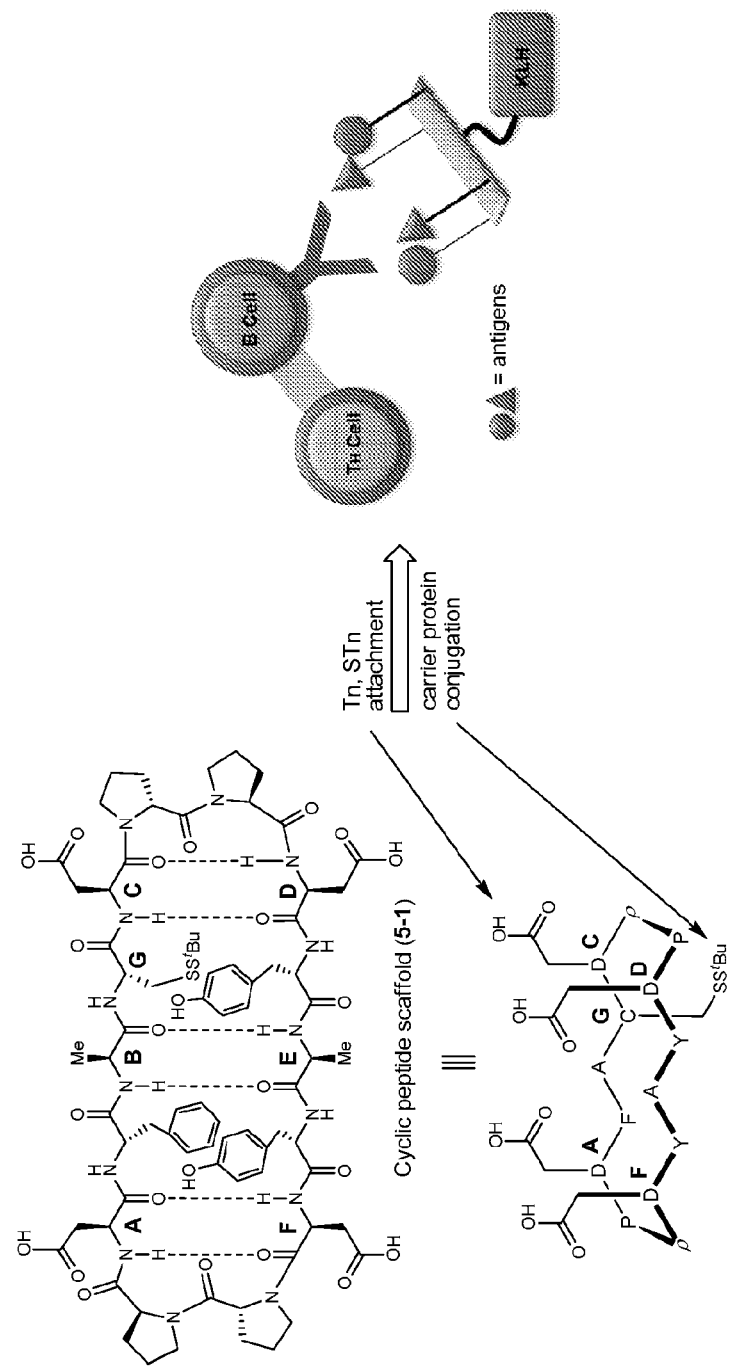
FIG. 25 depicts a cyclic peptide scaffold 5-1 (SEQ ID NO: 56) and antibody response to tetravalent-KLH conjugate.

To some extent, the lowered entropic penalty associated with the increase in valency enhances carbohydrate-protein interactions. However, the choice of template for multivalent carbohydrate display may be important; excessively flexible scaffolds will permit attached glycans to remain far from in most conformations, decreasing the effective clustering of the antigen. In considering a template for the presentation of the clustered carbohydrates, we have been attracted to the type of scaffold, depicted in FIG. 25, upon which the clustered glycans would be displayed in a well-defined orientation. Our design, inspired by Dumy (Dumy, P.; Eggleston, I. M.; Cervigni, S.; Sila, U.; Sun, X.; Mutter, M. *Tetrahedron Lett.* 1995, 36, 1225-1258; Dumy, P.; Renaudet, O. *Org. Lett.* 2003, 5, 243-246; Singh, Y.; Dolphin, G. T.; Razkin, J.; Dumy, P. *Chem Bio Chem* 2006, 7, 1298-1314) and Robinson (Jiang, L.; Moehle, K.; Dhanapal, B.; Obrecht, D.; Robinson, J. A. *Helv. Chim. Acta* 2000, 83, 3097-3112; Favre, M.; Moehle, K.; Jiang, J.; Pfeiffer, B.; Robinson, J. A. *J. Am. Chem. Soc.* 1999, 121, 2679-2685; Robinson, J. A. *Synlett* 2000, 429-441) is amenable to variations in the number and type of carbohydrates displayed, as well as the spacing of the carbohydrate domains. Moreover, the promise of such templates is evidenced by recent studies demonstrating their use for clustered antigen syntheses in our lab and elsewhere (Grigalevicius, S.; Chierici, S.; Renaudet, O.; Lo-Man, R.; Deriaud, E.; Leclerc, C.; Dumy, P. *Bioconjugate Chem.* 2005, 16, 1149-1159.

Wang, J.; Li, H.; Zou, G.; Wang, L. X. *Org. Biomol. Chem.* 2007, 5, 1529-1540). In fact, we have recently employed this scaffold in the context of a separate program, directed toward the development of an HIV vaccine (Krauss, I. J.; Joyce, J. G.; Finnefrock, A. C.; Song, H. C.; Dudkin, V. Y.; Geng, X. J.; Warren, D.; Chastain, M.; Shiver, J. W.; Danishefsky, S. J. *J. Am. Chem. Soc.* 2007, 129, 11042-11044; Joyce, J. G.; Krauss, I. J.; Song, H. C.; Opalka, D. W.; Grimm, K. M.; Nahas, D. D.; Esser, M. T.; Hrin, R.; Feng, M.; Dudkin, V. Y.; Chastain, M.; Shiver, J. W.; Danishefsky, S. J. *Proc. Natl. Acad. Sci. USA* 2008, 105, 15684-15689).

In some embodiments, a cyclic peptide comprises a pair of β-turn-inducing D-Pro-L-Pro sequences (Bean, J. W.; Kopple, K. D.; Peishoff, C. E. *J. Am. Chem. Soc.* 1992, 114, 5328-5334) at both ends of the macrocycle. Positions A-F (red, with side chain projecting "above" the plane of the scaffold) may contain handles for glycan attachment, whereas position G is a cysteine residue (blue, with side chain projecting from the "bottom" face of the scaffold), suitable for linkage to a carrier protein or biological marker. This scaffold is tunable in that differential placement of aspartate residues in positions A-F permits variation in the number and spacing of the glycan attachments (5-1, FIG. 25).

In certain embodiments, the present disclosure provides a construct comprising a cyclic peptide backbone, wherein two or more amino acids are independently substituted with a glycosidic moiety having the structure:

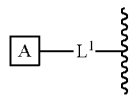

wherein each occurrence of $L^1$ is as defined above; and
each occurrence of A is independently a carbohydrate determinant having the structure:

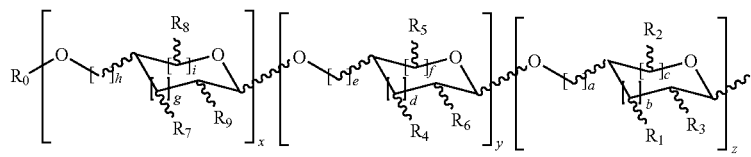

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0;

$R_0$ is hydrogen, or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R_1$, $R_2$, $R_3$, $R_4$, $R_5$, $R_6$, $R_7$, $R_8$ and $R_9$ is independently hydrogen, OH, OR, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur; or a saccharide moiety having the structure:

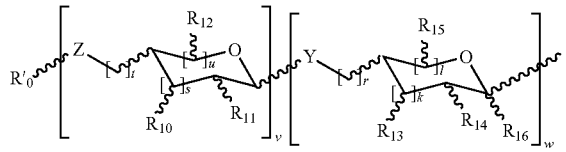

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0;

$R'_0$ is hydrogen, or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R_{10}$, $R_{11}$, $R_{12}$, $R_{13}$, $R_{14}$ and $R_{15}$ is independently hydrogen, OH, OR, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur;

each occurrence of $R_{16}$ is hydrogen, COOH, COOR, CONHR, a substituted or unsubstituted linear or branched chain alkyl or aryl group;

each R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur; or: two R on the same nitrogen atom are taken with the nitrogen to form a 4-7-membered heterocyclic ring having 1-2 heteroatoms independently selected from the group consisting of nitrogen, oxygen, and sulfur;

with the proviso that A is not a carbohydrate domain of formula:

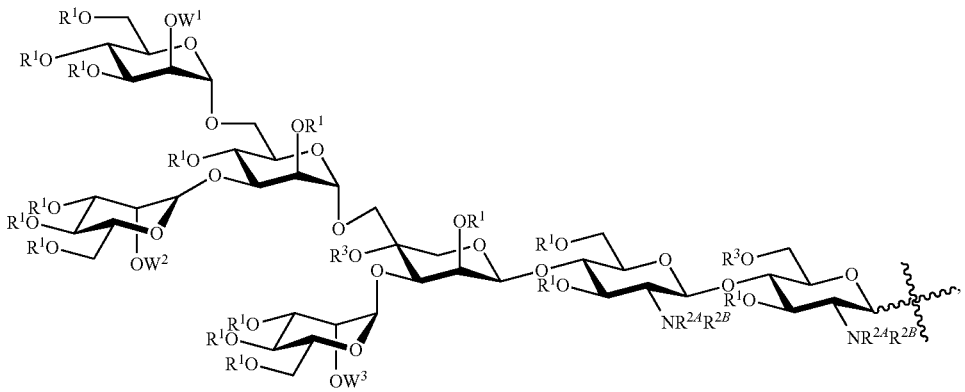

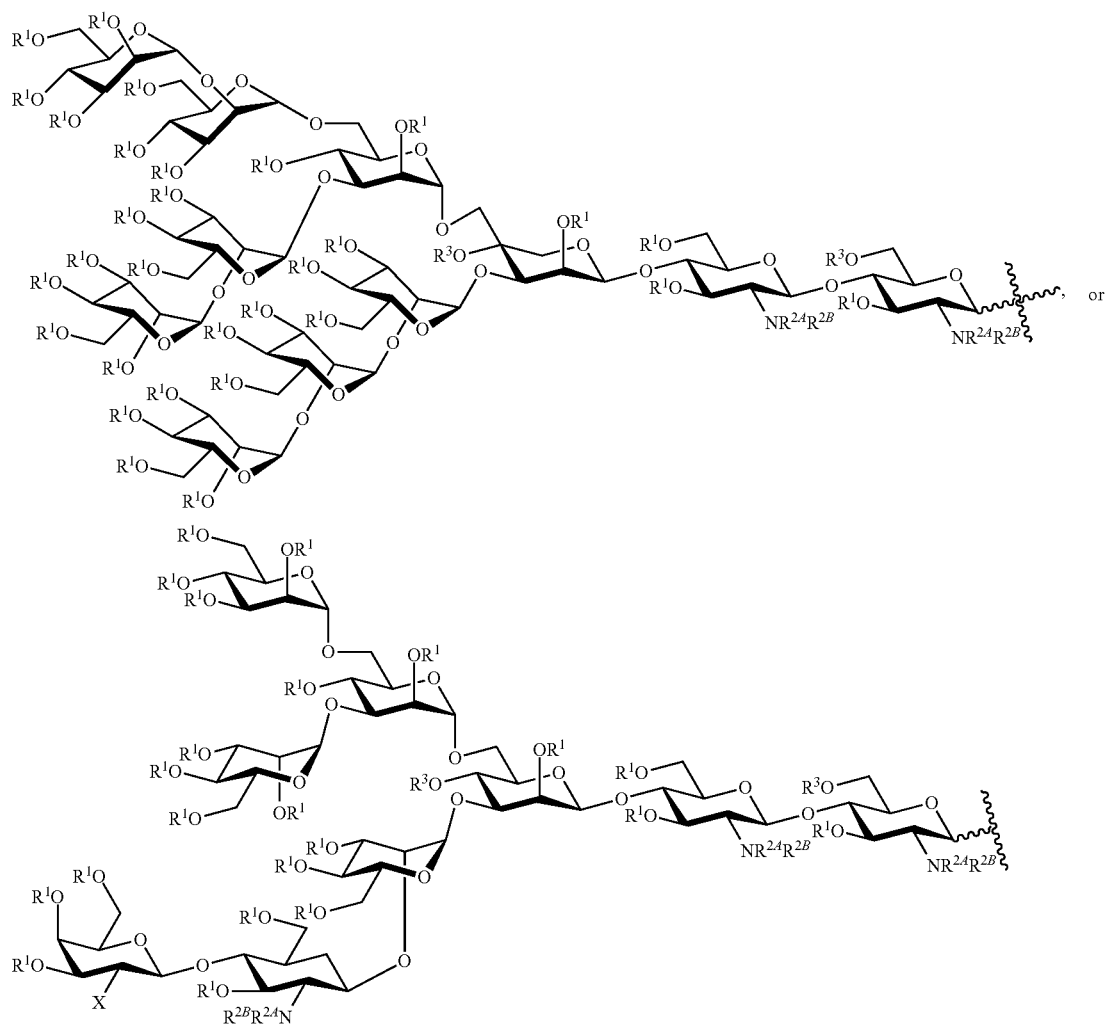

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

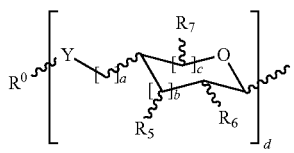

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group; and $W^1$, $W^2$ and $W^3$ are independently optionally substituted mannose, galactose or lactosamine moieties.

In certain embodiments, A is a carbohydrate determinant found on tumor cells. In certain embodiments, at least one occurrence of A is not a carbohydrate determinant found on gp120.

In some embodiments, a construct has the structure:

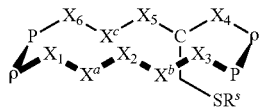

wherein each of $X^a$, $X^b$, $X^c$, $X^1$, $X^2$, $X^3$, $X^4$, $X^5$, and $X^6$ is independently a natural or unnatural amino acid, and $R^s$ is hydrogen or —SR, wherein R is as defined above and wherein at least one of $X^1$, $X^2$, $X^3$, $X^4$, $X^5$, or $X^6$ is an aspartate substituted with a glycosidic moiety having the structure:

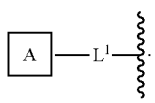

In certain embodiments, a cyclic peptide is further conjugated to a carrier as defined herein. In some embodiments, the carrier is KLH.

In certain embodiments, such constructs comprising a cyclic peptide comprise an amino acid sequence characterized in that the cyclic peptide adopts a β-sheet conformation in which alternating residues point their side chains above and below the macrocycle. In some embodiments, all amino acids of a cyclic peptide bearing a carbohydrate domain point their side chains in the same direction.

It will be appreciated that a variety of cyclic peptide sequences can be used in accordance with the present disclosure. In some embodiments, any amino acid sequence that provides such a β-sheet conformation may be used in accordance with the preceding cyclic peptide formula.

In some embodiments, one of $X^1$, $X^2$, $X^3$, $X^4$, $X^5$, or $X^6$ is substituted with a glycosidic moiety having the structure:

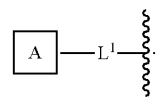

In some embodiments, two of $X^1$, $X^2$, $X^3$, $X^4$, $X^5$, or $X^6$ are independently substituted with a glycosidic moiety having the structure:

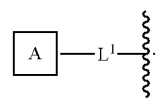

In some embodiments, three of $X^1$, $X^2$, $X^3$, $X^4$, $X^5$, or $X^6$ are independently substituted with a glycosidic moiety having the structure:

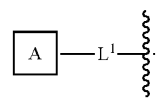

In some embodiments, four of $X^1$, $X^2$, $X^3$, $X^4$, $X^5$, or $X^6$ are independently substituted with a glycosidic moiety having the structure:

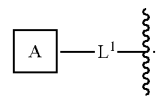

In some embodiments, five of $X^1$, $X^2$, $X^3$, $X^4$, $X^5$, or $X^6$ are independently substituted with a glycosidic moiety having the structure:

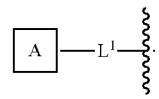

In some embodiments, each of $X^1$, $X^2$, $X^3$, $X^4$, $X^5$, and $X^6$ is independently substituted with a glycosidic moiety having the structure:

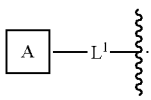

In some embodiments, each of $X^a$, $X^b$, and $X^c$ is selected from the group consisting of phenylalanine and tyrosine. In some embodiments, a provided construct has the structure:

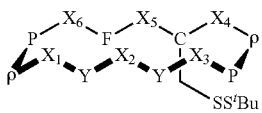

wherein at least one of $X^1$, $X^2$, $X^3$, $X^4$, $X^5$, or $X^6$ is an aspartate substituted with a glycosidic moiety having the structure:

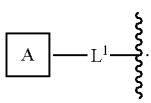

In certain embodiments, $L^1$ is a natural amino acid residue. In certain embodiments, $L^1$ is an unnatural amino acid residue. In certain embodiments, $L^1$ is

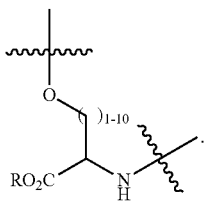

In certain embodiments, $L^1$ is

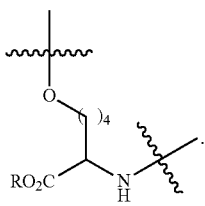

In certain embodiments, A is Tn. In certain embodiments, A is STn.

While a number of distinct combinations of variables are exemplified and described herein as genera and/or species, it will be appreciated that the present disclosure contemplates all possible combinations of variables as discrete species.

Formulations

As described above, the present invention provides compounds and synthetic methodologies useful in the development of novel therapeutic agents, particularly for fully synthetic cancer vaccines and/or therapeutics. In general, the compounds and glycopeptides prepared as disclosed herein can be conjugated to a protein carrier or a lipid to generate useful glycoconjugates for the treatment and/or prevention, (preferably the prevention of the recurrence), of cancer in a subject suffering therefrom. In addition, glycoconjugates prepared by processes disclosed herein are useful in adjuvant therapies as vaccines capable of inducing antibodies immunoreactive with various tumor cells. Such adjuvant therapies may reduce the rate of recurrence of certain cancers, and increase survival rates after surgery. Clinical trials on patients surgically treated for cancer who are then treated with vaccines prepared from a cell surface differentiation antigen found in patients lacking the antibody prior to immunization, a highly significant increase in disease-free interval may be observed (P. O. Livingston, et al., *J. Clin. Oncol.*, 1994, 12, 1036).

Thus, the present invention provides pharmaceutical compositions for treating cancer and/or for preventing the recurrence of cancer, comprising any compound of the present invention disclosed herein, as an active ingredient, optionally in combination with a pharmaceutically acceptable carrier. Pharmaceutical compositions of the present invention may further comprise other therapeutically active ingredients (e.g., chemotherapeutic and/or palliative). For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

In certain embodiments, pharmaceutical compositions of the invention comprise an immunological adjuvant, or a combination of immunological adjuvants.

In certain embodiments, the adjuvant is a saponin adjuvant (see, e.g., Marciani et al., *Vaccine*, 2000, 18, 3141, U.S. Pat. Nos. 6,080,725 and 5,977,081, the entire contents of which are hereby incorporated by reference). One example of a saponin adjuvant includes, but is not limited to, GPI-0100, (Galenica Pharmaceuticals, Inc., Frederick, Md.) which is a semi-synthetic adjuvant derived by modifying selected natural saponins

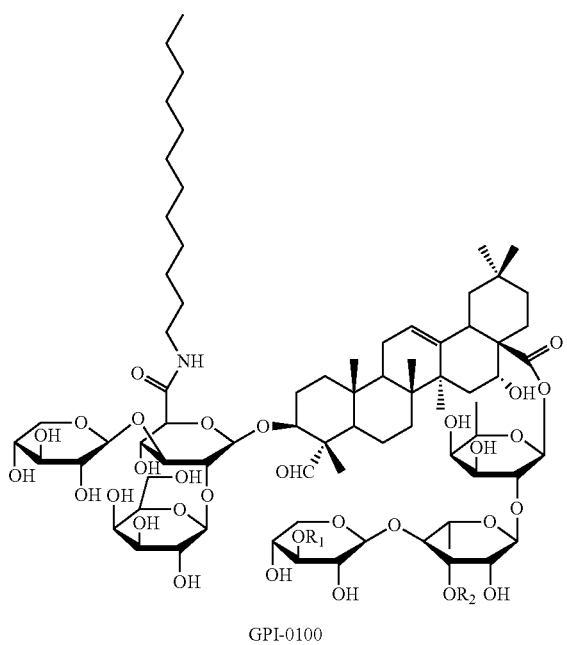

GPI-0100

Saponins isolated from *Quillaja soponaria* Molina contain two acyl moieties, a normonoterpene carboxylic acid and a normonoterpene carboxylic acid glycoside, which are linked linearly to a fucosyl residue attached at position C-28. It has been hypothesized that these lipophilic acyl groups may be responsible for these saponins' toxicity and their ability to stimulate cytotoxic T cells against exogenous antigens. The linkage between the fucosyl residue and the acyl group is unstable and hydrolyzes under mild conditions (pH≥6) with concomittant loss of saponins capability to stimulate cell-mediated immune response. Unlike their saponin precursors, GPI-0100 adjuvants comprise a stable non-toxic lipophilic moiety in the saponin's glucuronic residue. Methods for preparing these semi-synthetic adjuvants are well-known in the art. For example, GPI-0100 adjuvants may be prepared by hydrolizing *quillaja* saponins (which are commercially available) under basic conditions to yield the corresponding deacylated product. The deacylated intermediate may then be reacted with a suitable amine reagent using standard carboxylic acid moiety activation methodology to give the desired compounds. A wide variety of procedures are effective for extracting saponin compounds. They are generalized as follows: (i) defatting of the organic matter with a hydrophobic organic solvent such as petroleum ether; (ii) extraction with a suitable alcohol (e.g., methanol or ethanol) or alcohol-water mixture; (iii) evaporation of the carinol solvent; and (iv) partitioning of the dried alcohol extract between water and n-butanol saturated with water, followed by precipitation of the crude saponins from the n-butanol/water with a suitable organic solvent (e.g., diethyl ether). Purification of the saponin extract may require multiple separation steps. For example, preliminary fractionation may be carried out using conventional open column chromatography or flash chromatography on silica gel, in combination with a more sophisticated chromatographic technique such as High Pressure Liquid Chromatography (HPLC), droplet counter-current liquid chromatography (DCCC) or centrifugal Liquid Chromatography (RLCC). The integration of these techniques with preparative TLC typically affords separated and purified saponins.

In certain other embodiments, the adjuvant is or comprises bacteria or liposomes. In certain exemplary embodiments, the adjuvant includes but is not limited to, *Salmonella minnesota* cells, bacille Calmette-Guerin, GPI-0100, or QS-21.

Compounds of the present invention may be combined with a pharmaceutically acceptable carrier to form a pharmaceutical composition. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. In certain embodiments, the pharmaceutical composition includes a pharmaceutically acceptable amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such carriers as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Drug-eluting forms include coated or medicated stents and implantable devices. Drug-eluting stents and other devices may be coated with a compound or pharmaceutical preparation and may further comprise a polymer designed for time-release.

In certain embodiments, a compound or pharmaceutical preparation is administered orally. In other embodiments, the compound or pharmaceutical preparation is administered intravenously. In certain embodiments, a compound is attached via a cleavable linker to a solid support that is administered with a catheter. Alternative routes of administration include sublingual, intramuscular, and transdermal administrations.

When the compounds of the present invention are administered as pharmaceuticals, to humans and animals, they can be given per se or as a pharmaceutical composition containing, for example, 0.1% to 99.5%, or 0.5% to 90%, of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

These compounds may be administered to humans and other animals for therapy by any suitable route of administration, including orally, nasally, as by, for example, an aerosol, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six, or more sub-doses administered separately at appropriate intervals throughout the day, optionally, in unit dosage forms.

While it is possible for a compound of the present invention to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

The invention provides kits comprising pharmaceutical compositions of an inventive compound. In certain embodiments, such kits include the combination of a compound of the present invention and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of chemotherapy. In certain embodiments, the kit includes multiple cycles of chemotherapy.

Uses

In certain embodiments, a method of treatment is provided comprising administering to the subject a therapeutically effective amount of any of the glyconjugates disclosed herein, optionally in combination with a pharmaceutically acceptable carrier. In certain embodiments, the cancer is a solid tumor or an epithelial tumor. As mentioned above, methods for the treatment of cancer and/or for the prevention of recurrence of cancer are provided, which comprises administering to the subject an amount of any of the glycoconjugates disclosed above effective to induce antibodies. Also provide are methods for inducing antibodies in a human subject, wherein the antibodies are capable of specifically binding with human tumor cells. In certain embodiments, a carbohydrate antigen is linked to an immunogenic carrier either directly or through a crosslinker, wherein the carrier is a protein, peptide or lipid. In certain embodiments, a carrier is human serum albumin, aovine aerum albumin, cationized bovine serum albumin, polylysine or KLH. In certain other embodiments, the carrier is a lipid having the structure:

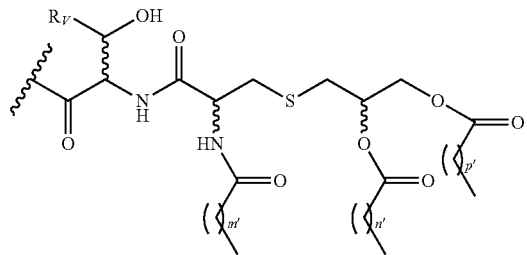

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-5-glycerylcysteinylserine (e.g., PamCys).

In certain embodiments, a provided method comprises administering to the subject a therapeutically effective amount of any of the compounds and/or glycopeptides disclosed herein, in combination with an immunogenic carrier, optionally in combination with a pharmaceutically acceptable carrier. Specifically, in certain embodiments, a provided method comprises administering a carbohydrate antigen conjugated to an immunogenic carrier. In certain embodiments, a provided method comprises administering a carbohydrate antigen and an immunogenic carrier that have not been conjugated. Rather, they are administered concurrently, or successively, as separate entities.

In certain embodiments, a provided method comprises administering a glycopeptide of the invention conjugated to an immunogenic carrier. In certain embodiments, a provided method comprises administering an inventive glycopeptide that has not been conjugated to an immunogenic carrier. Rather, a glycopeptide and an immunogenic carrier are administered concurrently, or successively, as separate entities. In certain embodiments, the immunogenic carrier is a protein, peptide or lipid. In certain embodiments, the carrier is human serum albumin, bovine aerum albumin, cationized bovine serum albumin, OMPC, polylysine or KLH. In certain other embodiments, the carrier is PamCys.

For the purpose of the invention, a compound/glycopeptide and a carrier are said to be administered concurrently when they are administered (i) as a single composition containing the compound/glycopeptide and the carrier, (ii) as two separate compositions or (iii) are delivered by separate routes within a short enough period of time that the effective result is equivalent to that obtained when both compound/glycopeptide and carrier are administered as a single composition.

In certain embodiments, the present disclosure provides methods of eliciting antibodies in a subject comprising administering to the subject a construct of the present disclosure. In some embodiments, the present invention provides methods of inducing antibodies which further comprise co-administering an immunological adjuvant, or a combination of immunological adjuvants. In certain embodiments, an adjuvant is a saponin adjuvant. In certain other embodiments, an adjuvant is bacteria or liposomes. In certain embodiments, the adjuvant includes but is not limited to, *Salmonella minnesota* cells, bacille Calmette-Guerin, GPI-0100, or QS21. Specifically, when a multi-antigenic glycopeptide comprising at least two different antigenic domains is used, it is possible to induce at least two different types of antibodies. In certain embodiments, each antigen present on the glycopeptide elicits an antibody type specific to that antigen. In certain embodiments, the antibodies produced are those that recognize at least one antigen present on the glycopeptide. In certain embodiments, an inventive multi-antigenic glycopeptide, when administered to a subject, produces antibodies to a subset of the antigens present on the glycopeptide backbone. In certain embodiments, some of the antibodies produced recognize two or more antigens of the glycopeptide. In certain embodiments, the inventive glycopeptides comprise carbohydrate domains, or truncated or elongated versions thereof, that are found on tumor cells.

Compounds of the present invention may be used in vitro or in vivo. The inventive compounds may be particularly useful in the treatment of neoplasms or other proliferative diseases in vivo. However, inventive compounds described above may also be used in vitro for research or clinical purposes (e.g., determining the susceptibility of a patient's disease to an inventive compound, researching the mechanism of action, elucidating a cellular pathway or process).

In some embodiments, compounds of the present invention are provided for use in medicine. In some embodiments, the present invention provides a method of treating a proliferative disease in a subject suffering therefrom, the method comprising administering to the subject a therapeutically effective amount of an inventive compound. In certain embodiments, the proliferative disease is a benign neoplasm. In certain embodiments, the proliferative disease is cancer.

Compounds of the present invention may be used in the treatment or prevention of neoplasms. In certain embodiments, the neoplasm is a benign neoplasm. In other embodiments, the neoplasm is a malignant neoplasm.

In some embodiments, the cancer is a hematological malignancy. In certain embodiments, the cancer is a solid tumor. Exemplary cancers that may be treated using inventive compounds include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, vaginal cancer, to name but a few. In some embodiments, the cancer is small cell lung cancer. In some embodiments, the cancer is ovarian cancer. In some embodiments, the cancer is breast cancer. In some embodiments, the cancer is lung cancer. In some embodiments, the cancer is of endometrial origin. In some embodiments, the cancer is colon cancer. In some embodiments, the cancer is prostrate cancer. In some embodiments, the cancer is gastric cancer. In some embodiments, the cancer is pancreatic cancer. In some embodiments, the cancer originates from any one of the above-mentioned organs or tissues.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with compounds of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, www.nci.nih.gov and The Merck Manual, Seventeenth Ed. 1999, the entire contents of which are hereby incorporated by reference.

In certain embodiments, inventive compounds are useful in treating a subject in clinical remission. In some embodiments, the subject has been treated by surgery and may have limited unresected disease.

EXEMPLIFICATION

Example 1

Synthesis of a MUC5AC-Based Glycopeptide Construct

This Example demonstrates the synthesis of a multi-antigenic glycopeptide comprising a mucin tandem repeat sequence.

All commercial materials (Aldrich, Fluka) were used without further purification. All solvents were reagent grade or HPLC grade (Fisher). Anhydrous THF, diethyl ether, $CH_2Cl_2$, toluene, and benzene were obtained from a dry solvent system (passed through column of alumina) and used without further drying. All reactions were performed under an atmosphere of pre-purified dry Ar(g). $^1$H NMR spectra and $^{13}$C NMR spectra were recorded on a Bruker Advance DRX-500 MHz at ambient temperature unless otherwise stated. Chemical shifts are reported in parts per million relative to residual solvent $CDCl_3$ ($^1$H, δ 7.24; $^{13}$C, δ 77.0), $CD_3OD$ ($^1$H, δ 3.31; $^{13}$C, δ 49.15). Data for $^1$H NMR are reported as follows: chemical shift, integration, multiplicity (app=apparent, par obsc=partially obscure, ovrlp=overlapping, s=singlet, d=doublet, t=triplet, q=quartet, m=multiplet) and coupling constants. All $^{13}$C NMR spectra were recorded with complete proton decoupling. Low-resolution mass spectral analyses were performed with a JOEL JMS-DX-303-HF mass spectrometer or Waters Micromass ZQ mass spectrometer. All reactions were carried out in oven-dried glassware under an argon atmosphere unless otherwise noted. Analytical TLC was performed on E. Merck silica gel 60 F254 plates and flash column chromatography was performed on E. Merck silica gel 60 (40-63 mm). Yields refer to chromatographically and spectroscopically pure compounds.

Figure 5:
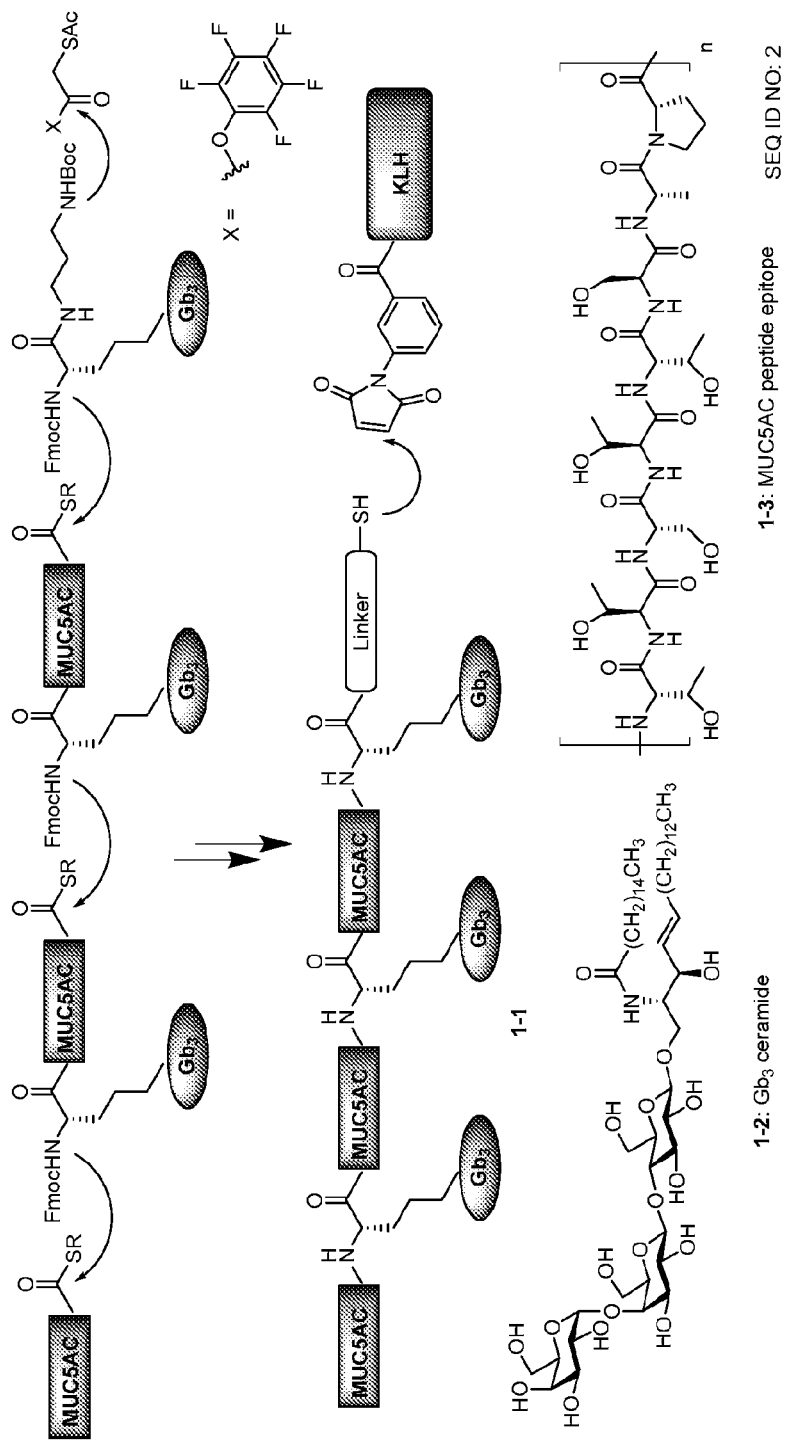
FIG. 5 depicts a design and synthetic strategy for a vaccine candidate targeting ovarian cancer 1-1.

Our initial program for the total synthesis of construct 1-1 required the assembly of three repeats of both the protected $Gb_3$ glycosylamino acid and the MUC5AC peptide C-terminal thioester, which would then be iteratively coupled to form the fully glycosylated polypeptide backbone, in analogy to our synthesis of unimolecular polyantigenic vaccine constructs. We have further refined our synthetic approach by preparing a $Gb_3$-MUC5AC thioester cassette, to be employed as a building block (FIG. 5). We elected to block the N-termini of the cassettes with fluorenylmethyl carbonate (Fmoc) protecting groups, so that the coupling sequence would consist of iterative peptide couplings following deprotection of the N-termini. The $Gb_3$ glycosylamino acid would ultimately be linked to the carrier protein (KLH) via a Boc-protected diaminopropyl unit.

Figure 6:
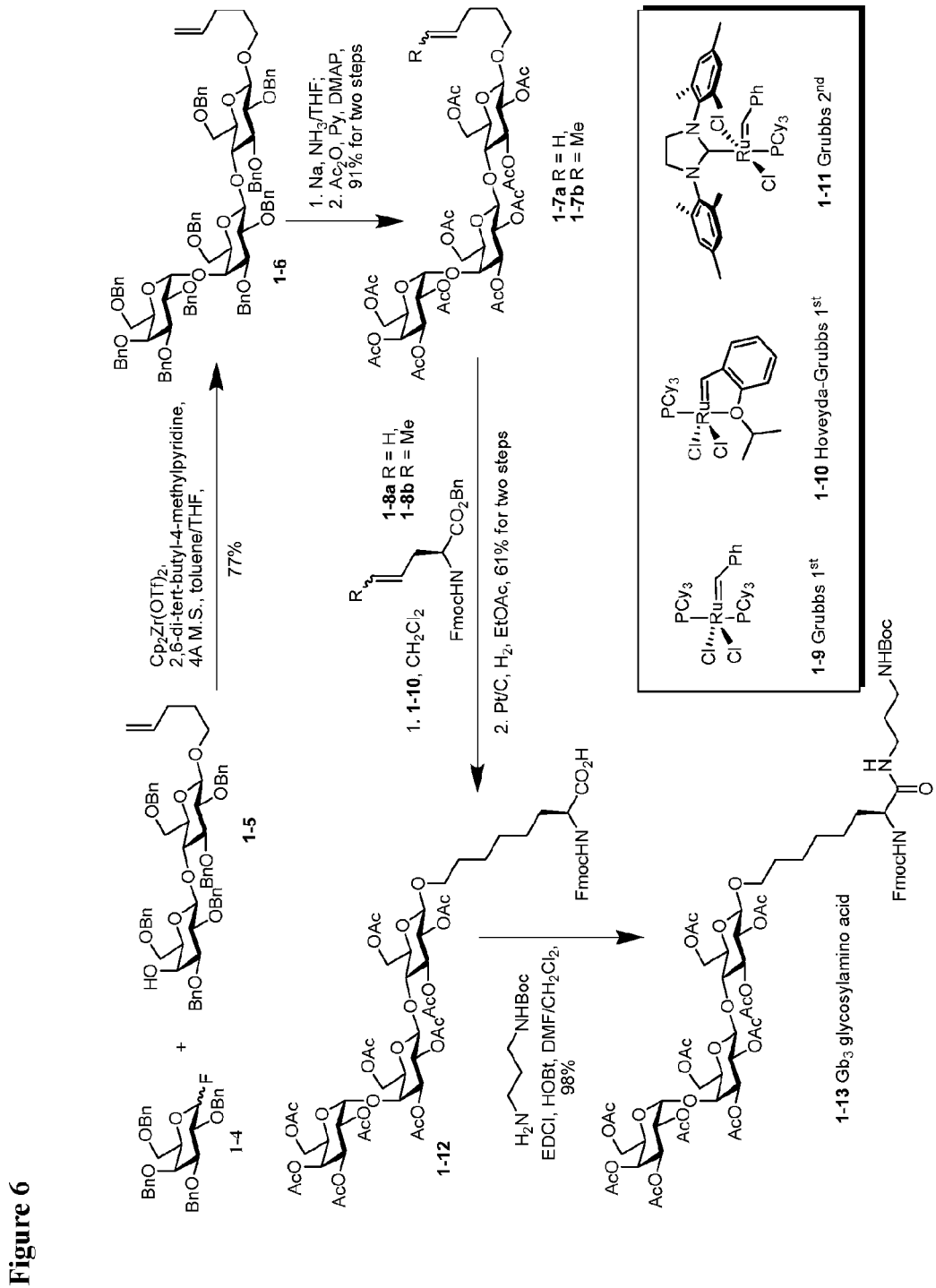
FIG. 6 depicts an improved synthesis of $Gb_3$ glycosylamino acid.
Figure 7:
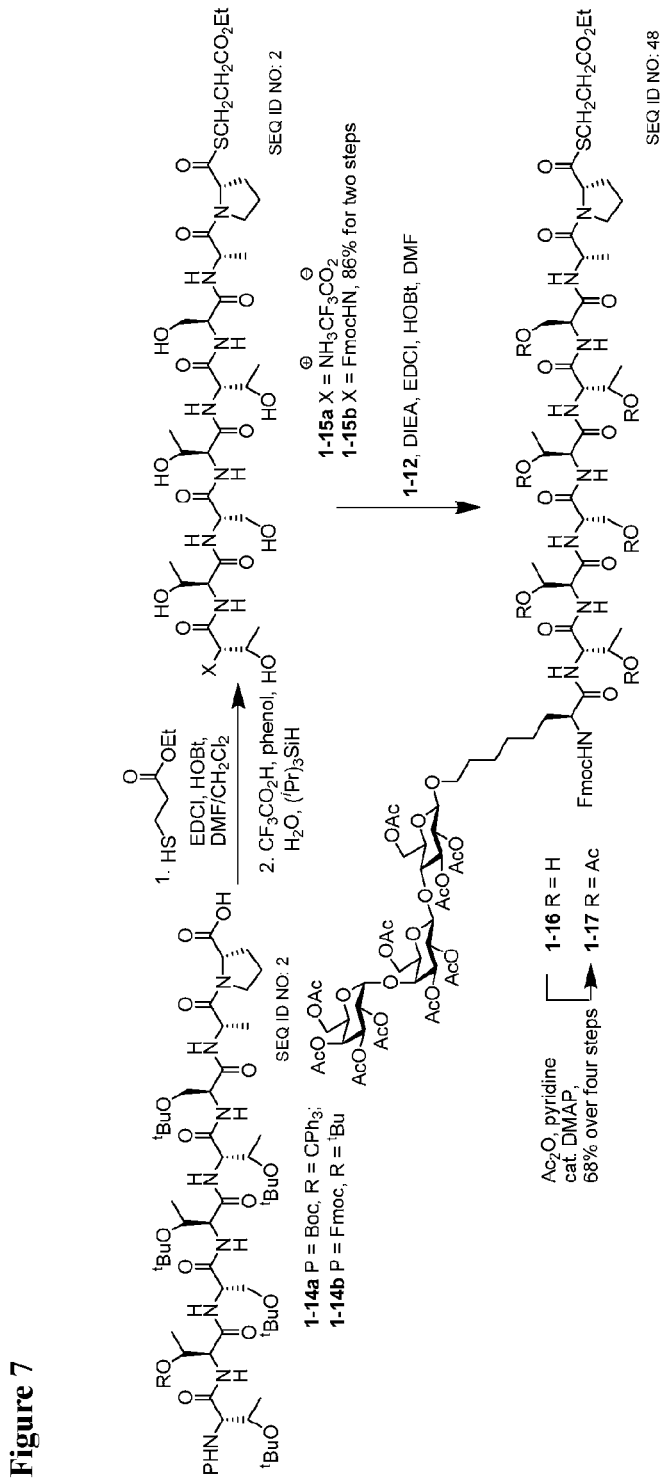
FIG. 7 depicts a synthesis of $Gb_3$-MUC5AC cassette 1-17.

The synthesis of the $Gb_3$ glycosylamino acid 1-12 commenced with glycosylation of fluoro-donor 1-4 (Fluoro donor 1-4 was prepared in 81% yield (α:β=1:1.4) by treatment of commercial available 2,3,4,6-tetra-O-benzyl-D-galactopyranose with DAST (diethylaminosulfur trifluoride) in THF. For a representative example of synthesis of fluoro donor 1-4, see: Nicolaou, K. C.; Caulfield, T.; Kataoka, H.; Kumazawa, T. *J. Am. Chem. Soc.* 1988, 110, 7910-7912) with disaccharide acceptor 1-5, under conditions previously developed in the Danishefsky group (Allen, J. R.; Allen, J. G.; Zhang, X.-F.; Williams, L. J.; Zatorski, A.; Ragupathi, G.; Livingston, P. O.; Danishefsky, S. J. *Chem. Eur. J.* 2000, 6, 1366-1375), to afford the desired perbenzylated trisaccharide 1-6 in 78% isolated yield (FIG. 6). Dissolving metal reduction of 1-6 followed by peracetylation afforded 1-7a (92%, two steps).

Earlier (Wan, Q.; Cho, Y. S.; Lambert, T. H.; Danishefsky, S. J. *J. Carbohydr. Chem.* 2005, 24, 425-440), we had noted that in the presence of Grubbs $2^{nd}$ generation catalyst (1-11), the direct cross-metathesis of the terminal olefins of 1-7a and 1-8a had been plagued by the formation of significant quantities of a truncated side product. To circumvent this complication, we had prepared compounds 1-7b and 1-8b through cross-metathesis of 1-7a and 1-8a with trans-2-butene, in the presence of catalyst 1-9. These modified substrates underwent cross-metathesis in the presence of catalyst 1-11. It was found that direct olefin cross metathesis of 1-7a and 1-8a can in fact be effectively accomplished through the use of the Grubbs-Hoveyda $1^{st}$ generation catalyst (1-10) (J. S. Kingsbury, J. P. A. Harrity, P. J. Bonitatebus, Jr.; A. H. Hoveyda *J. Am. Chem. Soc.* 1999, 121, 791) to provide the desired adduct, accompanied by only trace amounts of the truncated side product (Zhu, J.; Wan, Q.; Yang, G.; Ouerfelli, O.; Danishefsky, S. J. *Heterocycles*, 2008, submitted for publication). Hydrogenolysis, using Pt/C under a hydrogen atmosphere, provided the $Gb_3$ glycosylamino acid 1-12 in 66% yield over two steps. The latter was further coupled with tert-butyl N-(3-aminopropyl)carbamate to provide 1-13, incorporating the C-terminal partial linker for eventual conjugation to the carrier protein (FIG. 6).

Next, peptides 1-14a and 1-14b were prepared through Fmoc solid-phase synthesis using Novabiochem proline-TGT resin. Installation of a C-terminal thioester on both 1-14a and 1-14b, followed by standard side-chain deprotection afforded 1-15a and 1-15b in 93% and 86% yield over two steps, respectively. Compound 1-15b was to be a key intermediate for later stage fragment assembly, because the N-terminal Fmoc can be selectively removed in the presence of the N-Boc functionality. Our initial attempts at Fmoc deprotection of 1-15b afforded the desired free amine, together with significant amounts of the corresponding diketopiperizine. This side reaction presented difficulties in attempts at subsequent separation. We thus prepared compound 1-15a for coupling with $Gb_3$ glycosylamino acid 1-12. Standard coupling of 1-15a with $Gb_3$ glycosylamino acid 1-12 using EDCI/HOBt afforded compound 1-16, which was subsequently subjected to peracetylation to furnish the $Gb_3$-MUC5AC cassette 1-17 (70%, two steps). The acetate protection step facilitated isolation of the product. It will be noted that, in our peptide design, we chose to incorporate an activated L-proline thioester at the C-terminus of the peptide fragment, due to the rather non-racemizable nature of its α-stereocenter. This feature could prove useful in the subsequent cassette assembly stage.

Figure 8A:
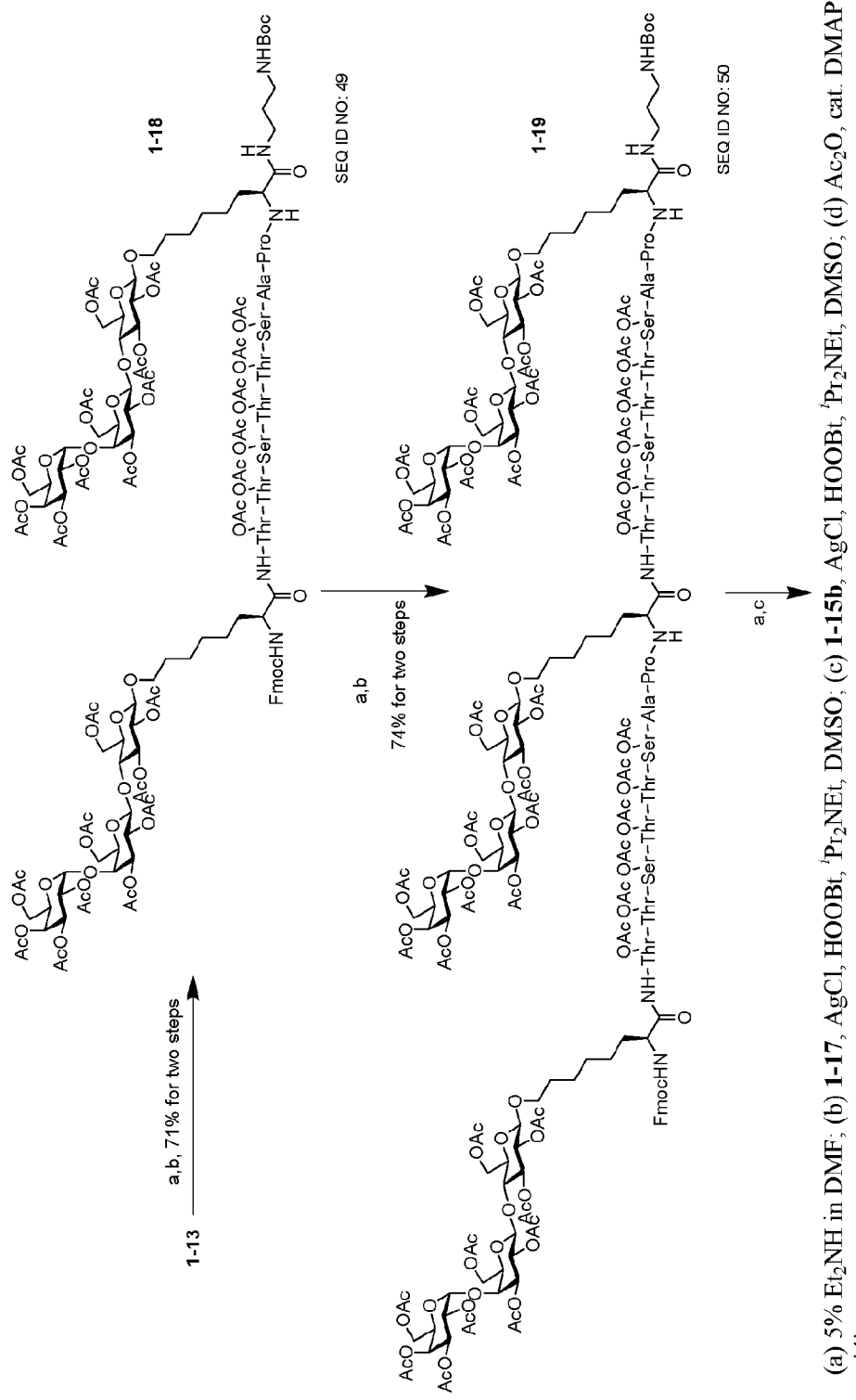
FIGS. 8a-c depict a synthesis of construct 1-22.
Figure 8B:
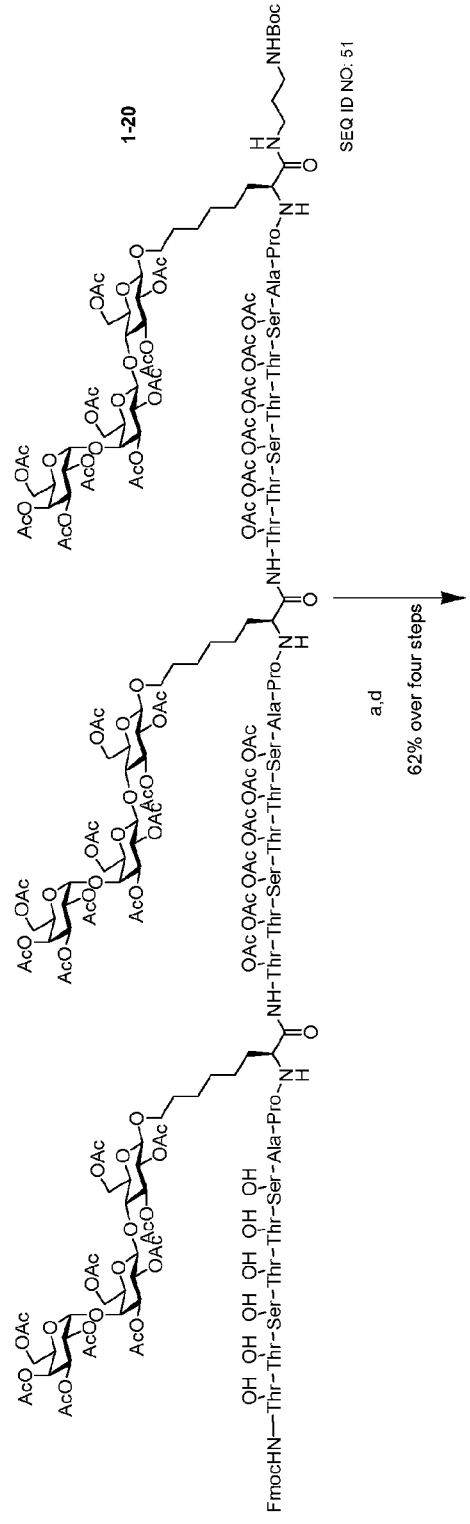
Figure 8C:
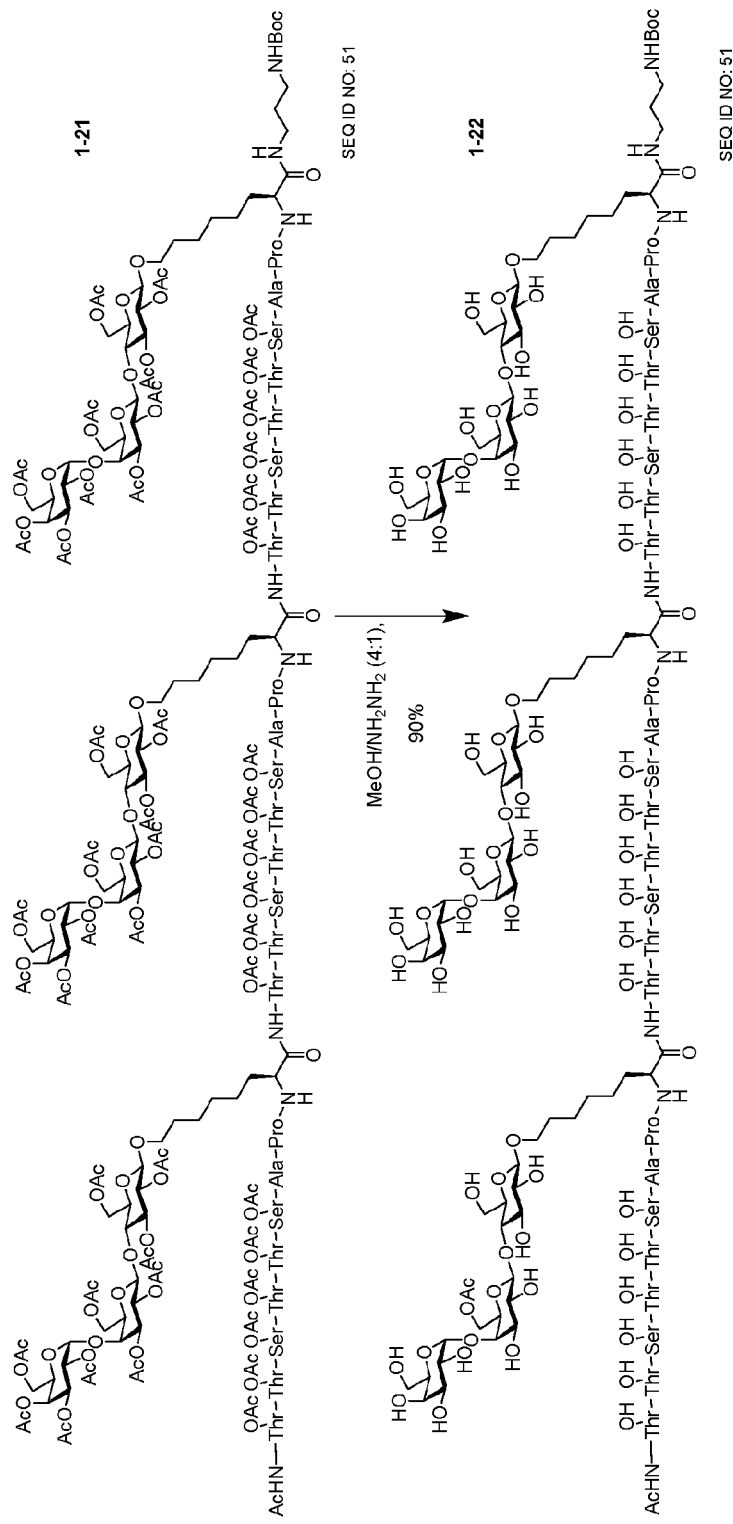

We were then able to devise a slightly modified procedure for Fmoc deprotection, using the relatively volatile diethylamine as a solvent, in lieu of piperidine in DMF (FIGS. 8a-c). With this modification, we needed only to remove the volatile reagents and solvents following Fmoc cleavage. The crude free amine thus exposed would be used in the next coupling step without further purification. Fmoc deprotection of the N-terminus of compound 1-13 afforded the desired free amine, which was subjected to peptide coupling with $Gb_3$-MUC5AC thioester cassette 1-17 under the AgCl/HOOBt protocol (Kawakami, T.; Yoshimura, S.; Aimoto, S. *Tetrahedron Lett.* 1998, 39, 7901-7904). There was obtained the desired bis-$Gb_3$-MUC5AC intermediate 1-18 (70% over two steps). This bis-$Gb_3$-MUC5AC 1-18 was subsequently elongated to produce compound 1-19, via a two-step sequence involving Fmoc deprotection and subsequent coupling with the $Gb_3$-MUC5AC thioester cassette 1-17 (72% over two steps). The next task would be that of installing the third MUC5AC peptidyl fragment. In an effort to facilitate a polarity-based separation of the target tris-$Gb_3$-tris-MUC5AC glycopeptide (cf. 1-20) from other potential side products, we elected to install the final MUC5AC fragment in its deprotected, free hydroxyl form.

Thus, as outlined in FIGS. 8a-c, Fmoc cleavage of tris-$Gb_3$-bis-MUC5AC compound 1-19, followed by coupling with the deprotected MUC5AC thioester, 1-15b, afforded the desired tris-$Gb_3$-tris-MUC5AC adduct, 1-20. As expected, glycopeptide 1-20 was readily separated from other side products. Next, N-terminal Fmoc cleavage followed by peracetylation furnished the desired clustered $Gb_3$-MUC5AC construct 1-21 (62% over four steps). Thus, through the use of the $Gb_3$-MUC5AC thioester cassette 1-17, we were indeed able to assemble, in a convergent manner, ample quantities of the clustered vaccine construct 1-21. Global deprotection of 1-21 using $NH_2NH_2$/MeOH (1:4, v/v) afforded the target fully synthetic clustered $Gb_3$-MUC5AC construct 1-22 (90%). Biological evaluations of conjugate 1-22 are described in Example 2.

A further objective would be that of installing an appropriate handle for conjugation to the KLH carrier protein. Toward this end, 1-21 was treated with trifluoroacetic acid in dichloromethane to cleave the Boc carbamate functionality. Next, direct amidation with activated S-acetylthioglycolic acid pentafluorophenyl ester (SAMA-OPfp), provided 1-23 in 66% yield for two steps. Final global deprotection of 1-23 using $NH_2NH_2$/MeOH (1:4, v/v) (Allen, J. R.; Harris, C. R.; Danishefsky, S. J. *J. Am. Chem. Soc.* 2001, 123, 1890-1897) followed by reduction with tris(2-carboxyethyl)phosphine (TCEP) afforded the vaccine construct 1-1 (86% yield).

Figure 9A:
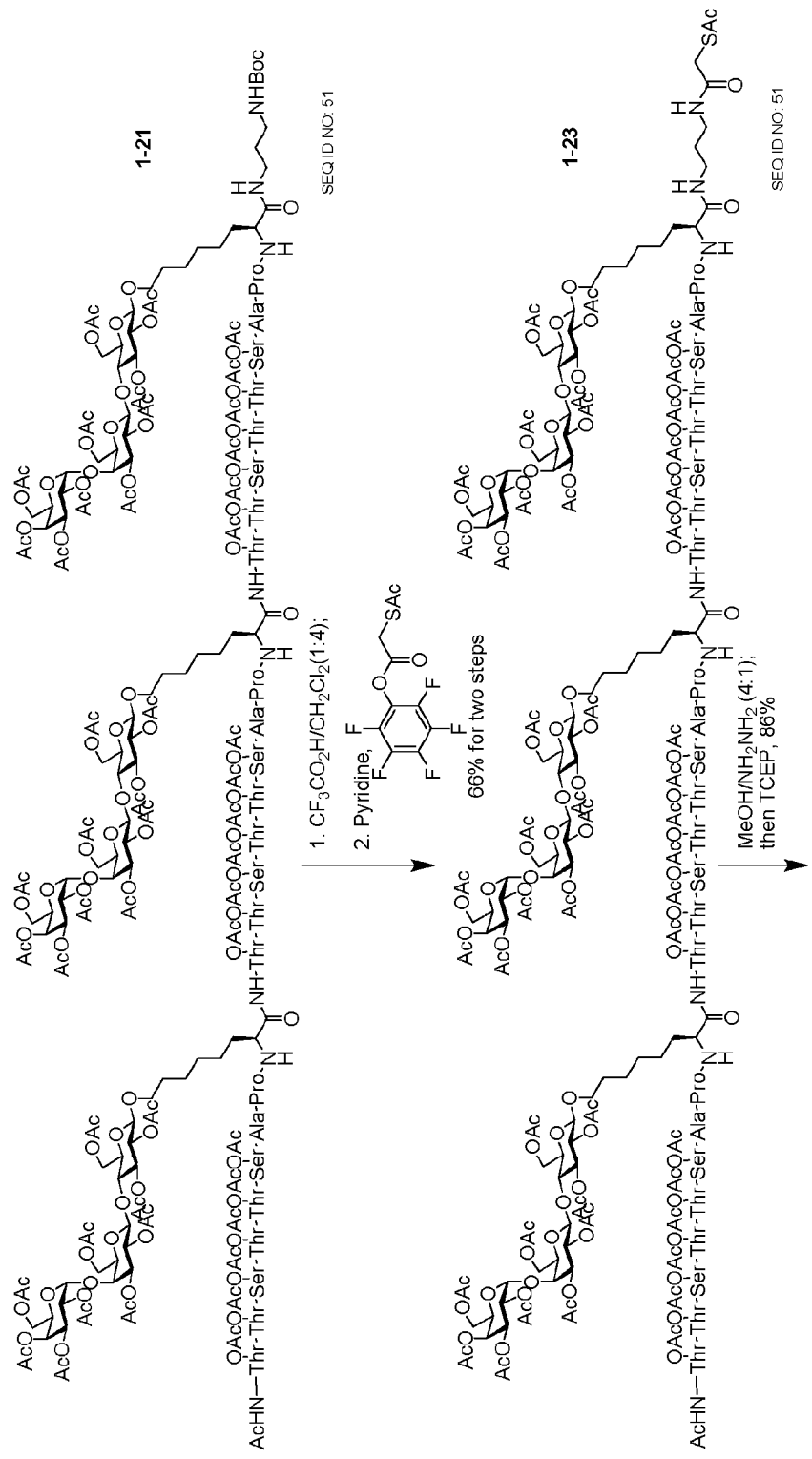
FIG. 9a-b depict a synthesis of vaccine construct 1-1 and KLH conjugate 1-24.
Figure 9B:
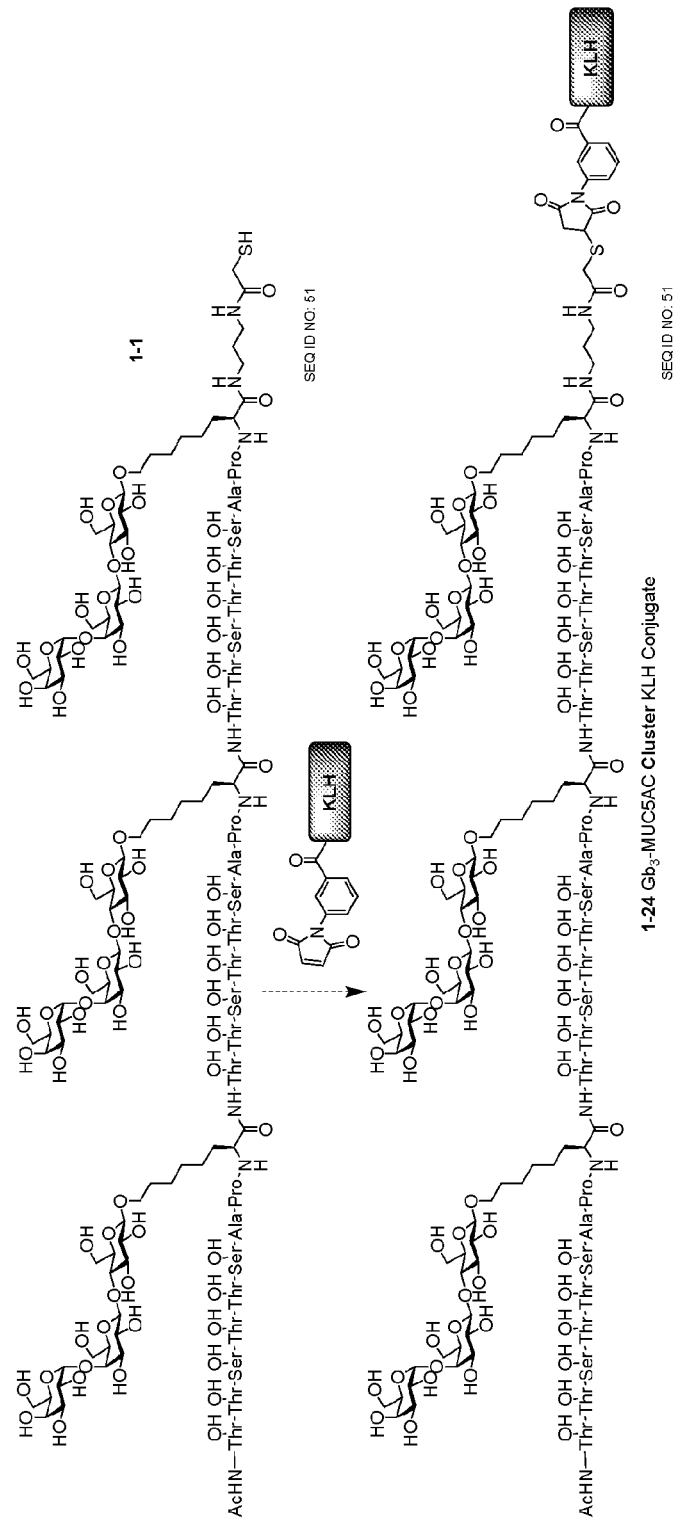
Figure 10:
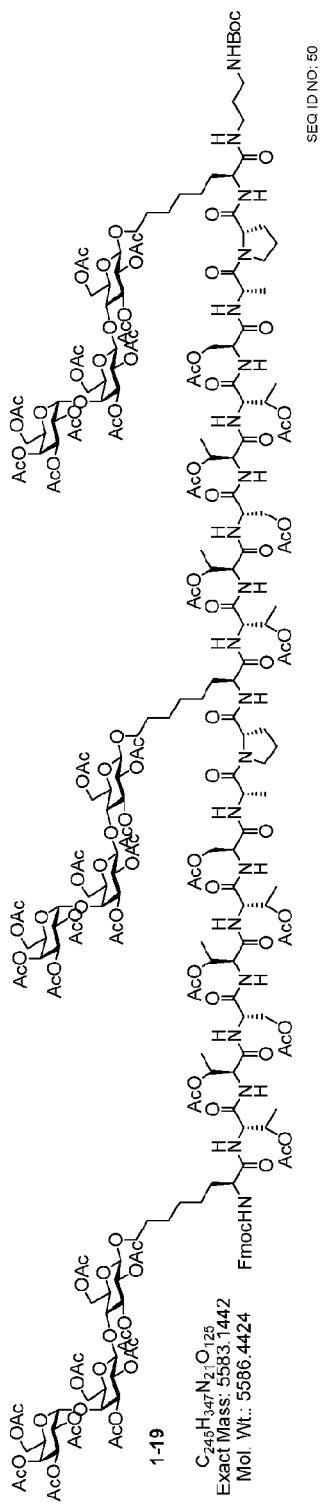
FIG. 10 depicts the structure of compound 1-19.
Figure 11A:
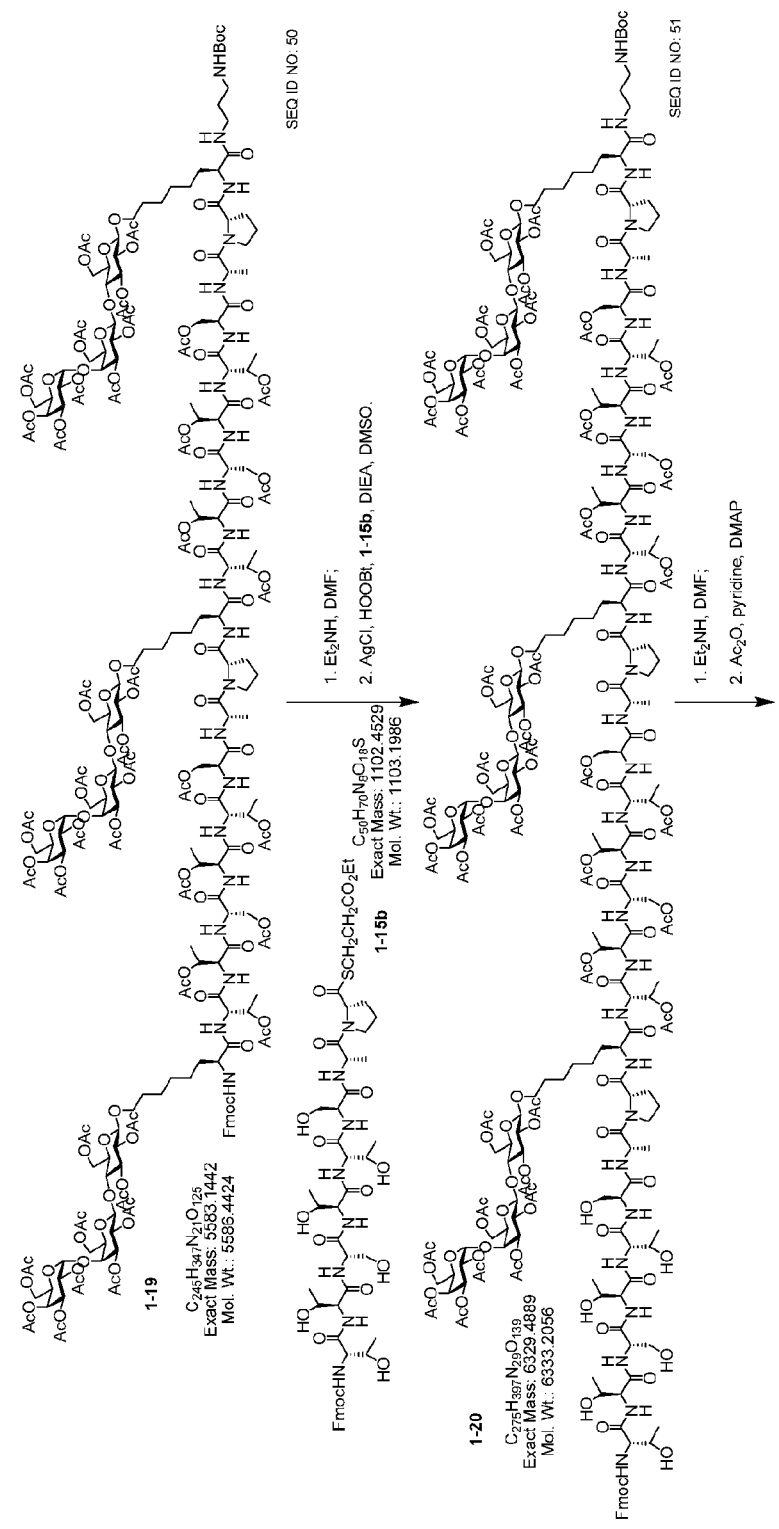
FIGS. 11a-b depict a synthesis of construct 1-21.
Figure 11B:
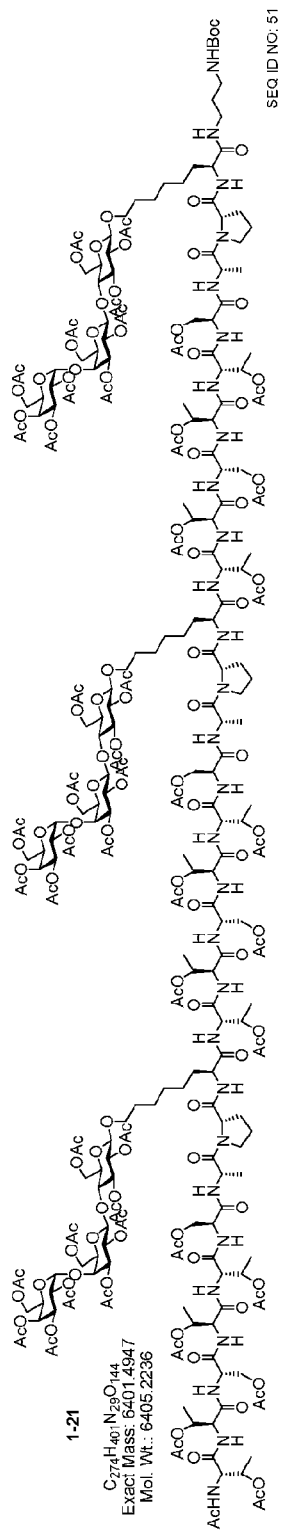

The corresponding KLH conjugate 1-24 was prepared via 1-1 in two steps. The first involved activation of the carrier protein KLH with sulfo-MBS (m-maleimidobenzoyl-N-hydroxysuccinimide). This was followed by subsequent addition of the terminating thiol on the glycopeptide 1-1 (in a presumed Michael fashion) to the maleimide olefin center of the activated carrier protein (FIG. 9b) (Zhang, S., Graeber, L. A., Helling, F., Ragupathi, G., Adluri, S., Lloyd, K. O. & Livingston, P. O. *Cancer Res.* 1996, 56, 3315-3319). The ratio of glycopeptide-to-protein for KLH conjugate 1-24, as determined by hydrolytic carbohydrate analysis (Lloyd, K. O.; Savage, A. *Glycoconjugate J.* 1991, 8, 439; Hardy, M. R.; Townsend, R. R. *Proc. Natl. Acad. Sci. USA* 1988, 85, 3289) and standard protein analysis (Bio-Rad dye-binding method) was ca. 698:1. This gratifyingly high ratio of construct incorporation into the carrier presumably reflects the steric accessibility of the linking thiol function in 1-1, as well as improved conjugation techniques. This phase of the synthesis is summarized in FIGS. 8a-c and 9a-b.

This Example illustrates the design and synthesize of a vaccine construct targeting ovarian carcinoma, which comprises clusters of $Gb_3$ carbohydrate antigen and MUC5AC peptide markers. The efficient synthesis was enabled by the preparation of a $Gb_3$-MUC5AC thioester cassette as a key building block for constructing three alternating repeats of $Gb_3$ and MUC5AC. Both non-conjugate and KLH-conjugate vaccine candidates have been prepared and the results of immunological evaluations are presented in Example 2.

Experimental Procedures:

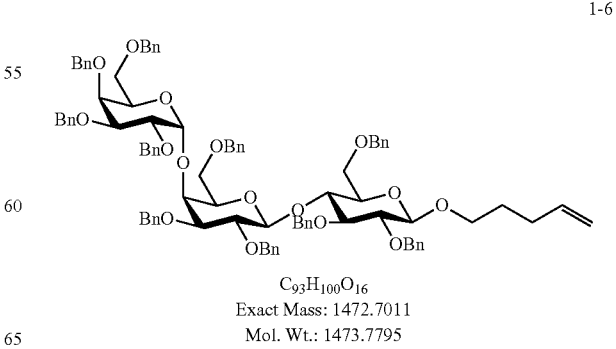

1-6

$C_{93}H_{100}O_{16}$
Exact Mass: 1472.7011
Mol. Wt.: 1473.7795

Perbenzylated Trisaccharide 1-6.

Prepared based on our previously reported glycosylation protocol with slight modification (Allen, J. R.; Allen, J. G.; Zhang, X.-F.; Williams, L. J.; Zatorski, A.; Ragupathi, G.; Livingston, P. O.; Danishefsky, S. J. *Chem. Eur. J.* 2000, 6, 1366-1375). A mixture of fluoro-donor 1-4 (618 mg, 1.14 mmol, 2.0 equiv) and lactoside acceptor 1-5 (540 mg, 0.57 mmol) was azeotroped with anhydrous benzene (3×10 mL) and further dried on high vacuum for 3 h. The above mixture was dissolved in toluene (5.0 mL) and THF (0.5 mL), and transferred via cannula to a flask containing 2,6-di-tert-butyl-4-methylpyridine (175 mg, 0.85 mmol) and freshly prepared 4 Å molecular sieves (900 mg) under argon. The flask was then cooled to −20° C. and $Cp_2Zr(OTf)_2$ (336 mg, 0.57 mmol, 1.0 equiv) was quickly added to the reaction mixture. The reaction was slowly warmed and stirred for 72 h at 7° C. under dark. The reaction mixture was diluted with EtOAc (15 mL) and filtered through a pad of anhydrous $MgSO_4$ with EtOAc (3×15 mL). The filtrate was washed with saturated $NaHCO_3$ (2×15 mL), dried over $Na_2SO_4$, and concentrated to dryness. Flash column chromatography (Hexane:EtOAc=12:1 to 7:1) gave the desired α-product 1-6 (653 mg, 78%). $^1$H NMR (500 MHz, $CDCl_3$) δ 7.44~7.12 (50H, m), 5.82 (1H, m), 5.11~5.08 (2H, ovrlp), 5.05~4.97 (2H, m), 4.91~4.87 (3H, ovrlp), 4.81~4.69 (6H, ovrlp), 4.56~4.46 (6H, ovrlp), 4.40~4.37 (3H, ovrlp), 4.28 (2H, dd, J=20.0 Hz, 12.0 Hz), 4.20 (1H, t, J=9.0 Hz), 4.14~3.92 (8H, ovrlp), 3.84 (1H, dd, J=11.0 Hz, 4.3 Hz), 3.75 (1H, d, J=9.7 Hz), 3.66 (1H, dd, J=9.8 Hz, 7.9 Hz), 3.61~3.50 (4H, ovrlp), 3.42~3.30 (4H, ovrlp), 3.20 (1H, dd, J=8.2 Hz, 4.6 Hz), 2.16 (2H, m), 1.76 (2H, m); $^{13}$C NMR (125.0 MHz, $CDCl_3$) δ 138.36, 138.04, 137.96, 128.39, 128.29, 128.20, 128.19, 128.16, 128.14, 128.12, 128.06, 128.05, 128.03, 128.00, 127.75, 127.59, 127.53, 127.51, 127.47, 127.41, 127.34, 127.31, 127.27, 127.23, 127.09, 114.80, 103.50, 102.79, 100.67, 82.60, 81.63, 81.60, 79.35, 77.19, 76.54, 75.16, 75.03, 74.95, 74.92, 74.81, 74.74, 73.64, 73.20, 73.10, 72.97, 72.94, 72.37, 72.01, 69.36, 69.17, 68.26, 67.75, 67.63, 30.16, 28.88; IR (thin film) 3030, 2921, 2865, 1495, 1452, 1364, 1093, 740 $cm^{-1}$; ESI-MS m/z 1496.0, $[M+Na]^+$. $[α]_D^{22}$=+26° (c=1.0, $CHCl_3$).

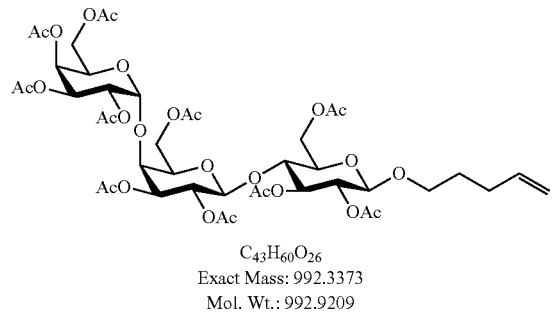

$C_{43}H_{60}O_{26}$
Exact Mass: 992.3373
Mol. Wt.: 992.9209

Peracetate of Globo-H Pentenyl Glycoside 1-7a:

To condensed liquid $NH_3$ (30 mL) cooled at −78° C. was added sodium (676 mg, 29.4 mmol) under positive argon pressure, and then the resulting blue solution was stirred at −78° C. for 20 min. Anhydrous THF (2.0 mL) was added to the blue solution, 10 minutes later perbenzylated trisaccharide 1-6 (722 mg, 0.49 mmol) in 4.0 mL THF was added. The resulting blue solution was stirred at −78° C. for 2 hours. The reaction was quenched with solid ammonium chloride (1.54 g) and anhydrous MeOH (3.0 mL), concentrated under a stream of dry $N_2$. To the residue was added 5.0 mL acetic anhydride, 10.0 mL pyridine and a crystal of 4-dimethylaminopyridine (DMAP), and then the reaction stirred at RT overnight. Concentration followed by purification by flash column chromatography (toluene/EtOAc=1/1 to 1/1.5) gave 446 mg desired product 1-7a as a white solid (92% yield). All data were consistent with our previously reported $^1$H, $^{13}$C NMR, IR, and CIHRMS data of 1-7a.

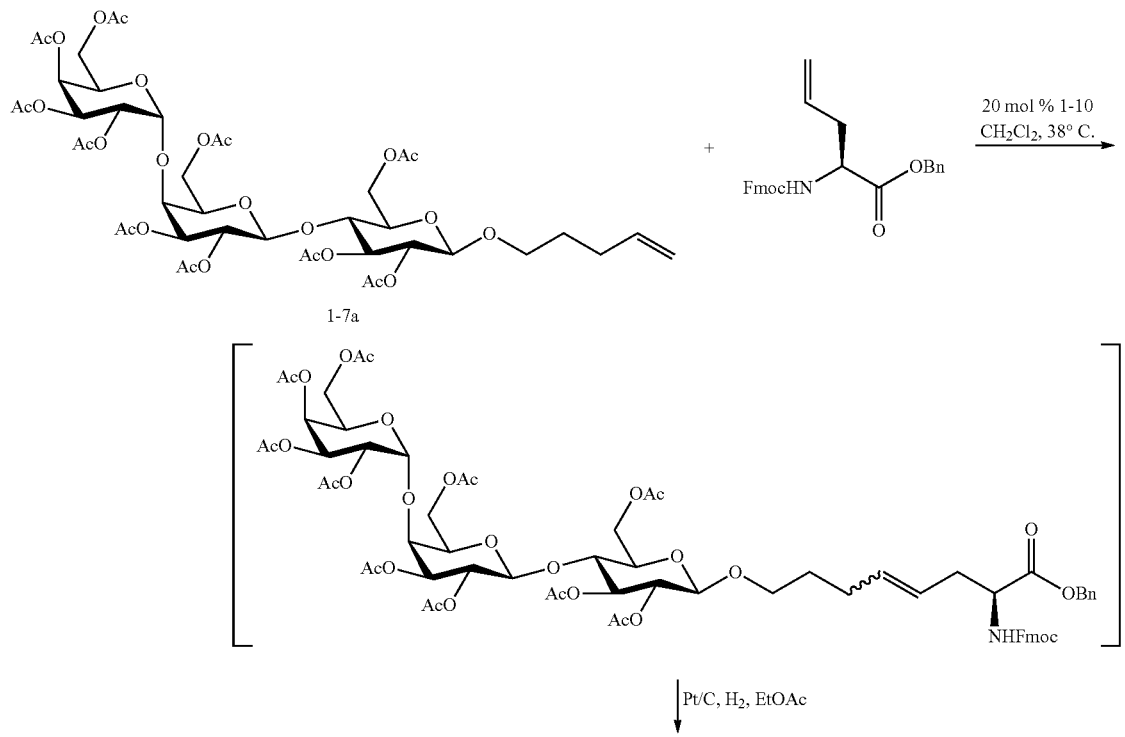

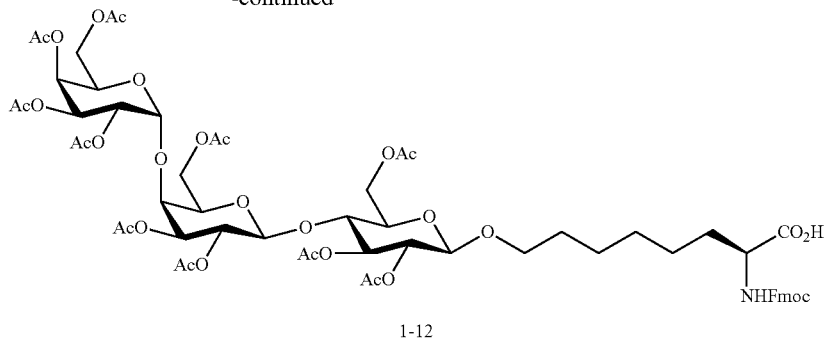

1-12

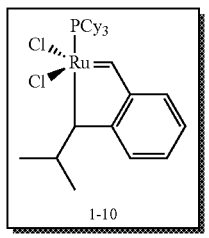

1-10

Gb₃ glycosylamino acid 1-12: To peracetate of globo-H pentenyl glycoside 1-7a (446 mg, 0.45 mmol), allylglycine benzylester (1.54 g, 3.6 mmol) and Hoveyda-Grubbs 1$^{st}$ generation catalyst 1-10 (67 mg, 0.11 mmol) was added degassed $CH_2Cl_2$ (6 mL), and then the mixture was heated at 37-38° C. with water cooling for 48 hours. The reaction mixture was purified on column chromatography (Hexanes/EtOAc=3/1 to 1/1 to 1/2) to afford 560 mg slightly impure cross-linked product. To this cross-linked compound (560 mg) was added 5% platinum on carbon (156 mg) and EtOAc (6.0 mL). The reaction mixture was stirred under $H_2$ atmosphere until full disappearance of starting material. Concentration followed by purification by flash column chromatography ($CH_2Cl_2$ to $CH_2Cl_2$/EtOAc=1.5/1 to $CH_2Cl_2$/MeOH=30/1 with 0.2% HOAc) gave 384 mg desired Gb₃ glycosylamino acid 1-12 (66% over two steps). All data were consistent with our previously reported $^1$H, $^{13}$C NMR, IR, and CIHRMS data of 1-12 (Wan, Q.; Cho, Y. S.; Lambert, T. H.; Danishefsky, S. J. *J. Carbohydr. Chem.* 2005, 24, 425-440).

SEQ ID NO: 2

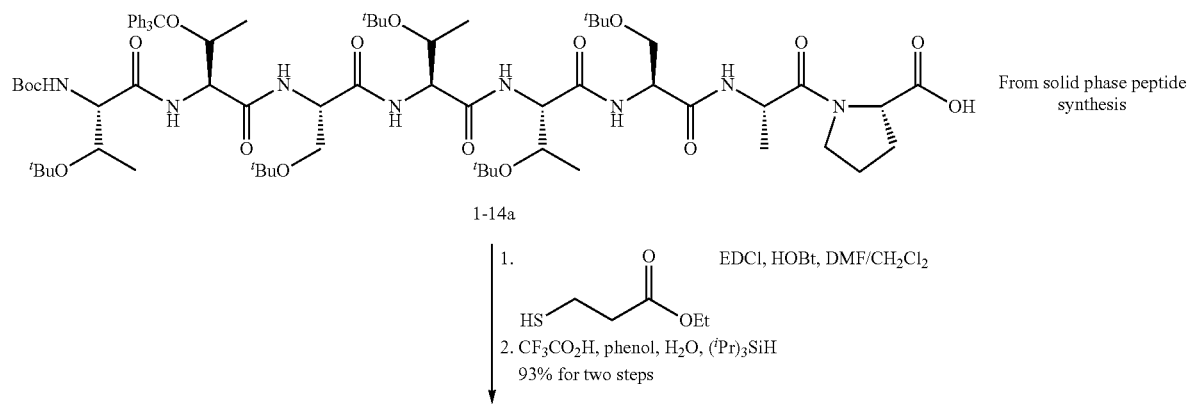

From solid phase peptide synthesis 1-14a

1. <br> HS⌒CO₂Et    EDCl, HOBt, DMF/$CH_2Cl_2$
2. $CF_3CO_2H$, phenol, $H_2O$, $(^iPr)_3SiH$
93% for two steps -continued
SEQ ID NO: 2
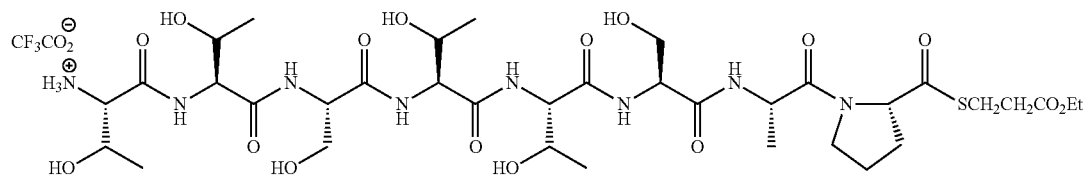
1-15a
Gb₃ glycosylamino acid 1-12.
DIEA, EDCl, HOBt, DMF;
SEQ ID NO: 48
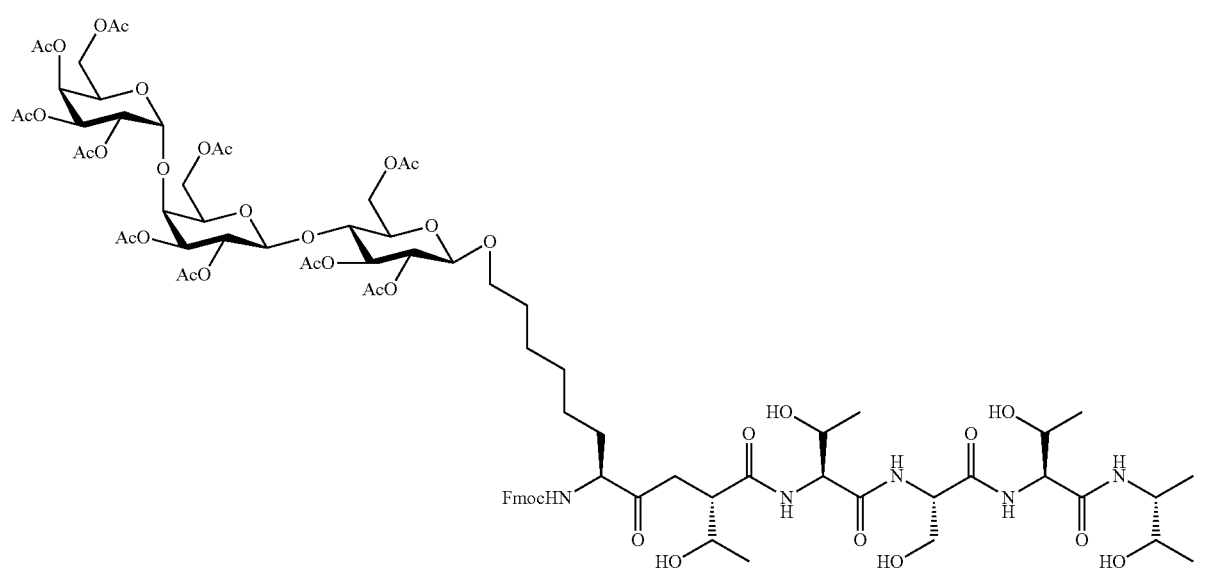
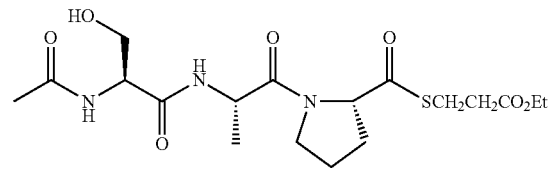
1-16
Ac₂O, pyridine, cat. DMAP, 70% over two steps

SEQ ID NO: 48

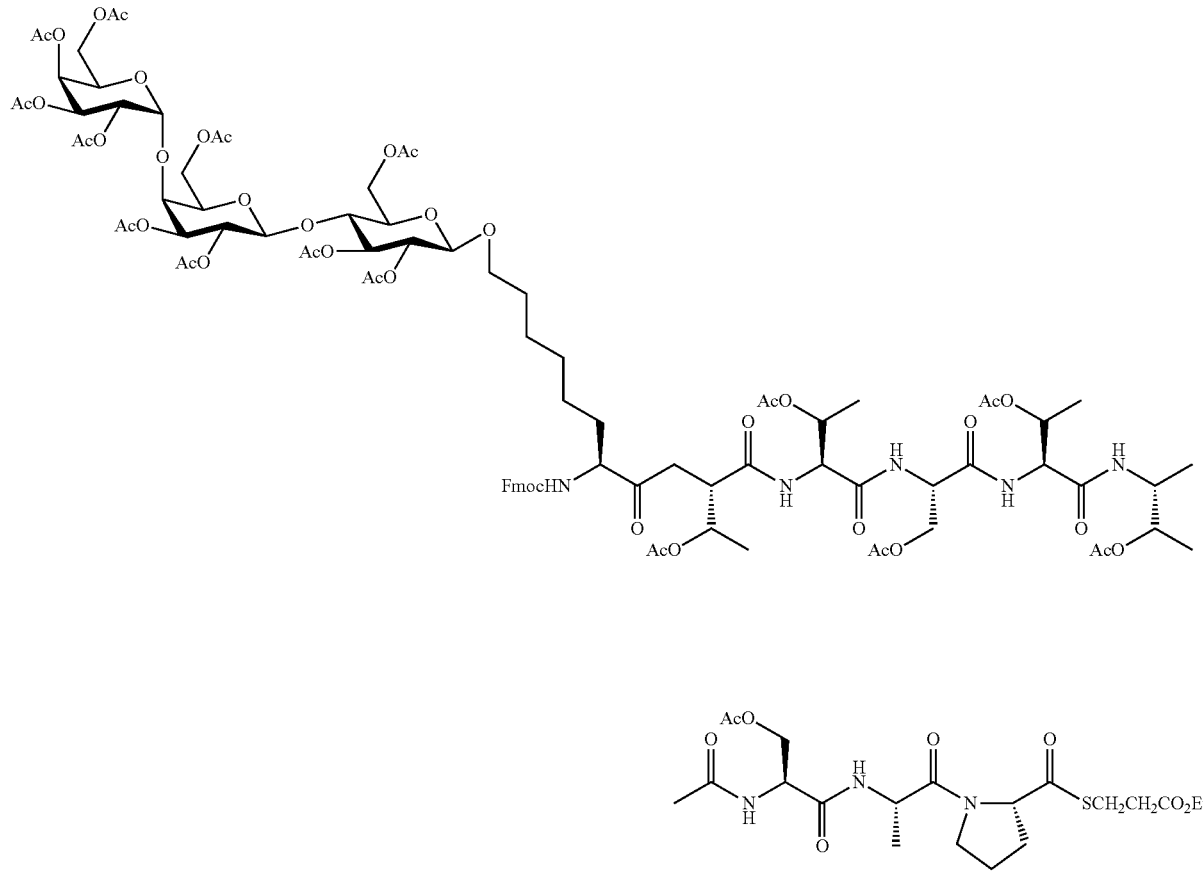

1-17

To a mixture of peptide 1-14a (prepared by solid phase peptide synthesis, 500 mg, 0.36 mmol), EDCI (414 mg, 2.16 mmol), HOBt (292 mg, 2.16 mmol) in DMF/CH$_2$Cl$_2$ (2.0/2.0 mL) was added ethyl 3-mercaptopropionate (456 μL, 3.6 mmol), the reaction was stirred at room temperature overnight. Nitrogen flow was applied to remove all of the volatiles and the residue was purified on flash column chromatography (CH$_2$Cl$_2$ to CH$_2$Cl$_2$/MeOH=40/1) to afford the desired thioester (504 mg, 93% yield). To this thioester (504 mg, 0.335 mmol) was added phenol (100 mg, 1.1 mmol), triisopropylsilane (251 μL, 1.23 mmol), water (335 μL, 18.6 mmol) and 5.0 mL trifluoroacetic acid, the reaction was stirred at room temperature for 3.5 hours before nitrogen flow was applied to remove all of the volatiles. Diethyl ether was added to the residue, the resulting heterogeneous mixture was shaken for 5 minutes and the ether layer was removed by centrifugation. This process was repeated three times to ensure complete removal of the impurities. The desired salt 1-15a (332 mg, quantitative yield) was obtained as white solid. ESI-MS m/z 881.6 [M+H]$^+$, 903.4 [M+Na]$^+$, 977.5 [M+CF$_3$CO$_2$H–H$_2$O+H]$^+$, 999.5 [M+CF$_3$CO$_2$H–H$_2$O+Na]$^+$, 1073.4 [M+2CF$_3$CO$_2$H–2H$_2$O+H]$^+$, 1095.6 [M+2CF$_3$CO$_2$H–2H$_2$O+Na]$^+$.

To salt 1-15a (292 mg, 0.293 mmol), Gb$_3$ glycosylamino acid 1-12 (180 mg, 0.138 mmol), EDCI (69 mg, 0.360 mmol), HOBt (65 mg, 0.48 mmol) was added DMF (3.0 mL) and N,N-diisopropylethylamine (48 μL), the reaction mixture was stirred at room temperature for 38 hours. Nitrogen flow was applied to remove all of the volatiles to afford crude 1-16 (ESI-MS m/z 2189.0 [M+Na]$^+$, 1106.1 [M+2Na]$^{2+}$). Compound 1-16 was next treated with Ac$_2$O (2.0 mL), pyridine (3.0 mL) and 4-dimethylaminopyridine (10 mg). The mixture was stirred at room temperature overnight before nitrogen flow was applied to remove all of the volatiles. The residue was first purified on column chromatography (CH$_2$Cl$_2$ to CH$_2$Cl$_2$/MeOH=10/1); then preparative TLC (CH$_2$Cl$_2$/MeOH=15/1); and further by preparative HPLC (C18 column, 45-95% CH$_3$CN in H$_2$O, 16 mL/min, 30 min) to afford 234 mg desired product Gb$_3$-MUC5AC cassettes 1-17 (70% yield for two steps). ESI-MS m/z 2440.8 [M+Na]$^+$, 1232.2 [M+2Na]$^{2+}$.

SEQ ID NO: 2

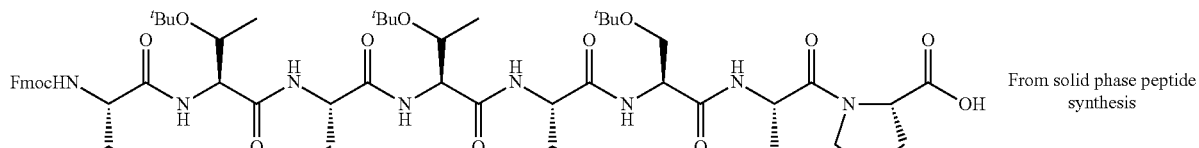

From solid phase peptide synthesis 1-14b

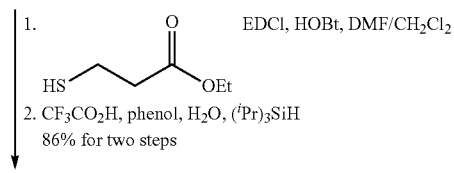

SEQ ID NO: 2

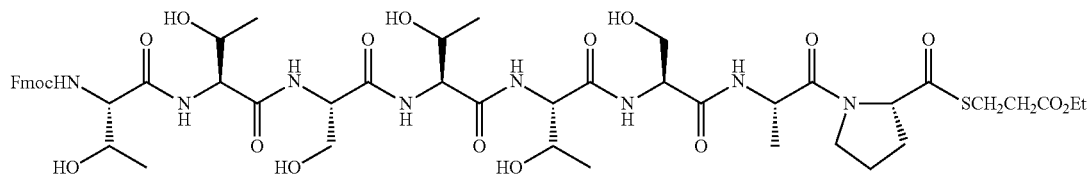

1-15b $C_{50}H_{70}N_8O_{18}S$
Exact Mass: 1102.4529
Mol. Wt.: 1103.1986

To a mixture of peptide 1-14b (prepared by solid phase peptide synthesis, 264 mg, 0.2 mmol), EDCI (384 mg, 2.0 mmol), HOBt (270 mg, 2.0 mmol) in DMF/CH$_2$Cl$_2$ (1.5/1.5 mL) was added ethyl 3-mercaptopropionate (506 μL, 4.0 mmol), the reaction was stirred at room temperature overnight. Nitrogen flow was applied to remove all of the volatiles and the residue was purified on flash column chromatography (CH$_2$Cl$_2$ to CH$_2$Cl$_2$/MeOH=25/1) to afford the desired thioester (280 mg, 97% yield). To this thioester (260 mg, 0.18 mmol) was added phenol (108 mg, 1.15 mmol), triisopropylsilane (300 μL, 1.47 mmol), water (360 μL, 20 mmol) and 5.4 mL trifluoroacetic acid, the reaction was stirred at room temperature for 3.5 hours before nitrogen flow was applied to remove all of the volatiles. The residue was purified on column chromatography (CH$_2$Cl$_2$/MeOH=20/1 to 15/1 to 10/1 to 6/1) to yield 177 mg desired product 1-15b (89% yield). ESI-MS m/z 1125.5 [M+Na]$^+$.

1-13

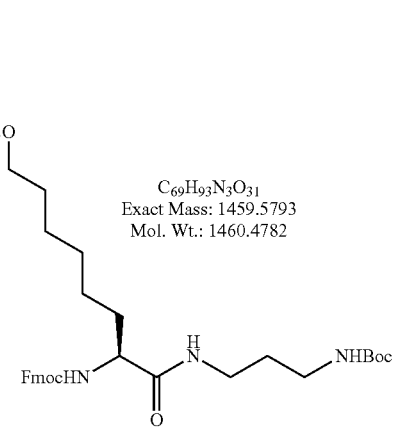

$C_{69}H_{93}N_3O_{31}$
Exact Mass: 1459.5793
Mol. Wt.: 1460.4782

To an oven-dried 5 ml round-bottomed flask was added Gb₃-glycosylamino acid 1-12 (112 mg, 86 μmol), 1-Hydroxybenzotriazole (17.5 mg, 129 μmol), and N-(3-Dimethylaminopropyl)-N'-ethylcarbodiimide hydrochloride (EDCI, 25 mg, 129 μmol). Anhydrous DMF (0.6 mL) and 16.5 mg of N-Boc-1,3-propanediamine in anhydrous CH₂Cl₂ (0.6 mL) was then added. The mixture was stirred at RT under argon for 30 minutes. The reaction mixture was diluted with EtOAc, sequentially washed with 1 M citric acid, saturated aqueous NaHCO₃ solution, saturated aqueous NaCl solution. The organic layer was separated, dried over Na₂SO₄ anhydrous, filtered, and concentrated. The residue was purified on column chromatography (CH₂Cl₂:MeOH=15:1) to yield 119 mg desired product 1-13 (95% yield). ESI-MS m/z 1482.9 [M+Na]⁺.

diethylamine and DMF. The residue was redissolved in CH₂Cl₂, and then N₂ flow was applied again applied to remove all volatiles. This process was repeated three times and further dried under high vacuum overnight to make sure excess diethylamine was completely removed. To this residue was sequentially added Gb₃-MUC5AC thioester 1-17 (97 mg, 40 μmol), AgCl (17.2 mg, 120 μmol), HOOBt (98 mg, 0.6 mmol), DMSO (2.0 mL) and N,N-diisopropylethylamine (70 μL, 0.4 mmol), and then this reaction mixture was stirred under dark for 48 h. After N₂ flow was applied to remove DMSO and N,N-diisopropylethylamine, the residue was first purified on column chromatography (CH₂Cl₂ to CH₂Cl₂/MeOH=10/1); then preparative TLC(CH₂Cl₂/MeOH=16/1); and further by preparative HPLC (C18 column, 45-95% CH₃CN in H₂O, 16 mL/min, 30 min) to afford

SEQ ID NO: 49

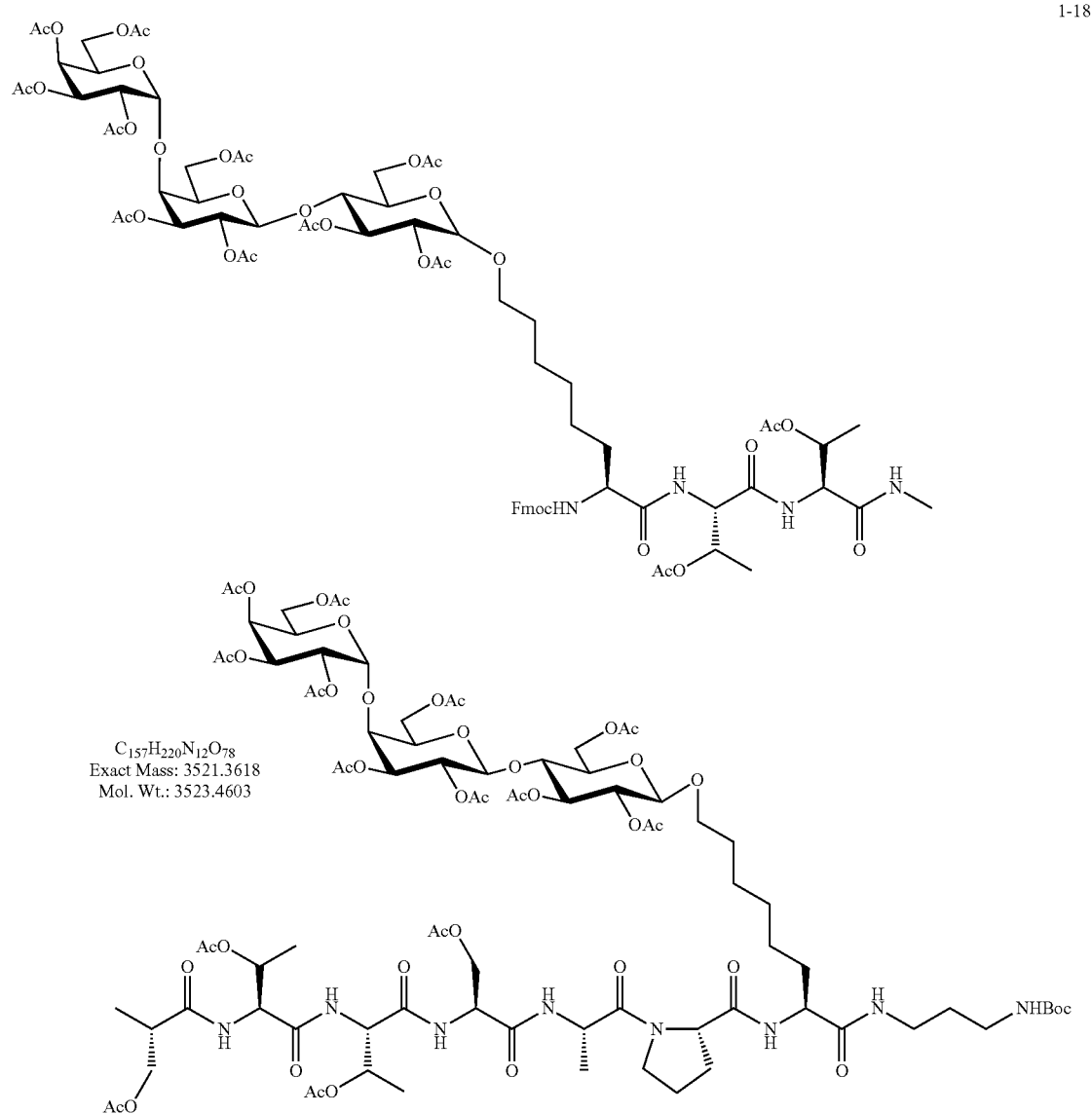

To construct 1-13 (67 mg, 46 μmol) was added 1.0 mL DMF and 50 μL diethylamine. The reaction mixture was stirred for 2 h before N₂ flow was applied to remove excess 98.5 mg desired product bis-Gb₃-mono-MUC5AC 1-18 (70% yield for two steps). ESI-MS m/z 1783.9 [M+2Na]²⁺, 1197.3 [M+3Na]³⁺.

To bis-Gb$_3$-mono-MUC5AC 1-18 (42.5 mg, 12 µmol) was added 0.8 mL DMF and 40 µL diethylamine. The reaction mixture was stirred for 2 h before N$_2$ flow was applied to remove excess diethylamine and DMF. The residue was redissolved in CH$_2$Cl$_2$, and then N$_2$ flow was applied again to remove all volatiles. This process was repeated three times and further dried under high vacuum overnight to make sure excess diethylamine was completely removed. To this residue was sequentially added Gb$_3$-MUC5AC thioester 1-17 (32 mg, 13.2 µmol), AgCl (5.7 mg, 40 µmol), HOOBt (31 mg, 192 µmol), DMSO (0.8 mL) and N,N-diisopropylethylamine (23 µL, 132 µmol), and then this reaction mixture was stirred under dark for 36 h. After N$_2$ flow was applied to remove DMSO and N,N-diisopropylethylamine, the residue was purified on column chromatography (CH$_2$Cl$_2$/MeOH=30/1 to 15/1) and further by preparative HPLC (C18 column, 45-95% CH$_3$CN in H$_2$O, 16 mL/min, 30 min) to afford 48.5 mg desired product tris-Gb$_3$-bis-MUC5AC 1-19 (72% yield for two steps). ESI-MS m/z 2814.4 [M+2Na]$^{2+}$, 1884.5 [M+3Na]$^{3+}$, 1418.9 [M+4Na]$^{4+}$.

To tris-Gb$_3$-bis-MUC5AC 1-19 (36.0 mg, 6.44 µmol) was added 0.6 mL DMF and 30 µL diethylamine. The reaction mixture was stirred for 2 h before N$_2$ flow was applied to remove excess diethylamine and DMF. The residue was redissolved in CH$_2$Cl$_2$, and then N$_2$ flow was applied again applied to remove all volatiles. This process was repeated three times and further dried under high vacuum overnight to make sure excess diethylamine was completely removed. To this residue was sequentially added MUC5AC thioester 1-15b (35.5 mg, 32.2 µmol), AgCl (13.8 mg, 96.6 µmol), HOOBt (31.5 mg, 193 µmol), DMSO (1.5 mL) and N,N-diisopropylethylamine (22.5 µL, 129 µmol), and then this reaction mixture was stirred under dark for 48 h. After N$_2$ flow was applied to remove DMSO and N,N-diisopropylethylamine, the residue was purified on preparative TLC (CH$_2$Cl$_2$/MeOH=9/1) afforded the desired product 1-20 which was directly used in the next step. ESI-MS m/z 2133.7 [M+3Na]$^{3+}$, 1606.2 [M+4Na]$^{4+}$, 1289.5 [M+5Na]$^{5+}$.

To the above construct 1-20 was added 0.6 mL DMF and 30 µL diethylamine. The reaction mixture was stirred for 2 h before N$_2$ flow was applied to remove excess diethylamine and DMF. The residue was redissolved in CH$_2$Cl$_2$, and then N$_2$ flow was applied again applied to remove all volatiles. This process was repeated three times and further dried under high vacuum overnight to make sure excess diethylamine was completely removed. To this residue was added acetic anhydride (0.6 mL), pyridine (0.9 mL) and a small crystal of 4-dimethylaminopyridine, and then this reaction mixture was stirred overnight. N$_2$ flow was applied again applied to remove all volatiles and the residue was purified by column chromatography (CH$_2$Cl$_2$/MeOH=30/1 to 10/1) to afford 25.4 mg desired tris-Gb$_3$-tris-MUC5AC 1-21 (62% over four steps). ESI-MS m/z 2156.7 [M+3Na]$^{3+}$.

To peracetate 1-21 (6.0 mg, 0.94 µmol) was added degassed NH$_2$NH$_2$/MeOH (500 µL, 1/4, v/v) at room temperature under argon. The reaction was stirred at room temperature for 36 hours before N$_2$ was applied to remove excess NH$_2$NH$_2$ and MeOH. The residue was dissolved in minimum amount of water and purified by bio-gel P4 column (water as eluant). All fractions containing the desired compound were combined and lyophilized to afford 3.7 mg pure construct 1-22 (90%). ESI-MS m/z 2215.5 [M+2Na]$^{2+}$, 1484.9 [M+3Na]$^{3+}$, 1119.2 [M+4Na]$^{4+}$.

To peracetate 1-21 (33 mg, 5.15 µmol) in 1.2 mL dichloromethane was added 0.3 mL trifluoroacetic acid, the reaction mixture was stirred at room temperature for 3 hours before nitrogen flow was applied to remove the volatiles. The residue was dried under high vacuum for 2 hours to afford corresponding crude amine salt. To this amine salt was added 0.8 mL pyridine and S-acetylthioglycolic acid pentafluorophenyl ester (SAMA-OPfp, 12.4 mg, 41 µmol) at room temperature. After stirring for 24 hours, nitrogen flow was applied to remove the volatiles and residue was purified on silica column (CH$_2$Cl$_2$/MeOH=15:1 to 10:1) to afford 22 mg desired product 1-23 as white solid (66% for two steps). ESI-MS m/z 2162.2 [M+3Na]$^{3+}$.

To peracetate 1-23 (21.0 mg, 3.27 µmol) was added degassed NH$_2$NH$_2$/MeOH (5.0 mL, 1/4, v/v) at 0° C. under argon. The reaction mixture was slowly warmed and stirred at room temperature for 36 hours before being concentrated to remove excess NH$_2$NH$_2$ and MeOH. To the residue was added 1.0 mL degassed water and tris(2-carboxyethyl)phosphine (TCEP, 150 µL, 0.5 M in neutral buffer) under argon pressure, and the reaction mixture was stirred for 1 hour at room temperature. This aqueous mixture was directly purified by bio-gel P4 column (degassed water as eluant). All fractions containing the desired compound were combined and lyophilized to afford 12.3 mg pure construct 1-1 (86%). ESI-MS m/z 1476.2 [M+3Na]$^{3+}$, 1112.9 [M+4Na]$^{4+}$.

Conjugation of Gb$_3$-MUC5AC Vaccine Construct to KLH:

Gb$_3$-MUC5AC glycopeptide 1-1 was covalently attached to KLH using the heterobifunctional crosslinker Sulfo-MBS (m-maleimidobenzoyl-N-hydroxysulfosuccinimide ester, Pierce Co., Rockford, Ill.) which couples the terminal free sulfhydryl functional to amino group on KLH as described earlier (Ragupathi, G.; Cappello, S.; Yi, S. S.; Spassova, M.; Bornmann, W.; Danishefsky, S. J.; Livingston, P. O. *Vaccine* 2002 20, 1030-1038; Ragupathi, G.; Coltart, D. M.; Williams, L. J.; Koide, F.; Kagan, E.; Allen, J.; Harris, C.; Glunz, P. W.; Livingston, P. O. Danishefsky, S. J. *Proc. Natl. Acad. Sci. USA* 2002, 99, 13699-13704). First KLH (9.0 mg, Sigma, molecular weight 8.6×10$^6$) was treated with Sulfo-MBS (3.0 mg), then the unconjugated Sulfo-MBS was eliminated by passage over a G25 Sephadex column. Maleimide activated KLH is then added to the freshly de-protected Gb$_3$-MUC5AC glycopeptide 1-1 (3.8 mg). The mixture was incubated at room temperature for 3 h, following incubation, unreacted glycopeptide was removed using a 30,000 molecular cut-off Centriprep filter. Finally the Gb$_3$-MUC5AC-KLH conjugate was obtained in a 6.0 mL buffer solution. The Gb$_3$-MUC5AC concentration in Gb$_3$-MUC5AC-KLH conjugate was determined using ion exchange chromatography with pulsed amperometric detection by measuring carbohydrate content of Gb$_3$-MUC5AC and KLH by a dye binding method (BioRad, Dye reagent). The epitope ratio of Gb$_3$-MUC5AC/KLH in the conjugate was 698/1 assuming a KLH molecular weight of 8.6 million.

Example 2

The present Example establishes that mucin-based glycopeptide constructs of the present disclosure give a positive immunogenic response as measured by IgG and IgM titer.

Gb3 is expressed on the cancer cell surface as a glycolipid and as an O-linked glycoprotein. It is highly expressed in colon and ovarian cancer. It is believed that Gb3 is be a good target for antibody mediated immunotherapy, including monoclonal antibodies and tumor vaccines. We have shown previously both in mice and in patients that conjugation of a variety of carbohydrate cancer antigens to keyhole limpet hemocyanin (KLH) and administration of this conjugate mixed with saponin adjuvants QS-21 or GPI-0100 are the most effective methods for induction of antibodies against carbohydrate cancer antigens (Ragupathi, G. et al., *J. Am. Chem. Soc.,* 2006, 128, 2715-2725; Ragupathi, G. et al., *Angew. Chem. Int. Ed.,* 1997, 36, 125-128). The preceding example demonstrated the total synthesis of Gb3 glycoside with MUC5AC and its conjugation to KLH to construct a Gb3-MUC5AC-KLH conjugate (compounds 1-1 and 1-24, respectively). The present example confirms that glycopeptide constructs comprising a mucin-based peptide epitope and a carbohydrate epitope are useful in obtaining an immunogenic response. These data demonstrate the utility of such constructs as vaccines.

Groups of five mice were vaccinated subcutaneously with Gb3-MUC5AC or Gb3-MUC5AC-KLH conjugate plus adjuvant with appropriate controls. Sera were tested against Gb3-ceramide by ELISA. The mice immunized with unconjugated Gb3-ceramide plus an adjuvant such as QS-21 or unconjugated Gb3-MUC5AC alone plus an adjuvant such as QS-21 failed to produce antibodies against Gb3. However mice immunized with Gb3-MUC5AC-KLH conjugate at various dose (1 µg, 5 µg and 10 µg) plus an adjuvant such as QS-21 induced significantly higher titer IgG and IgM antibodies against Gb3 by ELISA. Our preliminary evaluation showed that these antibodies did not cross react with a structurally similar antigen Globo H. Further evaluation of these antibodies on Gb3 positive cell-lines by FACS and testing for complement mediated cytotoxicity are expected to yield favorable results.

Vaccination of Mice.

Groups of five mice (C57BL/6J, female, 6-8 weeks old) were vaccinated three times with GB3-ceramide conjugate (5 µg equivalent of GB3), MUC5Ac peptide (5 µg equivalent of MUC5Ac), GB3-MUC5Ac-SH conjugate (5 µg equivalent of GB3-MUC5AC), GB3-MUC5Ac-KLH conjugate (1, 5 and 10 µg equivalent of GB3-MUC5Ac), Globo H-KLH conjugate (5 µg equivalent of GloboH) and KLH protein alone (5 µg equivalent of KLH) in 100 µL phosphate buffered saline (PBS) either with an adjuvant (20 µg) or without adjuvant. Vaccines were administered subcutaneously to each mouse on weeks 1, 2, 3, and 7. Mice were bled 7 days after the third vaccination and forth vaccination.

Measurement of Immunological Response.

The presence of antibodies was tested by an enzyme-linked immunosorbent assay (ELISA). ELISAs were performed to determine antibody response against GB3, Globo H and KLH. The ELISA plates were coated with either GB3 antigen or Globo H at 0.2 µg/well and 0.1 µg/well respectively in ethanol or KLH at 0.1 µg/well in carbonate buffer (pH 10). The GB3-coated and Globo H coated plates were kept overnight at room temperature to evaporate ethanol, and KLH coated plates were incubated at 4° C. overnight. ELISA plates were washed, blocked with 1% human serum albumin (HSA) in phosphate-buffered saline containing 0.05% Tween 20. Serially diluted pre- and post-vaccination sera in PBS with 1% HSA were added to wells of the coated plate with appropriate controls and incubated for 1 h at room temperature. After wash, goat anti-mouse IgM or IgG conjugated with alkaline phosphatase (Southern Biotechnology Associates, Inc., Birmingham, Ala.) was added to each well. Absorbance was measured at 405 nm. The titer was defined as the highest serum dilution that showed an absorbance of 0.1 or greater over that of the pre-sera (see FIGS. 76-79).

Example 3

Synthesis of Fucosyl-GM1 Glycopeptide Conjugate

This Example demonstrates the synthesis of a multi-antigenic glycopeptide comprising a MHC-II binding peptide.

Figure 12:
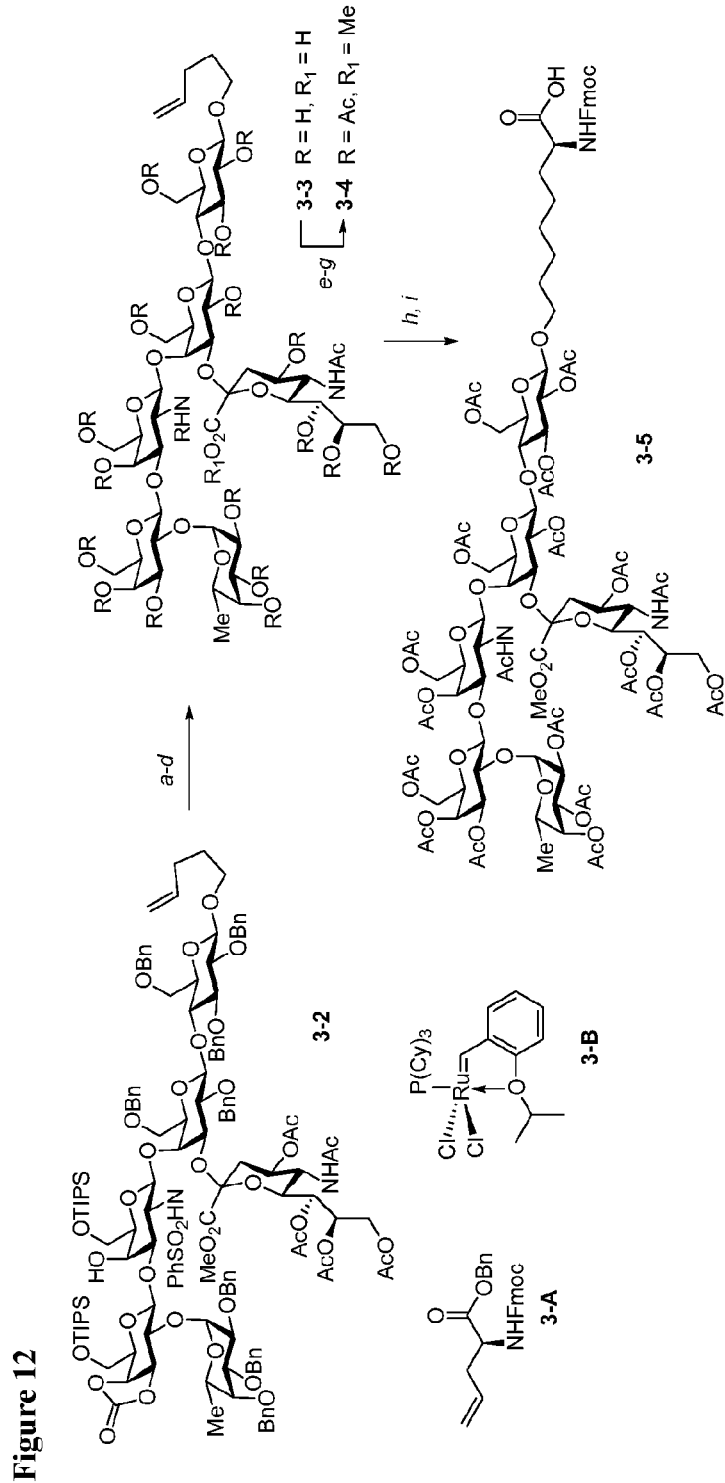
FIG. 12 depicts a synthesis of compound 3-5.

The construction of the vaccine began from the known Fuc-GM1 hexasaccharide 3-2, obtained through a previously disclosed sequence. After deprotection of the triisopropylsilyl groups with TBAF/acetic acid, and subsequent cleavage of acetates, carbonate and sialic acid methyl ester, the resultant product was debenzylated under Birch conditions (Wang, Z.-G.; Warren, J. D.; Dudkin, V. Y.; Zhang, X.; Iserloh, U.; Visser, M.; Eckhardt, M.; Seeberger, P. H.; Danishefsky, S. J. *Tetrahedron* 2006, 62, 4954-4978). The obtained acid 3-3, was exhaustively peracetylated to provide a corresponding lactone that was subsequently opened with methanol and DMAP. Acylation afforded 3-4 (56%, 7 steps). Glycoside 3-4 was treated with Fmoc-L-allylglycine benzyl ester (3-A) and Hoveyda-Grubbs catalyst (3-B) under the previously developed conditions and the resultant olefin cross-metathesis product was subjected to catalytic hydrogenation (Biswas, K.; Coltart, D. M.; Danishefsky, S. J. *Tetrahedron Lett.* 2002, 43, 6107-6110). The side-chain olefinic linkage was reduced with concomitant selective removal of the benzyl protecting group in the presence of Fmoc-protected amine to afford the cassette 3-5 (49%, 2 steps) ready for coupling (FIG. 12).

The synthesis of peptide 3-7 was accomplished by standard Fmoc solid phase peptide synthesis (SPPS), starting from the protected tyrosine, 3-6, preloaded on TGT-Nova Syn resin. Peptide 3-7 was obtained in 95% yield after cleavage from the resin, in more than 95% purity, as judged by LC/MS and $^1$H NMR analysis. The elaboration of 3-7 to peptide 3-8 was executed by first conjugating 3-7 to the linker C (Pittelkow, M.; Lewinsky, R.; Christensen, J. B. *Synthesis,* 2000, 15, 2195-2202) using the standard EDCI/HOBt protocol. The Fmoc protecting group was next removed by treatment with piperidine, providing fragment 3-8 in 71% yield (2 steps). The attachment of 3-8 to carbohydrate epitope 3-5 proceeded in 81% yield, thereby providing glycopeptide 3-9 (see FIG. 13).

Compound 3-9 was treated sequentially with piperidine/DMF and Ac$_2$O/Py. The allylcarboxy protecting group was exchanged to the acetate-protected 2-sulfhydrylacetate linker by reduction with Pd(PPh$_3$)$_4$/PhSiH$_3$ followed by acylation with SAMA-OPbf. Finally, three tert-butyl and one tert-butylcarboxy groups were removed by treating 3-10 with TFA/PhOH/H$_2$O/TIPS providing the corresponding deprotected product in 71% yield (5 steps) from 3-9 following purification by HPLC. This compound was treated with a degassed solution of NaOH in MeOH/H$_2$O (pH=10.5), providing the desired deprotected product 3-11 in 19% yield following HPLC purification (Glunz, P. W.; Hintermann, S.; Williams, L. J.; Schwarz, J. B.; Kuduk, S. D.; Kudryashov, V.; Lloyd, K. O.; Danishefsky, S. J. *J. Am. Chem. Soc.* 2000, 122, 7273-7279). Minor amounts of a dehydration side product (ca. 5% yield after HPLC) were also isolated.

Figure 14:
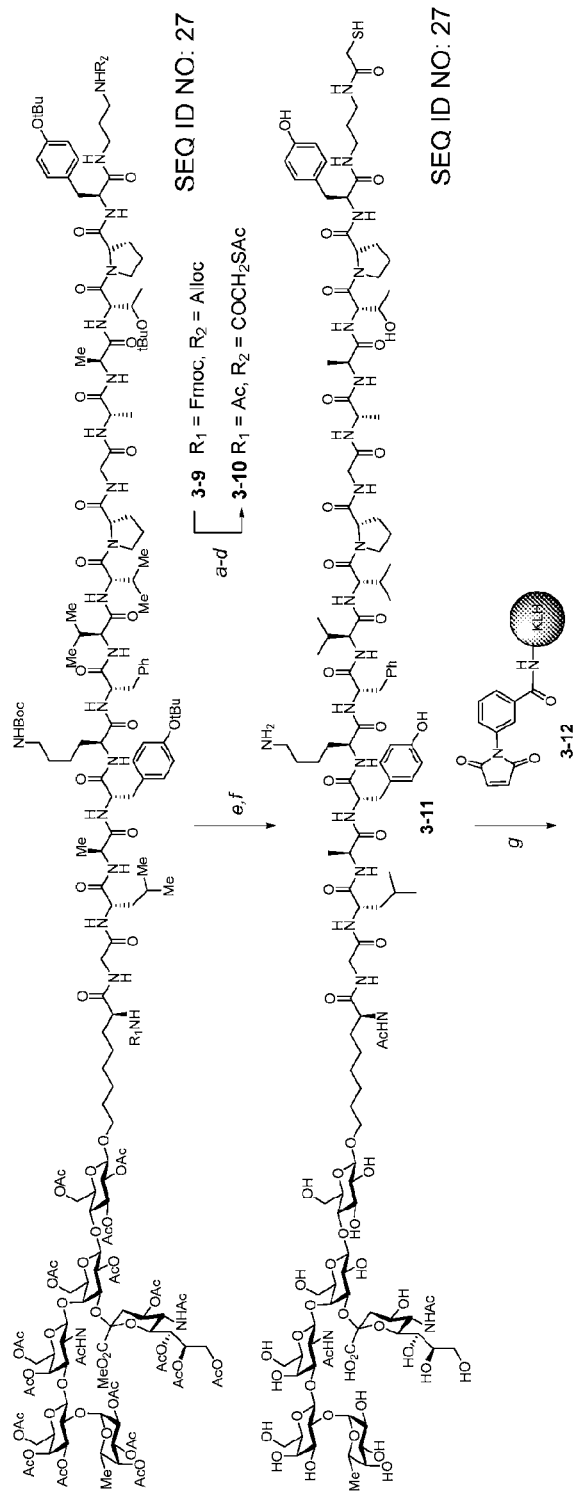
FIG. 14 depicts a synthesis of construct 3-1.

Next, the conjugation of construct 3-11 to maleimide activated KLH 3-12 was examined (FIG. 14). Thus, 3-11 was pretreated with TCEP gel for 2 h and then treated with freshly prepared 3-12 at pH=7.2. The efficiency of the coupling was estimated by a combination of Bradford protein essay (Bradford, M. *Anal. Biochem.* 1976, 72, 248-254) and neuraminic acid determination according to Svennerholm (Svennerholm, L. *Biochim. Biophys. Acta* 1957, 24, 604-611) to be 210 epitopes per molecule of KLH (MW=8 MDa).

Experimental:

All reactions were carried out under an atmosphere of dried nitrogen in flame-dried or oven-dried glassware with magnetic stirring, unless otherwise noted. Air-sensitive reagents and solutions were transferred via syringe or cannula and were introduced to the apparatus through rubber septa. Reactions were cooled via external cooling baths: ice water (0° C.), dry ice-acetone (−78° C.), ice-acetone (−10° C.), or immersion cooler (−20 to −80° C.). Heating was accomplished by heating mantle or silicon oil bath using a temperature controller. Analytical thin layer chromatography (TLC) was performed on 0.25 mm silica gel 60-F plates. Visualization was accomplished with UV light and exposure to aqueous ceric ammonium molybdate (CAM) solution or anisaldehyde followed by heating. Flash chromatography was performed using silica gel 60 (230-240 mesh). Solvents for extraction and chromatography were HPLC grade.

When necessary, solvents and reagents were dried prior to use. Tetrahydrofuran (THF), dichloromethane ($CH_2Cl_2$), toluene, diethyl ether ($Et_2O$) and benzene were filtered through a column of activated alumina under an argon atmosphere. Pyridine, N,N-diisopropylethylamine, and triethylamine were distilled from calcium hydride. DBU (Diazabicycloundecene) and piperidine were purchased and used without further purification. HATU (O-(7-azabenzotriazol-1-yl)-N,N,N',N'-tetramethyluronium hexafluorophosphate) was purchased and used without further purification.

Analytical Equipment: $^1$H- and $^{13}$C NMR spectra were recorded on a 500 MHz or 600 MHz spectrometer in $CDCl_3$, DMF-d7, $CD_3OD$ or $D_2O$. Chemical shifts (δ) are reported from tetramethylsilane with the solvent resonance as the internal standard ($CDCl_3$: δ 7.26; DMF-d7: δ 8.03; 2.92, 2.75; $CD_3OD$: δ 4.78, 3.34; $D_2O$: δ 4.65). Data are reported as follows: chemical shift (δ), multiplicity (s=singlet, d=doublet, t=triplet, q=quartet, br=broad, m=multiplet), coupling constants (Hz), integration, and assignment. $^{13}$C NMR spectra were recorded with complete proton decoupling. Chemical shifts are reported in ppm from tetramethylsilane with the solvent as the internal standard ($CDCl_3$: δ 77.0). HPLC purifications were run with TFA (trifluoroacetic acid)-buffered eluents: A=0.05% v/v TFA/Water, B=0.04% TFA/Acetonitrile using HPLC grade solvents.

Synthesis of Acetylated Glycoside 3-4 (Steps (a)-(c), FIG. 12)

To a solution of the hexasaccharide 3-2 (335 mg, 0.131 mmol) in THF (6.0 mL) was added glacial AcOH (0.12 mL) and TBAF (1.0 M in THF, 1.31 mL). The reaction mixture was stirred at rt for 2 days, poured into ice-water (25 mL), and extracted with EtOAc. The organic extracts were dried over $MgSO_4$ and concentrated. The resulting triol was dissolved in anhydrous MeOH (6 mL) and sodium methoxide was added (25% solution in MeOH, 0.6 mL). The contents were stirred at rt for 3 days, and then water (6.0 mL) and THF (6.0 mL) were added. Stirring at rt for an additional 2 days was followed by neutralization with Dowex-H$^+$, filtration with MeOH washing, and concentration. The crude material was allowed to dry under high vacuum for 1 day.

Figure 43:
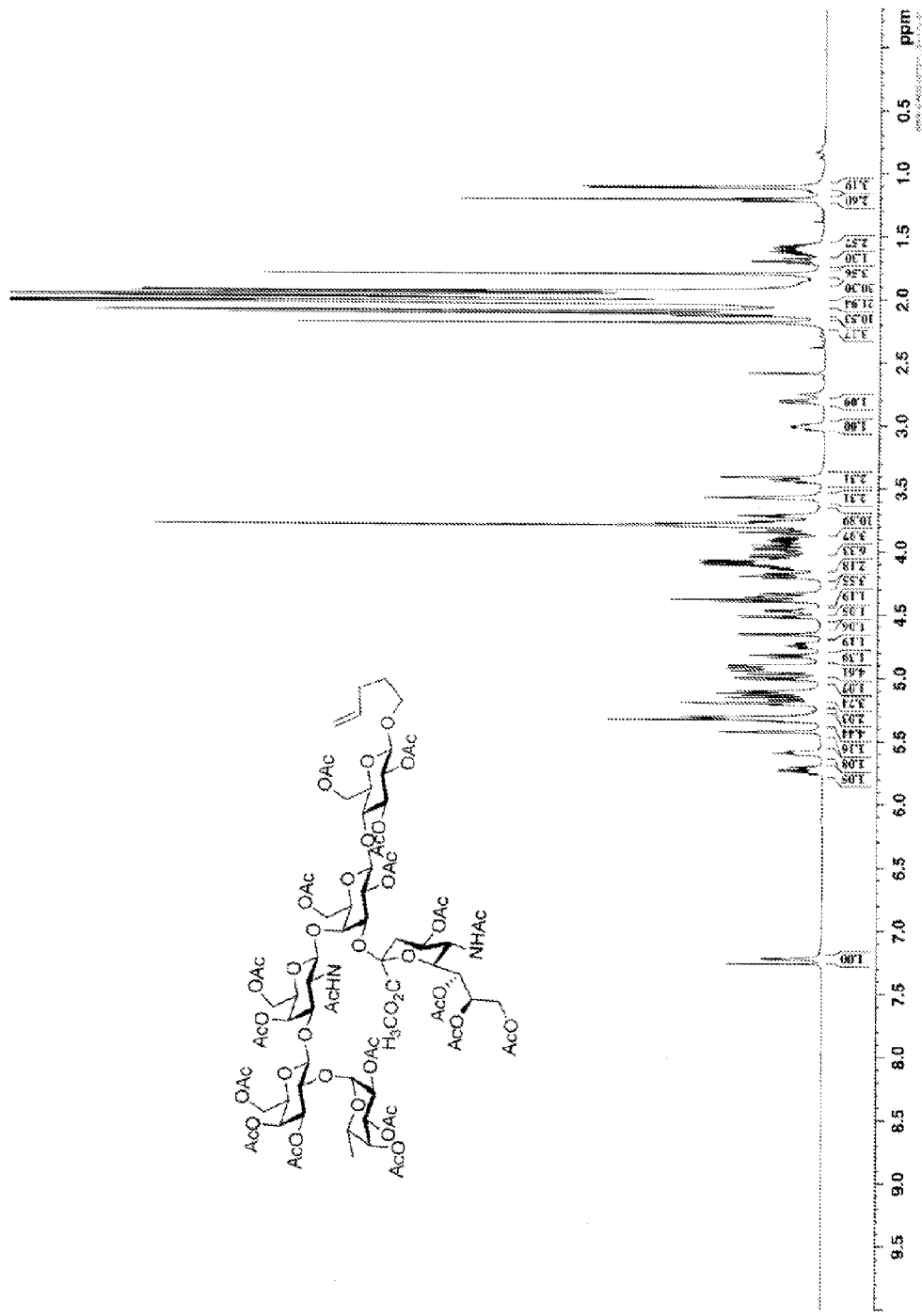
FIG. 43 depicts a $^1$H-NMR spectrum of compound 3-4.
Figure 44:
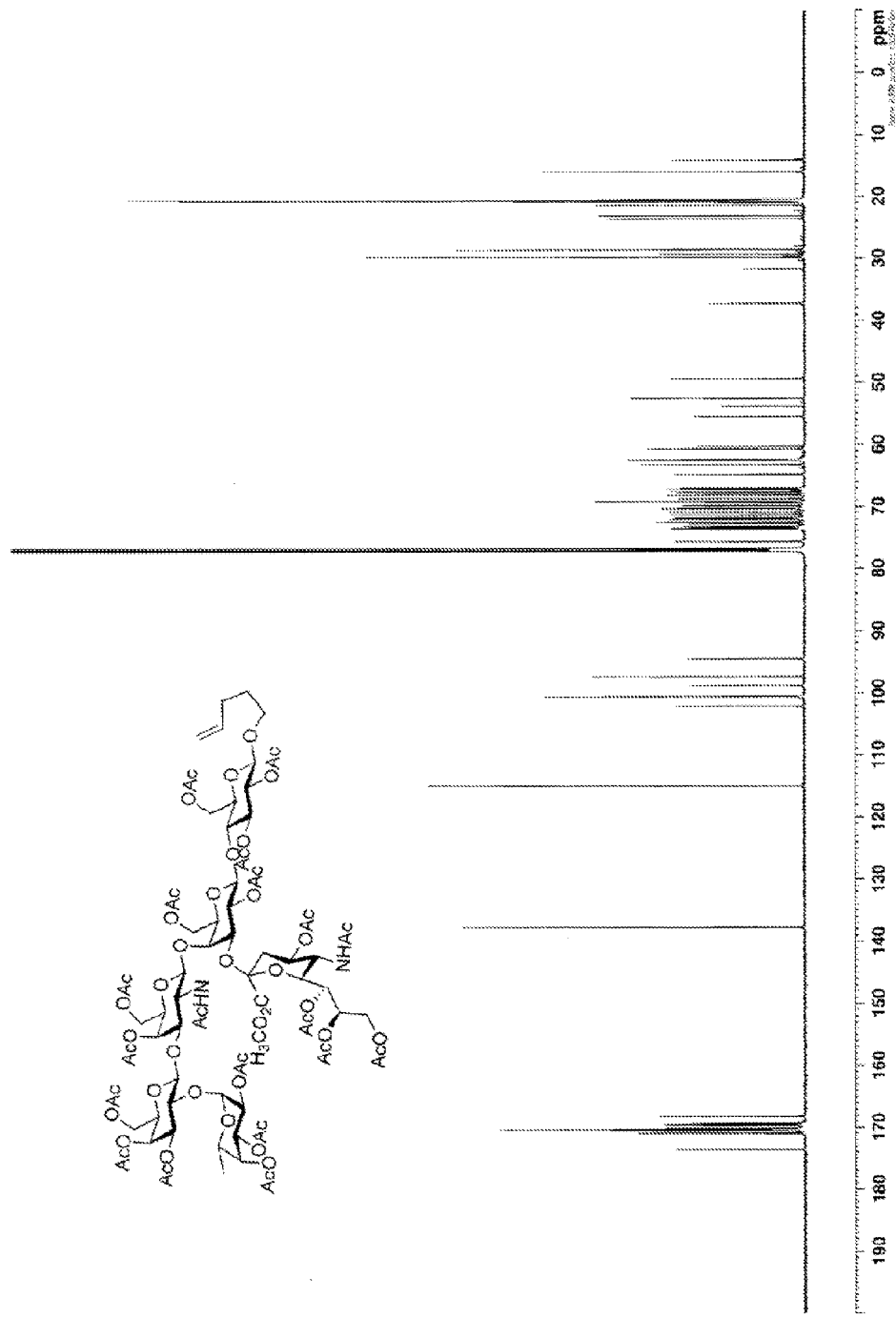
FIG. 44 depicts a $^{13}$C-NMR spectrum of compound 3-4.

Synthesis of Acetylated Glycoside 3-4 (Steps (d)-(g), FIGS. 12, 43, 44)

To a blue solution of sodium (160 mg) in liquid $NH_3$ (50 mL) was added a solution of the white solid from above in THF (5.0 mL), and the resulting mixture was stirred at −78° C. for 2 h. The reaction was quenched by the addition of anhydrous MeOH (20 mL), warmed to rt, and concentrated with a stream of dry argon. The residue was diluted with MeOH (70 mL) and treated with Dowex 50wX8-400 until pH was nearly 5-6. The mixture was filtered and concentrated to provide a solid. This solid was dissolved in a mixture of pyridine (12.0 mL) and $Ac_2O$ (6.0 mL) at rt. To the solution of tetrasaccharide was added DMAP (10 mg) and the mixture was stirred for an additional 2 days. The reaction mixture was cooled to 0° C. and treated with MeOH (24 mL). To this solution was added DMAP (15 mg) and the resultant mixture was stirred at rt for an additional 4 days. The reaction mixture was then concentrated and co-evaporated with toluene (4×100 mL). The residue was dissolved in pyridine (5.0 mL) and $Ac_2O$ (1.0 mL) at rt. The mixture was stirred for 1 day and then concentrated. The resultant oil was dissolved in MeOAc (10.0 mL) and MeI (0.2 mL). To the solution cesium carbonate (33 mg) was added, and the mixture was stirred for 1 h, and then diluted with methyl acetate (250 mL). The organic phase was washed with brine/$NH_4Cl_{(sat.)}$ (1:1, 100 mL), $NaHCO_{3(sat.)}$ (100 mL), brine (100 mL), and dried over $MgSO_4$. Concentration followed by flash chromatography (silica, 5% methanol/dichloromethane) provided the acetylated glycoside 3-4 (142 mg, 56% from 3-2). $[\alpha]^{24}_D$=−40.4 (c 1.00, $CHCl_3$); IR (film $CHCl_3$) 2969, 1746, 1689, 1530, 1371, 1231, 1131, 1058 cm$^{-1}$; $^1$H NMR ($CDCl_3$, 600 MHz) δ 7.22 (d, J=5.9 Hz, 1H), 5.76-5.69 (m, 1H), 5.61-5.58 (m, 1H), 5.43 (d, J=3.5 Hz, 1H), 5.34-5.30 (m, 4H), 5.21-5.10 (m, 5H), 5.00 (d, J=8.2 Hz, 1H), 4.97-4.89 (m, 4H), 4.82 (t, J=8.8 Hz, 1H), 4.74 (td, J=11.4, 3.6 Hz, 1H), 4.65 (d, J=7.7 Hz, 1H), 4.52 (d, J=7.8 Hz, 1H), 4.49-4.45 (m, 1H), 4.39-4.33 (m, 3H), 4.21-4.17 (m, 2H), 4.14-4.02 (m, 6H), 4.00-3.89 (m, 3H), 3.85-3.70 (m, 9H), 3.58-3.56 (m, 2H), 3.45-3.40 (m, 2H), 3.01 (dt, J=12.7, 5.6 Hz, 1H), 2.81 (dd, J=12.9, 4.1 Hz, 1H), 2.19 (s, 3H), 2.12 (s, 3H), 2.10 (s, 3H), 2.09 (s, 3H), 2.03-1.97 (m, 33H), 1.95 (s, 3H), 1.94 (s, 3H), 1.93 (s, 3H), 1.80 (s, 3H), 1.70 (t, J=12.8 Hz, 1H), 1.64-1.57 (m, 2H), 1.22-1.20 (m, 2H), 1.11 (d, J=6.4 Hz, 3H); $^{13}$C NMR ($CDCl_3$, 150 MHz) δ 173.6, 171.0, 170.9, 170.9, 170.4, 170.4, 170.4, 170.3, 170.3, 170.3, 170.3, 170.3, 170.2, 170.2, 170.0, 169.7, 169.6, 169.5, 169.4, 169.2, 168.2, 137.7, 114.9, 102.0, 100.4, 98.7, 97.3, 94.4, 75.6, 73.7, 73.5, 73.3, 73.2, 72.8, 72.5, 72.0, 71.8, 71.7, 71.3, 70.9, 70.3, 70.2, 69.8, 69.4, 69.2, 69.1, 68.7, 68.1, 67.7, 67.4, 67.2, 67.0, 65.0, 63.3, 62.4, 62.4, 62.4, 60.6, 60.3, 55.5, 53.7, 52.5, 49.3, 37.1, 31.6, 29.7, 29.2, 28.5, 23.5, 23.0, 21.3, 20.9, 20.8, 20.7, 20.7, 20.7, 20.7, 20.6, 20.6, 20.5, 20.4, 20.4, 15.9, 14.1; ESI/MS: Exact mass calcd for $C_{83}H_{116}N_2O_{50}$ [M+Na]$^+$: 1963.7; [M+Cl]$^-$: 1975.6. Found: 1963.9, 1977.0.

Synthesis of Amino Acid 3-5 (Step (h)).

The first generation Hoveyda-Grubbs catalyst (3-B, 9.6 mg, 0.016 mmol) was added to a solution of acetylated glycoside 3-4 (124 mg, 0.064 mmol) and allylglycine 3-A (273 mg, 0.640 mmol) in $CH_2Cl_2$ (1 mL) at rt. The reaction mixture was stirred for 12 h and exposed to air for 3 h. The mixture was concentrated and the resultant residue was purified by flash chromatography (100% ethyl acetate) to provide the coupled product.

Figure 45:
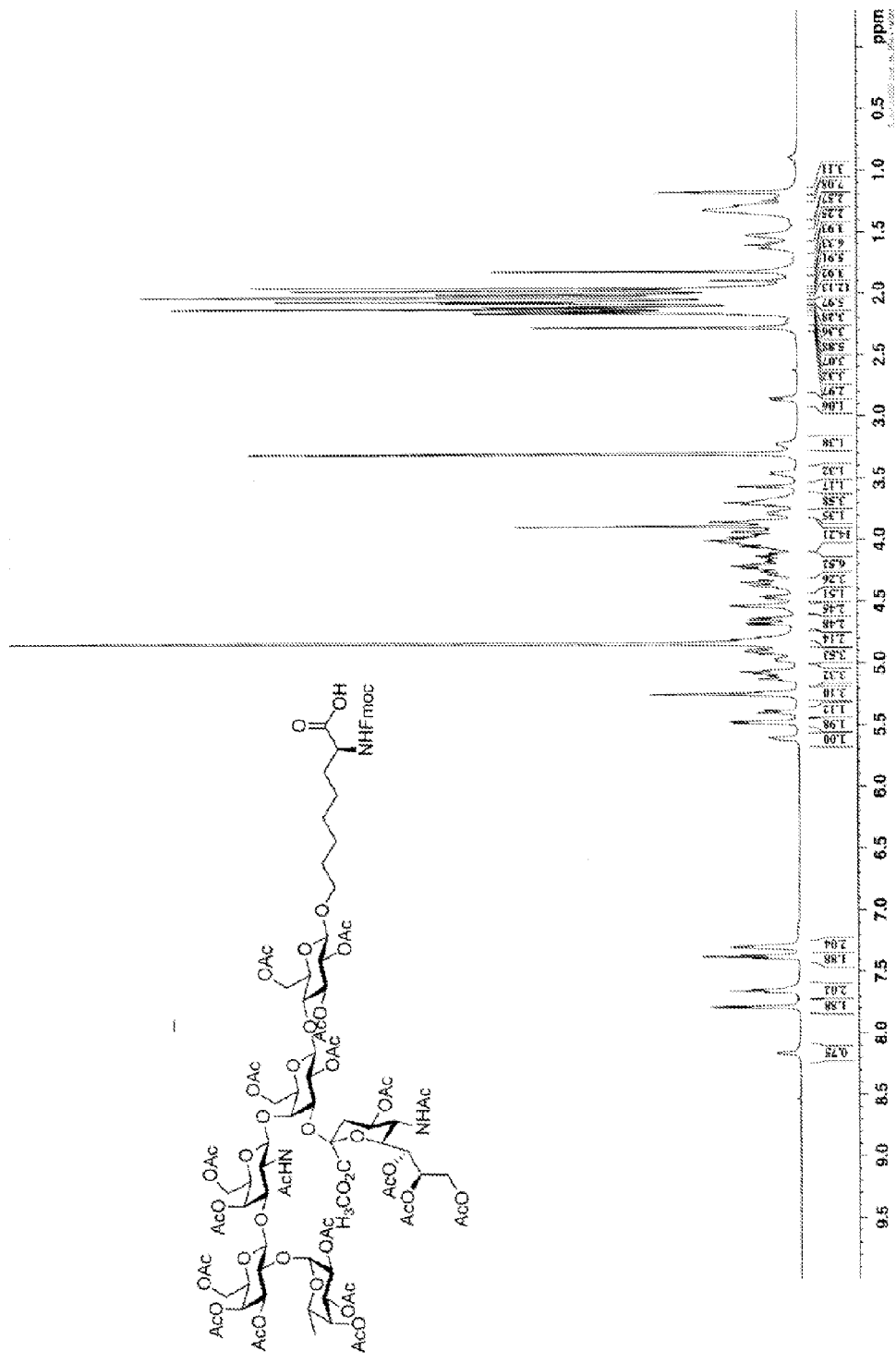
FIG. 45 depicts a $^1$H-NMR spectrum of compound 3-5.
Figure 46:
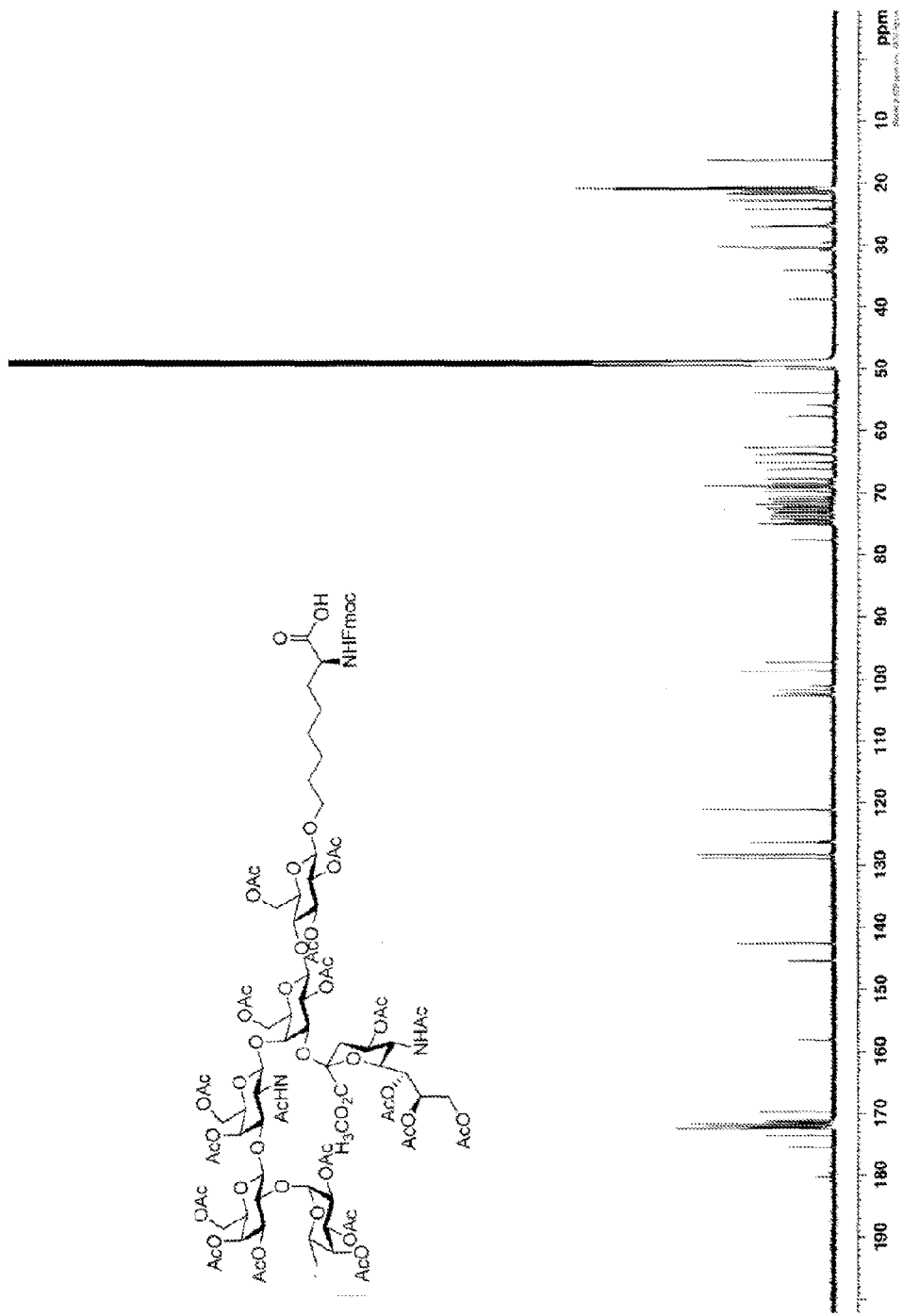
FIG. 46 depicts a $^{13}$C-NMR spectrum of compound 3-5.
Figure 47:
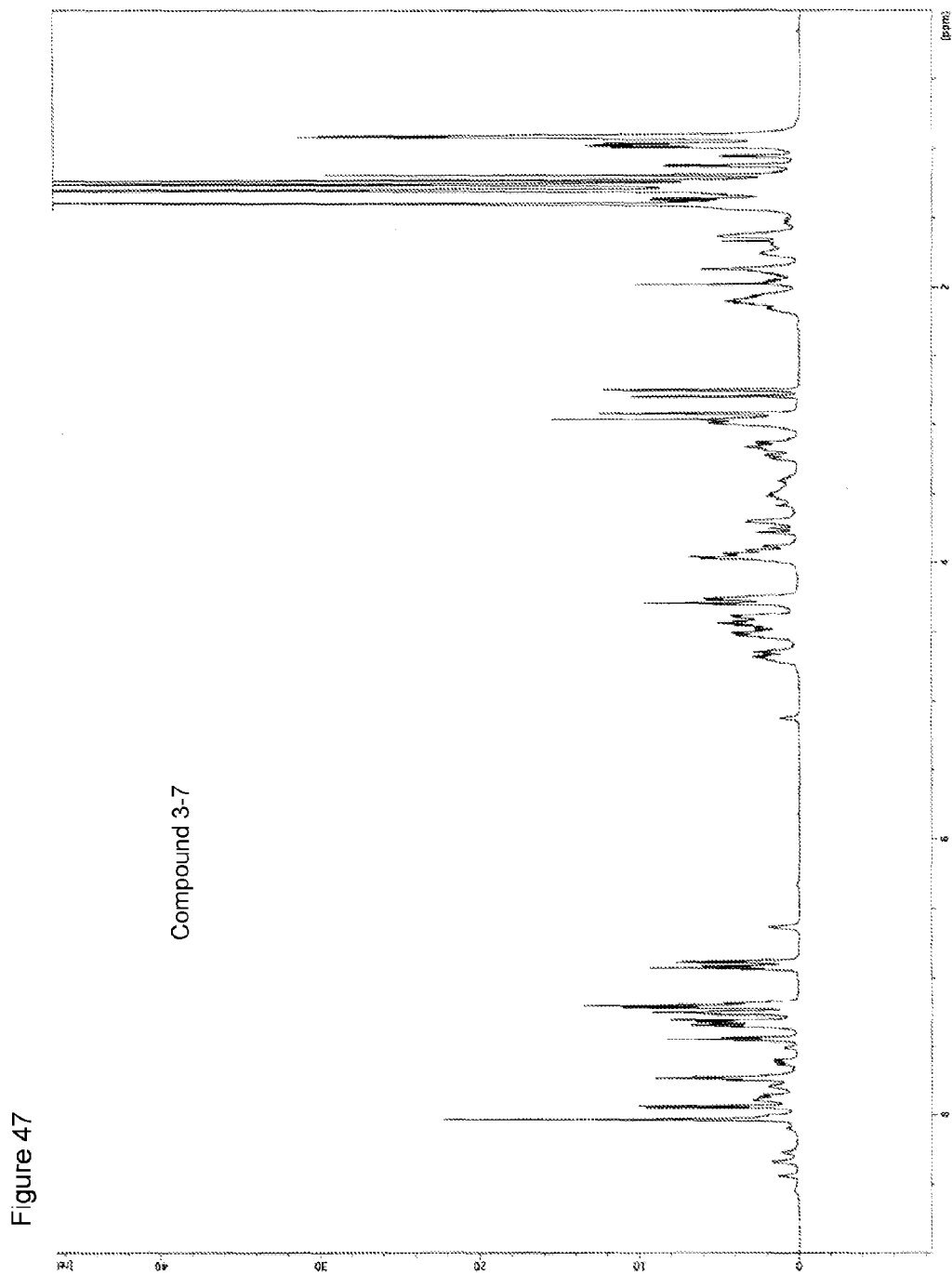
FIG. 47 depicts a $^1$H-NMR spectrum of compound 3-7.
Figure 48:
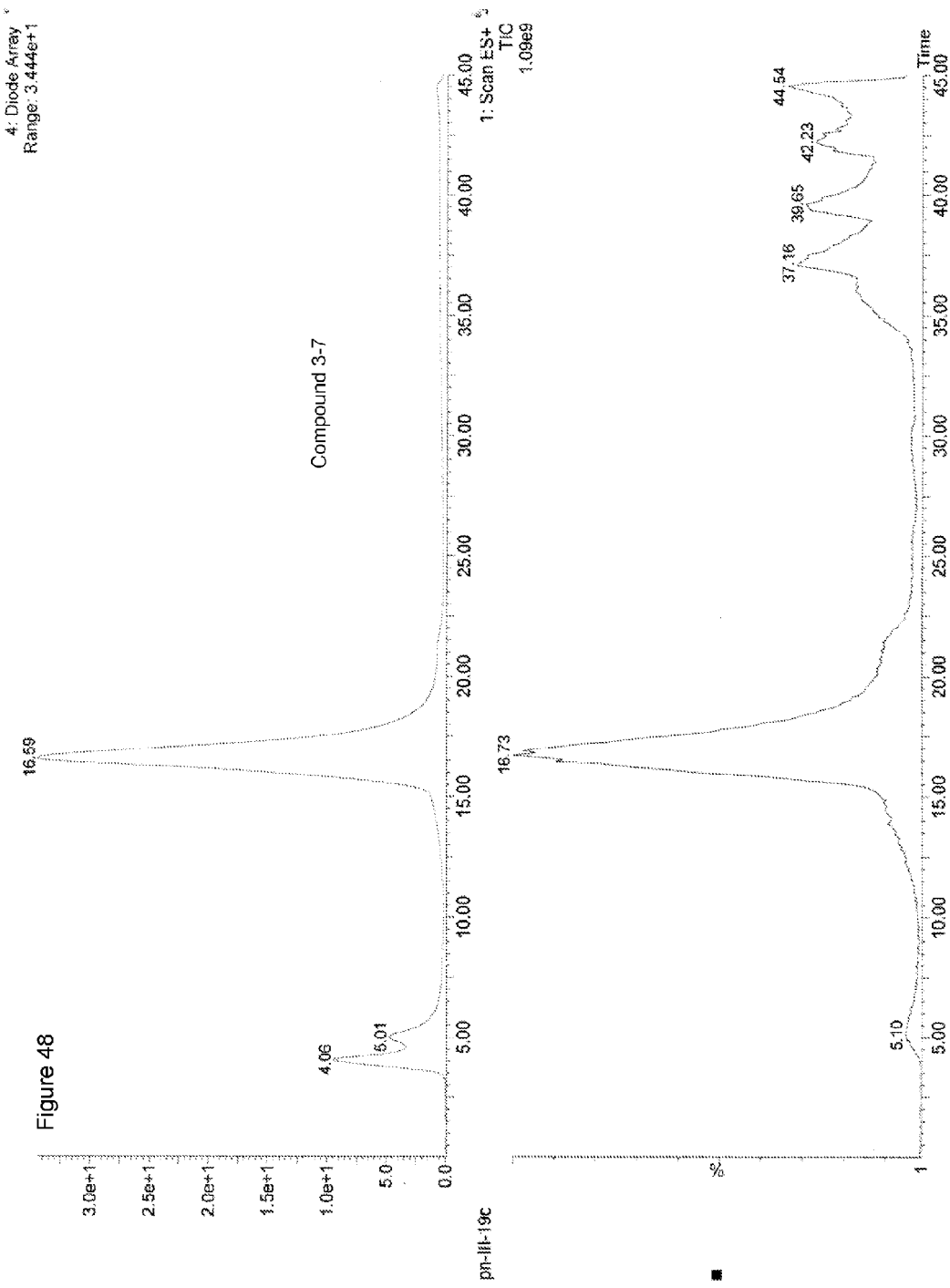
FIGS. 48-49 depict LCMS characterization data for compound 3-7.
Figure 49:
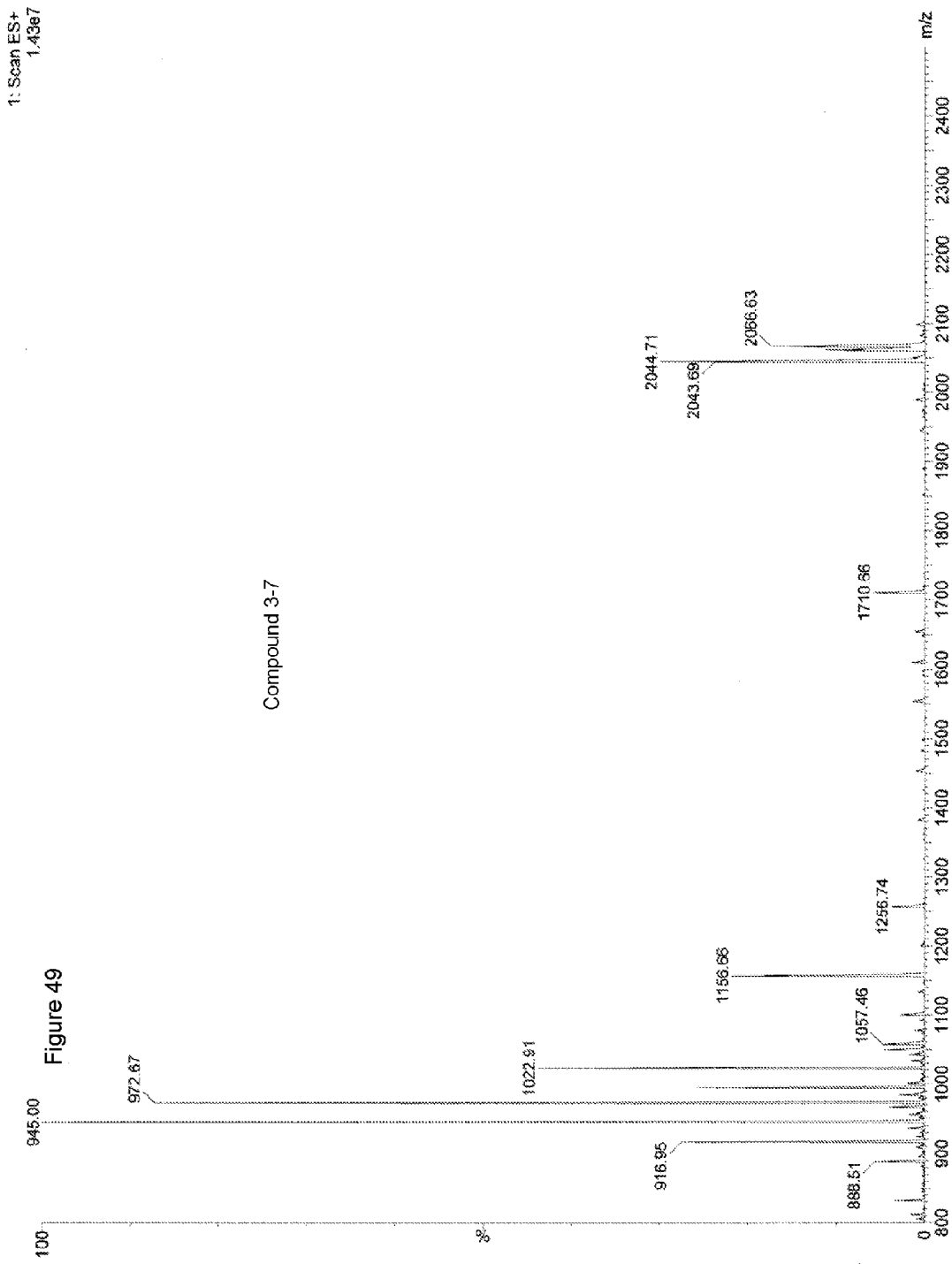

Synthesis of Amino Acid 3-5 (Step (i), FIGS. 12, 45, 46).

Pt/C (10% w/w, 15 mg) was added to a solution of the metathesis adduct from above in MeOH (3 mL) and $H_2O$ (0.2 mL) and the hydrogen atmosphere was established. The reaction mixture was stirred for 4 days at rt, filtered through a short pad of silica gel, and concentrated. The residue was purified by flash chromatography (10% MeOH in $CH_2Cl_2$) to give the amino acid 3-5 (70 mg, 49% over two steps). $[\alpha]^{24}_D$=−30.2° (c 1.00, $CHCl_3$); IR (film $CHCl_3$) 3470, 2928, 2854, 1746, 1429, 1370, 1232, 1057 cm$^{-1}$; $^1$H NMR ($CDCl_3$, 600 MHz) δ 8.16 (d, 1H, J=6.4 Hz), 7.79 (d, 2H, J=7.4 Hz), 7.67-7.65 (m, 2H), 7.39-7.37 (m, 2H), 7.30 (br.s, 2H), 5.62-5.60 (m, 1H), 5.48-5.47 (m, 2H), 5.39 (d, 1H, J=10 Hz), 5.25-5.23 (m, 3H), 5.14-5.05 (m, 3H), 4.98-4.78 (m, 6H), 4.68 (d, 1H, J=7.5 Hz), 4.64 (d, 1H, J=7.8 Hz), 4.54-4.53 (m, 2H), 4.47 (d, 1H, J=11.2 Hz), 4.40-4.32 (m, 3H), 4.29-4.10 (m, 7H), 4.07-3.76 (m, 15H), 3.72-3.65 (m, 3H), 3.57 (s, 1H), 3.48-3.44 (m, 1H), 3.25-3.17 (m, 1H), 2.86 (dd, 1H, J=3.9 and 12.5 Hz), 2.27 (s, 3H), 2.16 (s, 3H), 2.14 (s, 3H), 2.12 (s, 6H), 2.11 (s, 3H), 2.08 (s, 3H), 2.06 (s, 6H), 2.03 (s, 6H), 2.02 (s, 6H), 2.00 (s, 3H), 1.98 (s, 6H), 1.95 (s, 6H), 1.82 (s, 3H), 1.61 (t, 2H, 12.5 Hz), 1.52 (br.s, 2H), 1.37-1.25 (m, 7H), 1.18 (d, 3H, J=6.2 Hz); $^{13}$C NMR (CDCl$_3$, 150 MHz) δ 180.2, 175.4, 173.6, 172.4, 172.4, 172.4, 172.3, 172.2, 172.2, 172.1, 171.8, 171.7, 171.7, 171.5, 171.4, 171.1, 169.7, 158.2, 145.5, 145.4, 142.6, 128.8, 128.2, 126.3, 126.3, 121.0, 102.6, 102.3, 101.7, 101.1, 98.7, 97.3, 77.6, 75.2, 75.0, 74.8, 74.4, 74.3, 74.2, 73.8, 73.3, 73.2, 73.0, 72.7, 72.4, 72.2, 71.9, 71.3, 71.0, 70.6, 69.7, 69.2, 68.9, 68.4, 67.7, 66.2, 65.0, 63.8, 63.6, 63.5, 62.6, 57.6, 55.8, 53.8, 50.0, 49.6, 48.6, 38.7, 34.1, 30.6, 30.2, 27.0, 26.8, 24.2, 22.8, 21.7, 21.7, 21.3, 21.0, 21.0, 20.9, 20.9, 20.8, 20.8, 20.8, 20.7, 20.6, 20.6, 20.6, 16.3; ESI/MS: Exact mass calcd for C$_{101}$H$_{133}$N$_3$O$_{54}$ [M+Na]$^+$: 2275.8; [M+2Na]$^{2+}$: 1149.4. Found: 2275.5, 1149.3.

Synthesis of Peptide 3-7 (Step (a), FIGS. 13, 47-49).

NovaSyn TGT resin (purchased from NovaBiochem) was chlorinated, then esterified with Fmoc-Tyr(tBu)-OH for 3 hours, and then immediately Fmoc-deprotected according to the literature procedure. 0.21 g (ca. 0.05 mmol) of this resin was subjected to continuous flow automated peptide synthesis. For coupling steps, resin was treated with a 4-fold excess of HATU and Fmoc amino acids in 1 M DIEA/DMF, and for deblocking, a solution of 2% piperidine/2% DBU in DMF was used. The amino acids used were, in order of synthesis: Fmoc-Pro-OH, Fmoc-Thr(tBu)-OH, Fmoc-Ala-OH, Fmoc-Ala-OH, Fmoc-Gly-OH, Fmoc-Pro-OH, Fmoc-Val-OH, Fmoc-Val-OH, Fmoc-Phe-OH, Fmoc-Lys(Boc)-OH, Fmoc-Tyr(tBu)-OH, Fmoc-Ala-OH, Fmoc-Leu-OH, Fmoc-Gly-OH. The resin was then transferred to a manual peptide synthesis vessel and treated with a cleavage solution of 5 mL of 1:1:8 trifluoroethanol/acetic acid/dichloromethane for 1.5 h. The beads were filtered, rinsed with another 10 mL of cleavage solution, filtered again, and then treated for another 1 h with 10 mL of the cleavage solution. This process was repeated for a total of three 2-hour cleavage cycles, and the combined organic phase was concentrated in vacuo to afford 97 mg of peptide after cleavage (ca. 95% yield). This material was found to be >95% pure as judged by reverse-phase LC/ESI (Microsorb C4 column) MS and $^1$H NMR analysis: $^1$H-NMR (500 MHz, DMF-d7) (Due to the high degree of the NH exchange, the presence of the multiple peptide rotamers in the solution as well as the high overlap, there is an ambiguity associated in the tabulation and interpretation of the $^1$H NMR data. Please refer to the Figures for additional details) δ 8.44 (t, J=5.5 Hz, NH), 8.34 (br, NH), 8.27 (br, NH), 8.13 (t, J=8.6 Hz, NH), 8.00 (m, NH), 7.94 (d, J=7.6 Hz, 2H), 7.89 (d, J=6.5 Hz, NH), 7.86 (d, J=7.1 Hz, NH), 7.79 (br, NH), 7.73 (t, J=8.4 Hz, 2H, NH), 7.62 (d, J=7.9 Hz, NH), 7.60 (d, J=7.4 Hz, NH), 7.55 (d, J=6.0 Hz, NH), 7.45 (t, J=7.4 Hz, 2H), 7.34 (t, J=7.6 Hz, 2H), 7.31 (d, J=7.6 Hz, 2H), 7.25 (m, 2H), 7.22-7.17 (m, 5H), 6.93 (t, J=8.3 Hz, 2H), 6.88 (d, J=8.2 Hz, 2H), 6.63 (m, NH), 5.12 (t, J=4.7 Hz, NH), 4.71-4.67 (m, 2H), 4.66-4.59 (m, 1H), 4.54-4.47 (m, 3H), 4.46-4.41 (m, 2H), 4.41-4.37 (m, 2H), 4.30 (m, 2H), 4.29-4.23 (m, 2H), 4.00-3.85 (m, 4H), 3.77 (d, J=16.7 Hz, 1H), 3.70 (m, 2H), 3.52 (br t, J=8.8 Hz, 2H), 3.40 (q, J=8.5 Hz, 1H), 3.23 (d, J=10.6 Hz, 1H), 3.19-3.08 (m, 3H), 3.08-2.96 (m, 3H), 2.96 (s, 2H), 2.79 (s, 2H), 2.18-2.05 (m, 4H), 2.02-1.93 (m, 1H), 1.92-1.83 (m, 3H), 1.77-1.72 (m, 1H), 1.71-1.66 (m, 2H), 1.63 (m, 2H), 1.54 (m, 1H), 1.40 (s, 9H), 1.42-1.33 (m, 6H), 1.31 (s, 9H), 1.30 (s, 9H), 1.26 (s, 9H), 1.3-1.23 (m, 2H), 1.23 (s, 6H), 1.19 (s, 3H), 1.12 (d, J=6.2 Hz, 6H), 1.05 (d, J=6.2 Hz, 3H), 0.99 (d, J=6.8 Hz, 3H), 0.97 (d, J=6.6 Hz, 3H), 0.92 (d, J=6.2 Hz, 6H), 0.90 (d, J=5.2 Hz, 6H); LC/MS (ESI): Rf=16.6 min (C4 Microsorb column, 50-95% MeCN in H$_2$O, 30 min); Exact mass calcd for C$_{108}$H$_{154}$N$_{16}$O$_{23}$ [M+H]$^+$: 2045.2; [M+Na]$^+$: 2067.1; [M+2H]$^{2+}$: 1023.1. Found: 2044.7, 2066.6, 1022.9.

Figure 50:
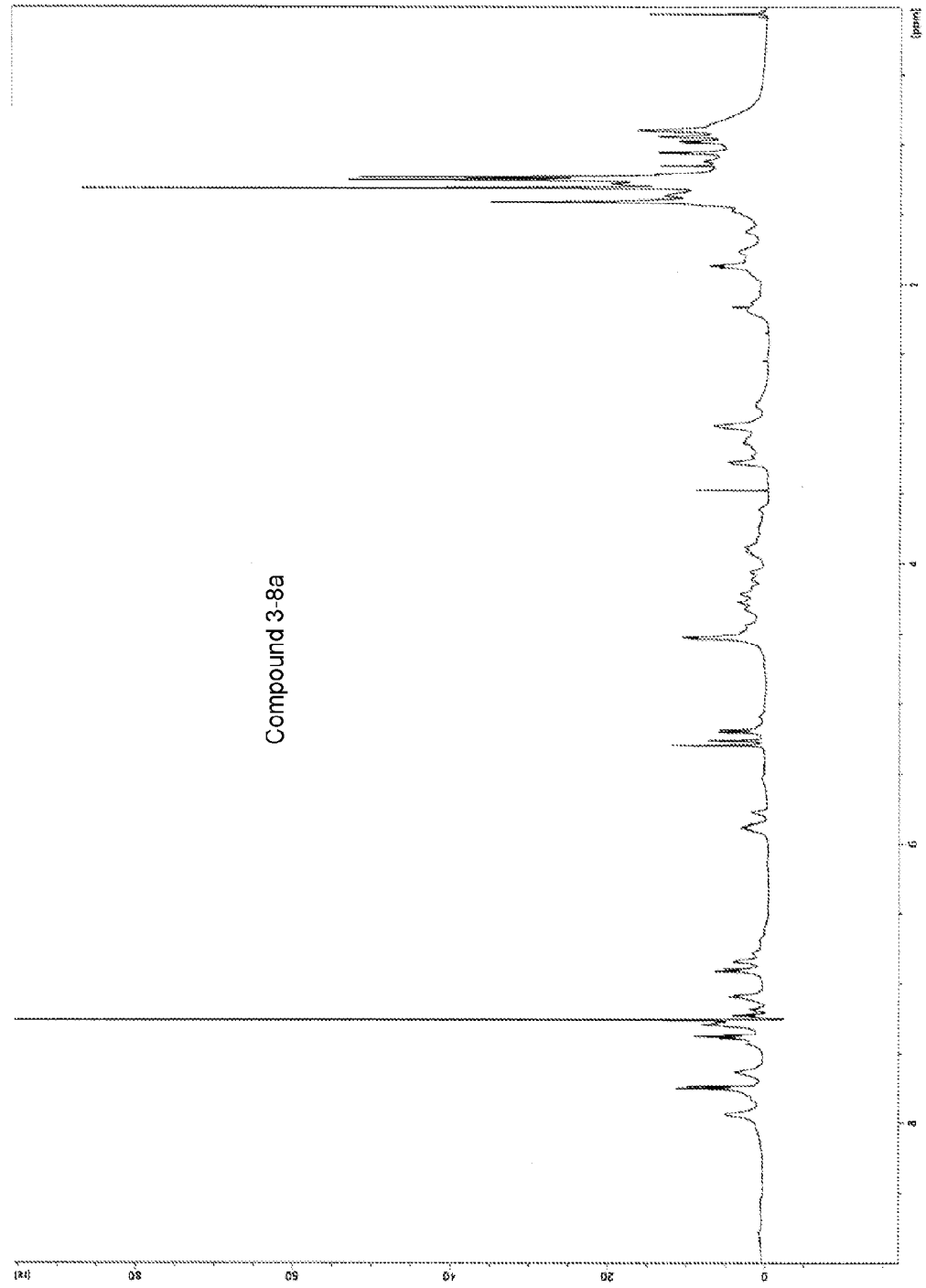
Figure 51:
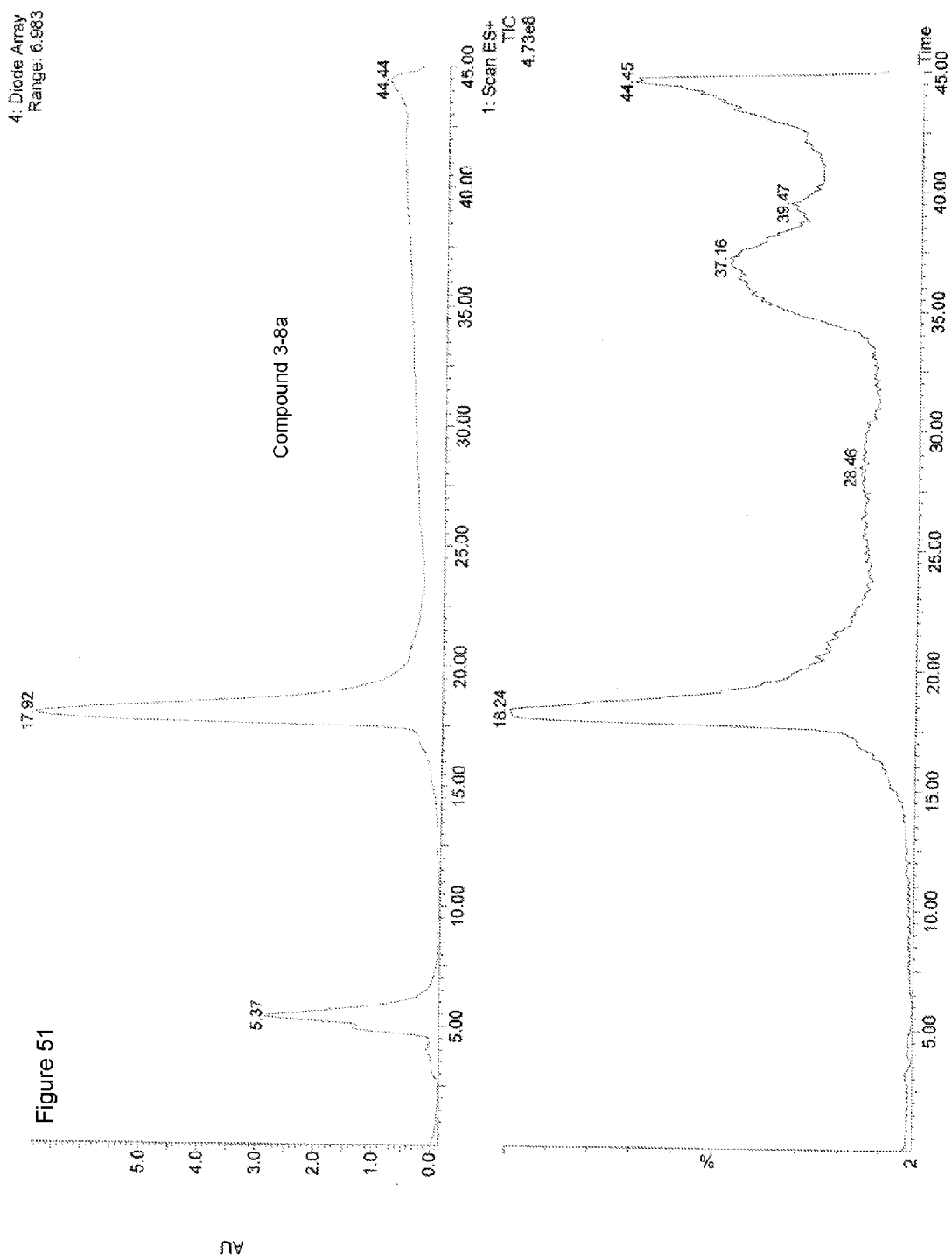
Figure 52:
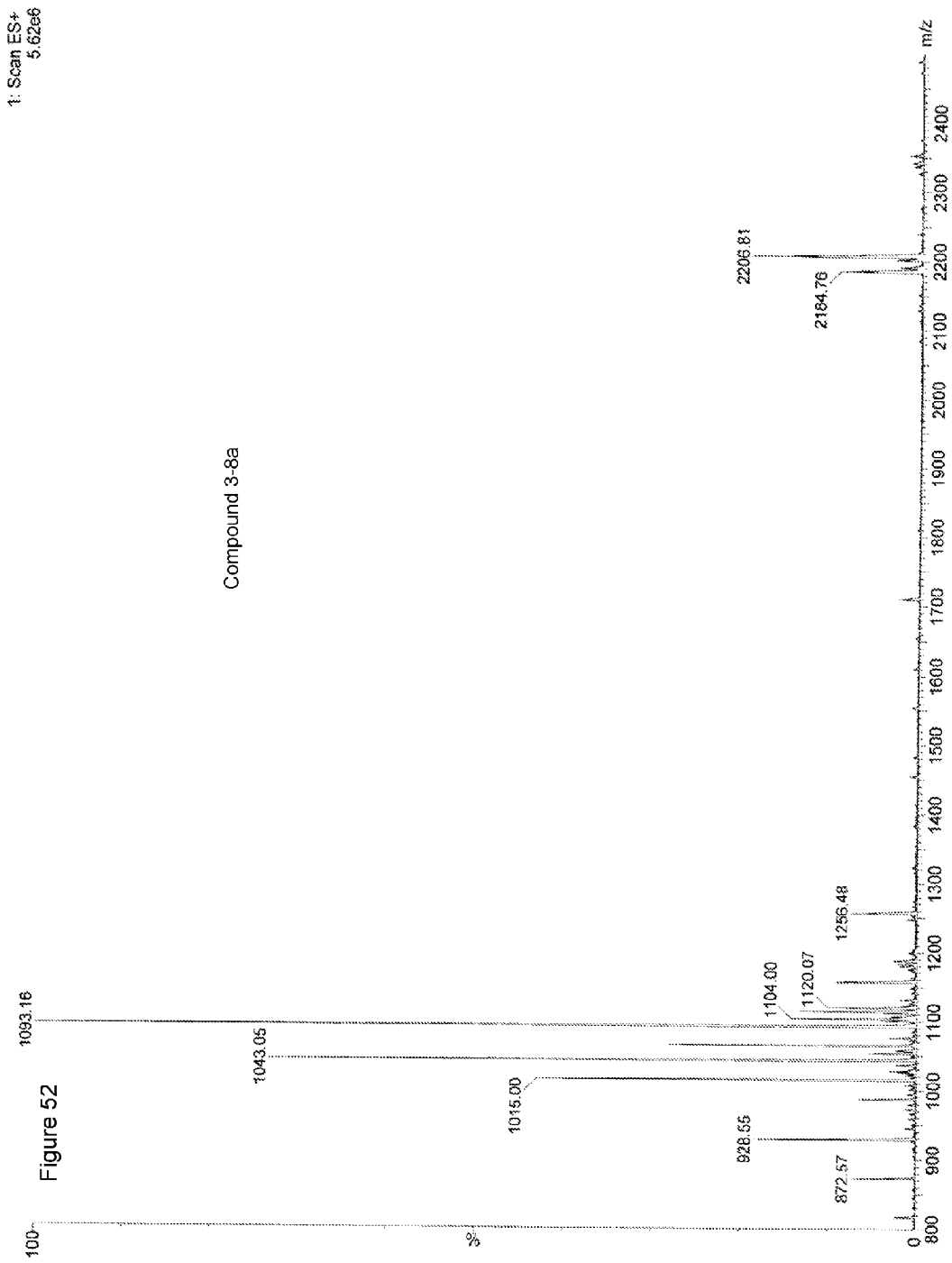

Synthesis of Compound 3-8a (Step (b), FIGS. 50-52).

To compound 3-7 (30 mg, 0.0147 mmol), linker 3-C (5.6 mg, 0.0352 mmol), HOOBt (5.7 mg, 0.0352 mmol) in 1:3 trifluoroethanol/CHCl$_3$, EDC (6.2 mL, 0.0352 µmol) was added. After 2 h, LC/MS indicated completion of the reaction. The mixture was concentrated under reduced pressure and purified via flash chromatography (silica, 2%→10% MeOH/CH$_2$Cl$_2$) and the appropriate fractions were concentrated (R$_f$ 0.5, 10% MeOH/CH$_2$Cl$_2$) to afford 30 mg of product in 94% yield. This material was found to be >95% pure as judged by reverse-phase LC/ESI (Microsorb C4 column). MS: Exact mass calcd for C$_{115}$H$_{166}$N$_{18}$O$_{24}$ [M+H]$^+$: 2185.2; [M+Na]$^+$: 2207.2; [M+2H]$^{2+}$: 1093.1. Found: 2184.8, 2206.8, 1093.2.

Figure 13:
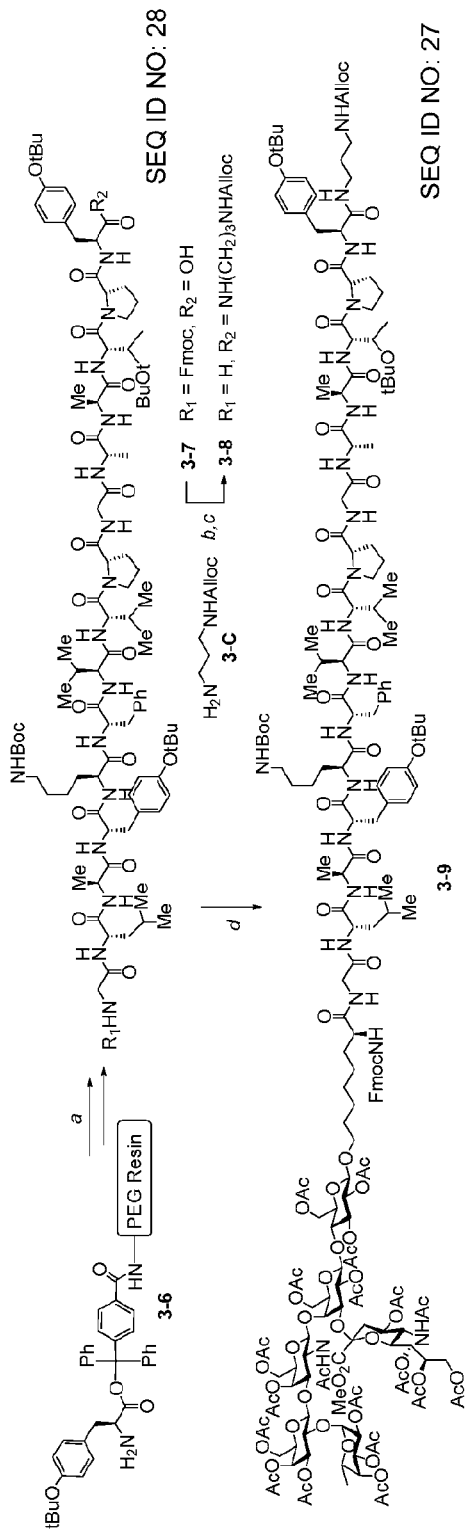
FIG. 13 depicts a synthesis of compound 3-9.
Figure 53:
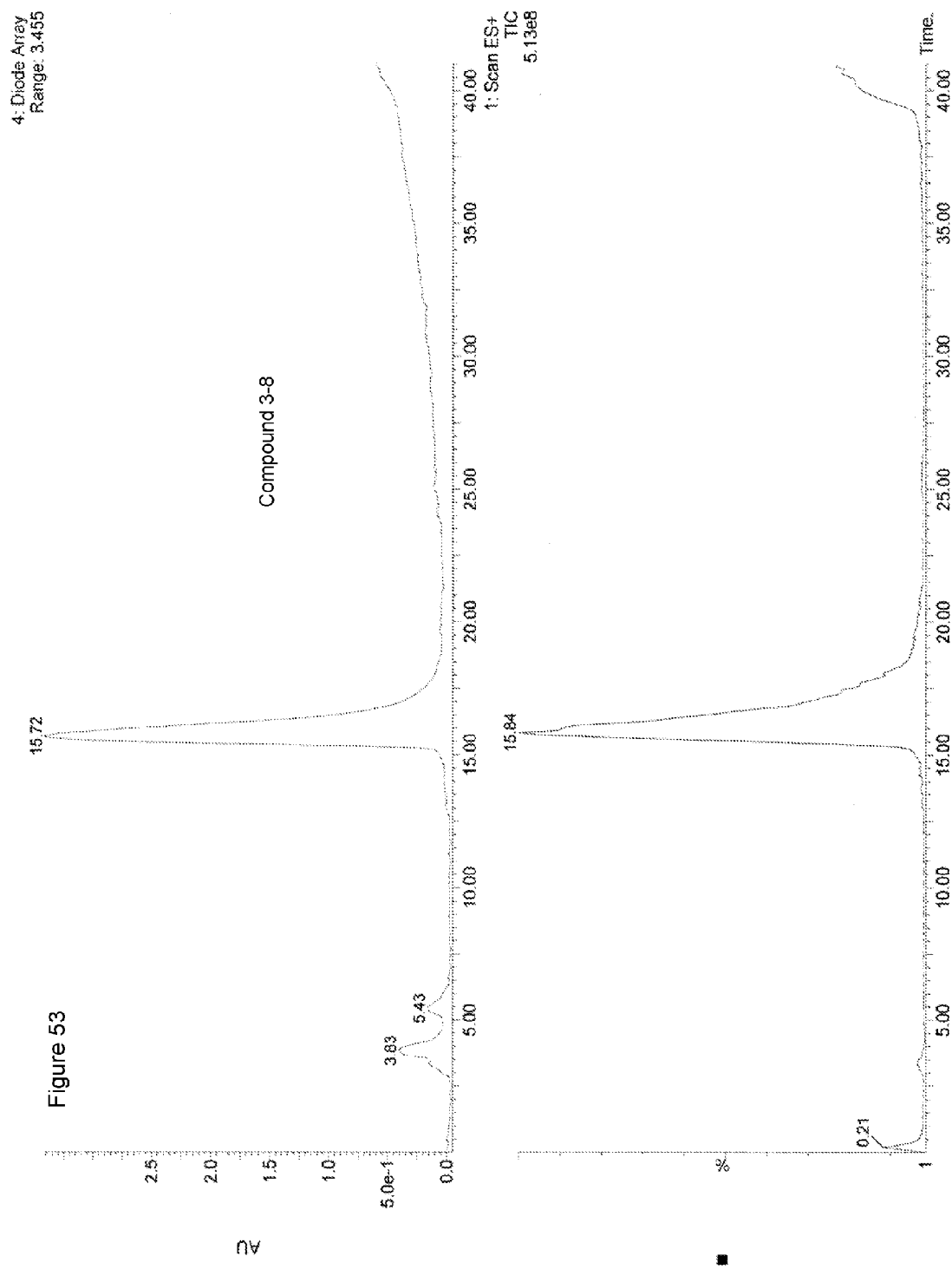
FIGS. 53-54 depict LCMS characterization data for compound 3-8.
Figure 54:
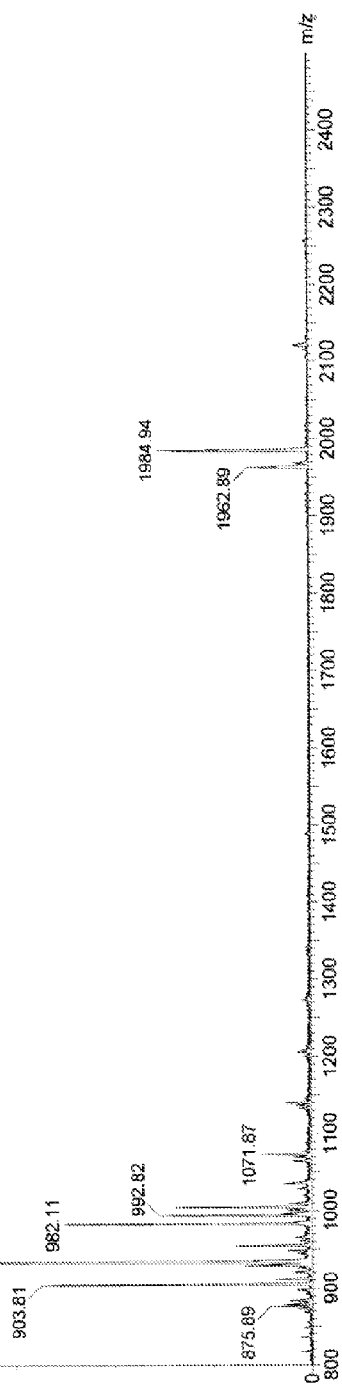
Figure 55:
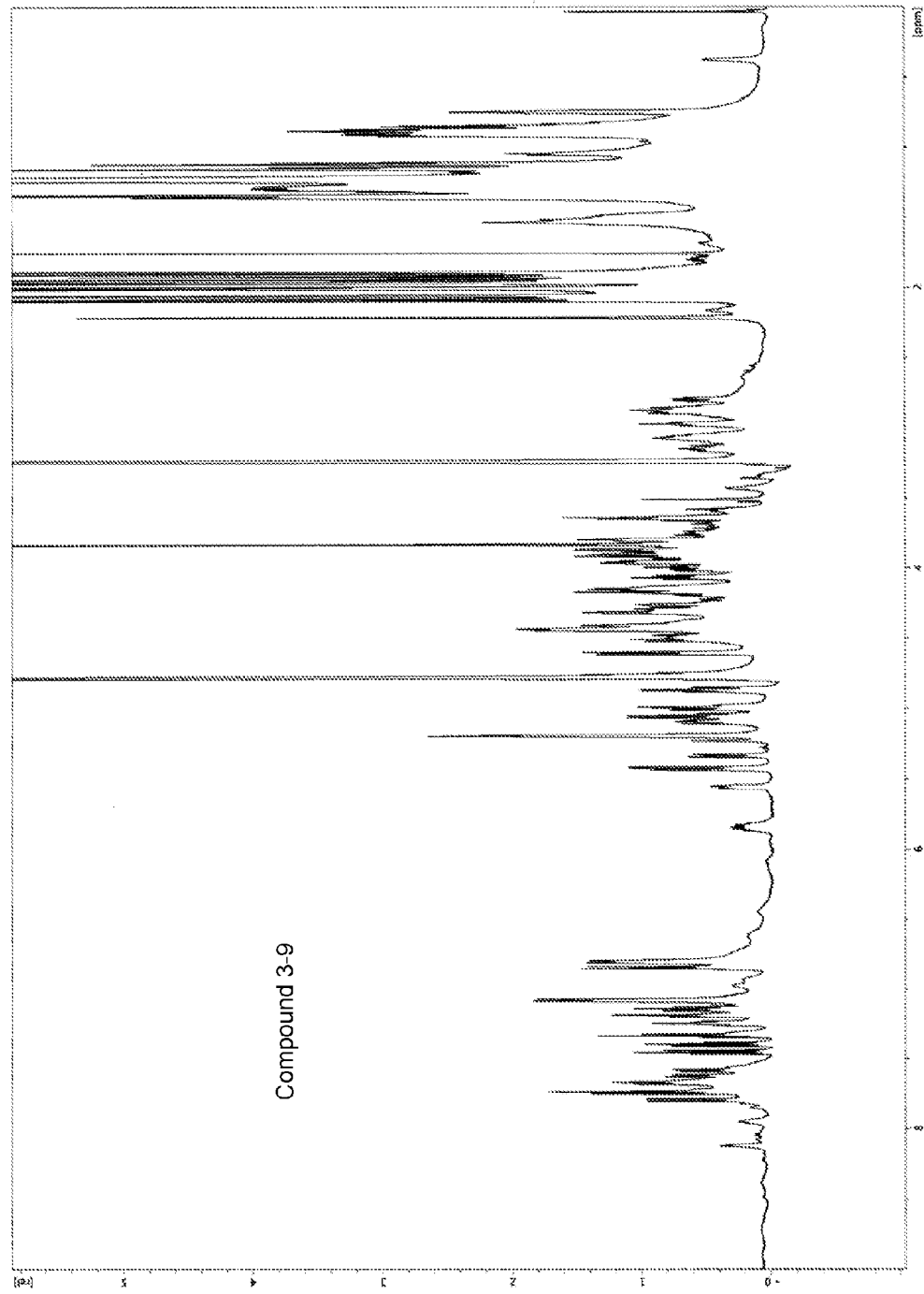
FIG. 55 depicts a $^1$H-NMR spectrum of compound 3-9.
Figure 56:
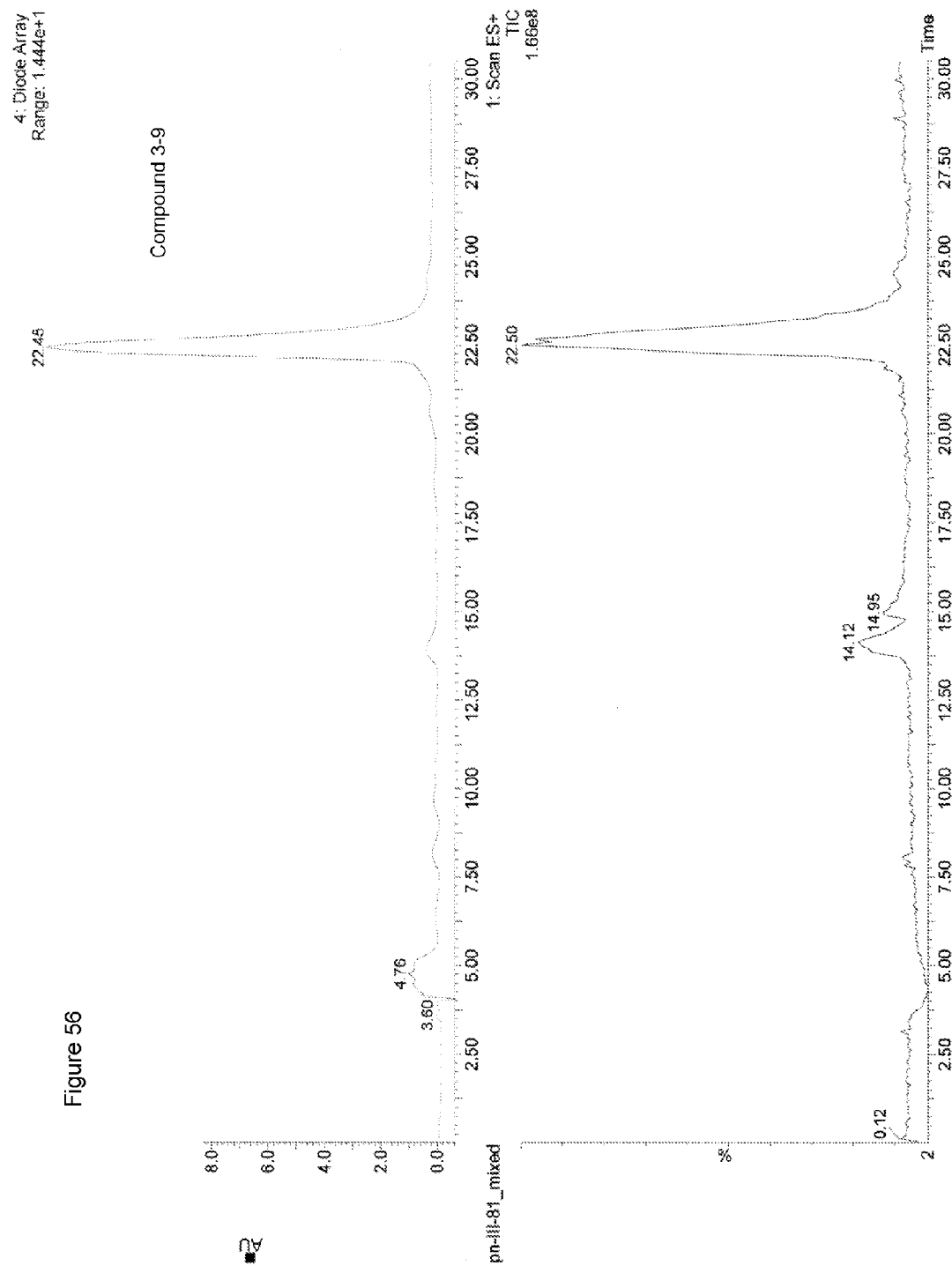
FIGS. 56-57 depict LCMS characterization data for compound 3-9.
Figure 57:
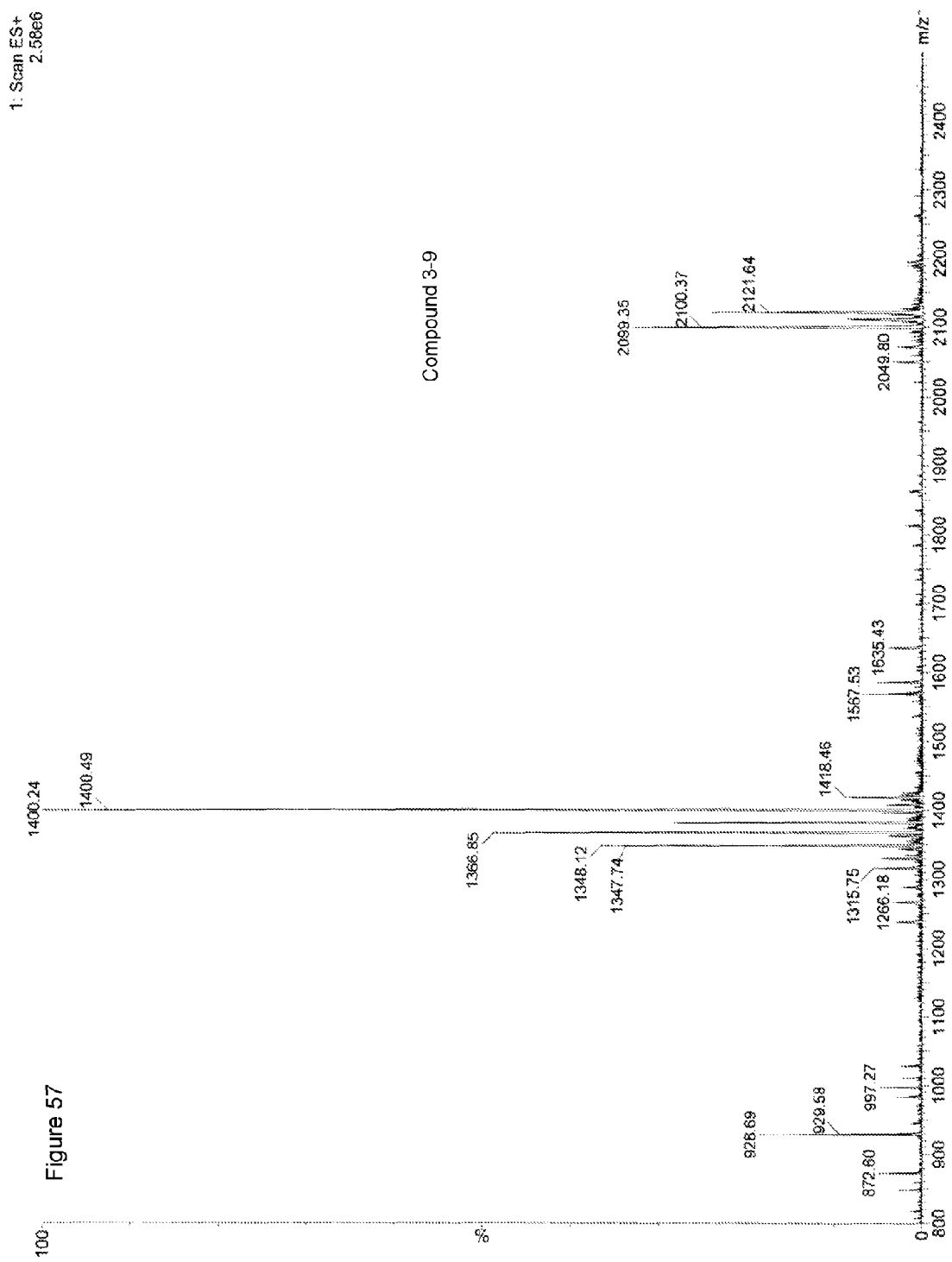

Synthesis of Compound 3-8 (Step (c), FIGS. 13, 53, 54).

The product from above (26.8 mg, 0.0123 mmol) was dissolved in 1.0 mL of DMF, and to this solution piperidine (0.25 mL) was added. After 1 h, LC/MS analysis indicated the completion of the reaction. The mixture was concentrated under reduced pressure and purified via flash chromatography (silica, 10%→12% MeOH/CH$_2$Cl$_2$) and the appropriate fractions were concentrated (R$_f$ 0.15, 10% MeOH/CH$_2$Cl$_2$) to afford 18 mg of product 3-8 in 75% yield. This material was found to be >95% pure as judged by reverse-phase LC/ESI analysis: Rf=15.7 (C4 Microsorb column, 40-85% MeCN in H$_2$O, 30 min); Exact mass calcd for C$_{100}$H$_{156}$N$_{18}$O$_{22}$ [M+H]$^+$: 1963.2; [M+Na]$^+$: 1985.2; [M+2H]$^{2+}$: 982.1. Found: 1962.9, 1984.9, 982.1.

Synthesis of Compound 3-9 (Step (d), FIGS. 13, 55-57).

Amine 3-8 (9.5 mg, 0.048 mmol) was combined with acid 3-5 (6.6 mg, 0.029 mmol), EDCI (1.8 mg, 0.093 mmol), and HOBt (1.3 mg, 0.0093 mmol) and this mixture was dissolved in 0.30 mL of 1:1 DMF/CH$_2$Cl$_2$. After 3 h of stirring under argon, the solvents were removed under high vacuum, and the resultant oil was purified via flash chromatography (silica, 5%→10% MeOH/CH$_2$Cl$_2$) and the appropriate fractions concentrated (R$_f$ 0.5, 10% MeOH/CH$_2$Cl$_2$) to afford 10 mg of product 3-9 in 81% yield. This material was found to be >90% pure as judged by reverse-phase LC/ESI MS (Microsorb C4 column) and $^1$H NMR analysis: $^1$H-NMR (500 MHz, CD$_3$OD) (Due to the high degree of the NH exchange, the presence of the multiple peptide rotamers in the solution as well as the high overlap, there is an ambiguity associated in the tabulation and interpretation of the $^1$H NMR data. Please refer to the $^1$H NMR spectrum in the Figures for additional details.) Selected peaks: δ 8.12 (d, 1H), 7.95 (m, 1H), 7.80 (d, J=9.1 Hz, 2H), 7.74 (d, J=7.6 Hz, 2H), 7.72 (m, 1H), 7.67 (d, J=8.2 Hz, 2H), 7.66 (m, 1H), 7.62 (d, J=7.4 Hz, 1H), 7.57 (d, J=7.5 Hz, 1H), 7.56 (m, 1H), 7.45 (t, J=7.2 Hz, 1H), 7.39 (t, J=7.7 Hz, 1H), 7.33 (t, J=7.4 Hz, 1H), 7.24 (dt, J=7.3, 4.1 Hz, 1H), 7.18 (d, J=7.3 Hz, 1H), 7.14 (t, J=7.6 Hz, 1H), 7.08 (d, J=5.5 Hz, 4H), 6.97 (m, NH), 6.93 (m, NH), 6.85 (d, J=7.9 Hz, 2H), 6.80 (d, J=8.0 Hz, 4H), 5.85 (ddd, J=16.2, 10.5, 5.5 Hz, 1H), 5.55 (dt, J=9.5, 4.1 Hz, 1H), 5.42 (dd, J=9.5, 2.8 Hz, 2H), 5.32 (dd, J=9.6, 2.1 Hz, 1H), 5.19 (m, 4H), 5.07 (m, 4H), 4.97 (m, 2H), 4.75 (m, 1H), 4.60 (d, J=7.5 Hz, 3H), 4.49 (dt, J=16.3, 8.1 Hz, 1H), 4.47-4.37 (m, 8H), 4.33-4.24 (m, 8H), 4.20-4.08 (m, 7H), 4.06 (dd, J=11.2, 6.0 Hz, 2H), 4.05 (dt, J=9.1, 4.0 Hz, 2H), 3.95 (m, 2H), 3.94-3.81 (m, 8H), 3.83 (s, 3H), 3.80 (m, 3H), 3.75 (m, 1H), 3.71 (m, 1H), 3.68 (m, 1H), 3.64 (m, 3H), 3.58 (m, 1H), 3.50 (s, 1H), 3.42 (m, 1H), 3.15 (dd, J=13.3, 6.2 Hz, 2H), 3.12 (m, 1H), 3.11-3.03 (m, 4H), 2.97 (t, J=6.2 Hz, 2H), 2.93-2.83 (m, 4H), 2.80 (dd, J=12.7, 4.4 Hz, 1H), 2.21 (s, 3H), 2.20-2.13 (m, 2H), 2.11 (s, 3H), 2.09 (s, 3H), 2.06 (s, 9H), 2.01 (s, 3H), 2.00 (s, 3H), 1.99 (s, 3H), 1.97 (s, 6H), 1.96 (s, 6H), 1.94 (s, 3H), 1.92 (s, 3H), 1.91 (s, 3H), 1.89 (s, 3H), 1.89 (s, 3H), 2.13-1.77 (m, 13H), 1.75 (s, 3H), 1.58-1.48 (m, 12H), 1.36 (s, 3H), 1.36 (s, 3H), 1.34-1.24 (m, 8H), 1.23 (s, 18H), 1.21 (s, 9H), 1.15 (s, 6H), 1.15-1.09 (m, 6H), 1.05 (d, J=6.2 Hz, 3H), 0.91 (d, J=6.7 Hz, 3H), 0.89 (d, J=8.6 Hz, 6H), 0.87 (d, J=7.0 Hz, 6H), 0.85 (d, J=6.6 Hz, 3H), 0.75 (m, 3H): Rf=22.5 (C4 Microsorb column, 50-95% MeCN in $H_2O$, 30 min); Exact mass calcd for $C_{201}H_{287}N_{21}O_{75}$ $[M+2H]^{2+}$: 2099.5, $[M+2Na]^{2+}$: 2121.5, $[M+3H]^{3+}$: 1400.0. Found: 2099.4, 2121.6, 1400.2.

Synthesis of Compound 3-10 (Step (a)).

Compound 3-9 (10.5 mg, 0.00250 mmol) was dissolved in 1.0 mL of DMF, and piperidine (0.25 mL) was added. After 1 h, LC/MS analysis indicated the completion of the reaction: Rf=15.3 (C4 Microsorb column, 50-95% MeCN in $H_2O$, 30 min); Exact mass calcd for $C_{186}H_{277}N_{21}O_{71}$ $[M+2H]^{2+}$: 1988.4; $[M+Na+H]^{2+}$: 1999.4; $[M+2Na]^{2+}$: 2010.4, $[M+3Na]^{3+}$: 1326.0. Found: 1988.4, 1999.37, 2010.45, 1326.1.

Figure 58:
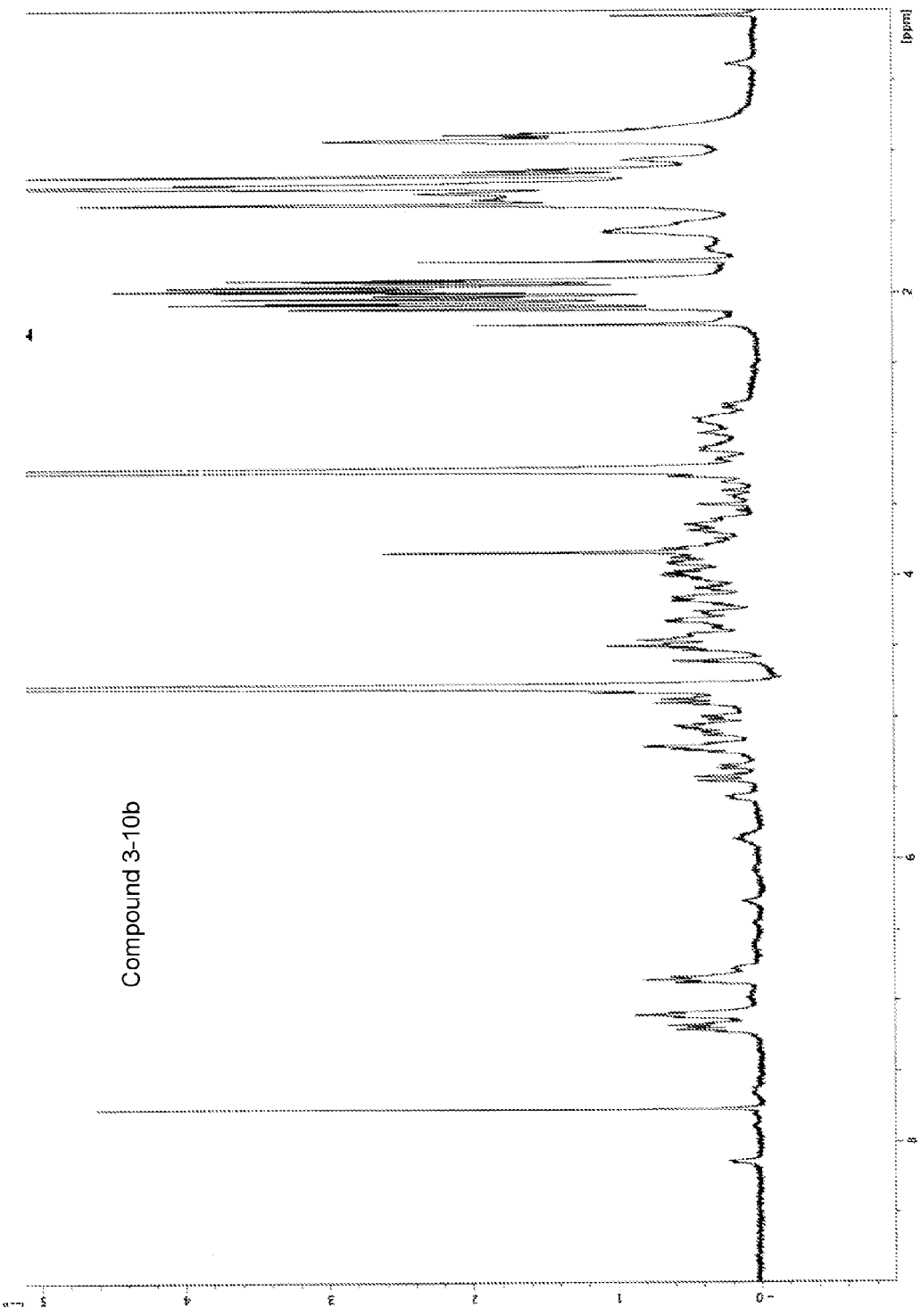
FIG. 58 depicts a $^1$H-NMR spectrum of compound 3-10b.
Figure 59:
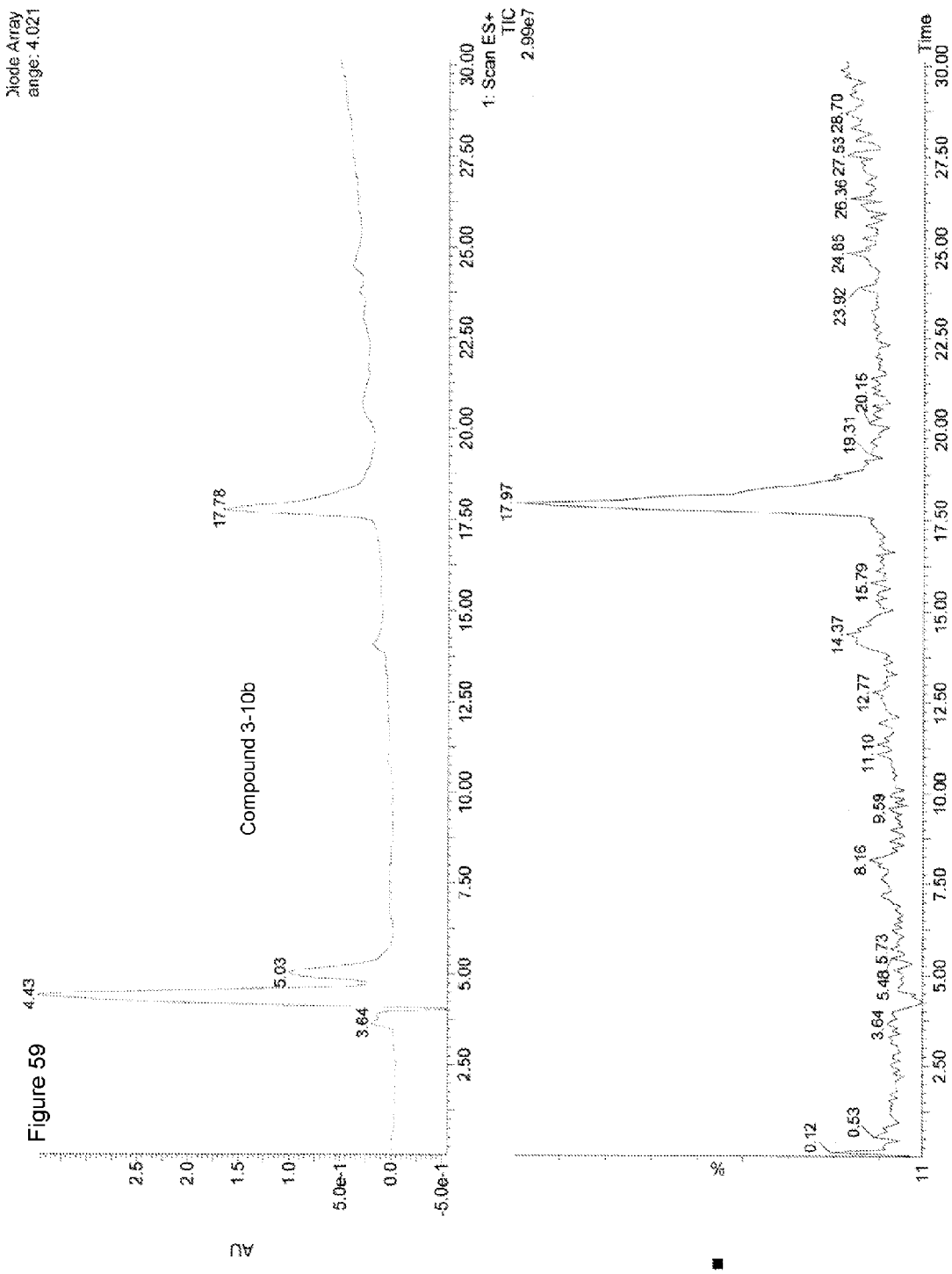
FIGS. 59-60 depict LCMS characterization data for compound 3-10b.
Figure 60:
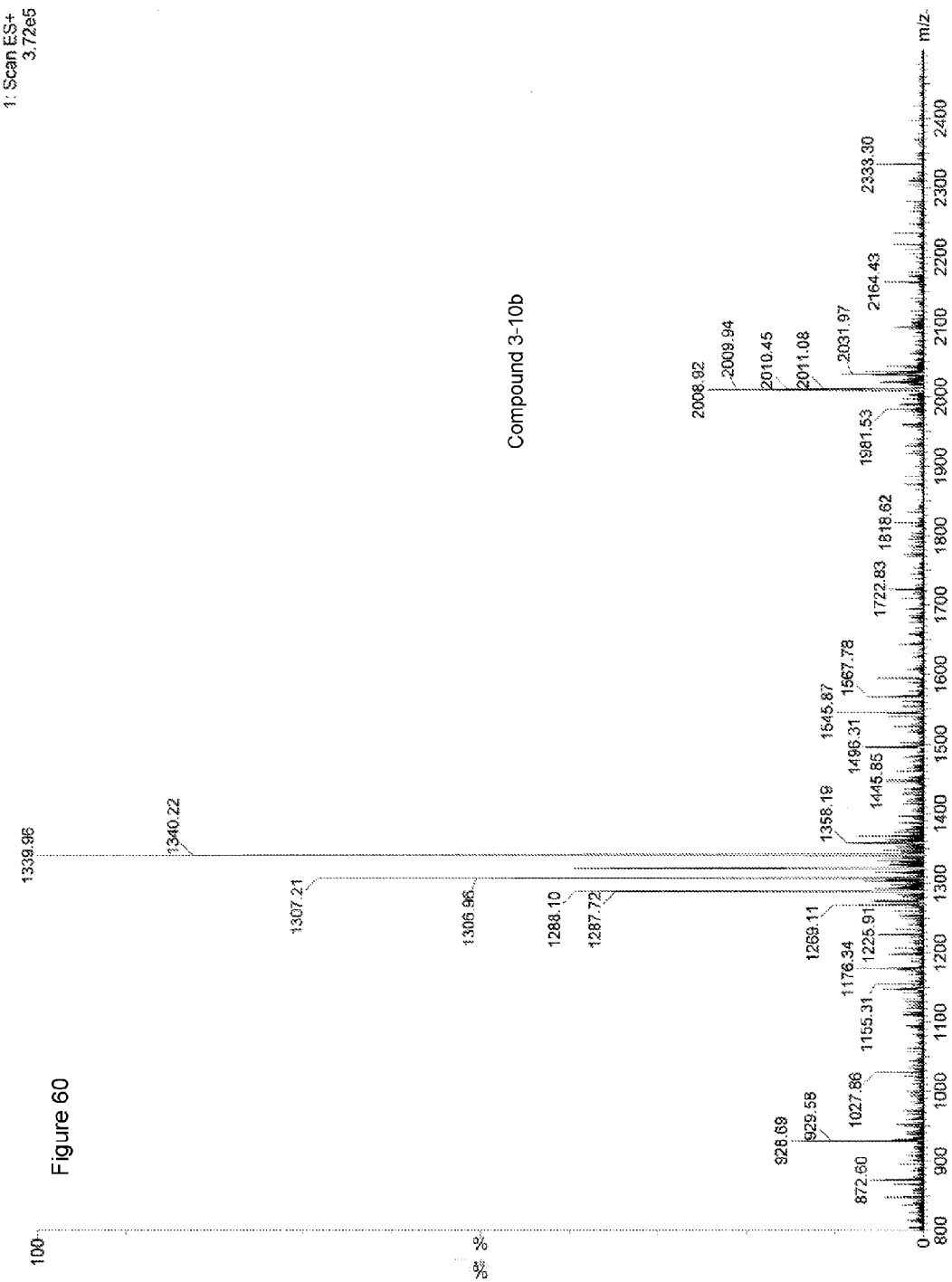

Synthesis of Compound 3-10b (Step (b), FIGS. 58-60).

The mixture from above was concentrated under reduced pressure, re-dissolved in pyridine (1.0 mL) and treated with acetic anhydride (0.5 mL). After 4 h, the reaction mixture was concentrated and purified via flash chromatography (silica, 10% $MeOH/CH_2Cl_2$) and the appropriate fractions were concentrated ($R_f$ 0.2, 10% $MeOH/CH_2Cl_2$) to afford 10 mg (quantitative yield) of product 3-9a. This material was found to be >85% pure as judged by reverse-phase LC/ESI analysis: Rf=17.8 (C4 Microsorb column, 50-95% MeCN in $H_2O$, 30 min); Exact mass calcd for $C_{188}H_{279}N_{21}O_{74}$ $[M+2H]^{2+}$: 2009.5; $[M+2Na]^{2+}$: 2031.4; $[M+3H]^{3+}$: 1340.0. Found: 2009.4, 2032.0, 1340.0.

Synthesis of Compound 3-10 (Step (c)).

A solution of $Pd(PPh_3)_4$ (14 mg, 0.0125 mmol) and phenylsilane (46 μL, 0.373 mmol) in 3.5 mL of $CH_2Cl_2$ was prepared, and 0.35 mL of this solution was added to the solution of compound 3-9a (10 mg, 0.00249 mmol) in DMF (0.35 mL). After 30 min, LC/MS analysis indicated the completion of the reaction. Pyridine (0.1 mL) was added, and the resultant mixture was concentrated under vacuum to provide crude product: Rf=16.4 (C4 Microsorb column, 50-95% MeCN in $H_2O$, 30 min); Exact mass calcd for $C_{184}H_{275}N_{21}O_{72}$ $[M+2H]^{2+}$: 1966.9; $[M+Na+H]^{2+}$: 1977.9; $[M+2Na]^{2+}$: 1988.9, $[M+3Na]^{3+}$: 1311.6. Found: 1967.5, 1978.6, 1989.7, 1312.6.

Figure 61:
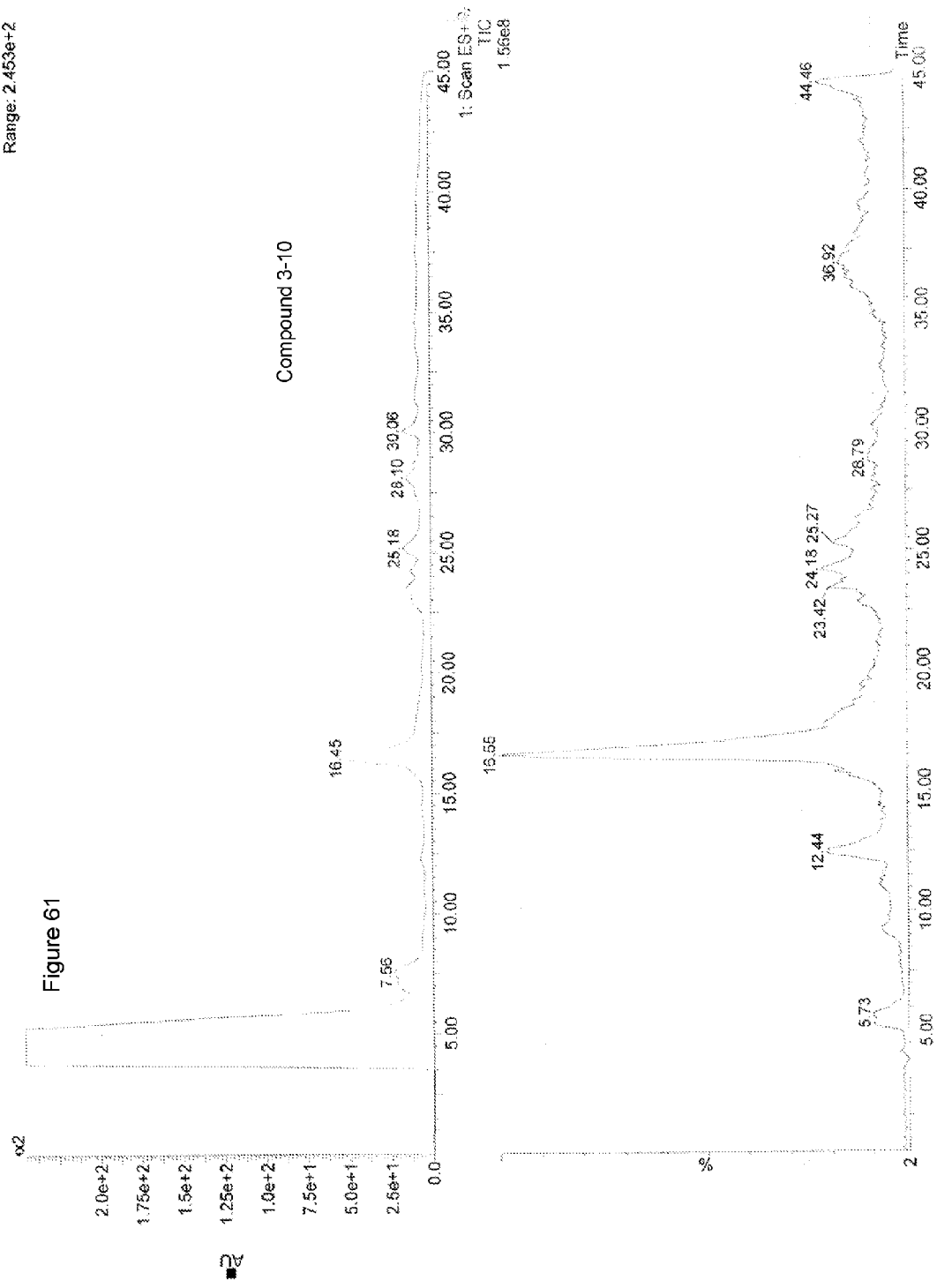
FIGS. 61-62 depict LCMS characterization data for compound 3-10.
Figure 62:
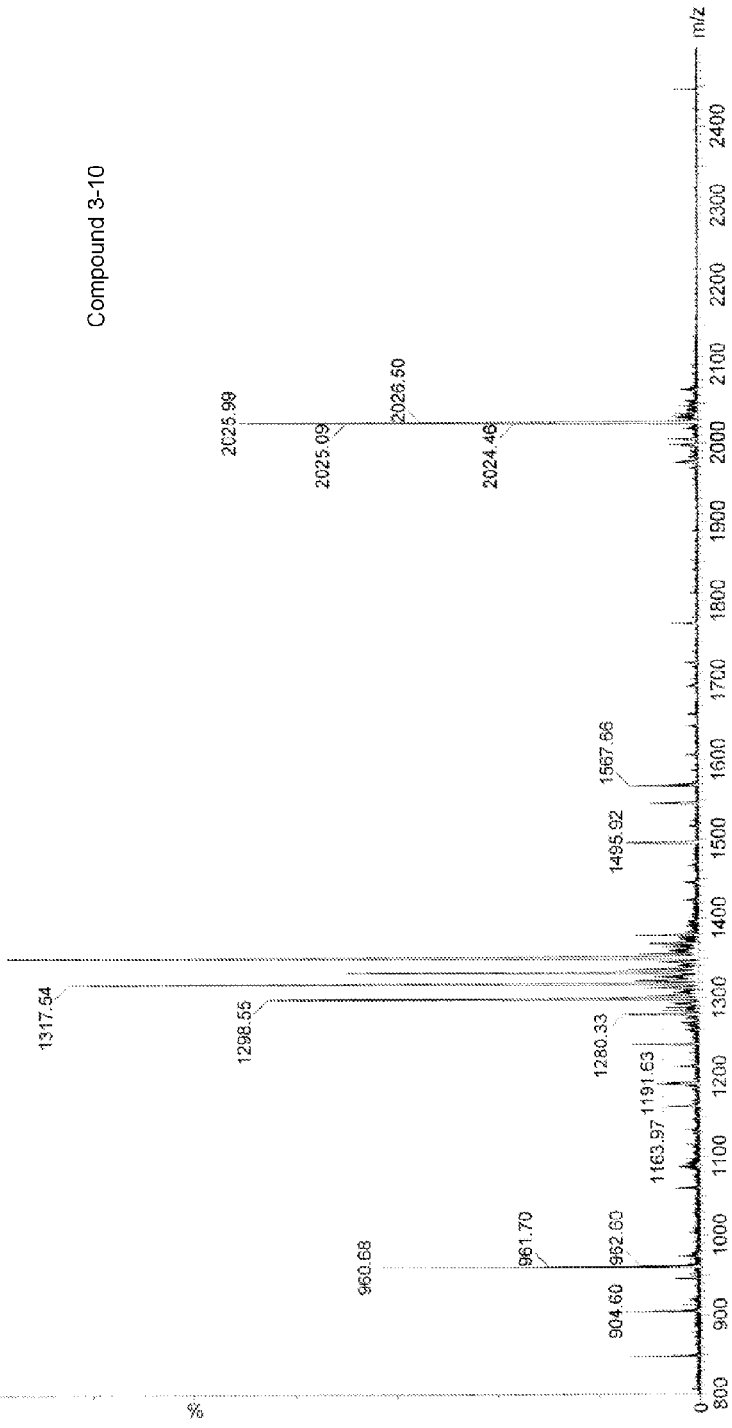

Synthesis of Compound 3-10 (Step (d), FIGS. 14, 61, 62).

The residue was re-dissolved in pyridine (0.35 mL) and triethylamine (0.15 mL), and SAMAOPbf (11.2 mg, 0.0373 mmol) was added to this solution. The reaction mixture was stirred for 3 h, concentrated and purified by flash chromatography (silica, 5%→10% $MeOH/CH_2Cl_2$) and the appropriate fractions were concentrated ($R_f$ 0.3, 10% $MeOH/CH_2Cl_2$) to afford product 3-10 contaminated with SAMAOPbf decomposition products (70% purity as judged by LC/MS): Rf=16.5 (C4 Microsorb column, 50-95% MeCN in $H_2O$, 30 min); Exact mass calcd for $C_{188}H_{279}N_{21}O_{74}S$ $[M+2Na]^{2+}$: 2026.4; $[M+3Na]^{3+}$: 1351.3. Found: 2026.0, 1350.8. This product was advanced to the next step without further purification.

Figure 63:
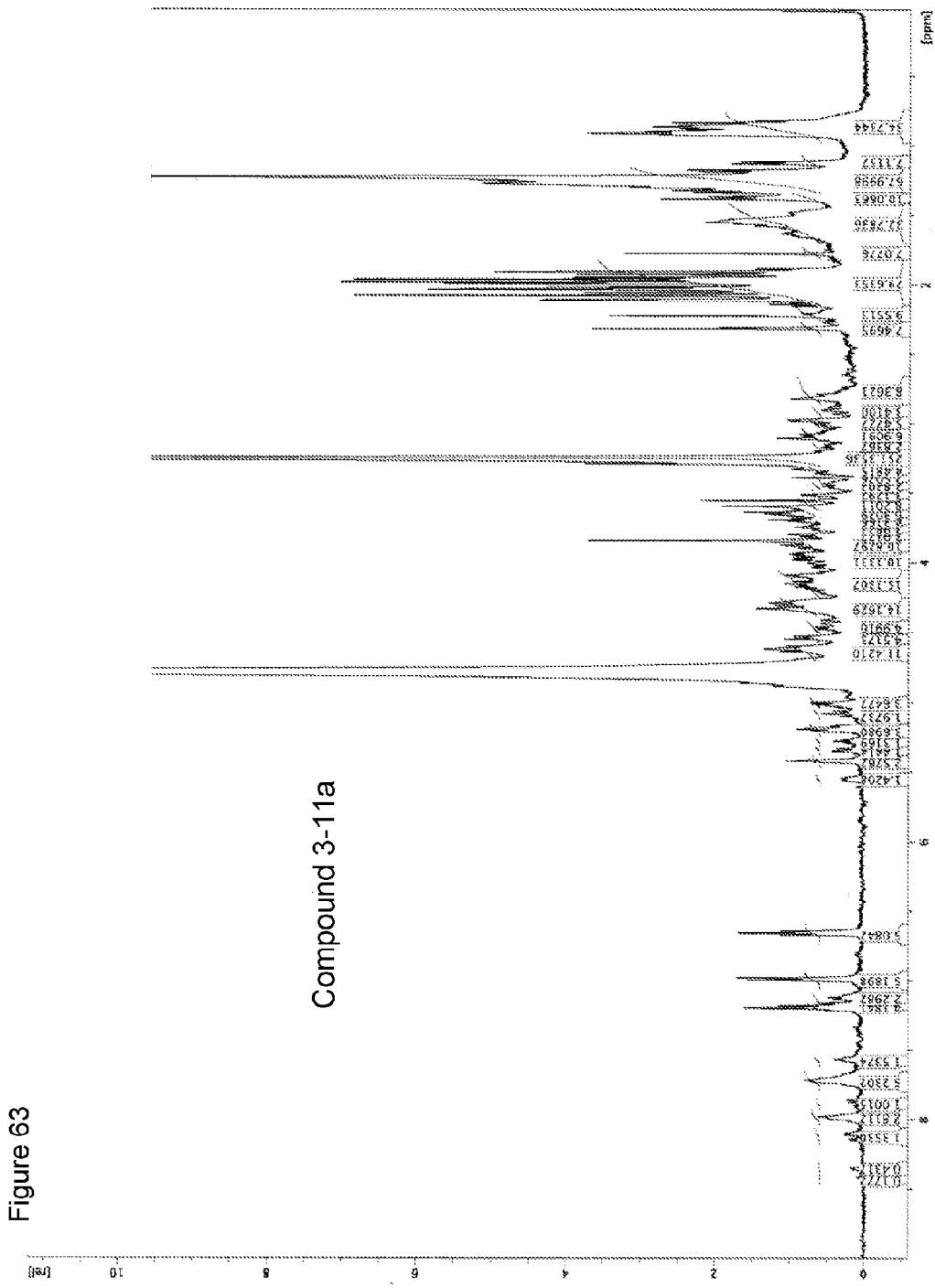
Figure 64:
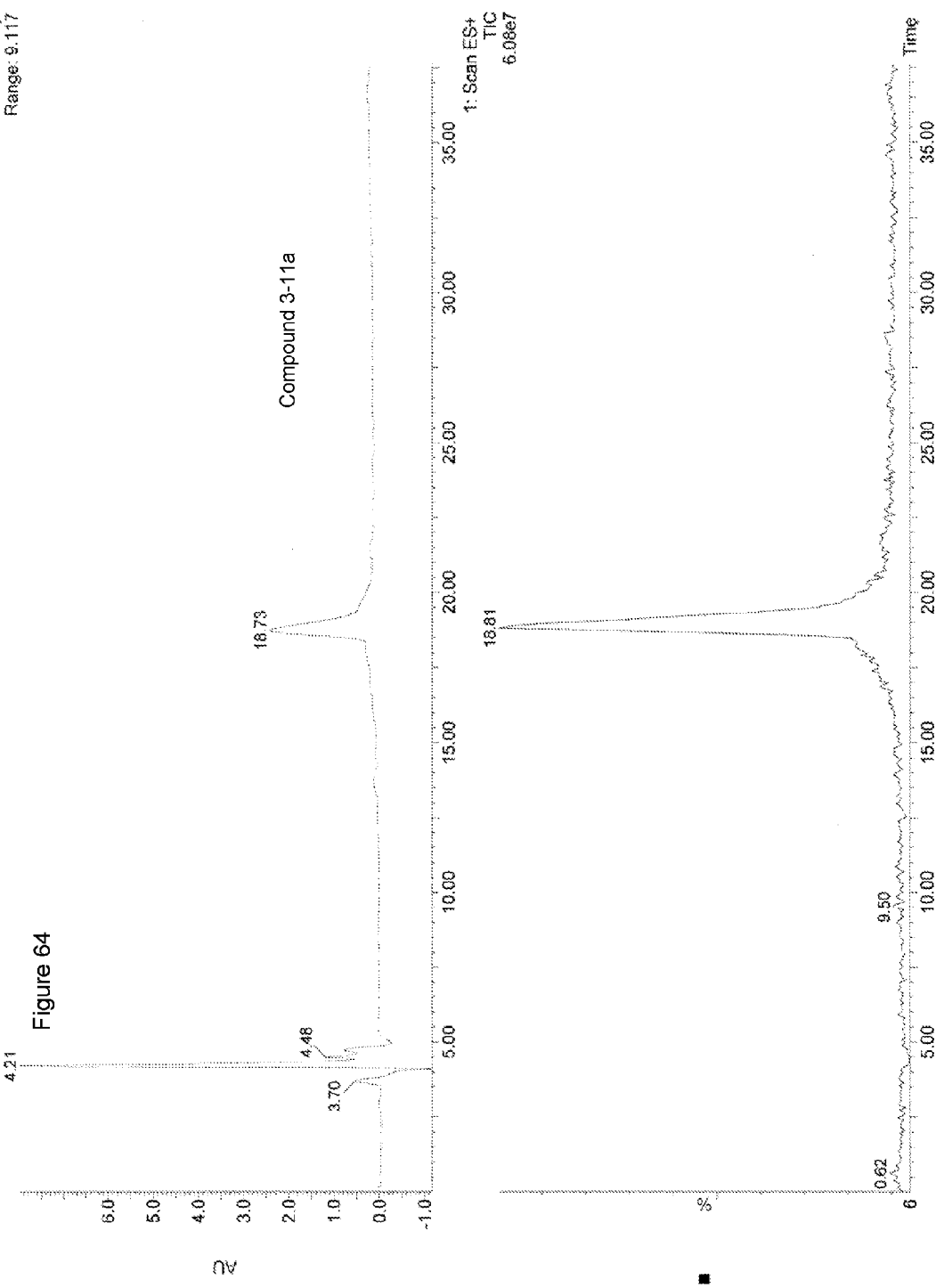
Figure 65:
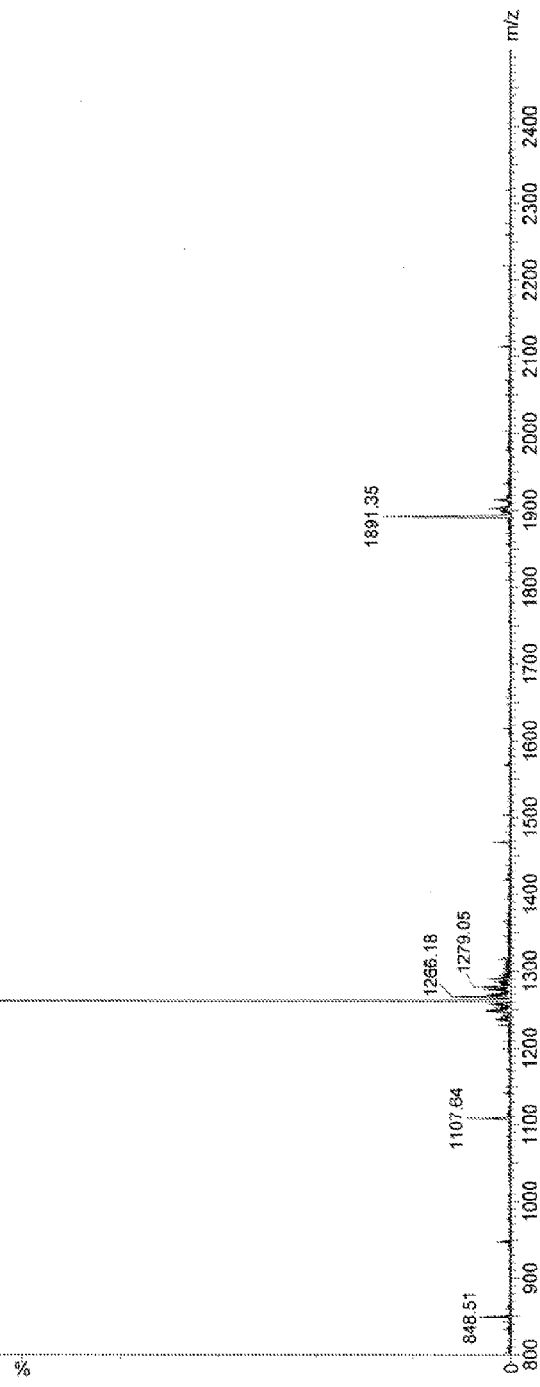

Synthesis of Compound 3-11a (Step (e), FIGS. 63-65).

Phenol (60 mg), triisopropylsilane (0.15 mL), and water (0.2 mL) were added to trifluoroacetic acid (3.0 mL). The resultant solution (1.0 mL) was added to a vial with compound 3-10 from above (ca. 10 mg, 0.00249 mmol). The reaction mixture was stirred for 40 min before being diluted with dichloromethane (3 mL), concentrated, and purified by reverse-phase HPLC: Rf=18.7 (Microsorb C4 column, 35-75% MeCN in $H_2O$, 30 min) to afford pure product (6.7 mg, 71% yield from 3-9). The product was >95% pure as judged by LC/MS: Exact mass calcd for $C_{171}H_{247}N_{21}O_{72}S$ $[M+2H]^{2+}$: 1891.3; $[M+3H]^{3+}$: 1261.2. Found: 1891.4, 1261.5.

Figure 66:
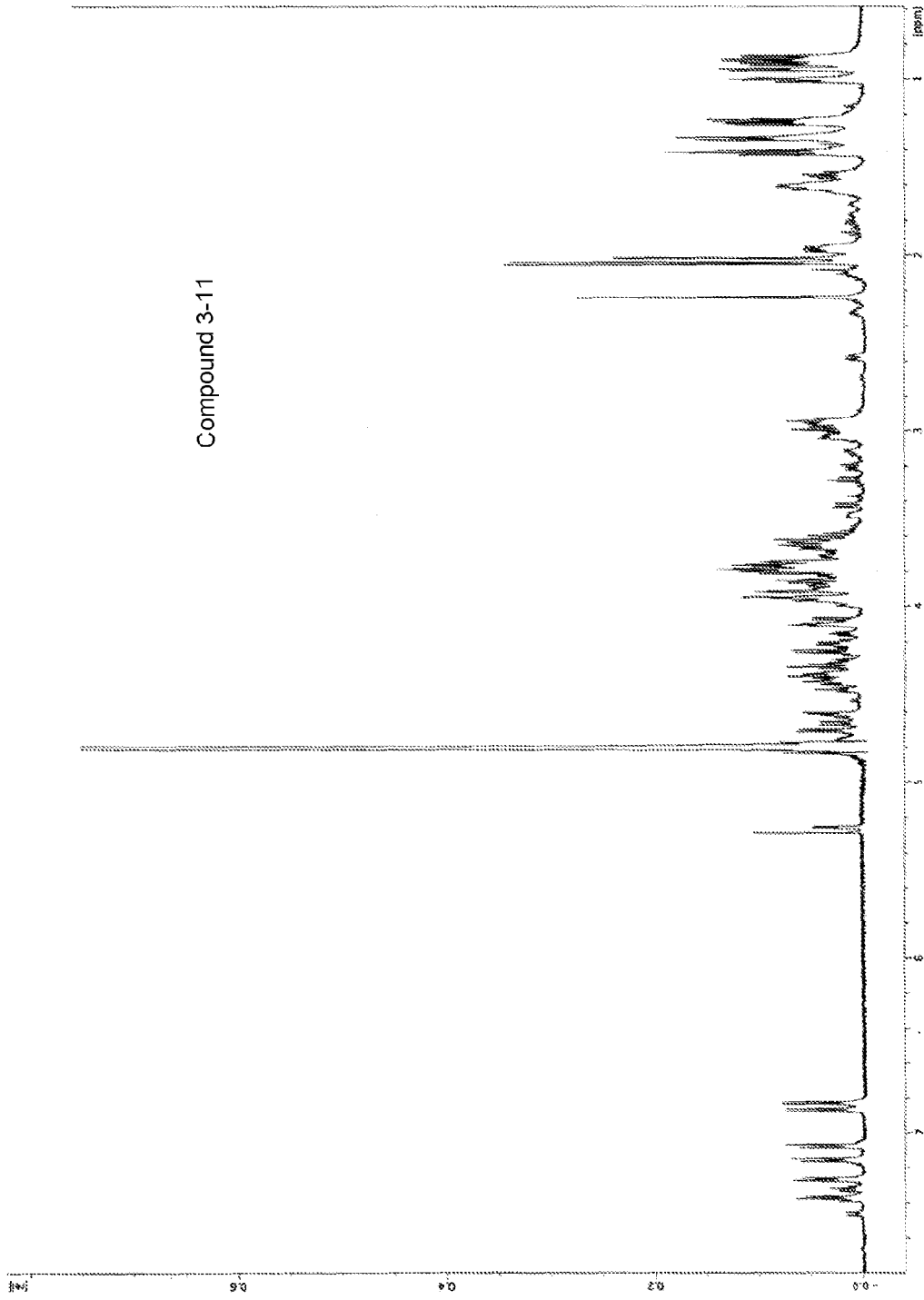
FIG. 66 depicts a $^1$H-NMR spectrum of compound 3-11.
Figure 67:
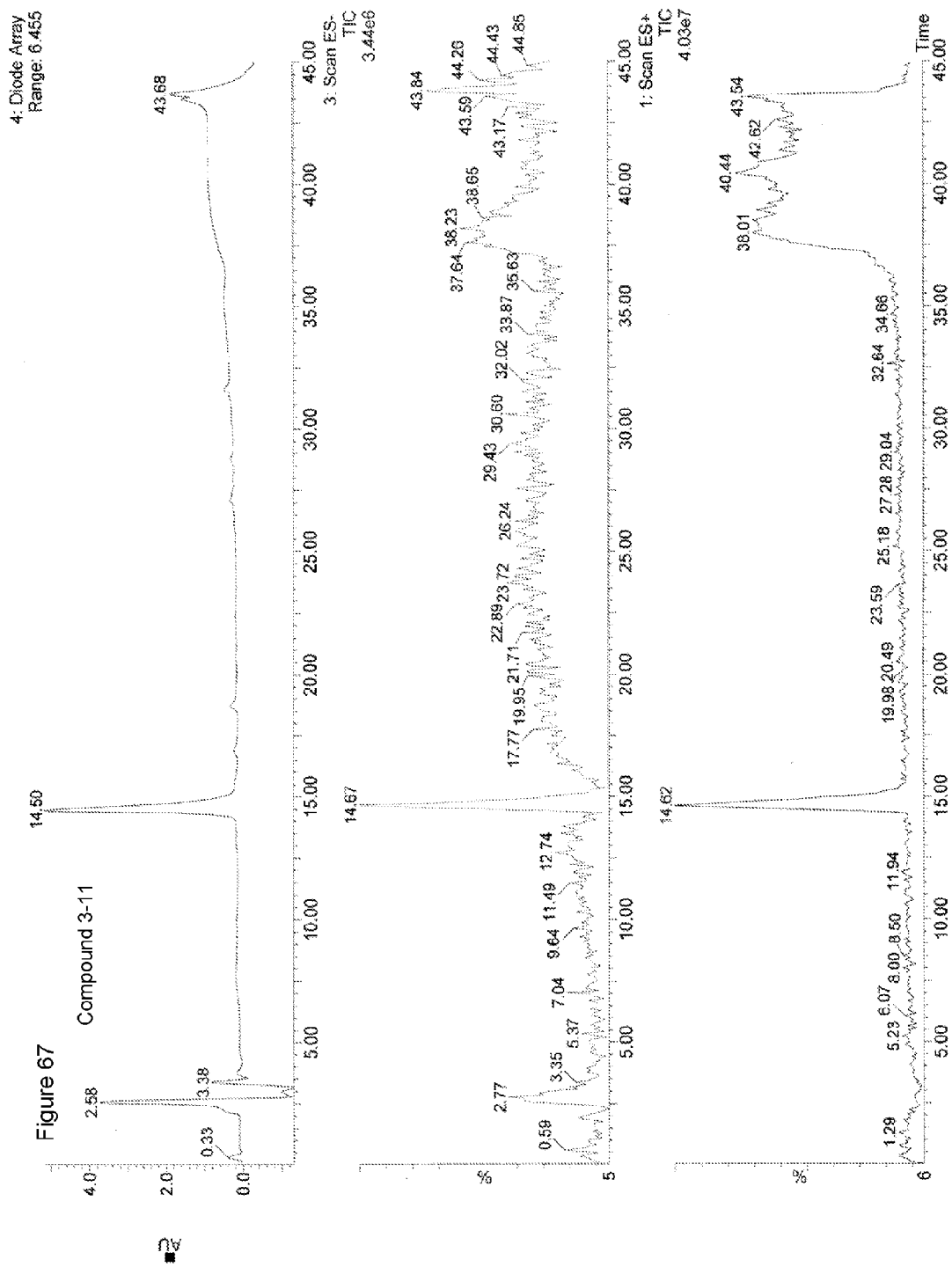
FIGS. 67-68 depict LCMS characterization data for compound 3-11.
Figure 68:
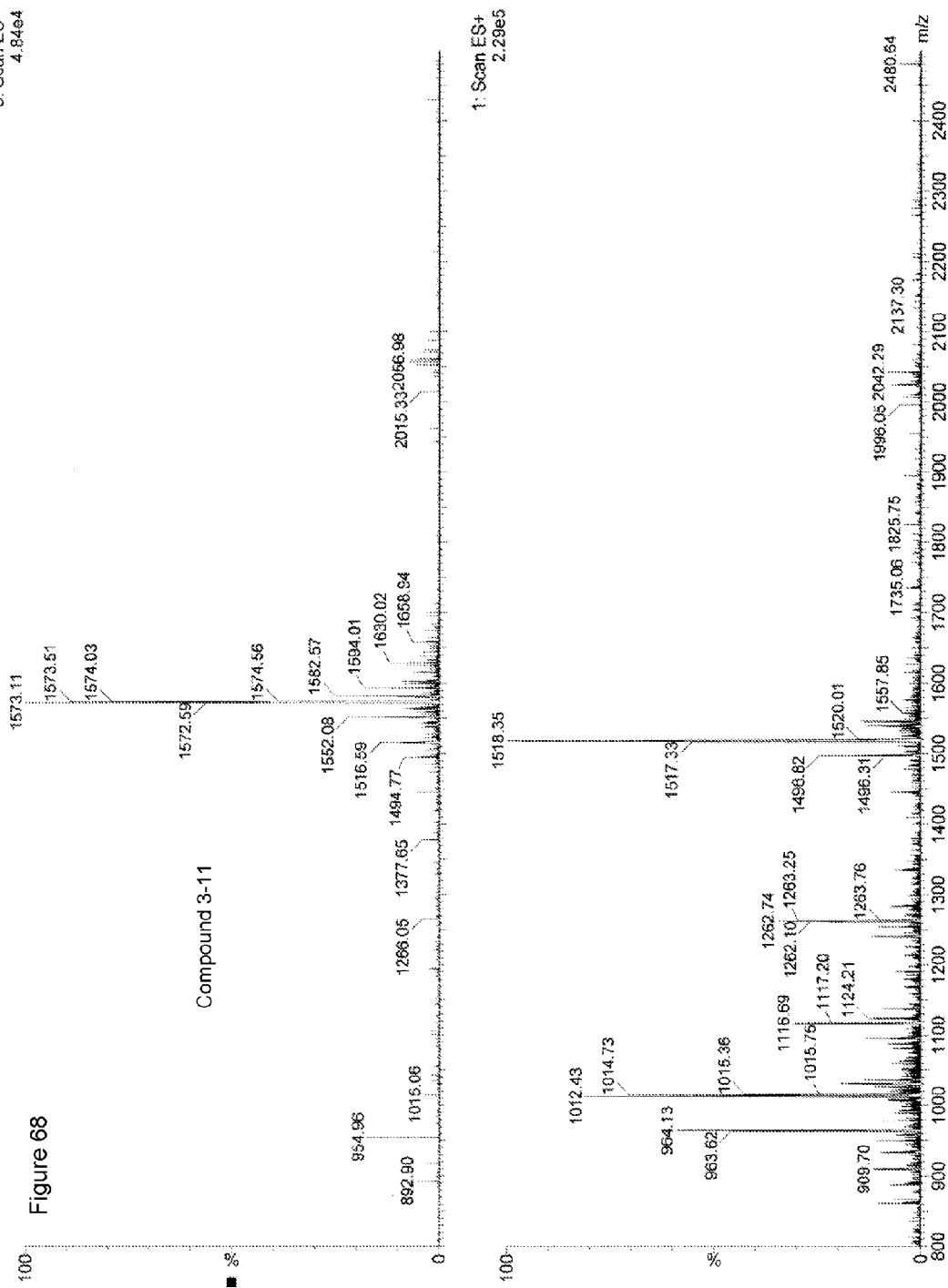
Figure 69:
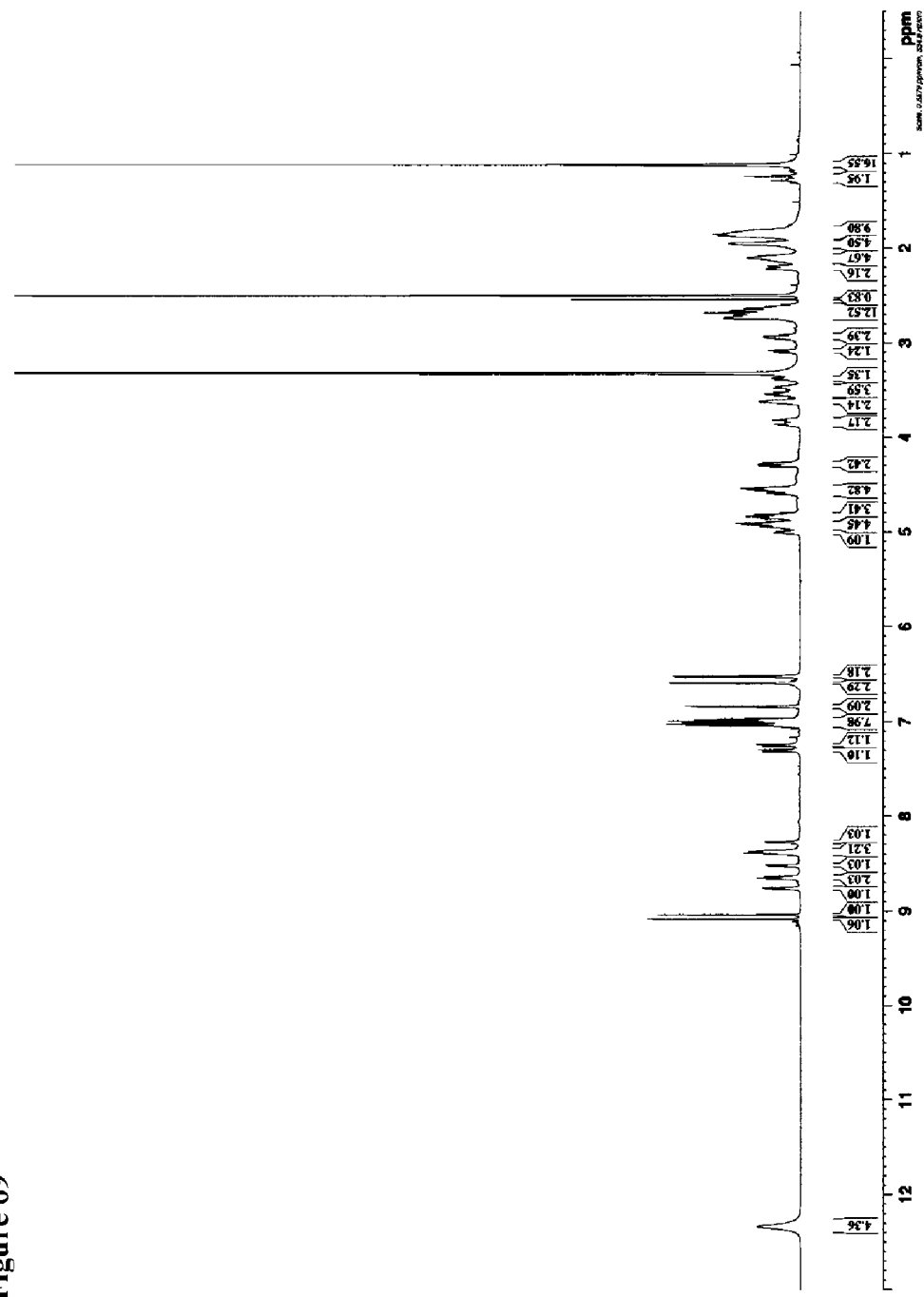
FIG. 69 depicts a $^1$H-NMR spectrum of compound 5-1 in $d_6$-DMSO.
Figure 70:
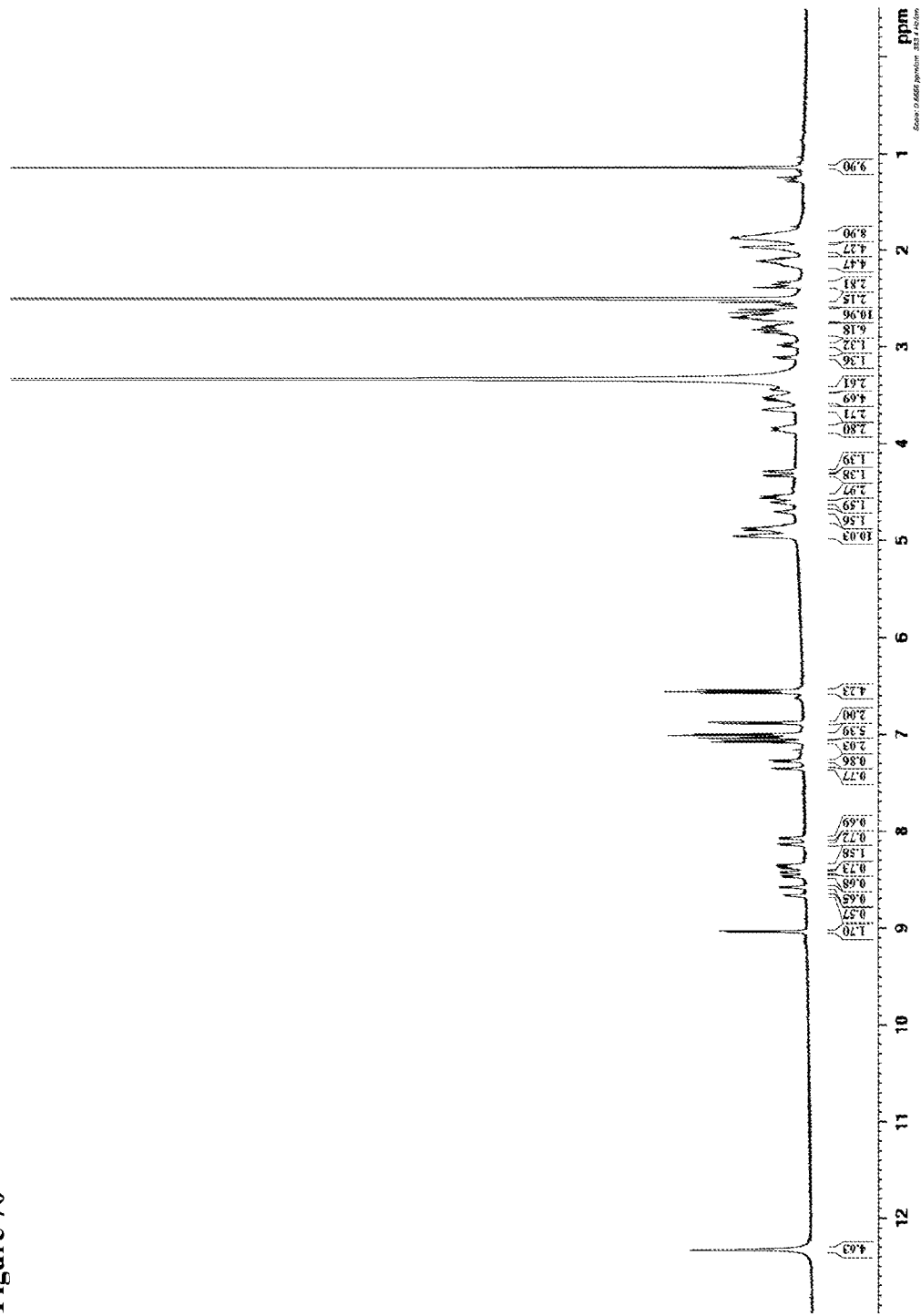
FIG. 70 depicts a $^1$H-NMR spectrum of compound 5-12 in $d_6$-DMSO.
Figure 71:
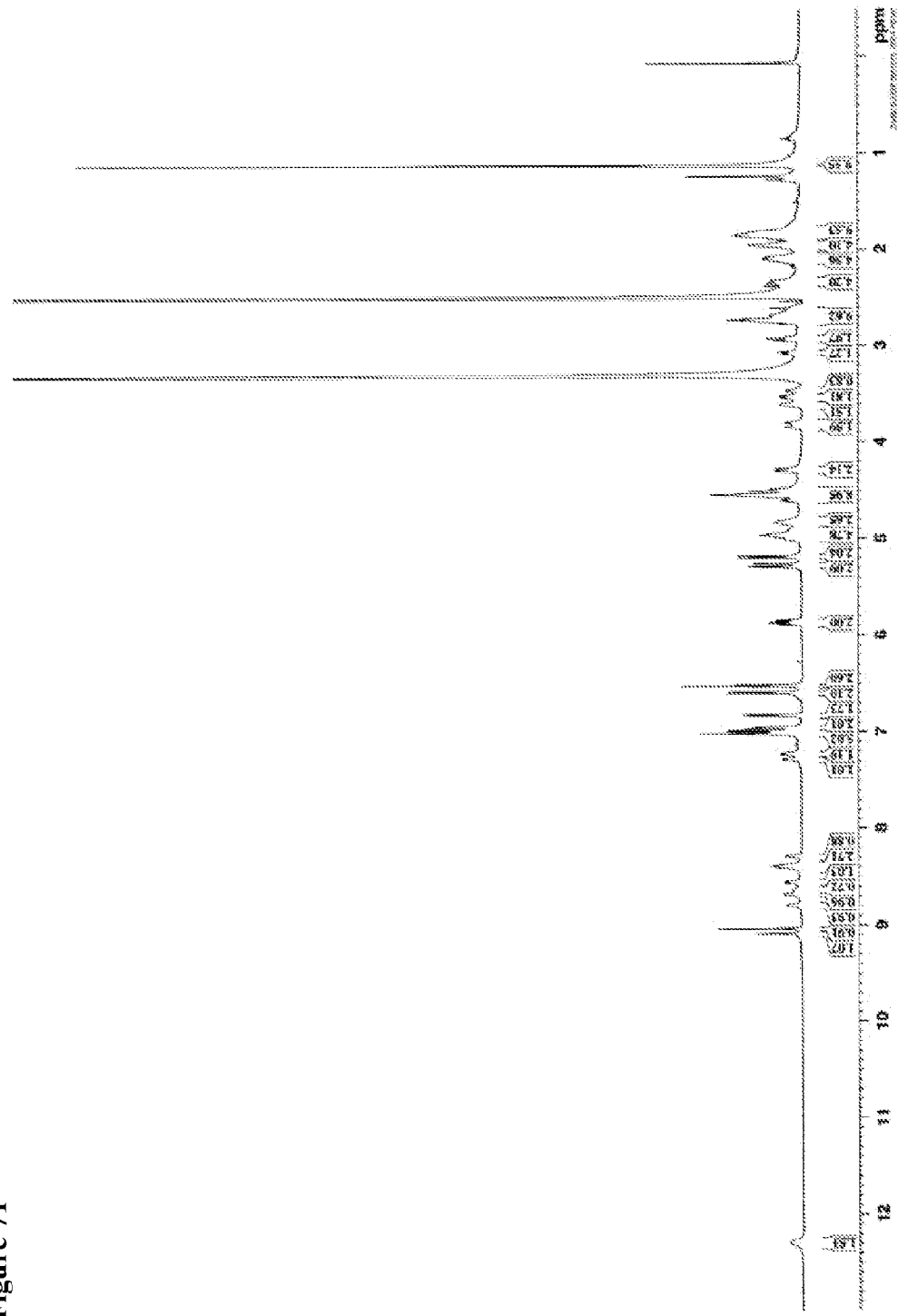
FIG. 71 depicts a $^1$H-NMR spectrum of compound 5-13 in $d_6$-DMSO.
Figure 72:
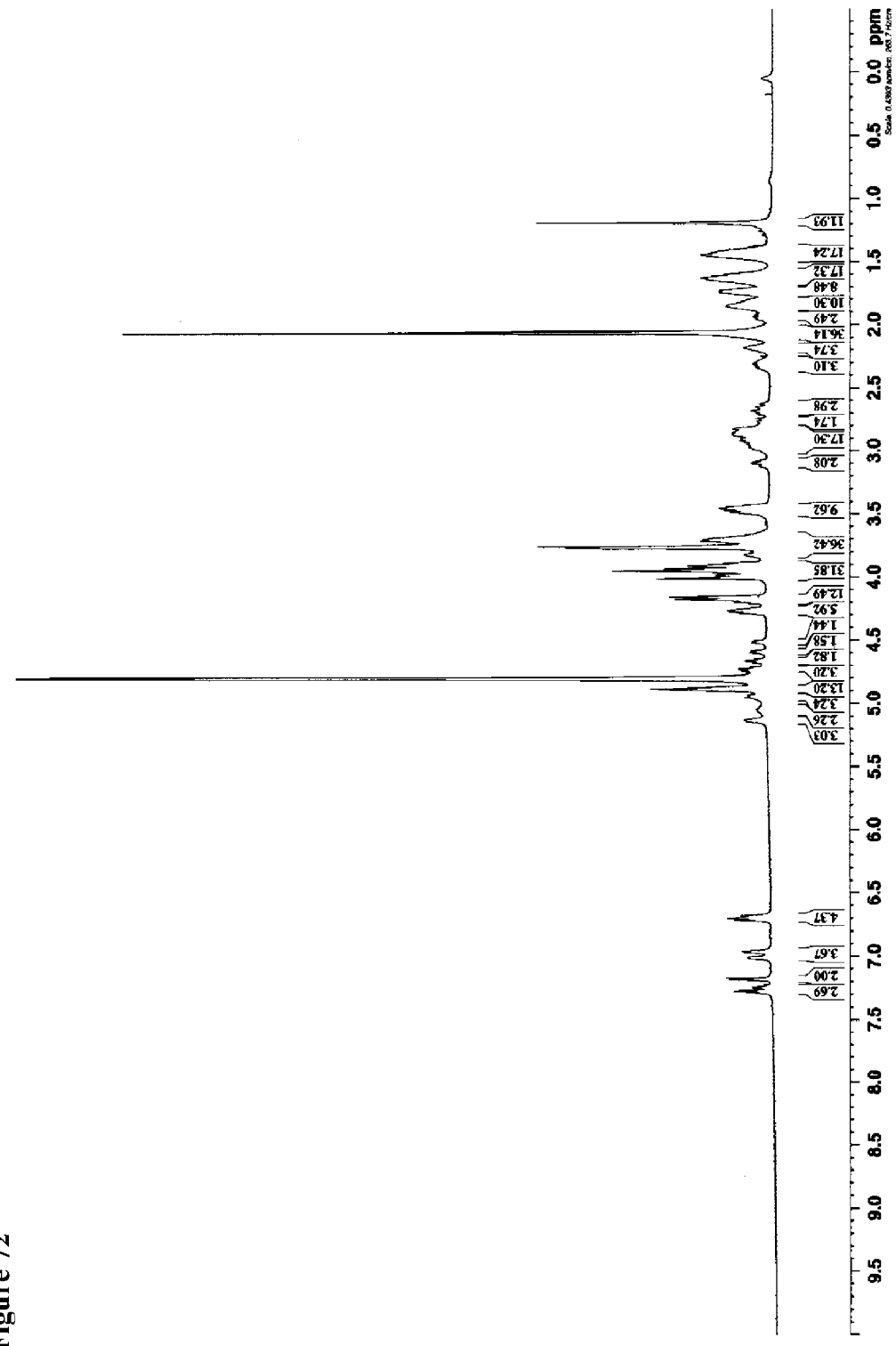
FIG. 72 depicts a $^1$H-NMR spectrum of compound 5-4 in $D_2O$.
Figure 73:
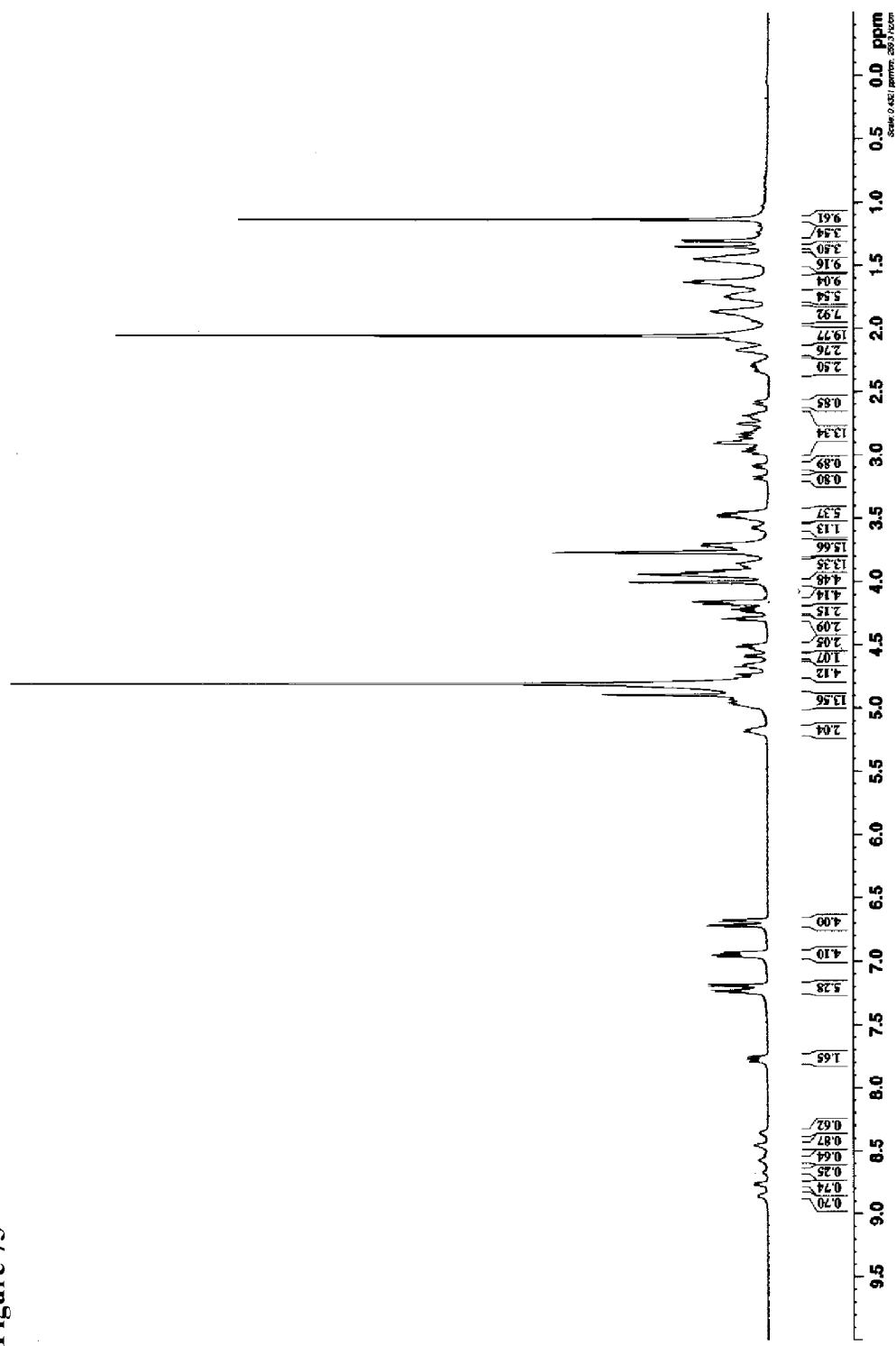
FIG. 73 depicts a $^1$H-NMR spectrum of compound 5-5 in $D_2O$.
Figure 74:
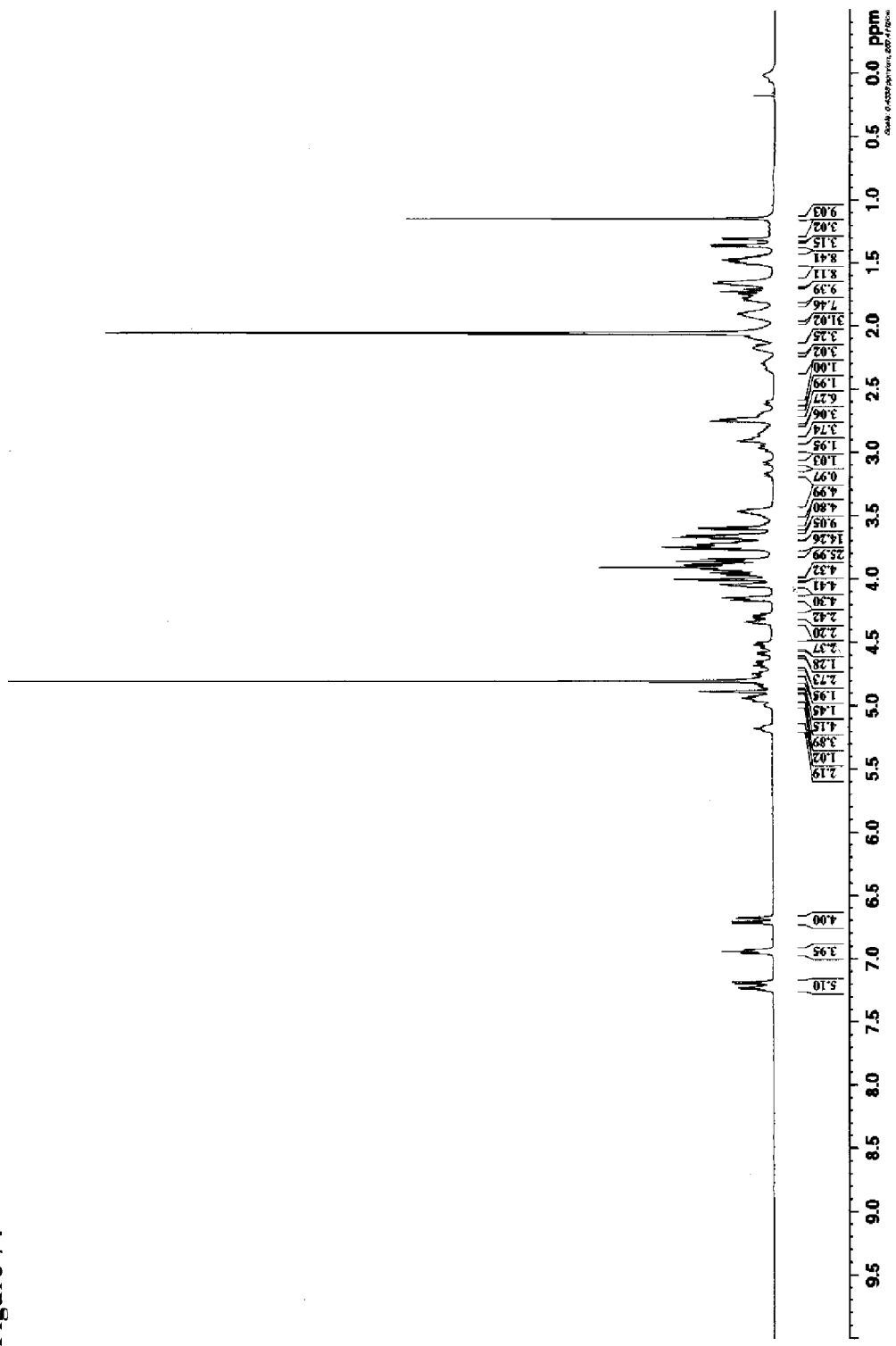
FIG. 74 depicts a $^1$H-NMR spectrum of compound 5-6 in $D_2O$.
Figure 75:
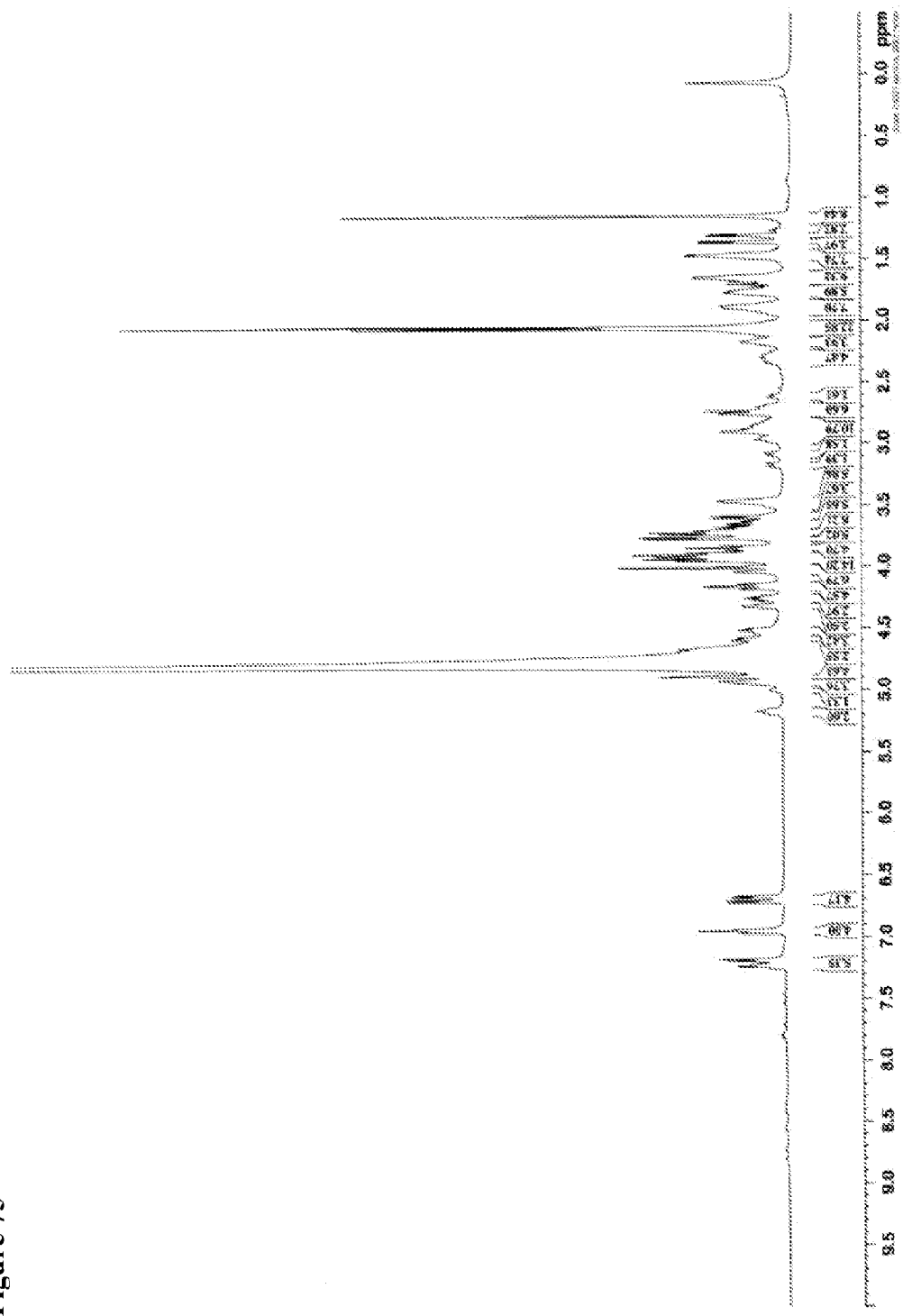
FIG. 75 depicts a $^1$H-NMR spectrum of compound 5-7 in $D_2O$.
Figure 76:
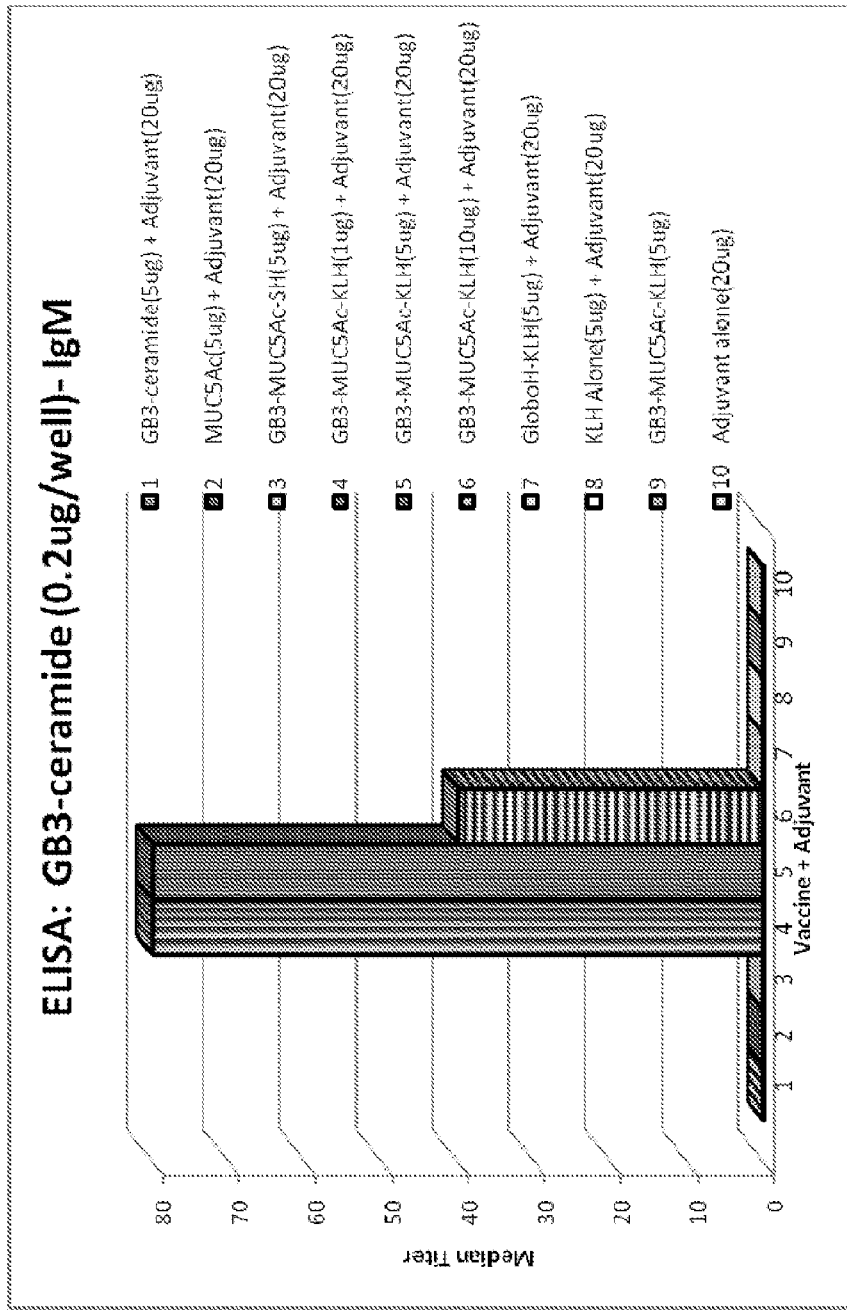
FIG. 76 depicts ELISA results obtained from vaccination sera as described in Example 2. The positive control used was a commercially available antibody (Gene Tex, Inc.) CD77 [38-13] used at a 1:40 dilution. The median titer was 240.
Figure 77:
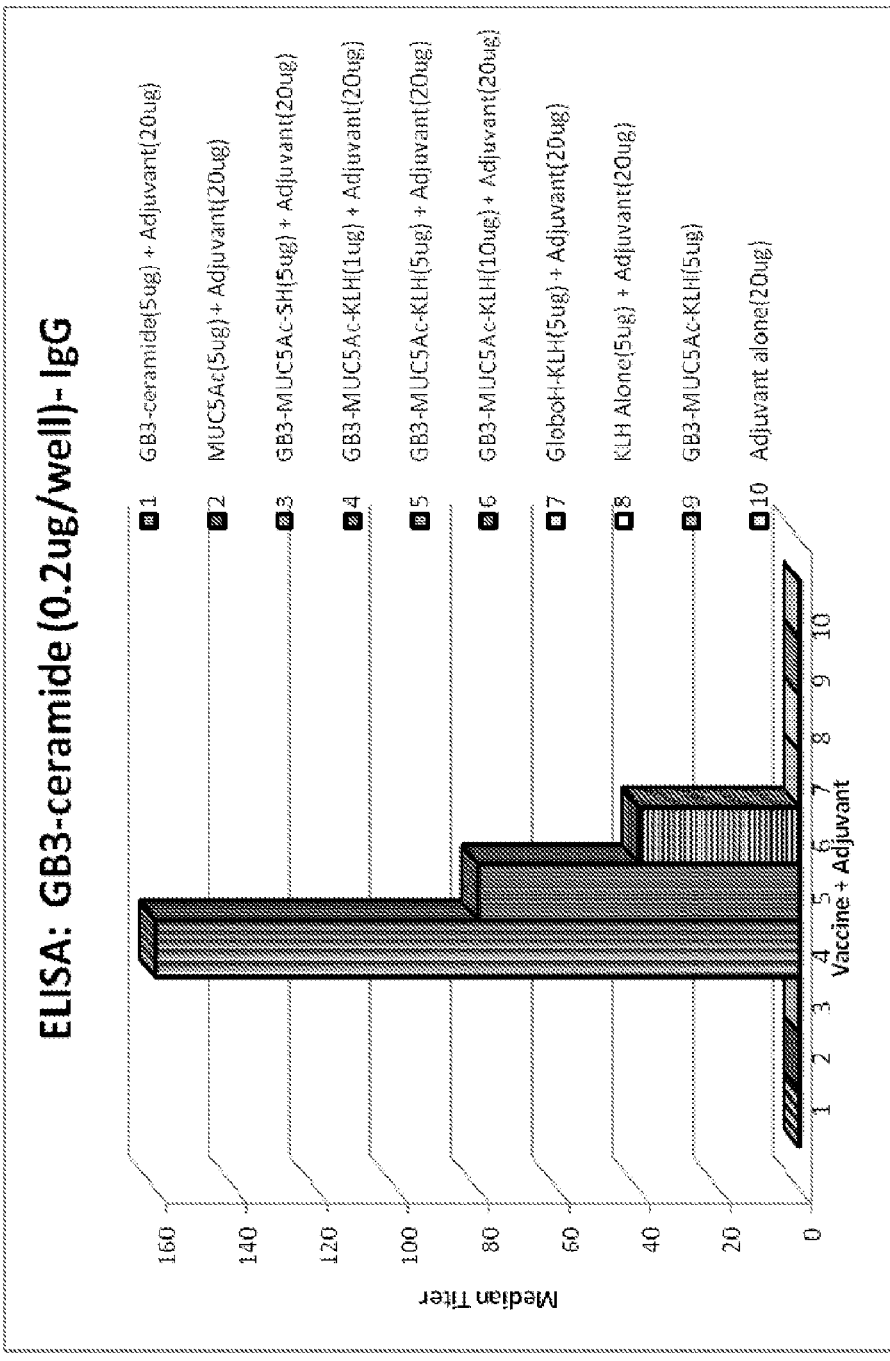
FIG. 77 depicts ELISA results obtained from vaccination sera as described in Example 2. The positive control used was a commercially available antibody (Gene Tex, Inc.) CD77 [38-13] used at a 1:40 dilution. The median titer was 320.
Figure 78:
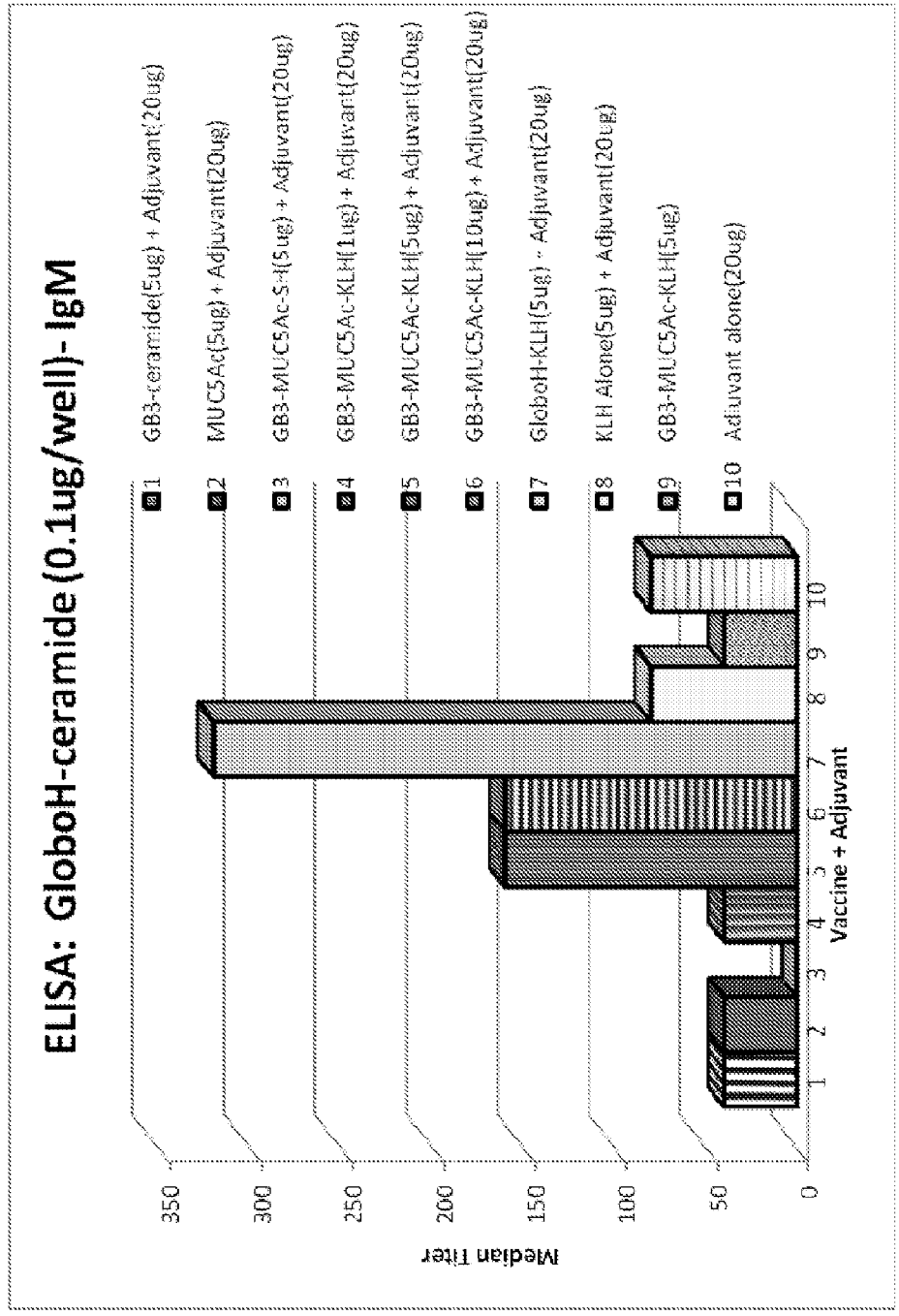
FIG. 78 depicts ELISA results obtained from vaccination sera as described in Example 2. The positive control was serum from female black mice vaccinated thrice with GloboH-KLH (3 ug). The median titer was 1280.
Figure 79:
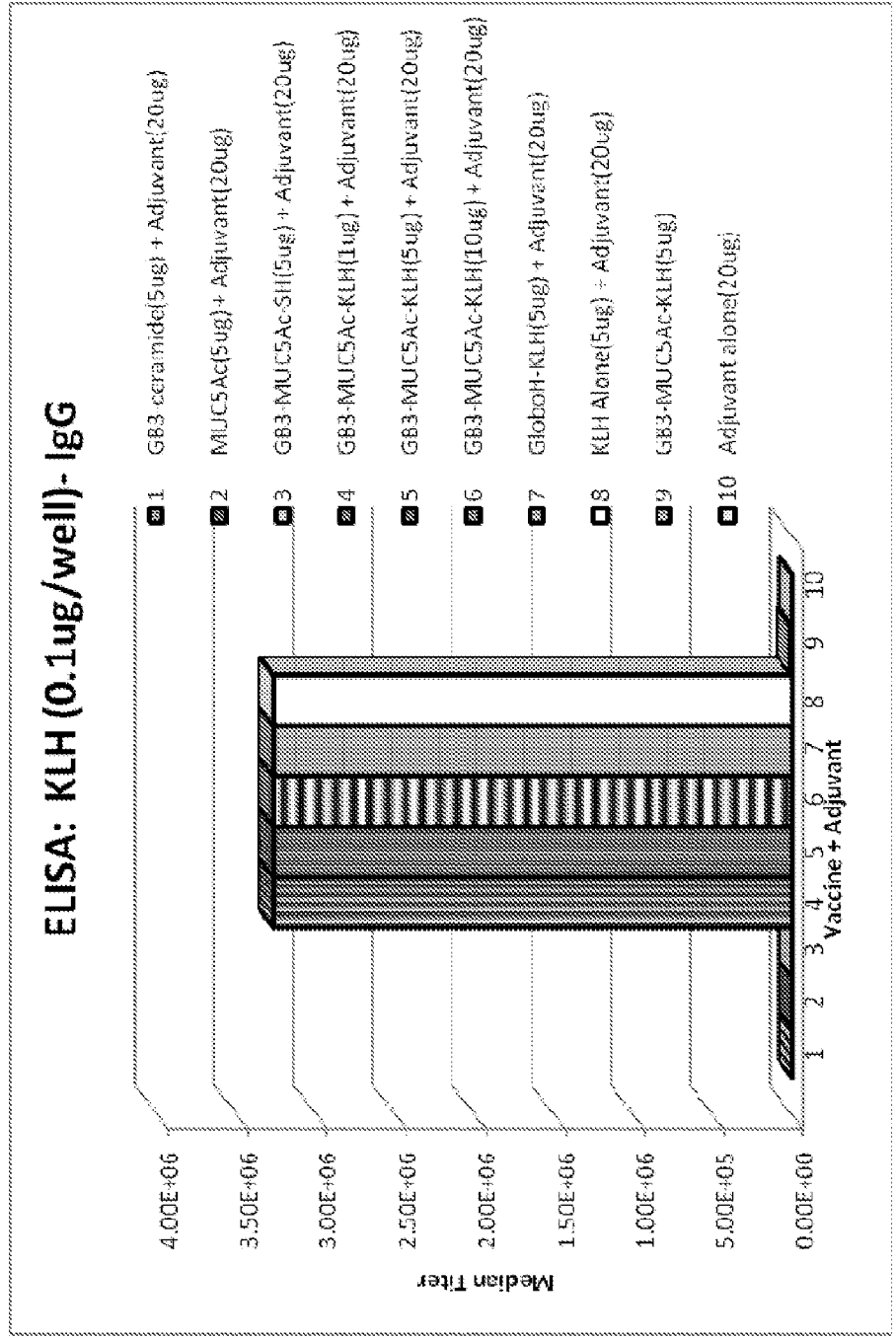
FIG. 79 depicts ELISA results obtained from vaccination sera as described in Example 2. The positive control was serum from female black mice vaccinated thrice with GloboH-KLH (5 ug). The median titer was $3.2 \times 10^6$. The median titer for the five groups with KLH maximized at a titer of $3.2 \times 10^6$.

Synthesis of Compound 3-11 (Step (f), FIGS. 66-68).

The product from above was re-dissolved in degassed 1:1 MeOH/water (10 mL), and degassed 0.03 M NaOH (0.75 mL) was added. The reaction mixture was stirred for 40 h before being neutralized with MAC-3 Dowex resin to pH=5, filtered and purified by HPLC: Rf=14.5 (Microsorb C18 column, 10-85% MeCN in $H_2O$, 30 min) to afford 3-11 (1.0 mg, 19% yield from 3-11a, 13% from 3-9). The product was found to be >95% pure as judged by LC/MS and $^1$H NMR: $^1$H-NMR (500 MHz, $D_2O$) (Due to the high degree of the NH exchange, the presence of the multiple peptide rotomers in the solution as well as the high overlap, there is an ambiguity associated in the tabulation and interpretation of the $^1$H NMR data. Please refer to the attached $^1$H NMR spectrum in the Figures for additional details.) δ 7.46 (d, J=9.7 Hz, 1H), 7.38 (d, J=7.4 Hz, 1H), 7.37 (d, J=7.6 Hz, 2H), 7.32 (t, J=7.4 Hz, 2H), 7.26 (d, J=7.0 Hz, 2H), 7.07 (d, J=8.5 Hz, 2H), 6.87 (d, J=8.6 Hz, 2H), 6.81 (d, J=7.4 Hz, 2H), 5.28 (s, 1H), 5.26 (d, J=3.9 Hz, 1H), 4.70 (dd, J=5.2, 1.5 Hz, 2H), 4.66 (d, J=6.9 Hz, 2H), 4.62 (d, J=8.0 Hz, 1H), 4.60 (d, J=5.5 Hz, 2H), 4.47 (t, J=7.5 Hz, 2H), 4.16 (t, J=6.1 Hz, 2H), 4.10 (at, J=5.5 Hz, 4H), 4.07 (d, J=8.5 Hz, 2H), 3.48 (m, 1H), 3.42 (dd, J=10.0, 2.0 Hz, 1H), 3.28 (t, J=8.9 Hz, 1H), 3.20 (dt, J=13.1, 6.4 Hz, 1H), 3.12 (dd, J=13.5, 6.8 Hz, 1H), 2.58 (dd, J=12.1, 4.4 Hz, 1H), 2.31 (m, 1H), 2.24 (s, 3H), 2.05 (s, 3H), 2.04 (s, 3H), 2.01 (s, 3H), 1.87 (t, J=13.2 Hz, 1H), 1.81 (dd, J=6.5 Hz, 1H), 1.42 (d, J=8.5 Hz, 3H), 1.26 (d, J=6.1 Hz, 3H), 1.24 (d, J=6.6 Hz, 3H), 1.01 (d, J=6.8 Hz, 3H), 0.99 (d, J=6.8 Hz, 3H), 0.94 (d, J=6.3 Hz, 3H), 0.91 (d, J=6.7 Hz, 3H), 0.89 (d, J=6.3 Hz, 3H), 0.87 (d, J=6.7 Hz, 3H). Exact mass calcd for sodium salt $C_{134}H_{208}N_{21}NaO_{54}S$ $[M+2H]^{2+}$: 1516.7; $[M+3H]^{3+}$: 1011.5; $[M+CF_3CO_2^-]^{2-}$: 1572.2. Found: 1517.7, 1012.3, 1572.9.

Preparation of Conjugate 3-1 (Step (g), FIG. 14).

Solution of sulfo-SMCC (10 mg/mL, 0.10 mL) in 0.1 M sodium phosphate, 0.9 M NaCl (pH=7.2) was added to the reconstituted with water solution of KLH (Aldrich, H7017, 10 mg/mL, 1.0 mL). The resultant solution was stirred for 1 h and then purified over G-25 sephadex column using 0.1 M sodium phosphate, 0.9 M NaCl, 0.1 M EDTA, pH=7.2 for elution. The fractions containing KLH were collected and combined giving the total volume of 3.0 mL. Compound 3-11 (2 mg, 0.665 μmol) in 0.2 mL of the pH=7.2 buffer was treated with TCEP gel for 2 h, filtered, combined with the solution of KLH (0.6 mL), and reacted under argon for 2 h. The resultant solution was purified by repetitive centrifugation over molecular filter (30 kDa cut off) resulting in ca. 1 mL of the final solution of the vaccine construct. The degree of the epitope incorporation was estimated to be 210 epitopes per molecule of KLH using Bradford protein assay with KLH as a standard and Svennerholm sialic acid assay to determine the carbohydrate concentration.

Example 4

Figure 15:
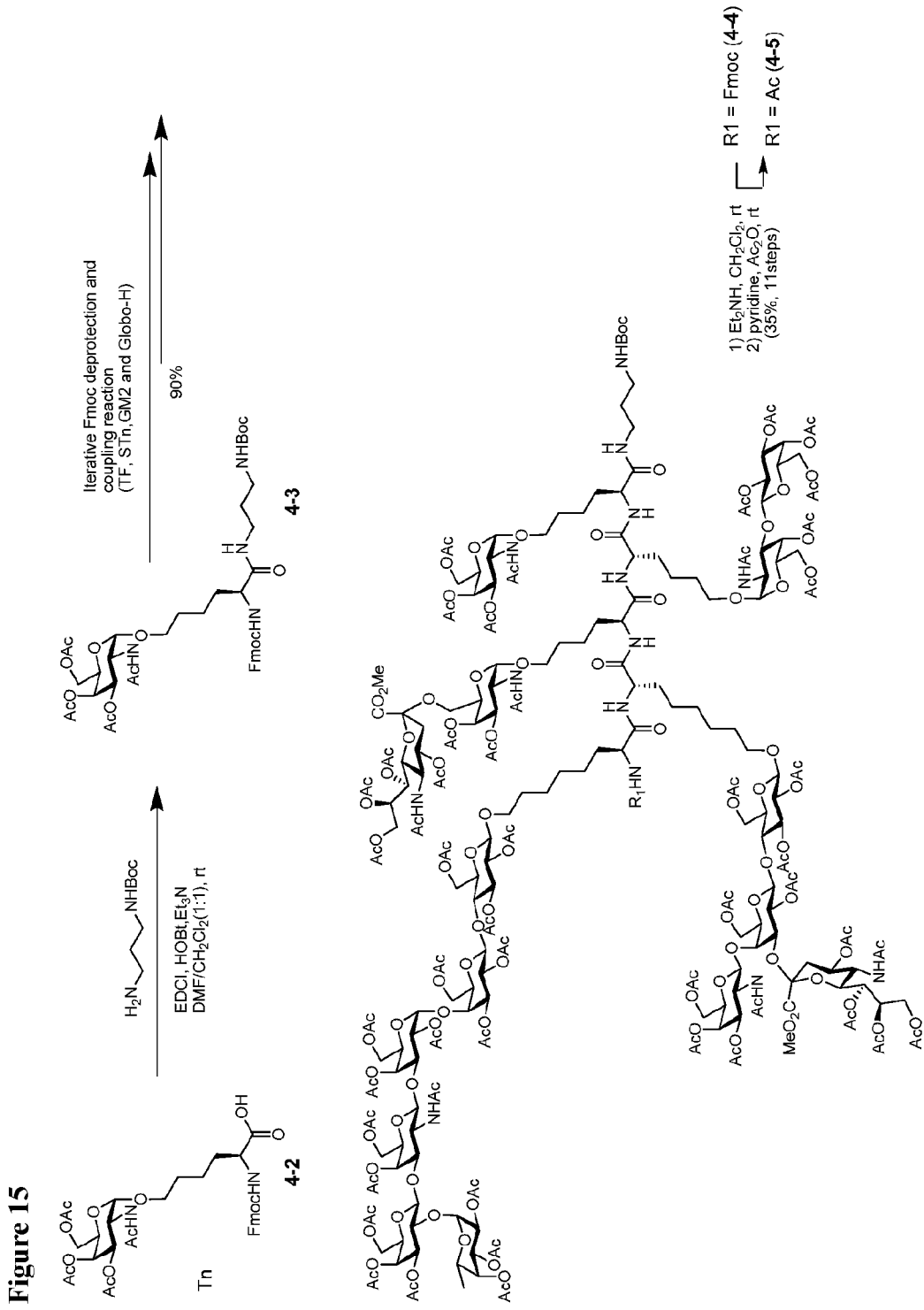
FIG. 15 depicts a preparation of the unimolecular pentavalent carbohydrate domain 4-5.

The unimolecular pentavalent carbohydrate domain (4-5) was prepared though the "cassette" approach, developed by our laboratory (FIG. 15) (Allen, J. R.; Harris, C. R.; Danishefsky, S. J. *J. Am. Chem. Soc.* 2001, 123, 1890-1897; Biswas, K.; Coltart, D. M.; Danishefsky, S. J. *Tetrahedron Lett.* 2002, 43, 6107-6110; Keding, S. J.; Endo, A.; Biswas, K.; Zatorski, A.; Danishefsky, S. J. *Tetrahedron Lett.* 2003, 44, 3413-3416; Keding, S. J.; Endo, A.; Danishefsky, S. J. *Tetrahedron* 2003, 59, 7023-7031; Cho, Y. S.; Wan, Q.; Danishefsky, S. J. *Bioorg. Med. Chem.* 2005, 13, 5259-5266; Wan, Q.; Cho, Y. S.; Lambert, T. H. *J. Carbohydr. Chem.* 2005, 24, 425-440). Thus, the pre-assembled, protected glycosylamino acids were coupled via iterative Fmoc deprotection and coupling reactions, as described previously, leading to the fully glycosylated polypeptide backbone. Each deprotection and coupling step proceeded in >75% yield, and our coupling conditions allowed us to access 4-5 in 35% overall yield for eleven transformations.

Figure 16:
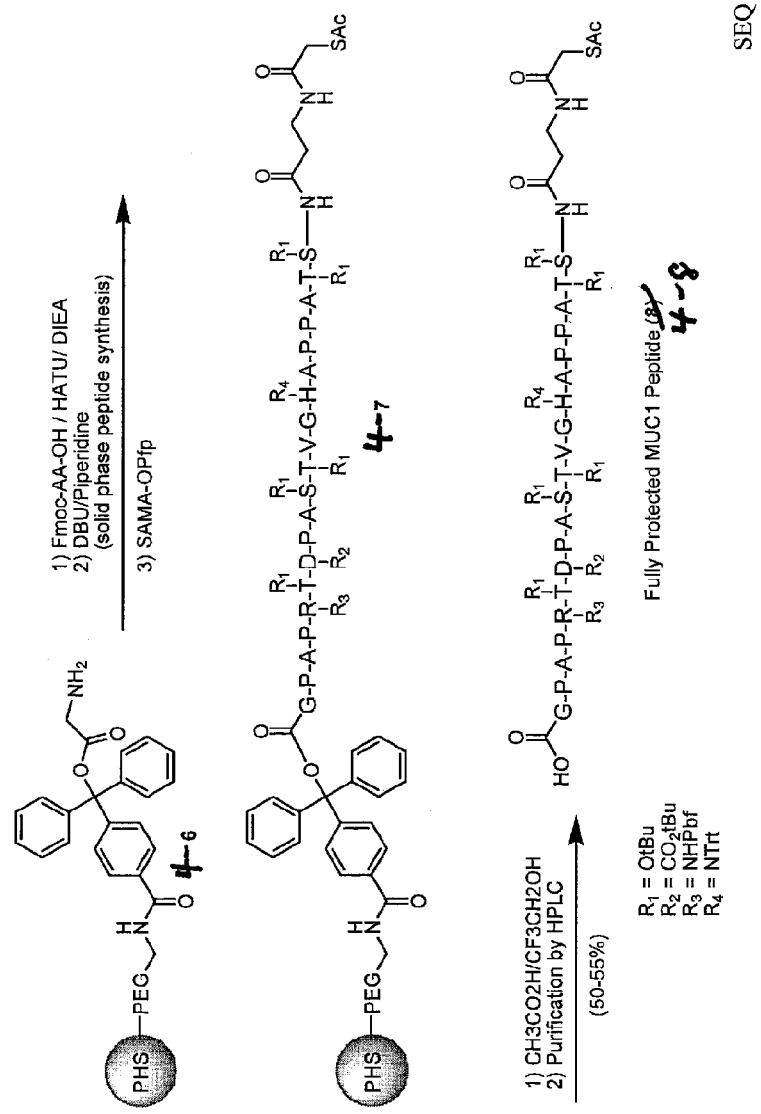
FIG. 16 depicts a preparation of compound 4-8.

We next turned to the preparation of the peptide domain (4-8) (FIG. 16). In designing the unglycosylated MUC1 peptide, it was decided to position a glycine on the C-terminus, to avoid the possibility of α-epimerization during the subsequent coupling phase. We also elected to install a protected thiol functionality, to be utilized in the late-stage conjugation to KLH, at the N-terminus during the solid phase peptide synthesis. The fully protected unglycosylated MUC1 tandem repeat (4-8) was thus prepared by automated solid-phase peptide synthesis on a commercially available trityl resin (4-6) using Fmoc amino acid derivatives, according to standard procedures (Atherton E.; Sheppard, R. C. *Solid phase synthesis: A practical approach*, IRL Press, Oxford University Press, Oxford, 1989). Cleavage from the resin using TFA/TFE furnished the desired MUC1 peptide (4-8) (LC/MS analysis showed (60-80% MeCN/H$_2$O, Microsorb C18, 300-5, 2×150 mm, 0.2 mL/min) showed that the peptide (4-8) at 13.57 min and MS spectrum with base peaks of 1453.86 (M+2H$^+$, [1452.76 calc])) as a carboxylic acid.

Figure 17A:
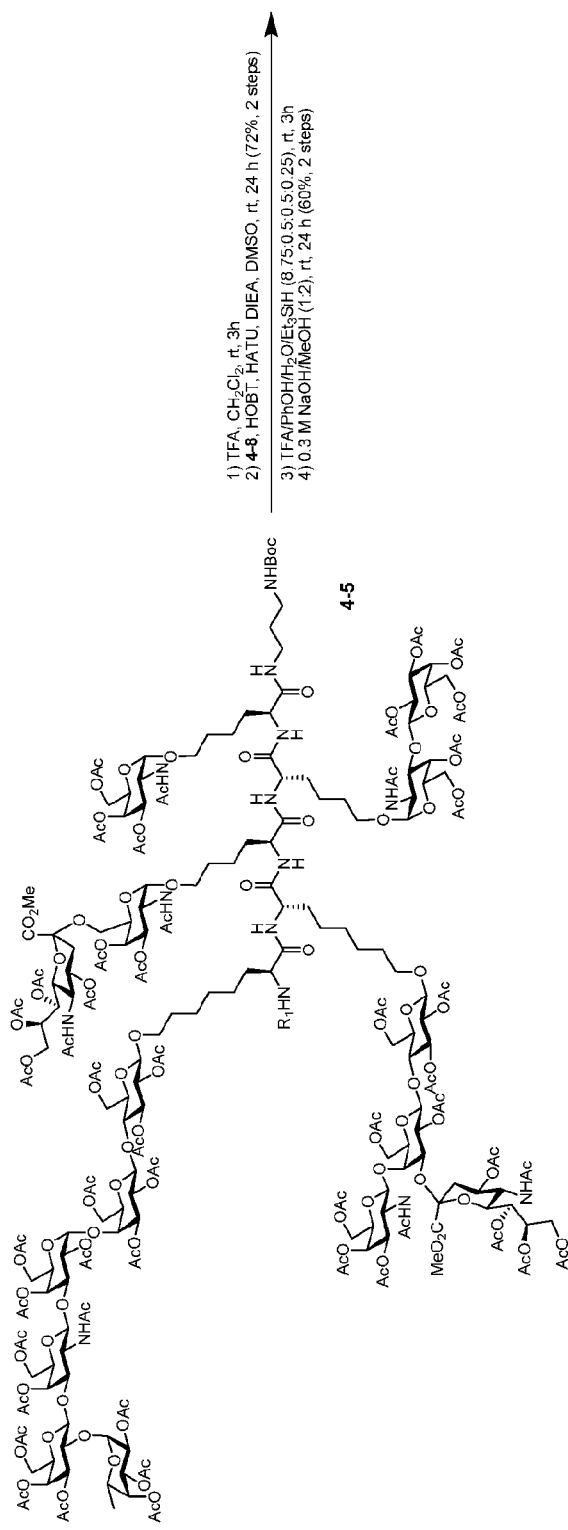
FIGS. 17a-b depict a preparation of the unimolecular pentavalent-MUC1 glycopeptide construct 4-9.
Figure 17B:
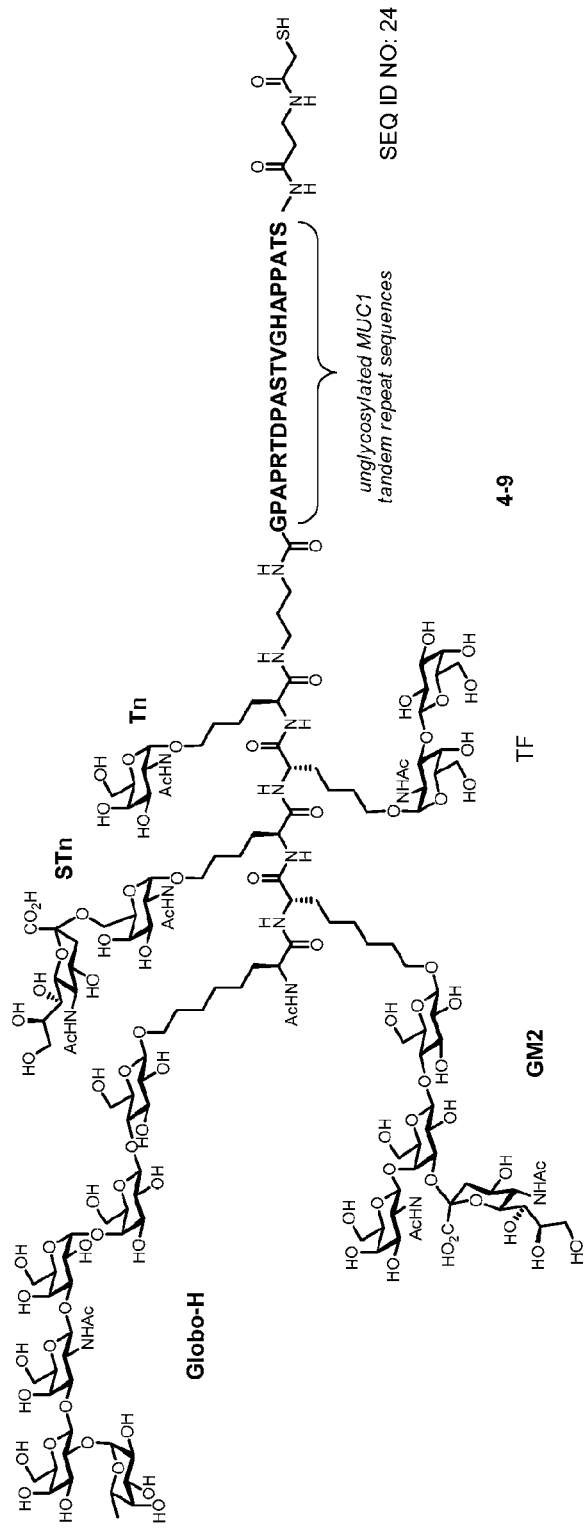
Figure 18A:
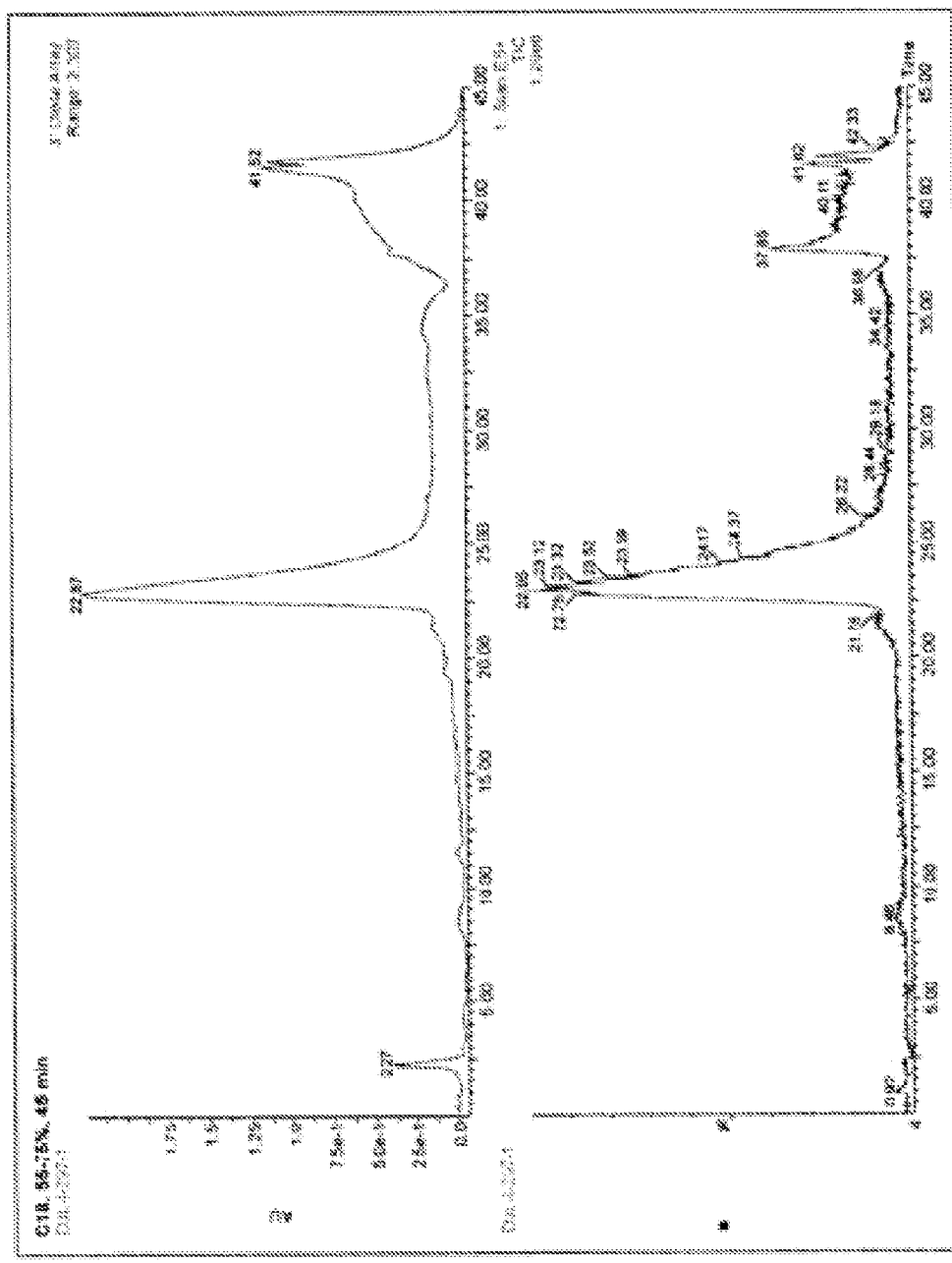
FIGS. 18a-b depict LCMS characterization data for compound 4-8.
Figure 18B:
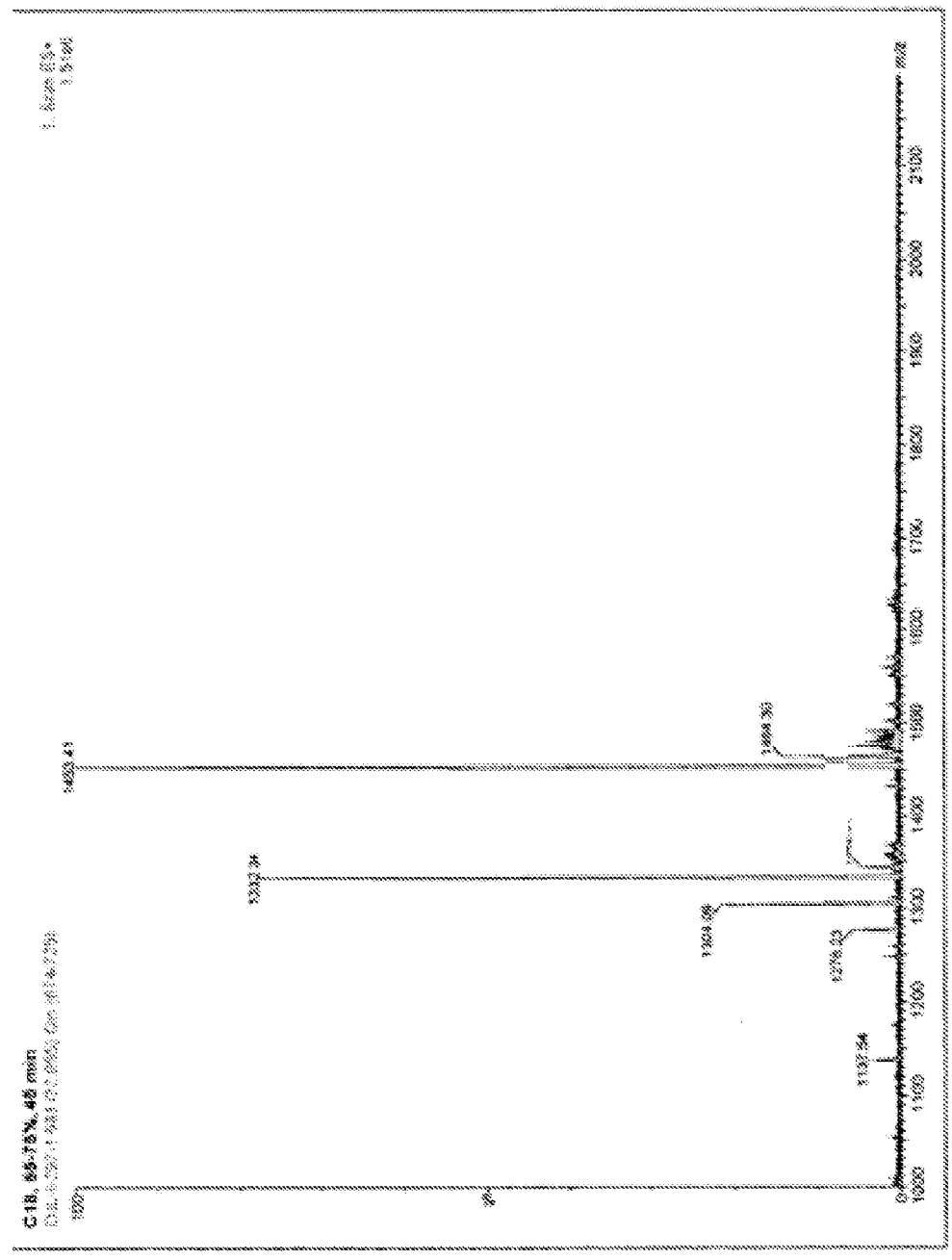
Figure 19:
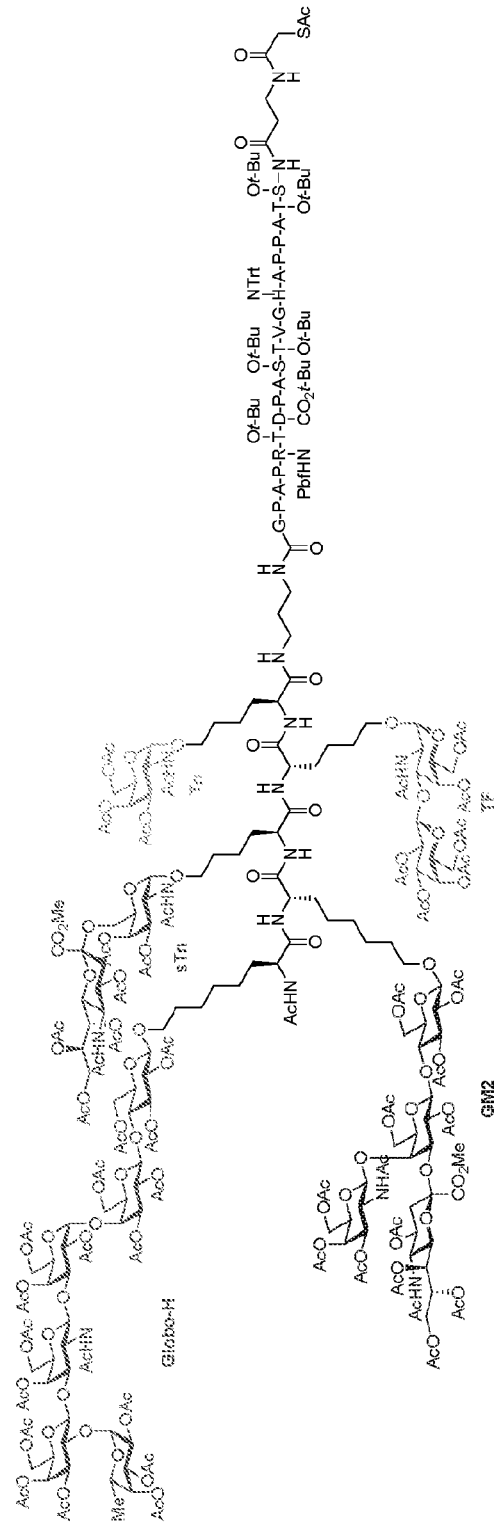
FIG. 19 depicts a protected unimolecular pentavalent-MUC1 glycopeptide.
Figure 20A:
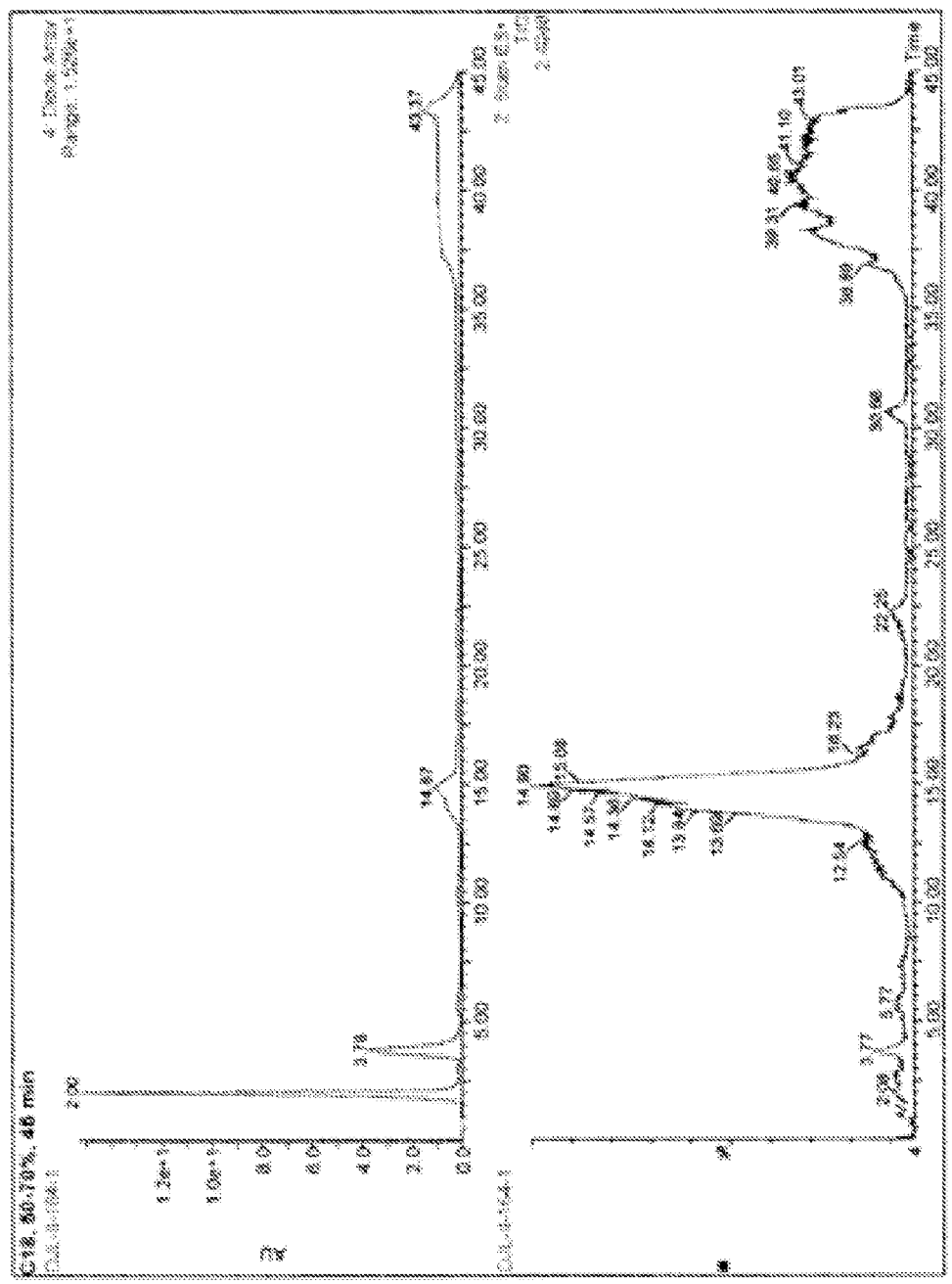
FIGS. 20a-b depicts LCMS characterization data for deprotected compound 4-5.
Figure 20B:
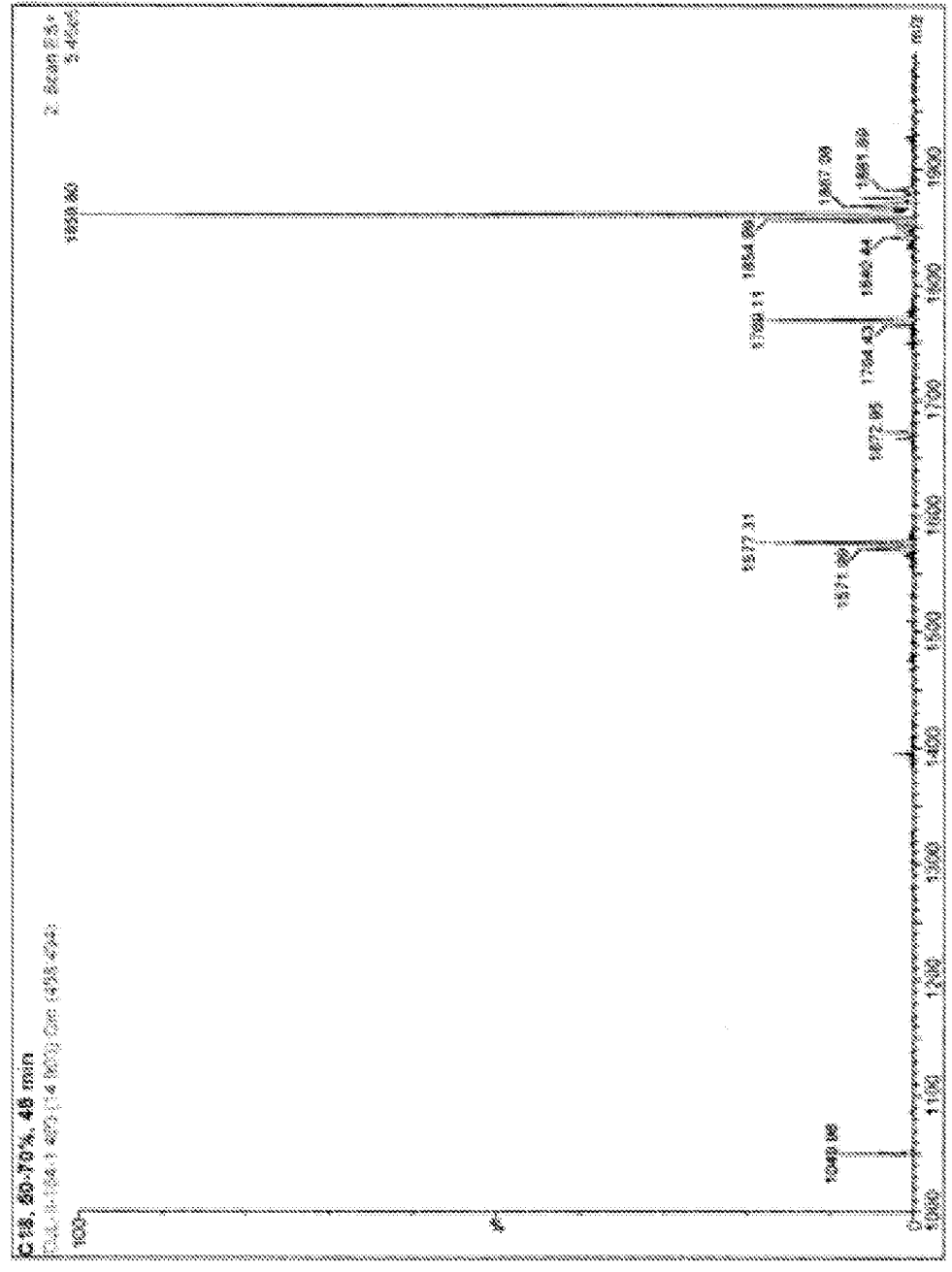
Figure 21A:
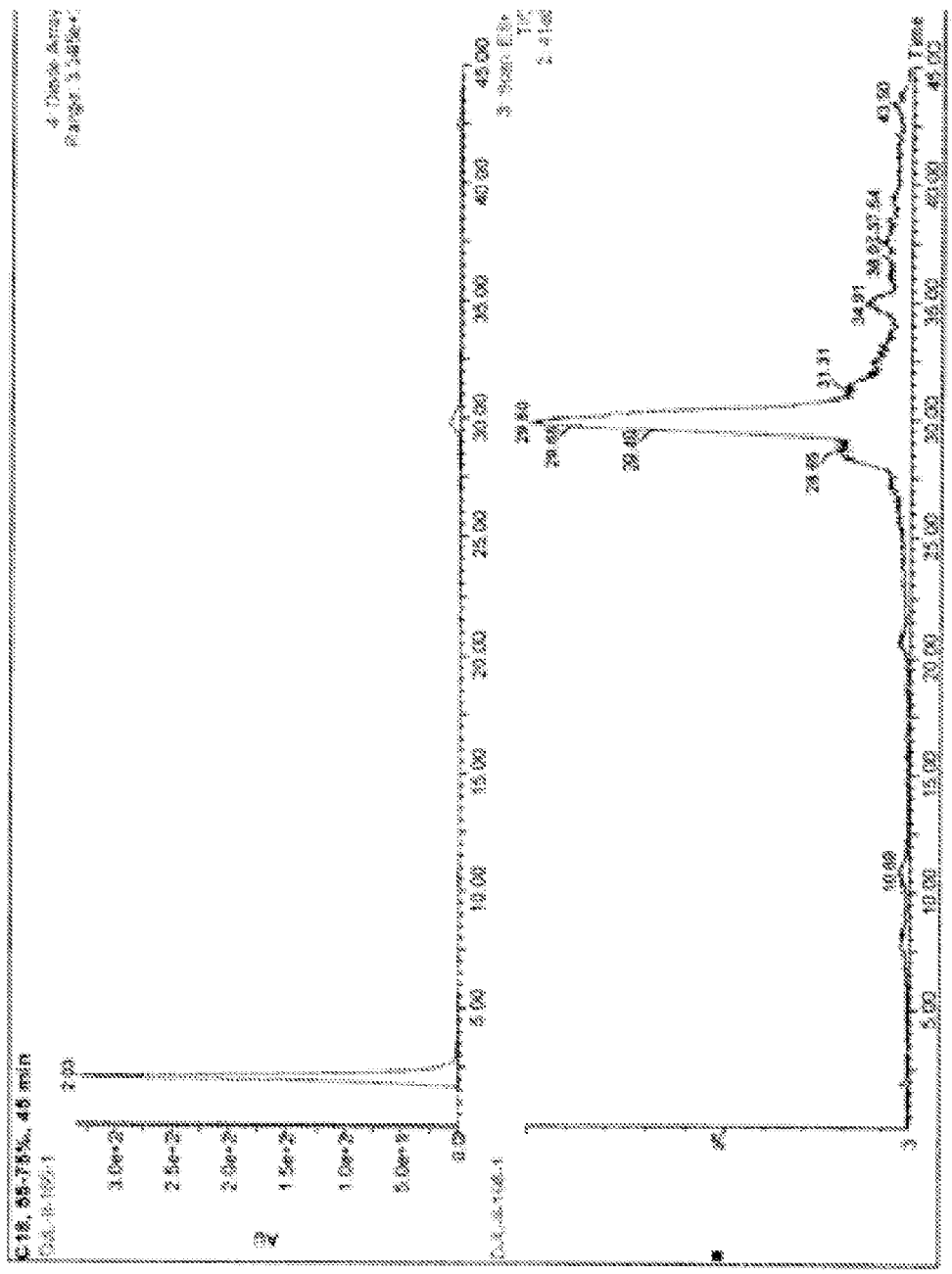
FIGS. 21a-b depict LCMS characterization data for the compound depicted in FIG. 19.
Figure 21B:
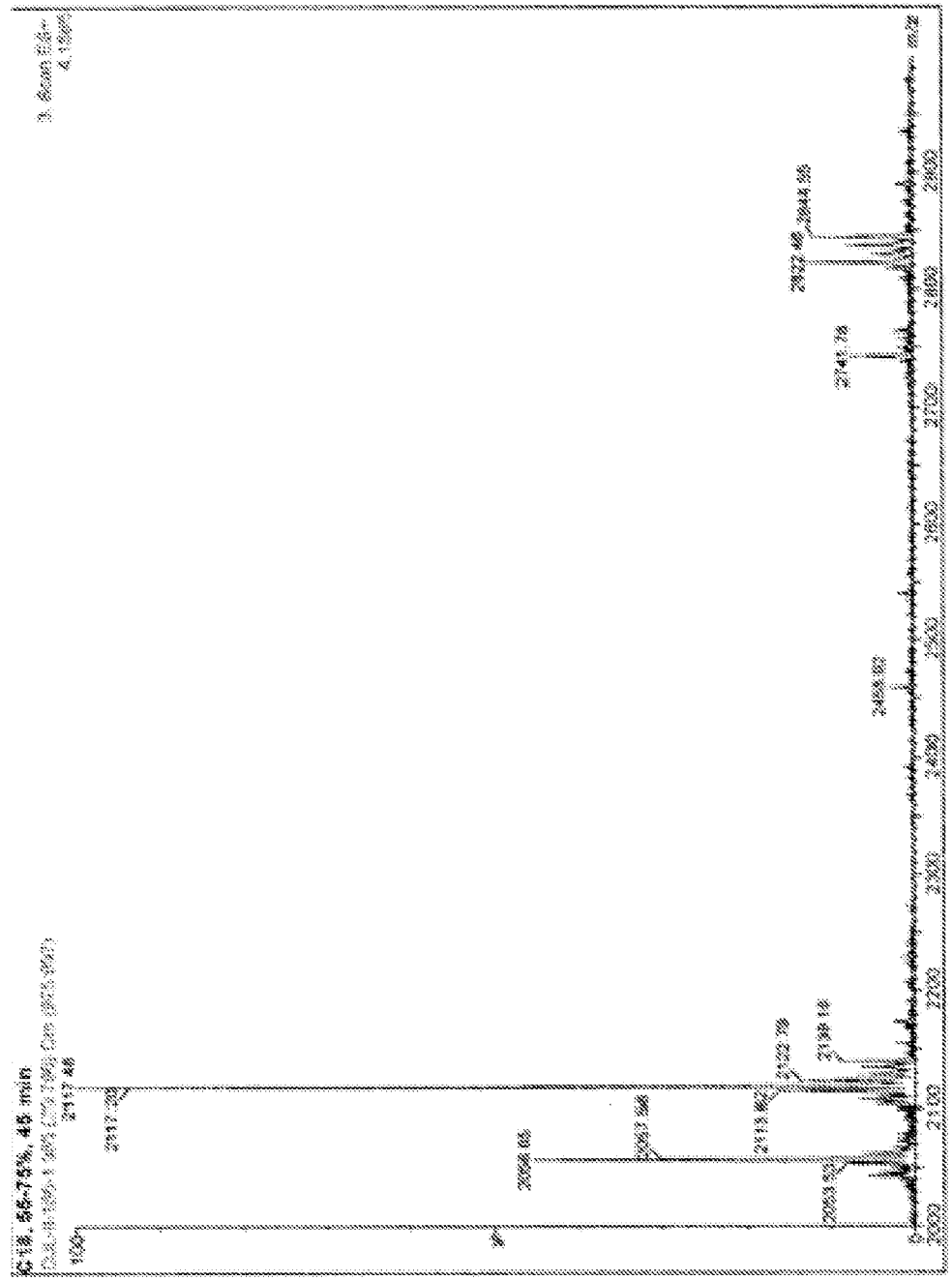
Figure 22:
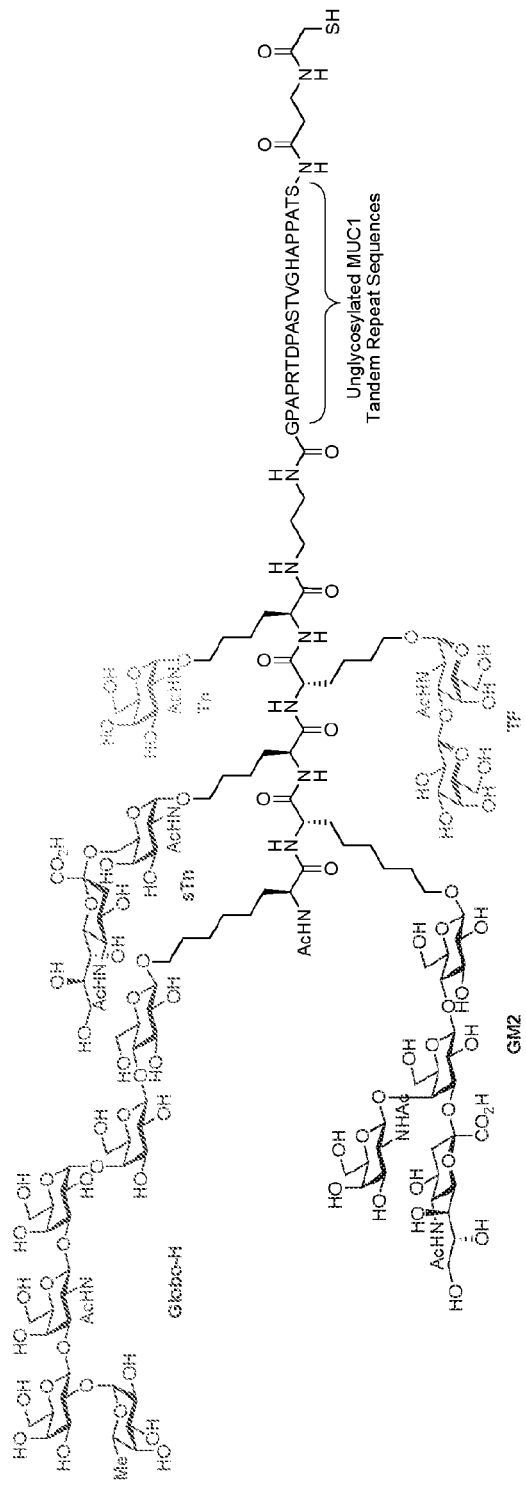
FIG. 22 depicts unimolecular pentavalent-MUC1 glycopeptide 4-9.
Figure 23:
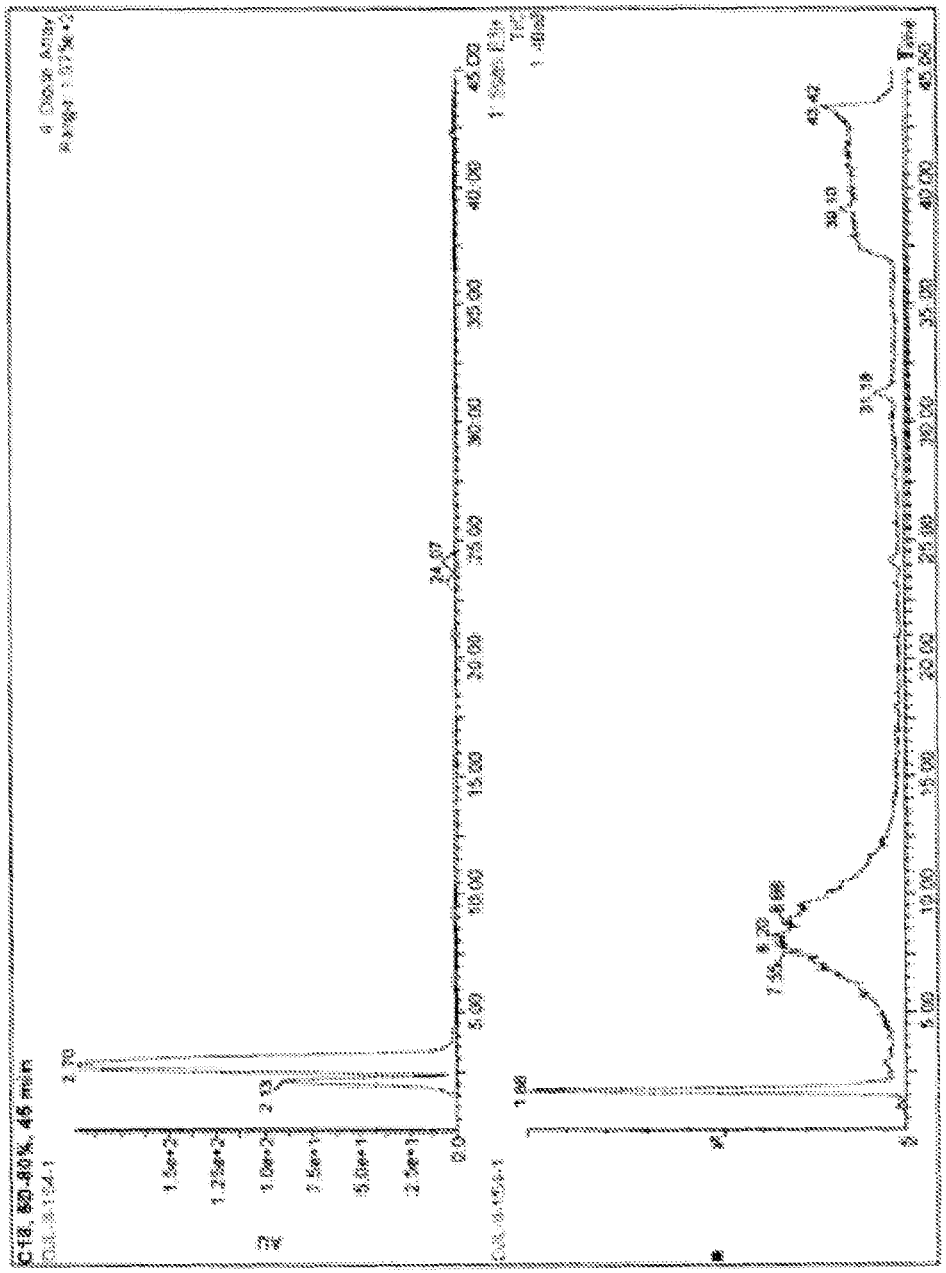
FIGS. 23-24 depict LCMS characterization data for the compound depicted in FIG. 19 after treatment with a cleavage solution (150 μL, $TFA/H_2O/PhOH/Et_3SiH=8.75:0.5:0.5:0.25$).
Figure 24:
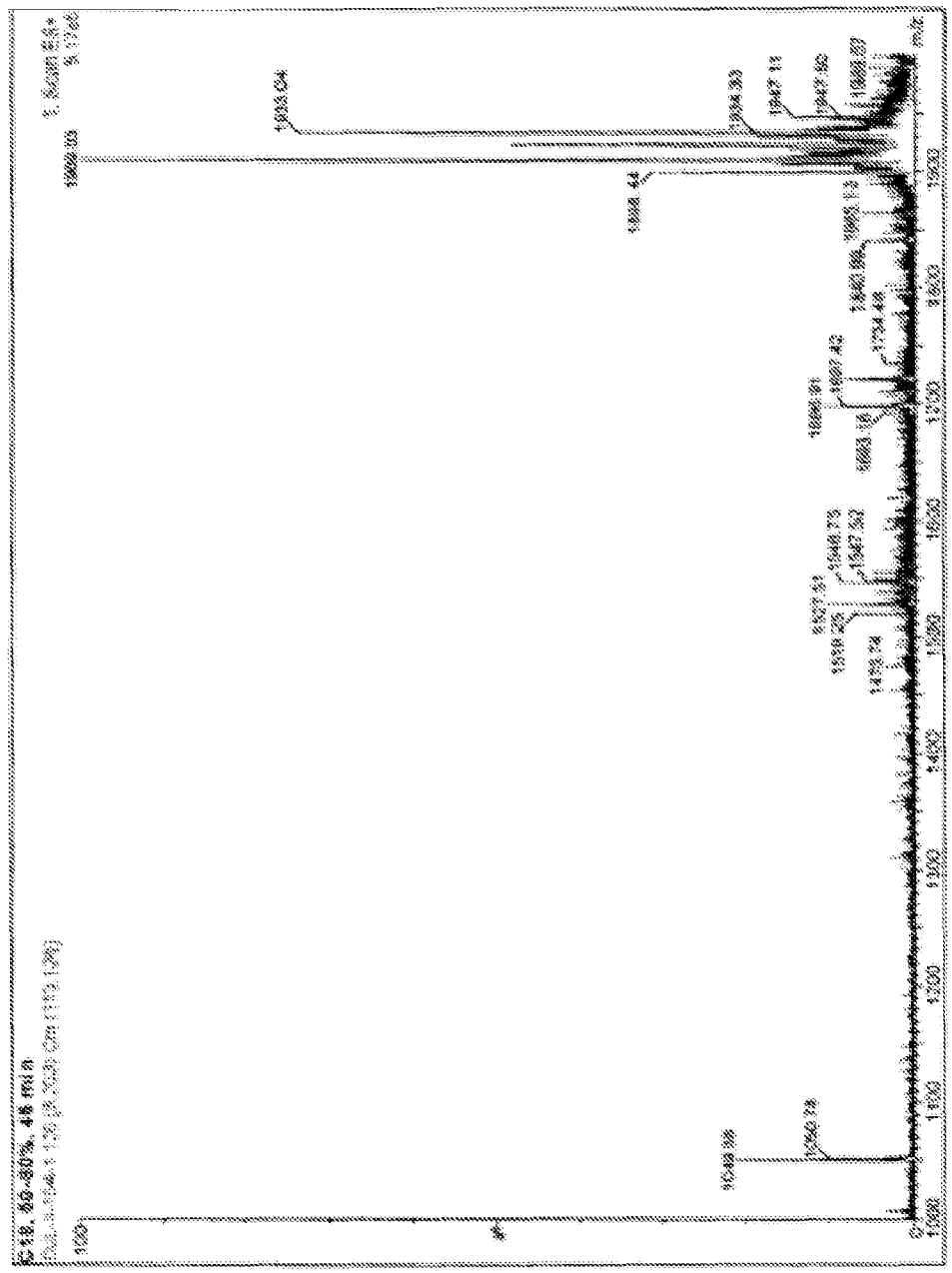

Having gained synthetic access to both the pentavalent carbohydrate domain (4-5) and the desired peptide (4-8), we now sought to merge the two domains, thus assembling the complete framework of the target vaccine. First, the C-terminal Boc group on the diaminopropyl spacer (4-5) was removed under acidic conditions (TFA/CH$_2$Cl$_2$). Next, the fully protected MUC1 peptide (4-8), activated with HATU/HOBT, was coupled to the carbohydrate domain (4-5) in the presence of DIEA, leading to the desired fully protected glycopeptide in 72% yield over 2 steps after purification by preparative HPLC (FIGS. 17a-b). All acid-labile side chain protecting groups of the peptide were simultaneously removed by a cleavage cocktail (TFA/PhOH/H$_2$O/Et$_3$SiH). Finally, global deprotection of the O-acetyl and methyl groups with NaOH/MeOH afforded the desired unconjugated unimolecular pentavalent-MUC1 glycopeptide (4-9) (LC/MS analysis showed (1-10% MeCN/H$_2$O (5 min), 20-50% MeCN/H$_2$O (30 min), Microsorb C18, 300-5, 2×150 mm, 0.2 mL/min) showed that the glycopeptide (4-9) at 12.15 min and MS spectrum with base peaks of 1904.76 (M+3H$^+$, [1903.84 calc])) in 60% over 2 steps after purification by preparative HPLC.

In summary, this Example demonstrates the synthesis of a pentavalent-MUC1 glycopeptide construct in a highly convergent and efficient way. Conjugation to KLH carrier protein and immunological testing of the resultant vaccine conjugate (4-1) will be carried out shortly using procedures described herein.

Experimental Procedures:
I. Materials and Methods:
Reagents:

All commercial materials were used as received unless otherwise noted. Trifluoroethanol (TFE), trifluoroacetic acid (TFA), acetic acid (CH$_3$CO$_2$H), N,N-diisopropylethyl amine (DIEA), diazabicycloundecene (DBU), piperidine, N-hydroxybenzotriazole (HOBT), triethyl silane (Et$_3$SiH), phenol (PhOH), anhydrous methanol (MeOH), anhydrous methyl sulfoxide (DMSO), and anhydrous N,N-dimethyl formamide (DMF) were purchased from Aldrich. [O-(7-azabenzotriazol-1-yl)-N,N,N',N'-tetramethyluronium hexafluorophosphate] (HATU) was purchased from GenScript and used without further purification. All amino acids and resins for solid phase peptide synthesis were purchased from NovaBiochem; all other solvents from Fisher Scientific (HPLC grade).

HPLC:

All separation involved a mobile phase of 0.05% TFA (v/v) in water (solvent A)/0.0425% TFA in acetonitrile (solvent B). Preparative and analytical HPLC separation were performed using a Rainin HXPL solvent delivery system equipped with a Rainin UV-1 detector and Microsorb Dynamax-100 Å C18 axial compression columns. LC-MS chromatographic separations were performed using a Waters 2695 Separations Module and a Waters 996 Photodiode Array Detector equipped with Varian Microsorb C18 2×150 mm, and C4 2×250 mm columns at a flow rate of 0.2 mL/min.

ESMS and LC-MS:

Electrospray mass spectroscopy and LCMS analyses were obtained on a Waters Micromass ZQ mass spectrometer in conjugation with the Waters HPLC apparatus described above.

II. Detailed Experimental Procedures
1. Preparation of the Peptide (4-8)

SEQ ID NO: 24

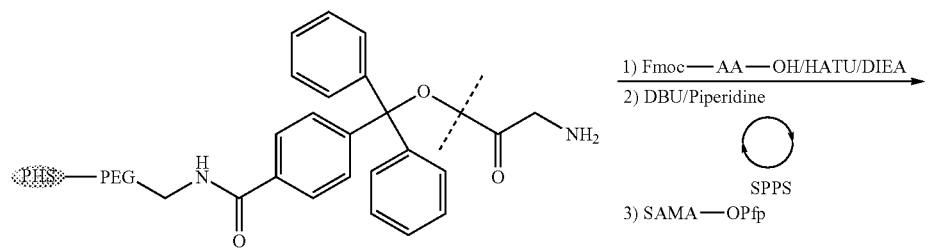

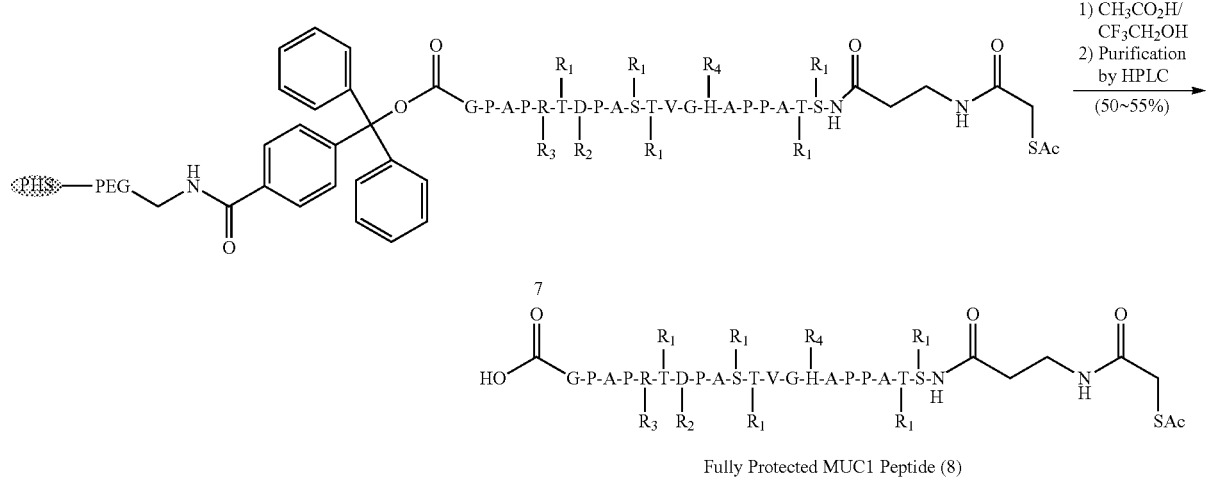

Fully Protected MUC1 Peptide (8)

$R_1 = OtBu$
$R_2 = CO_2tBu$
$R_3 = NHPbf$
$R_4 = NTrt$

The Fully Protected MUC1 Peptide (4-8):

Fmoc-Gly-NovaSyn® TGT resin (purchased from NovaBiochem) was used. Fmoc quantitation of the resin prior to deprotection indicated a loading of 0.23 mmol/g. 217.4 mg of this resin (4-6) was subjected continuous flow automated peptide synthesis. For coupling steps, resin was treated with a 4-fold excess of HATU and Fmoc amino acids in DIEA/DMF, and for deblocking, a solution of 2% piperidine/2% DBU in DMF was used. The amino acids used were, in order of synthesis, Fmoc-Pro-OH, Fmoc-Ala-OH, Fmoc-Pro-OH, Fmoc-Arg(Pbf)-OH, Fmoc-Thr(O-tBu)-OH, Fmoc-Asp(O-tBu)-OH, Fmoc-Pro-OH, Fmoc-Ala-OH, Fmoc-Ser(O-tBu)-OH, Fmoc-Thr(O-tBu)-OH, Fmoc-Val-OH, Fmoc-Gly-OH, Fmoc-His(N-Trt)-OH, Fmoc-Ala-OH, Fmoc-Pro-OH, Fmoc-Pro-OH, Fmoc-Ala-OH, Fmoc-Thr(O-tBu)-OH, Fmoc-Ser(O-tBu)-OH, Fmoc-β-Ala-OH, SAMA-Opfp (S-acetylthioglycolic acid pentafluorophenyl ester). The resin was then transferred to a manual peptide synthesis vessel and treated with a cleavage solution (10 mL, $CH_3CO_2H/TFE/CH_2Cl_2=1:1:8$) for 1 hour. The beads were filtered, rinsed with another 10 mL cleavage solution. This 1-hour cleavage cycle process was repeated for two times, and the combined filtrate was concentrated by nitrogen ($N_2$) flow and lyophilized to afford 73 mg (51%) as the crude peptide. This crude peptide (8.0 mg) was purified by preparative reverse-phase HPLC using a gradient of 60-80% B buffer over 30 minutes, flow rate 16 mL/min, 265 nm UV detection. The peak with retention time of 22.13 minutes was collected and lyophilized to afford 5.90 mg of 4-8 as a white solid (74% yield based on the loaded crude material). Post-purification analytical LC-MS analysis showed a clean product spectrum with a base peak of 2905.09 [M+H] and 1453.41 $[M+2H]^+$.

The Fully Protected Unimolecular Pentavalent-MUC1 Glycopeptide:

To a stirred solution of 4-5 (2.70 mg, 0.48 μmol, 1 equiv) in $CH_2Cl_2$ (300 μL) was added trifluoroacetic acid (TFA, 30 μL) at room temperature. The resulting reaction mixture was stirred for 3 hours. 3 μL of aliquot of the reaction mixture was taken out and diluted with 30 μL of $CH_3CN$ for LC-MS analysis; C18 column, B: 50-70% over 30 minutes, retention time: 14.87 minutes, MS (ESI): $C_{239}H_{346}N_{14}O_{135}$, Calc. 5572.06, Observed 2788.94 $[M+2H]^{2+}$, 1859.80 $[M+3H]^{3+}$. The solvent was removed by nitrogen flow ($N_2$), and the crude material was used for the next step without further purification.

To a stirred solution of amine prepared above (theoretically 2.65 mg, 0.48 μmol, 1 equiv) and peptide (4-8) (1.66 mg, 0.57 μmol, 1.2 equiv) in DMSO (250 μL), a solution of HATU (0.90 mg, 2.38 μmol, 5 equiv) and HOBT (0.32 mg, 2.38 μmol, 5 equiv) in DMSO, and DIEA (0.83 μL, 4.76 μmol, 10 equiv) were added at room temperature. The resulting reaction mixture was stirred for 24 hours. 3 μL of aliquot of the reaction mixture was taken out and diluted with 30 μL of $CH_3CN$ for LC-MS analysis; C18 column, B: 55-75% over 30 minutes, retention time: 29.80 minutes, MS (ESI): $C_{382}H_{558}N_{40}O_{168}S_2$, Calc. 8457.5792, Observed 2117.46 $[M+4H]^{4+}$, 1694.00 $[M+5H]^{5+}$. The final reaction mixture was diluted with 1 mL of $CH_3CN/H_2O$ (1:1), and this crude mixture was purified by preparative reverse-phase HPLC using a gradient of 60-80% B buffer over 30 minutes, flow rate 16 mL/min, 264 nm UV detection. The peak with retention time of 26.50 minutes was collected and lyophilized to afford 2.90 mg as a white solid (72% yield over 2 steps). Post-purification analytical LC/ESI MS analysis showed a clean product spectrum with a base peak of 2117.46 $[M+4H]^{4+}$, 1693.87 $[M+5H]^{5+}$.

3. Preparation of the Unimolecular Pentavalent-MUC1 Glycopeptide (4-9)

The Unimolecular Pentavalent-MUC1 Glycopeptide (4-9):

The fully protected unimolecular pentavalent-MUC1 glycopeptide (1.1 mg, 0.14 μmol) was treated with a cleavage solution (150 μL, $TFA/H_2O/PhOH/Et_3SiH=8.75:0.5:0.5:0.25$). The resulting mixture was stirred for 3.5 hours at room temperature. 3 μL of aliquot of the reaction mixture was taken out and diluted with 30 μL of $CH_3CN$ for LC-MS analysis; C18 column, B: 50-80% over 30 minutes, retention time: 9.13 minutes, MS (ESI): $C_{326}H_{480}N_{40}O_{168}S$, Calc. 7627.0120, Observed 1909.03 $[M+4H]^{4+}$. The reaction mixture was dried by nitrogen flow ($N_2$), and rinsed with $Et_2O$, and dried in vacuo. The crude material was used for the next step without further purification.

To a stirred solution of the glycopeptide prepared above in MeOH (120 μL), 0.3 M aqueous NaOH (60 μL) solution at room temperature. The resulting reaction mixture was stirred for 24 hours, which was then acidified with 1 M aqueous HCl solution until the pH of the reaction mixture reached 4-5.3 μL of aliquot of the reaction mixture was taken out and diluted with 30 μL of $CH_3CN$ for LC-MS analysis; C18 column, B: 01-10% over 30 minutes, retention time: 35.85 minutes, MS (ESI): $C_{234}H_{386}N_{40}O_{120}S$, Calc. 5708.5053, Observed 1905.54 $[M+3H]^{3+}$, 1429.18 $[M+4H]^{4+}$. The final reaction mixture was diluted with 1 mL of $CH_3CN/H_2O$ (1:1), and this crude mixture was purified by preparative reverse-phase HPLC using a gradient of 1-10% (5 minutes), 20-50% (30 minutes) B buffer, flow rate 16 mL/min, 220 nm UV detection. The peak with retention time of 12.10 minutes was collected and lyophilized to afford 0.5 mg of 4-9 as a white solid (60% yield over 2 steps). Post-purification analytical LC/ESI MS analysis showed a clean product spectrum with a base peak of 1905.02 $[M+3H]^{3+}$.

Example 5

Figure 26:
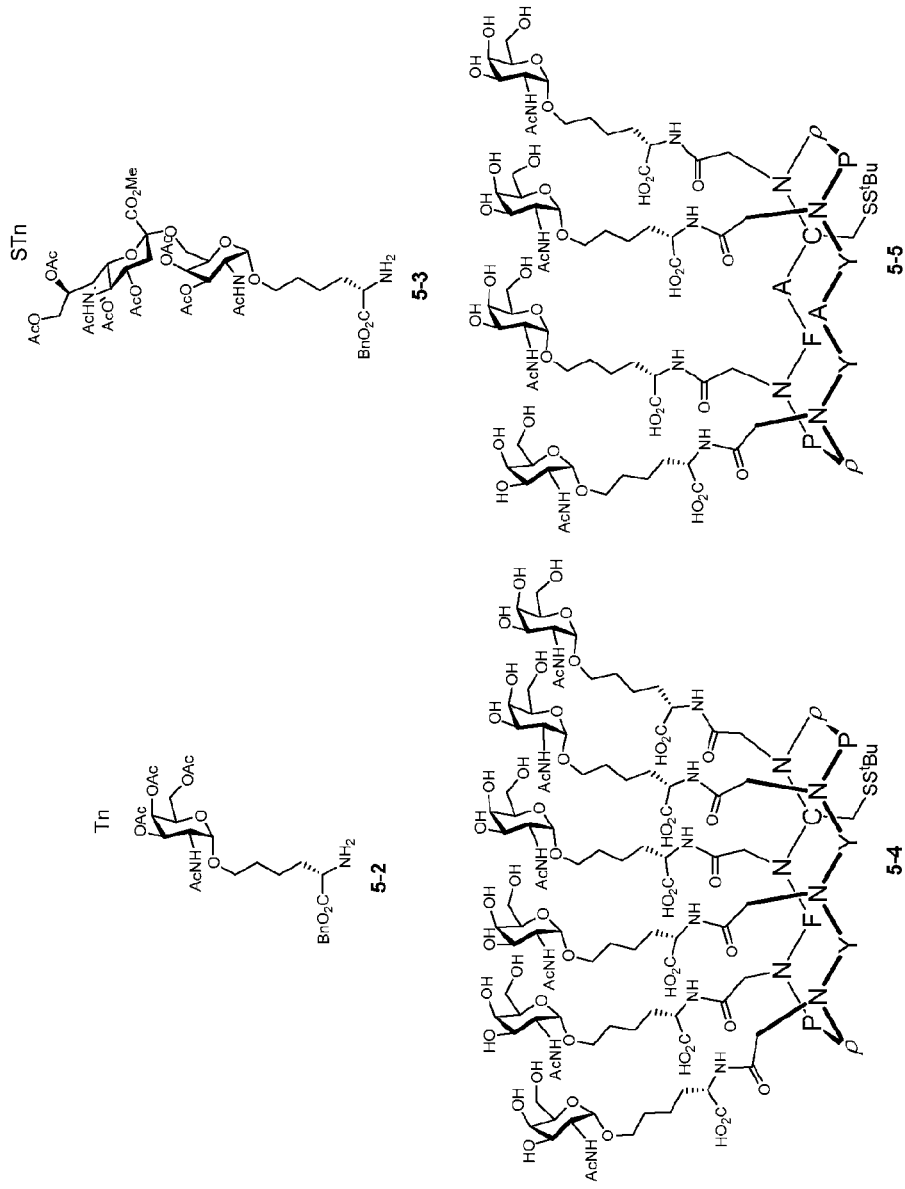
FIGS. 26-27 depict protected glycosylamino acids and clustered antigens.
Figure 27:
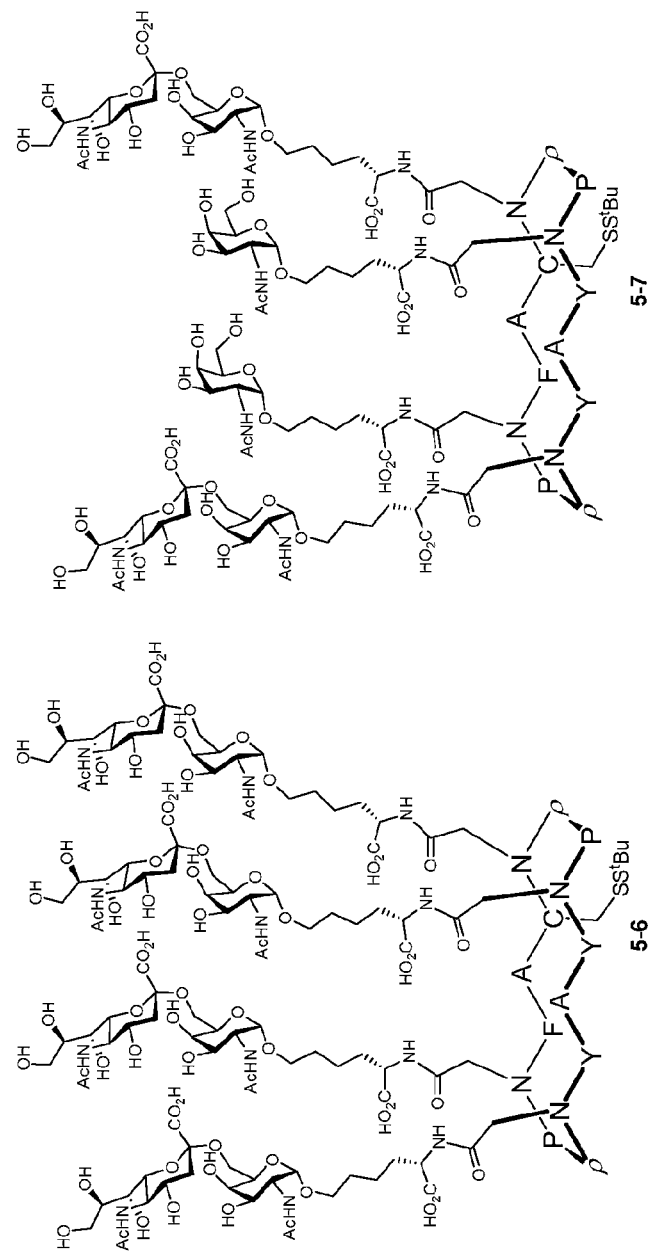

This Example demonstrates the assembly of multiantigenic constructs comprising a cyclic peptide that displays multiple carbohydrate determinants in a clustered fashion. In an effort to identify an exemplary presentation of the carbohydrates on the cyclic peptide scaffold, we chose as our targets the four constructs shown in FIGS. 26 and 27. Structures 5-4 and 5-5 incorporate six and four replicate copies of the Tn antigen, respectively, and construct 5-6 presents four copies of the STn disaccharide. We also sought to prepare a multiantigenic construct, 5-7, incorporating both the Tn and STn antigens.

The protected O-linked glycosylamino acids 5-2 and 5-3 (FIG. 26) were prepared from the L-hydroxynorleucine benzyl ester, according to our previously established protocol (Keding, S. J.; Endo, A.; Danishefsky, S. J. *Tetrahedron* 2003, 59, 7023-7031). These Tn and STn "cassettes," which we originally employed in earlier approaches to the synthesis of clustered antigens, serve as useful building blocks for glycal assembly. In this system, the N-termini of both the Tn and STn cassettes serve as handles for coupling to the peptide scaffold, and the remaining carboxyl function may provide a handle for further elaboration (i.e., as T-helper or additional B-epitope attachments).

Figure 28:
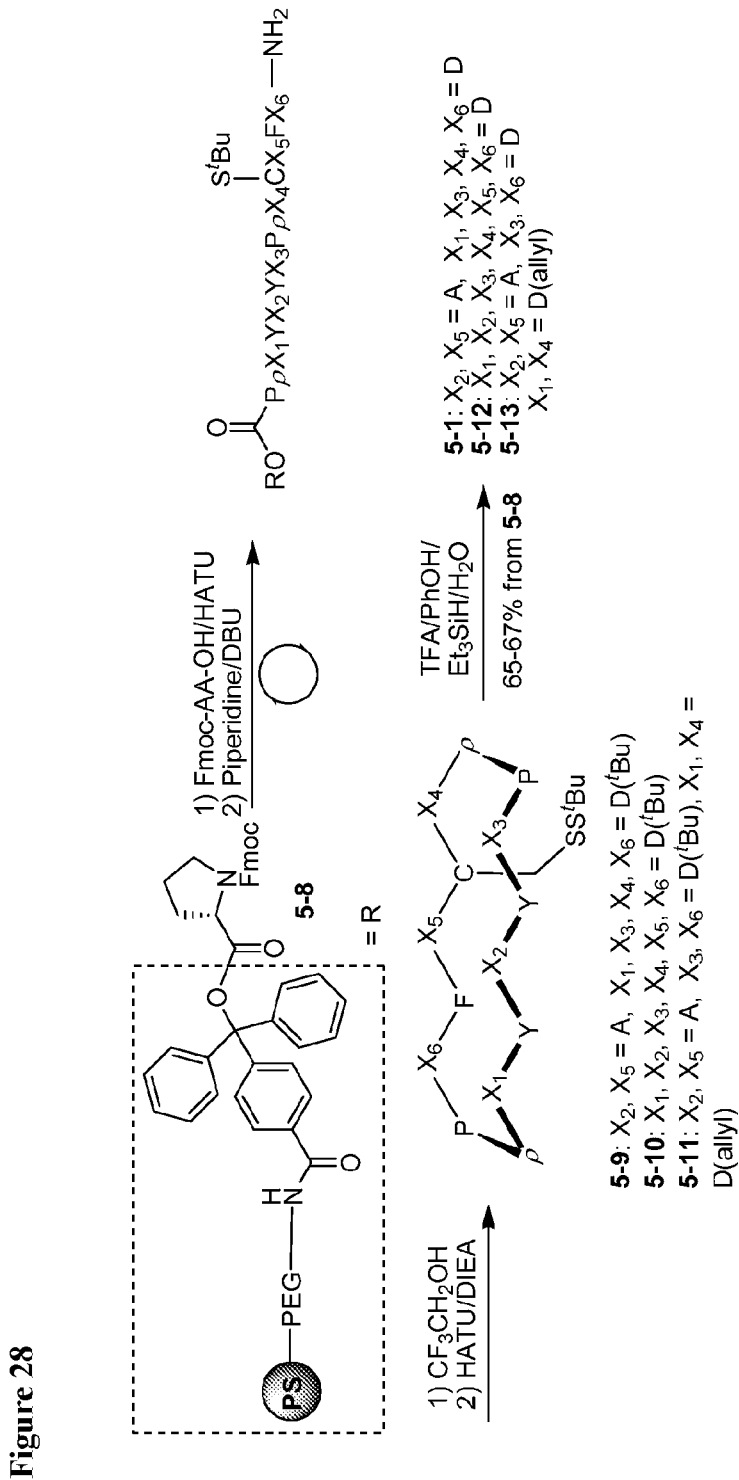
FIG. 28 depicts a synthesis of cyclic peptide scaffolds.

Cyclic peptides 5-9, 5-10, and 5-11 (containing 4 or 6 aspartate residues) were prepared in parallel through automated solid-phase synthesis from the prolinated trityl resin 5-8 (FIG. 28). Cleavage from the resin, macrocyclization (the macrocyclization was essentially instantaneous at room temperature, indicating that cross-strand hydrogen bonding may preorganize the acyclic peptide for cyclization. Moreover, downfield $^1H$ NMR chemical shifts of selected NH resonances, slow $D_2O$ exchange times, and the temperature profile of these chemical shifts provided preliminary evidence of the desired β-sheet character of the peptide scaffold), and tert-butyl deprotection of the aspartate and tyrosine residues furnished 5-1, 5-12, and 5-13 in good overall yields.

Figure 29A:
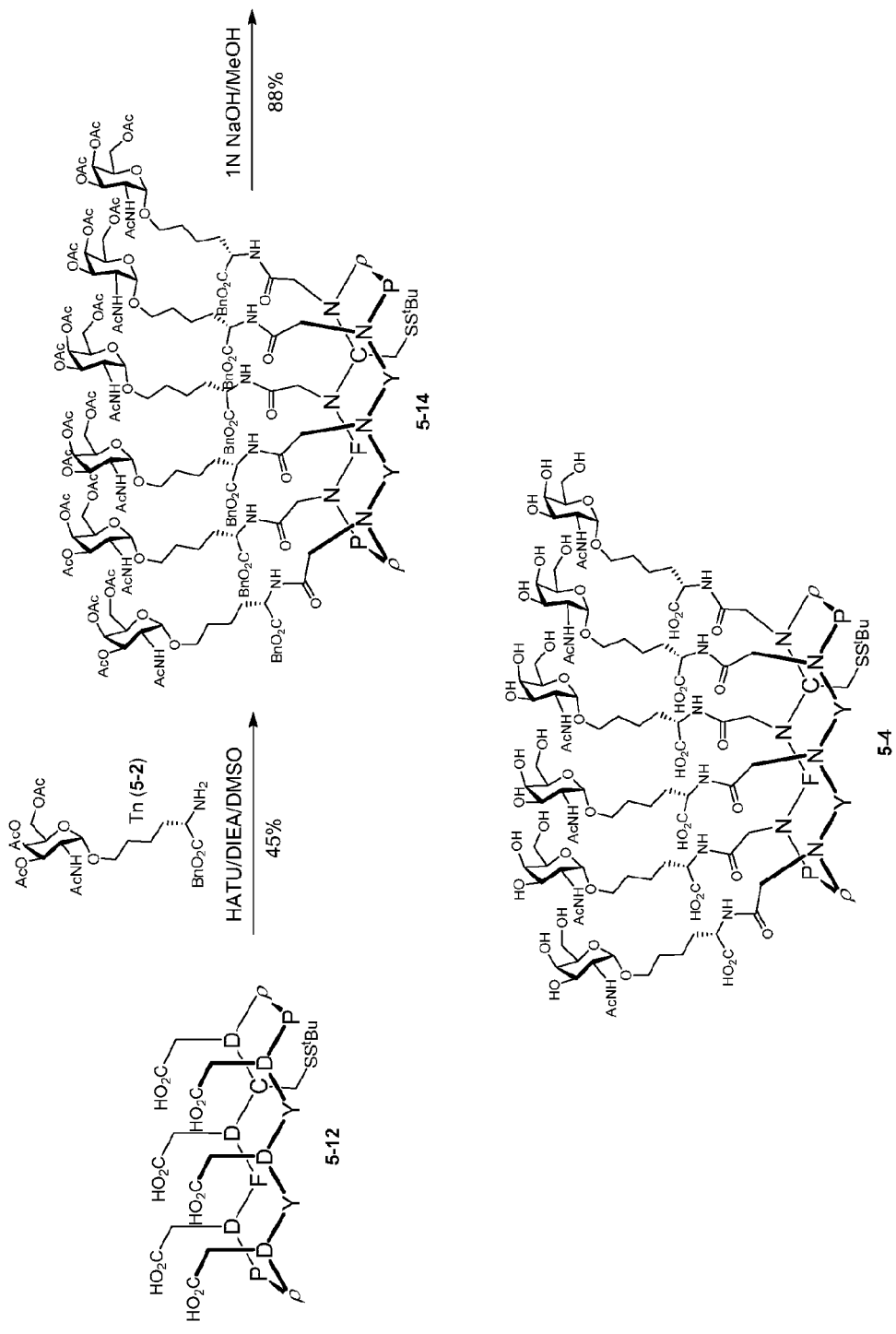
FIGS. 29a-c depict a synthesis of clustered glycopeptides.

With the components of the target structures in hand, we directed our efforts toward the covalent attachment of the carbohydrate antigens to the scaffolds. The Lansbury aspartylation reaction (Cohen-Anisfeld, S. T.; Lansbury, P. T. *J. Am. Chem. Soc.* 1993, 115, 10531-10537) is a useful tool in glycopeptide synthesis. However, the standard Lansbury aspartylation protocol employs a glycosidic amine as the coupling partner of activated aspartic acid, rather than the primary amino acid nitrogen which could be used by our strategy. In considering the application of this protocol to our own system, there was concern that attenuated nucleophilicity of the amine might result in the emergence of nonproductive pathways. For example, the competing, relatively facile intramolecular cyclization of the peptide itself might lead to the formation of aspartimide (Bodanszky, M.; Natarajan, S. *J. Org. Chem.* 1975, 40, 2495-2499; Bodanszky, M.; Kwei, J. Z. *Int. J. Pept. Protein Res.* 1978, 12, 69-74; Tam, J. P.; Riemen, M. W.; Merrifield, R. B. *Pept. Res.* 1988, 1, 6-18; Mergler, M.; Dick, F.; Sax, B.; Weiler, P.; Vorherr, T. *J. Peptide Sci.* 2003, 9, 36-46; Lauer, J. L.; Fields, C. G.; Fields, G. B. *Lett. Peptide Sci.* 1994, 1, 197-205). Indeed, this side reaction was observed in the coupling reaction of peptide 5-12 with glycosylamino acid 5-2. Under standard reaction conditions (HOAt, HATU, DIEA/DMSO), formation of the undesired aspartimide was predominant, with little indication of the requisite hexavalent product, 5-14. Upon close investigation, it was found that the HOAt, which is generally used as an activation additive, along with HATU, plays a significant role in promoting undesired aspartimide formation. Fortunately, activation of the aspartic acids with HATU alone in the presence of DIEA in DMSO effectively minimized aspartimide formation, and consequently allowed high yielding conversion to the desired hexavalent product, 5-14 (FIG. 29a).

Figure 29B:
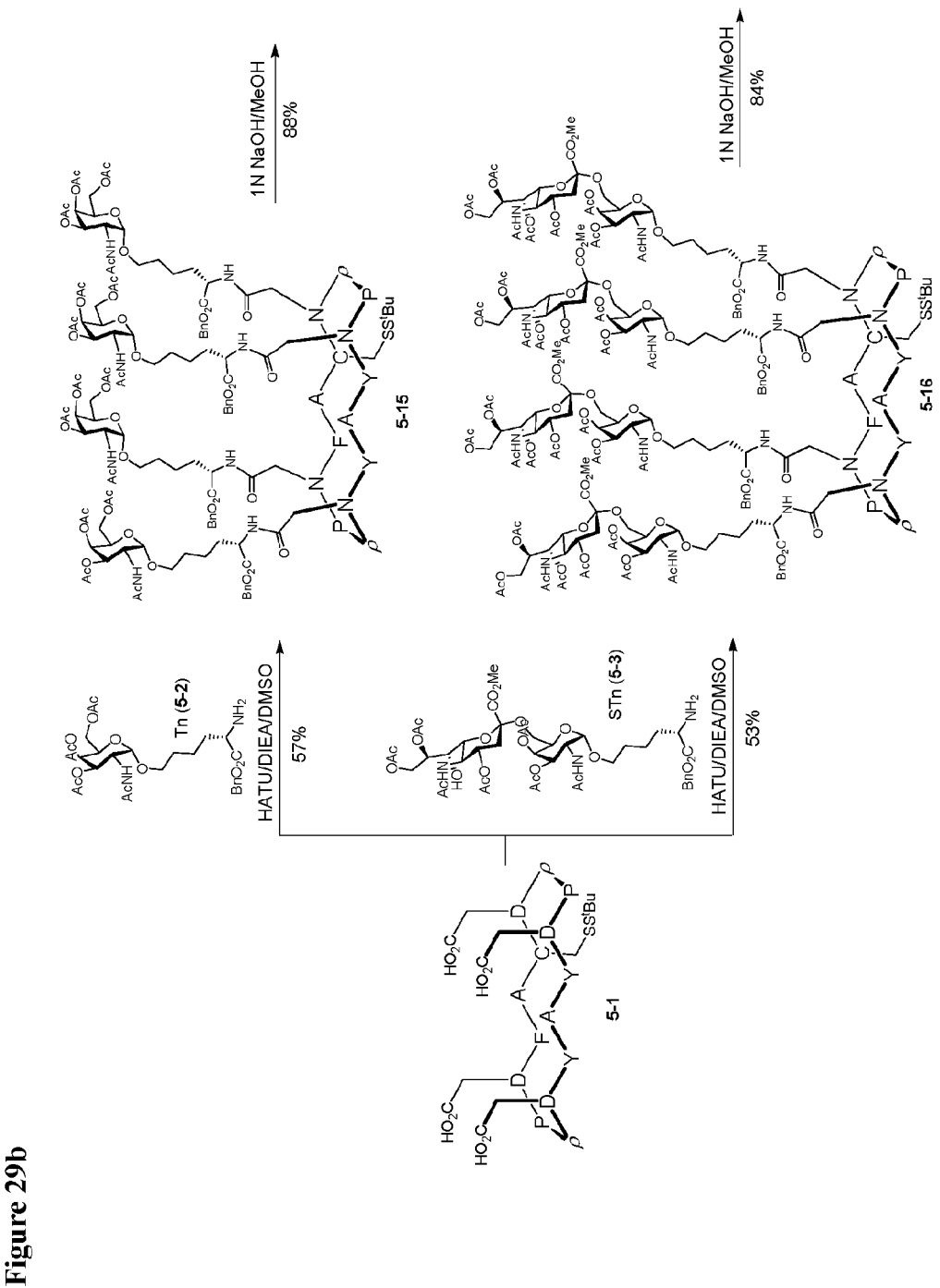
Figure 29C:
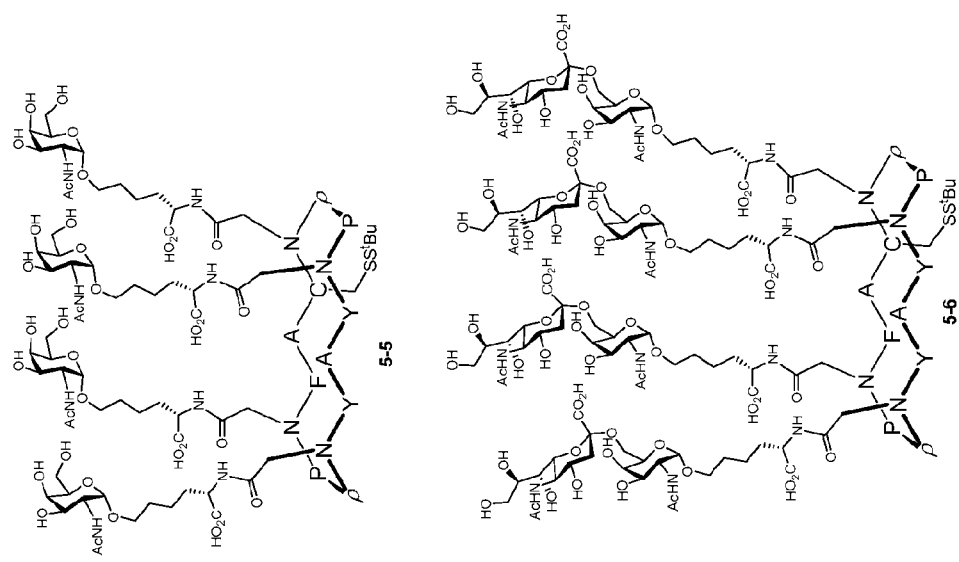

Having identified useful coupling conditions, we were able to successfully assemble the tetravalent constructs 5-15 and 5-16 in a similar fashion. These relatively less congested glycopeptides exhibit different spatial arrangements, yet they still express the epitopes in highly clustered fashions. Following global deprotection, the highly clustered antigens 5-4, 5-5, and 5-6 were in hand (FIGS. 29a-c).

We next turned our attention to the synthesis of the unimolecular multiantigenic construct, 5-7 (Ragupathi, G.; Koide, F.; Livingston, P. O.; Cho, Y. S.; Endo, A.; Wan, Q.; Spassova, M. K.; Keding, S. J.; Allen, J.; Ouerfelli, O.; Wilson, R. M.; Danishefsky, S. J. *J. Am. Chem. Soc.* 2006, 128, 2715-2725; Allen, J. R.; Harris, C. R.; Danishefsky, S. J. *J. Am. Chem. Soc.* 2001, 123, 1890-1897; Ragupathi, G.; Coltart, D. M.; Williams, L. J.; Koide, F.; Kagan, E.; Allen, J.; Harris, C.; Glunz, P. W.; Livingston, P. O.; Danishefsky, S. J. *Proc. Natl. Acad. Sci. U.S.A.* 2002, 99, 13699-13704; Keding, S. J.; Danishefsky, S. J. *Proc. Natl. Acad. Sci. U.S.A.* 2004, 101, 11937-11942), wherein both the Tn and STn carbohydrate antigens are displayed on the peptidic backbone. This type of multivalent construct is intended to reflect the actual degree of carbohydrate heterogeneity associated with most cancers (Zhang, S. L.; Cordon-Cardo, C.; Zhang, H. S.; Reuter, V. E.; Adluri, S.; Hamilton, W. B.; Lloyd, K. O.; Livingston, P. O. *Int. J. Cancer* 1997, 73, 42-49; Zhang, S. L.; Zhang, H. S.; Cordon-Cardo, C.; Reuter, V. E.; Singhal, A. K.; Lloyd, K. O.; Livingston, P. O. *Int. J. Cancer* 1997, 73, 50-56). There is a significant degree of variation in the types of carbohydrates over-expressed on the tumor cell surface, even within a particular cancer type. By combining clusters of both the Tn and STn antigens within a single cyclic peptide scaffold, we would hope to induce a more robust immune response, in which the antibodies raised would target a greater proportion of transformed tumor cells. In a practical sense, the realization of a unimolecular multiantigenic construct relies on careful strategic considerations in the peptide scaffold design.

Figure 30A:
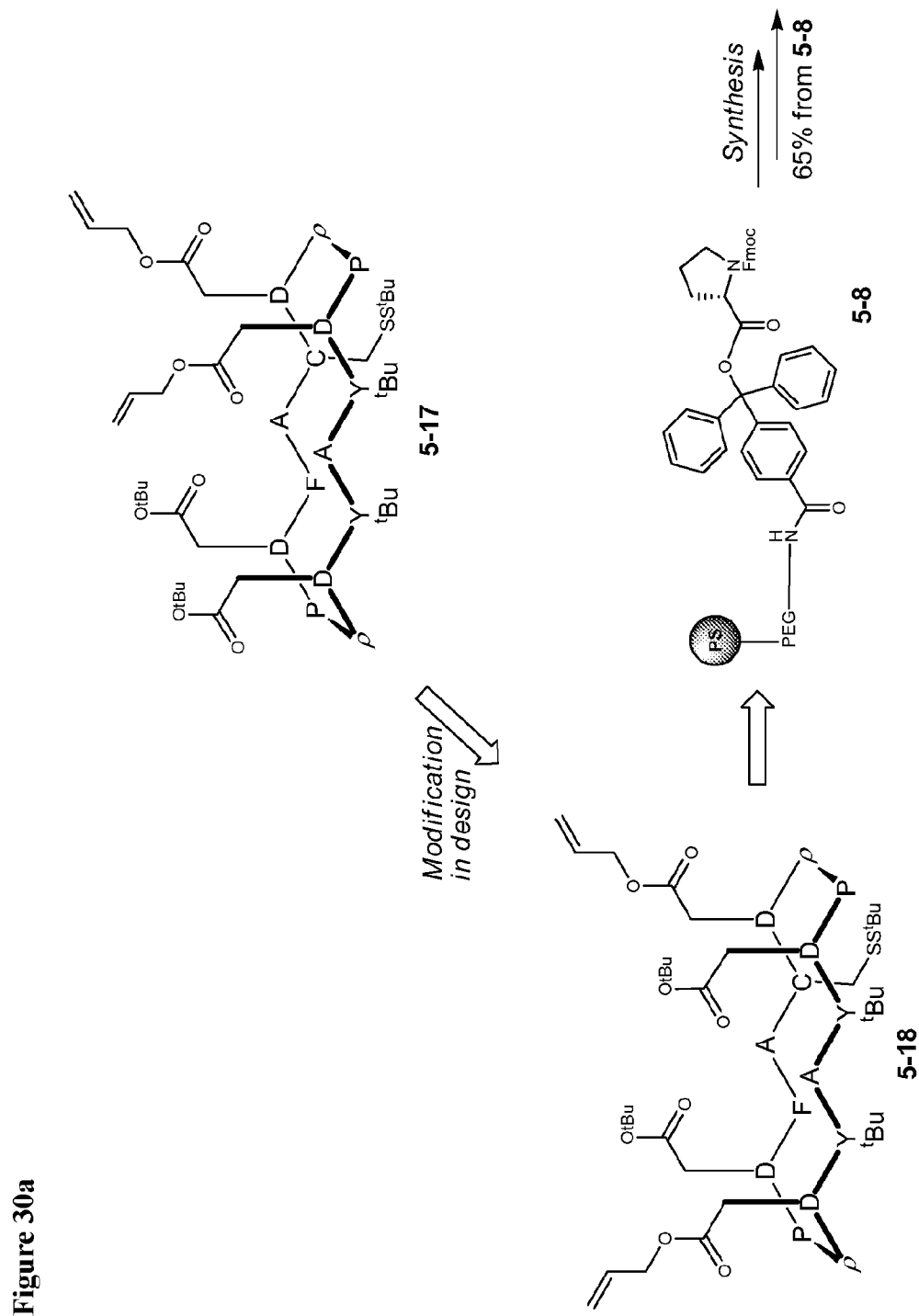
FIGS. 30a-b depict a cyclic peptide scaffold for multiantigen attachments.
Figure 30B:
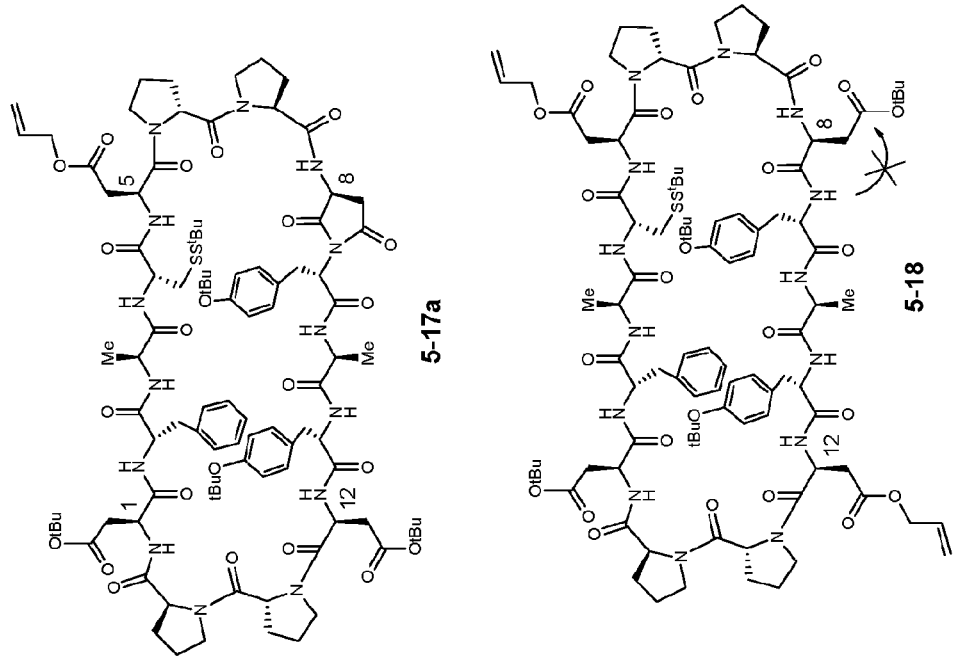

Initial efforts toward cyclic peptide 5-17 were unsuccessful, due to complications arising from aspartimide formation at position 8, leading to the undesired product, 5-17a (FIGS. 30a-b). Unlike the bulky Asp-β-tert-butyl esters, the less hindered Asp-β-allyl ester is susceptible to undesired aspartimide formation, arising from intramolecular nucleophilic attack by the amide nitrogen at the aspartyl C-terminus (Mergler, M; Dick, F.; Sax, B.; Weiler, P.; Vorherr, T. *Peptide Sci.* 2003, 9, 36-46). However, aspartimide formation of the Asp-β-allyl ester at position 5 was impeded by the presence of proline in position 6. Thus, we made the design decision of transposing the -β-allyl and -β-tert-butyl protecting groups of positions 8 and 12. Indeed, no evidence of aspartimide formation was found in the synthesis of cyclic peptide 5-18.

Figure 31A:
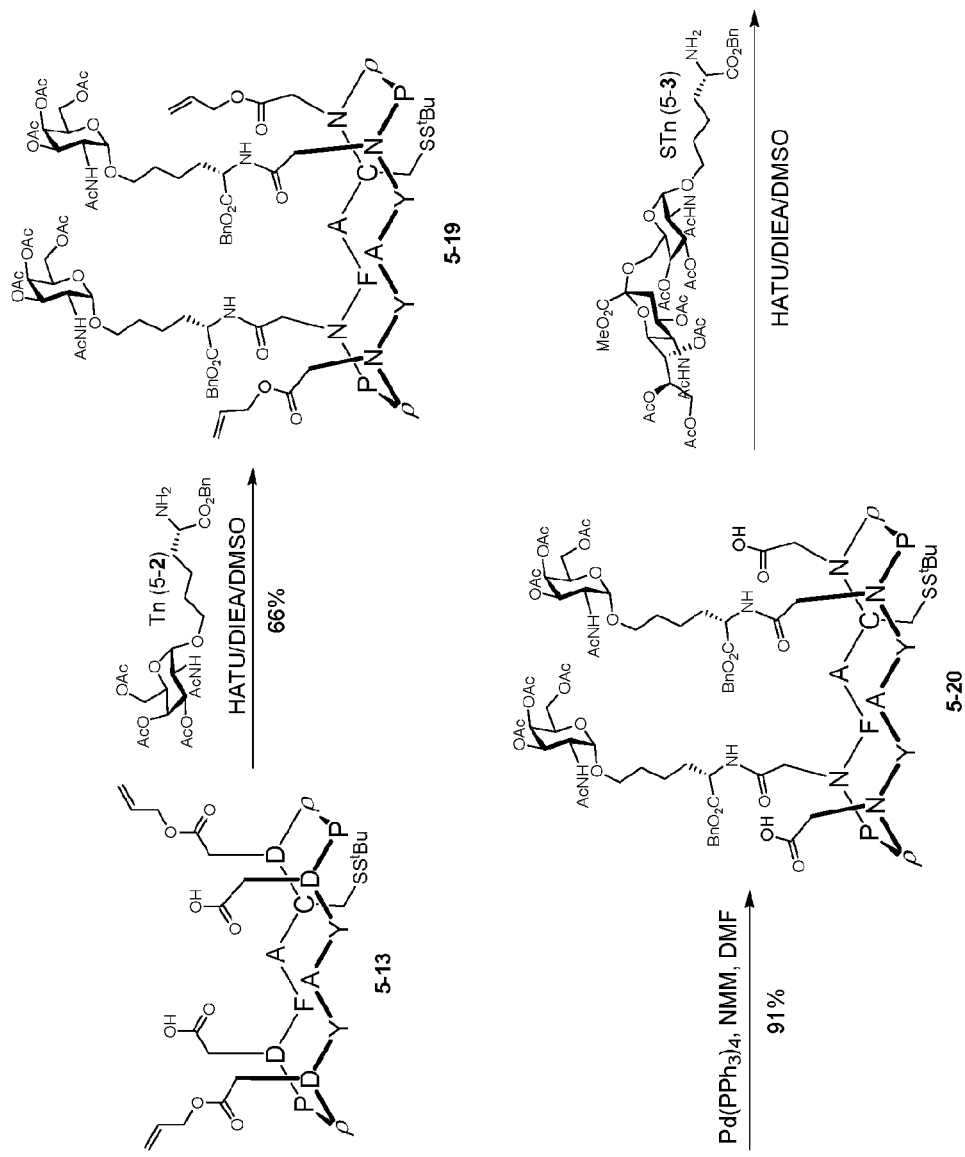
FIGS. 31a-b depict a synthesis of unimolecular multiantigenic glycopeptide 5-7.
Figure 31B:
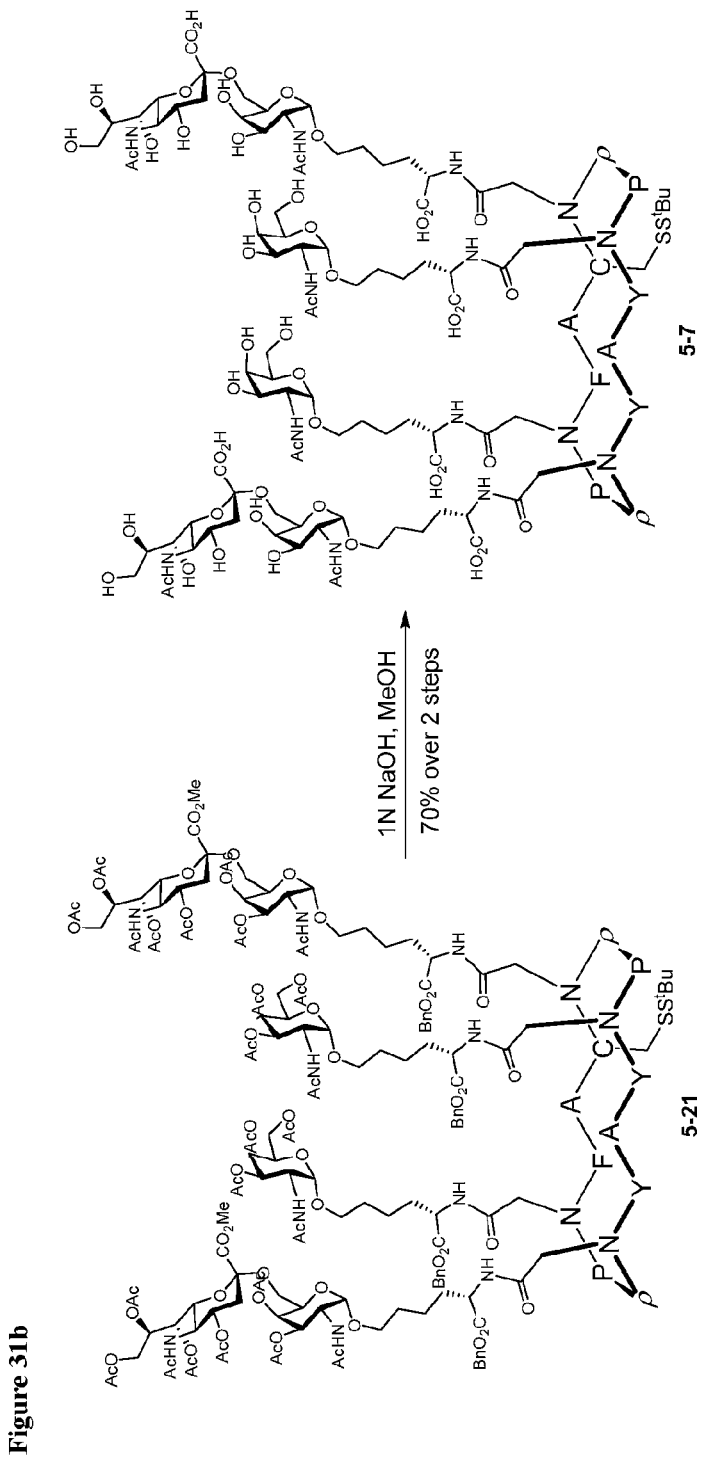
Figure 32A:
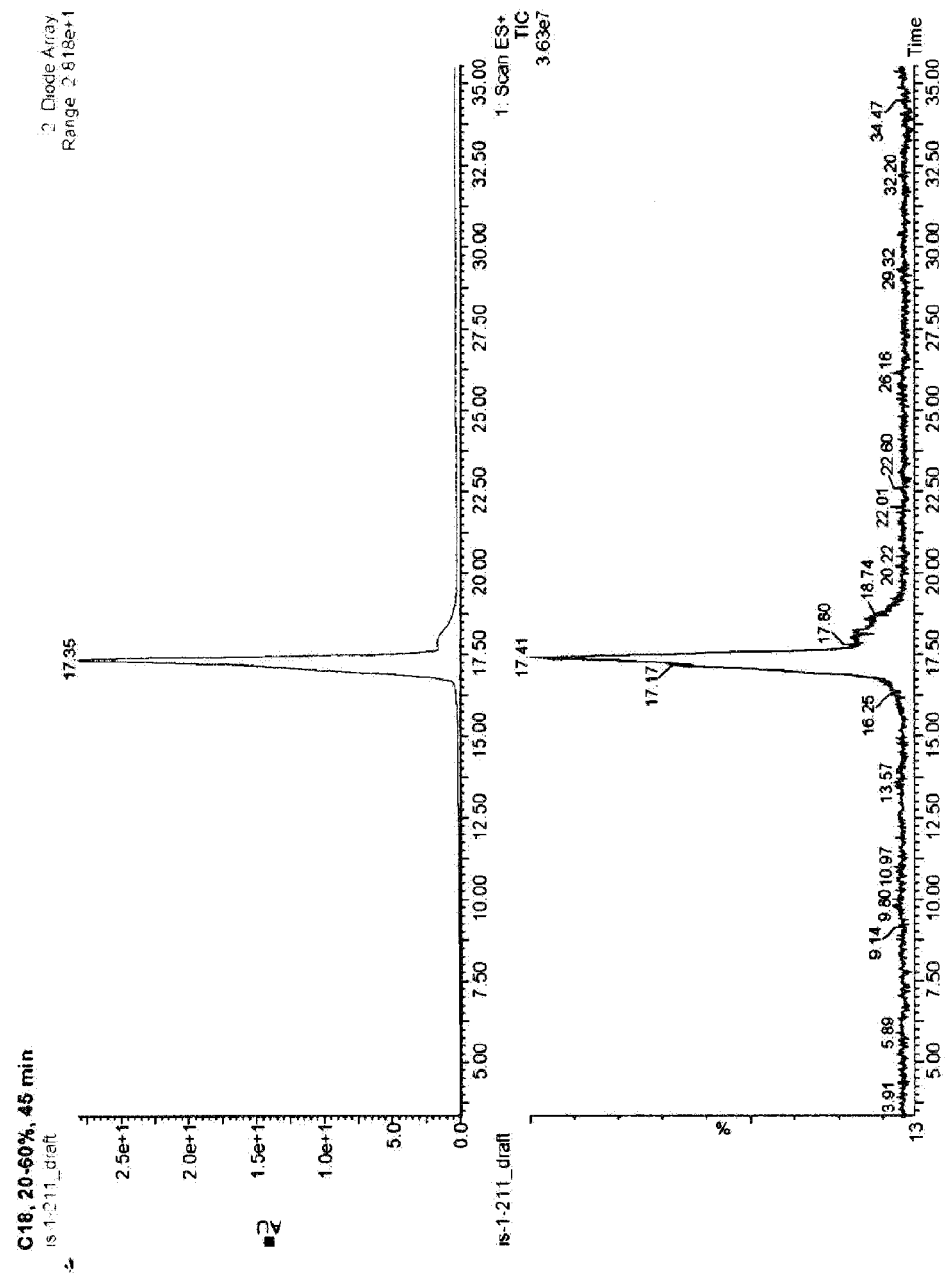
Figure 33A:
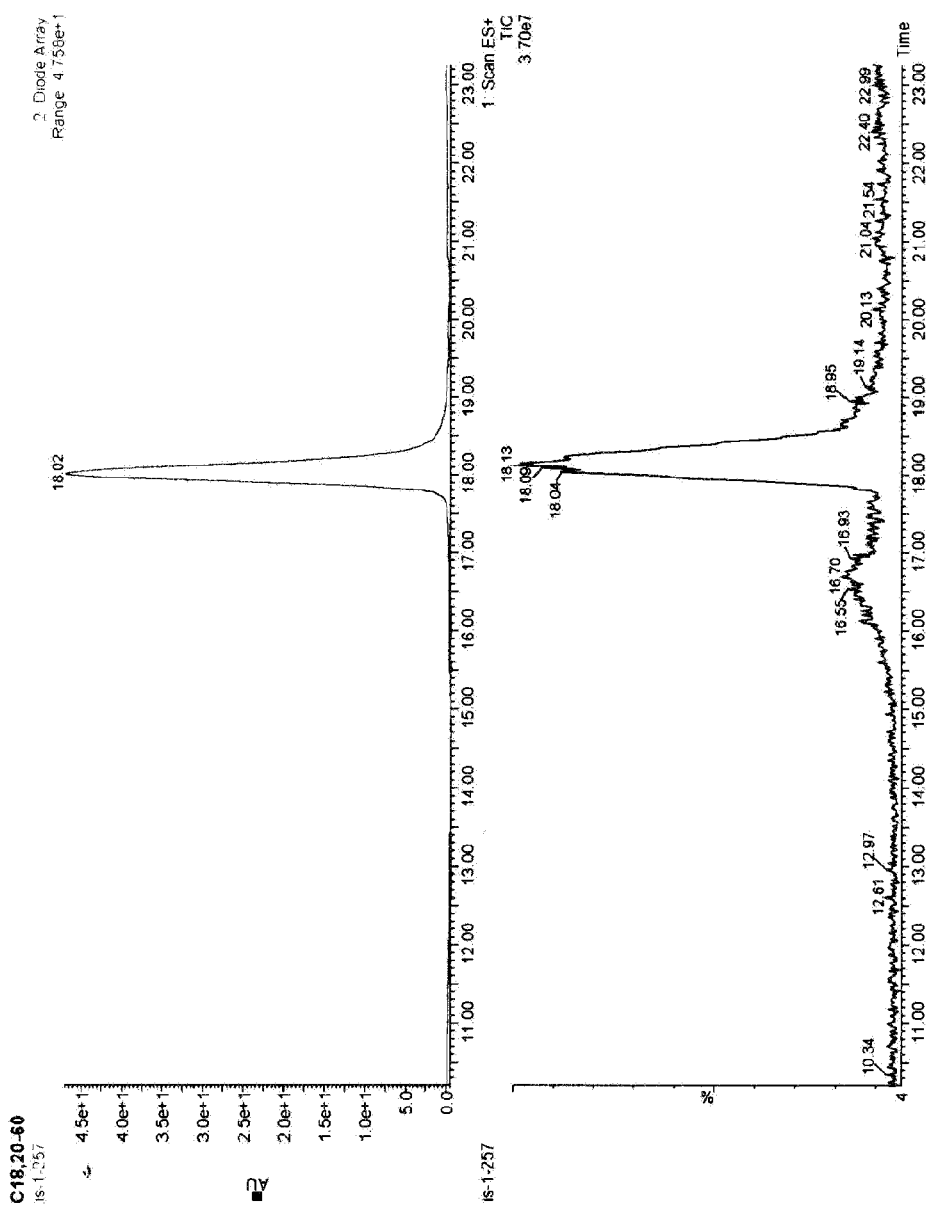
FIGS. 33a-b depict LCMS characterization data for purified peptide 5-12.
Figure 33B:
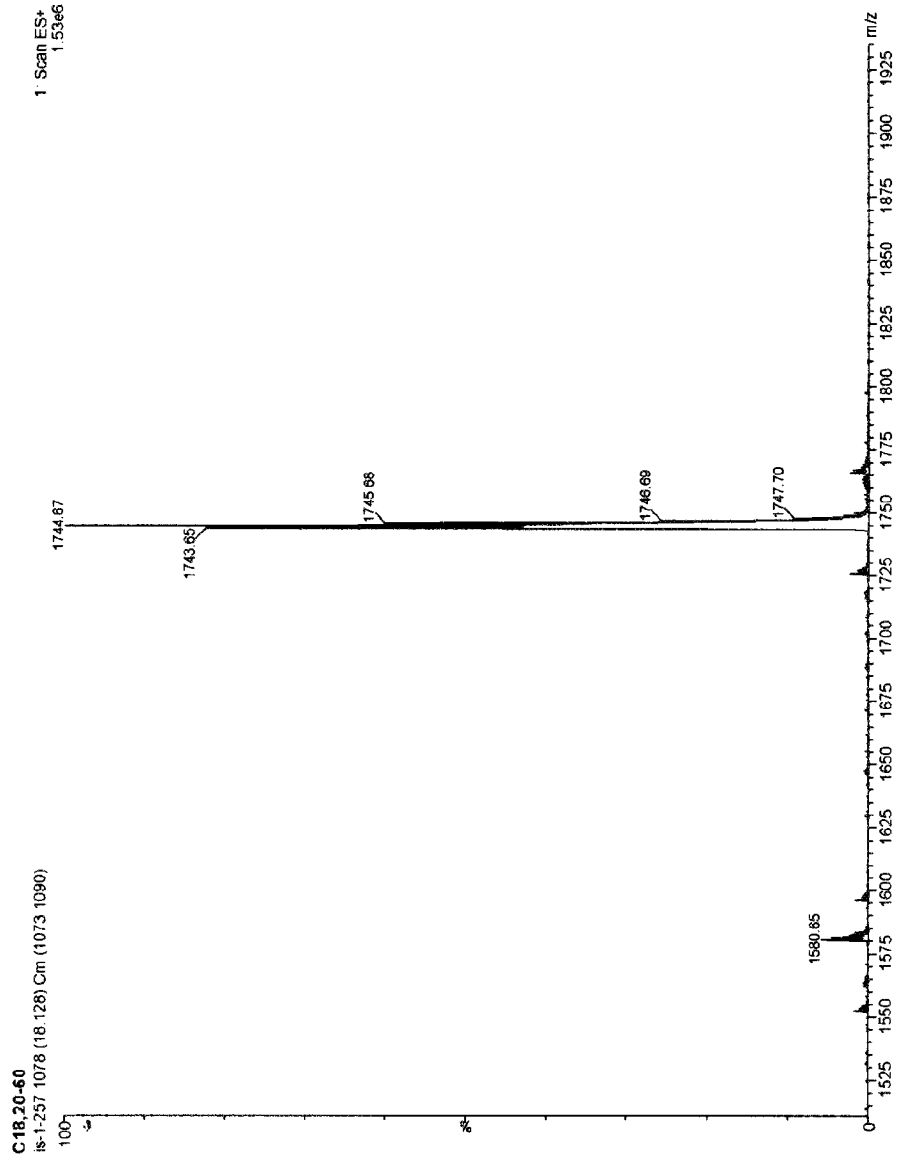
Figure 34A:
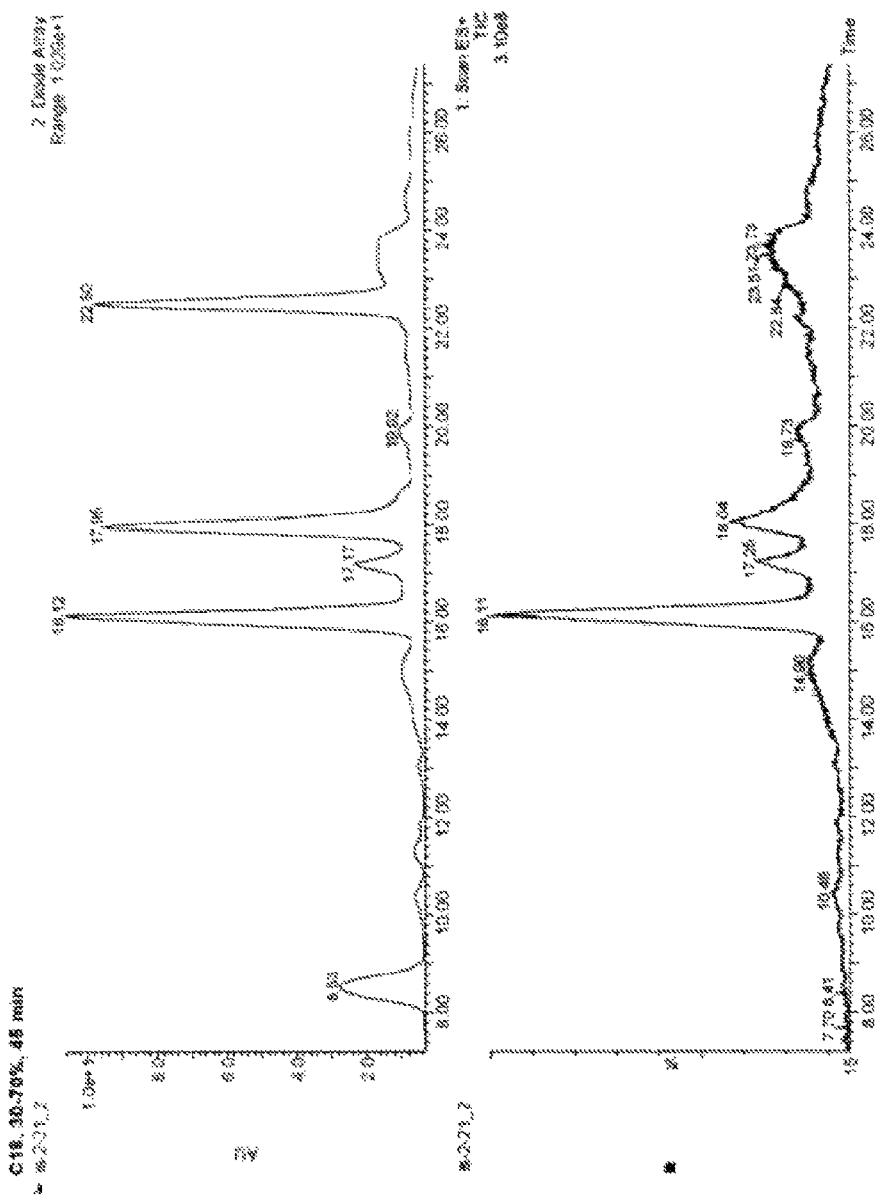
FIGS. 34a-c depict LCMS characterization data for compound 5-13.
Figure 34B:
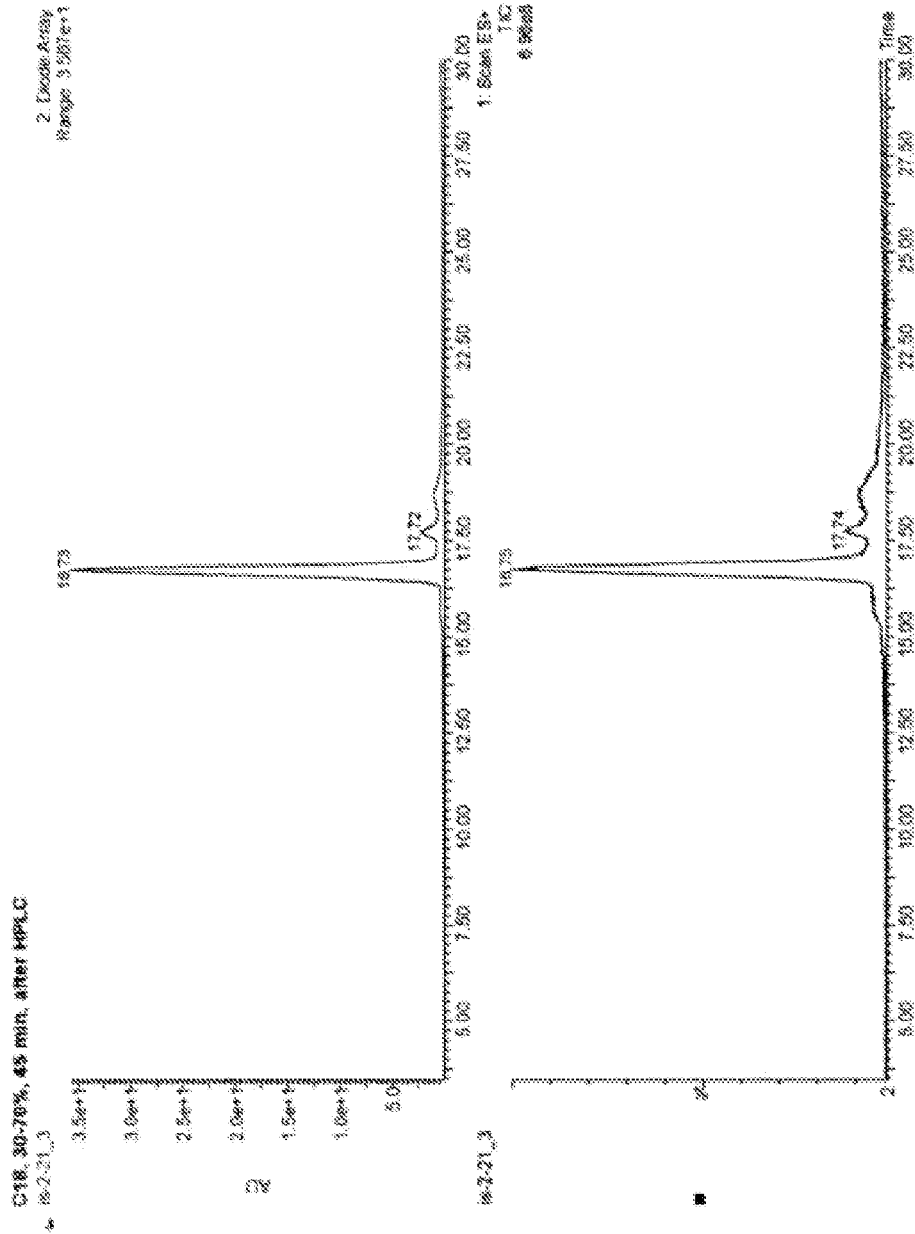
Figure 34C:
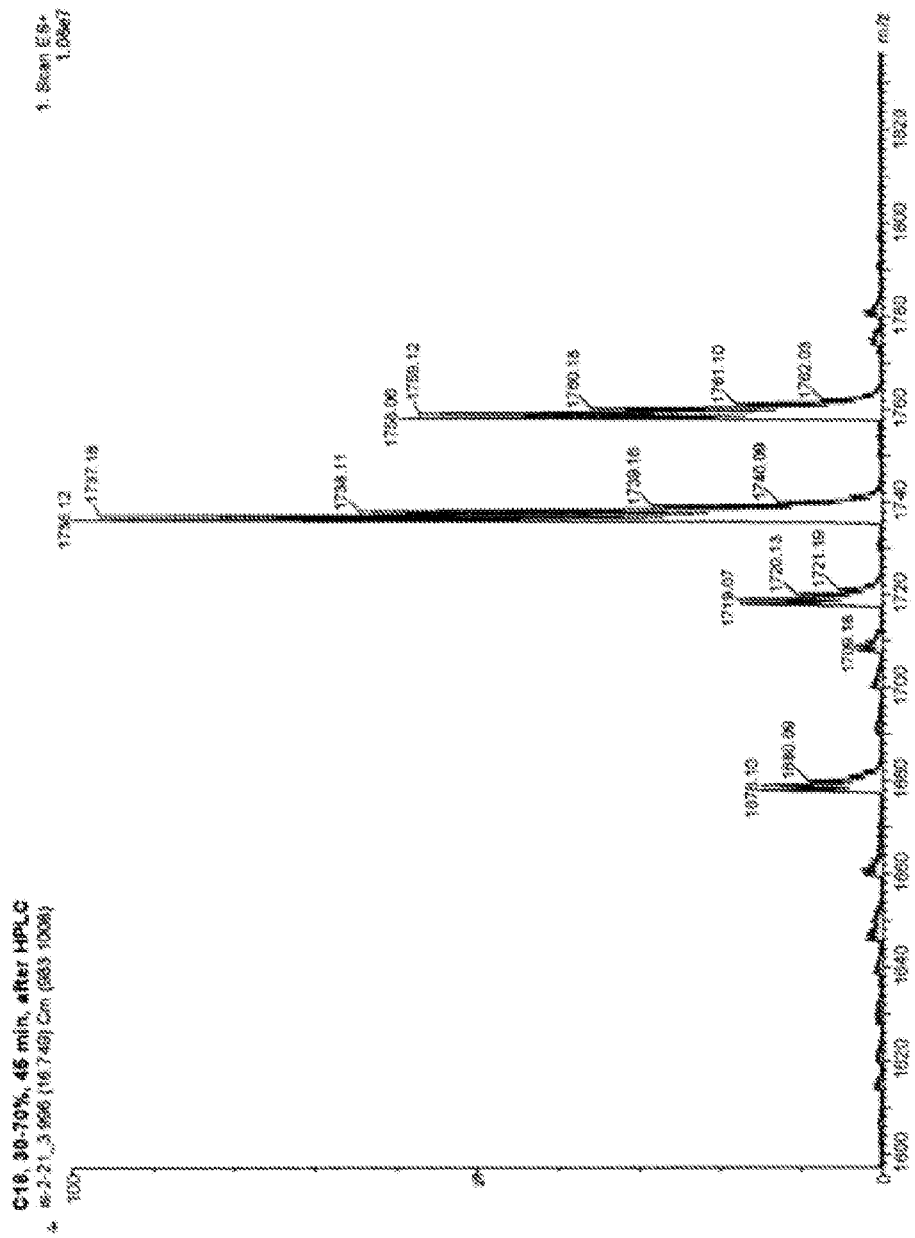
Figure 35A:
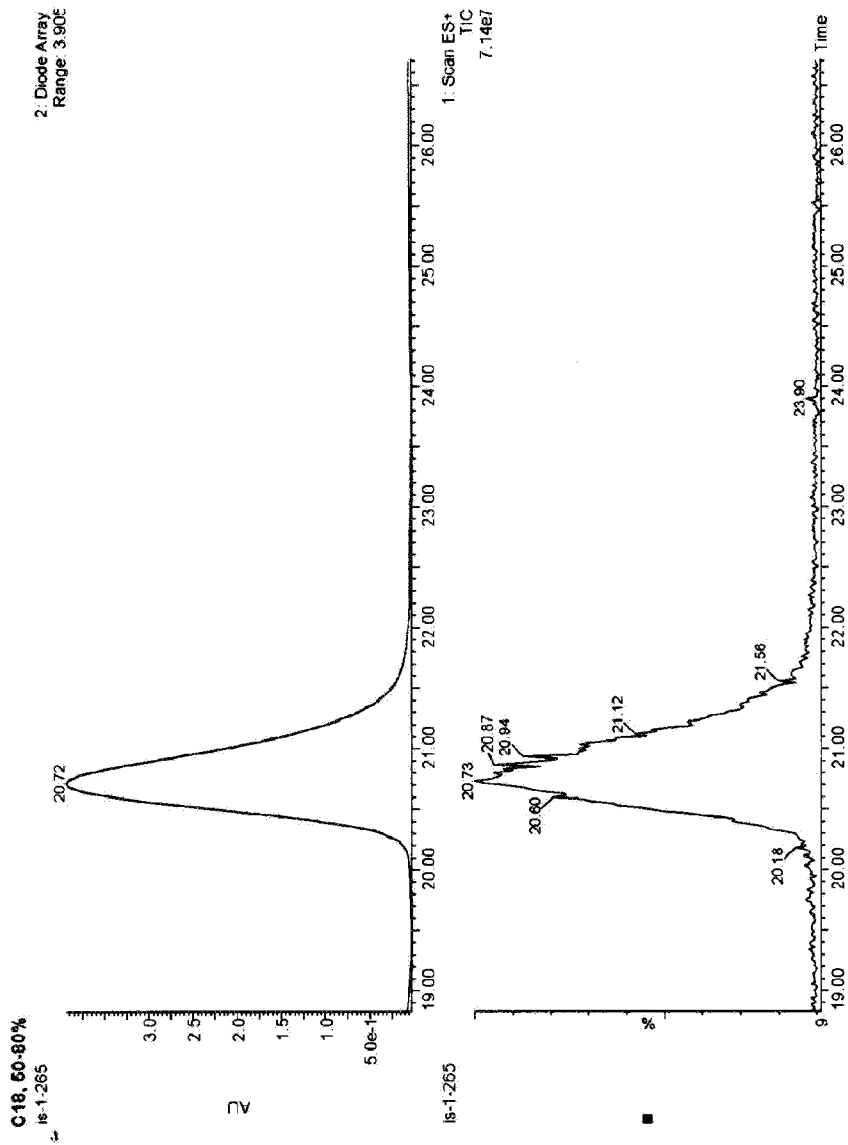
FIGS. 35a-c depict LCMS characterization data for purified glycopeptide 5-14.
Figure 35B:
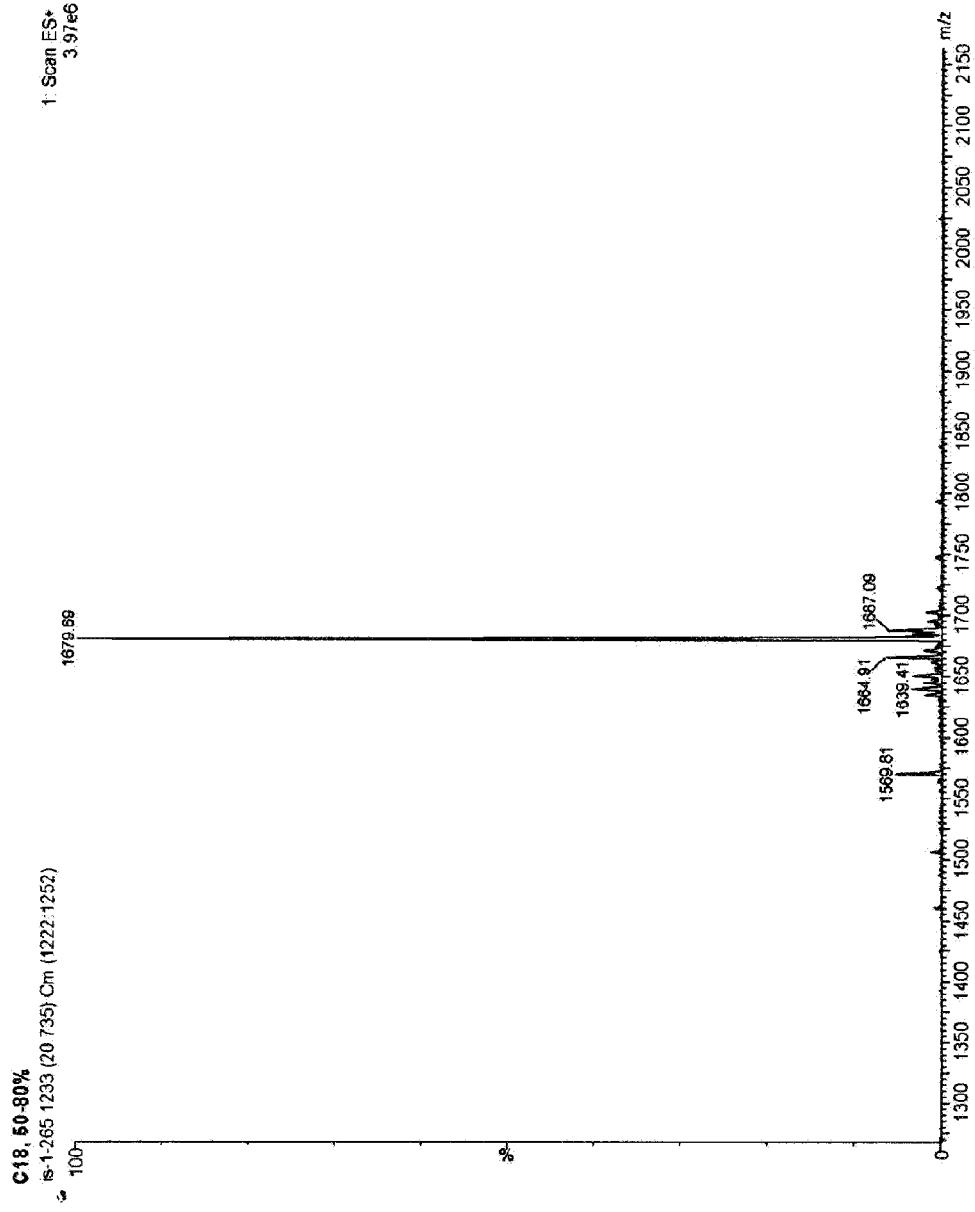
Figure 35C:
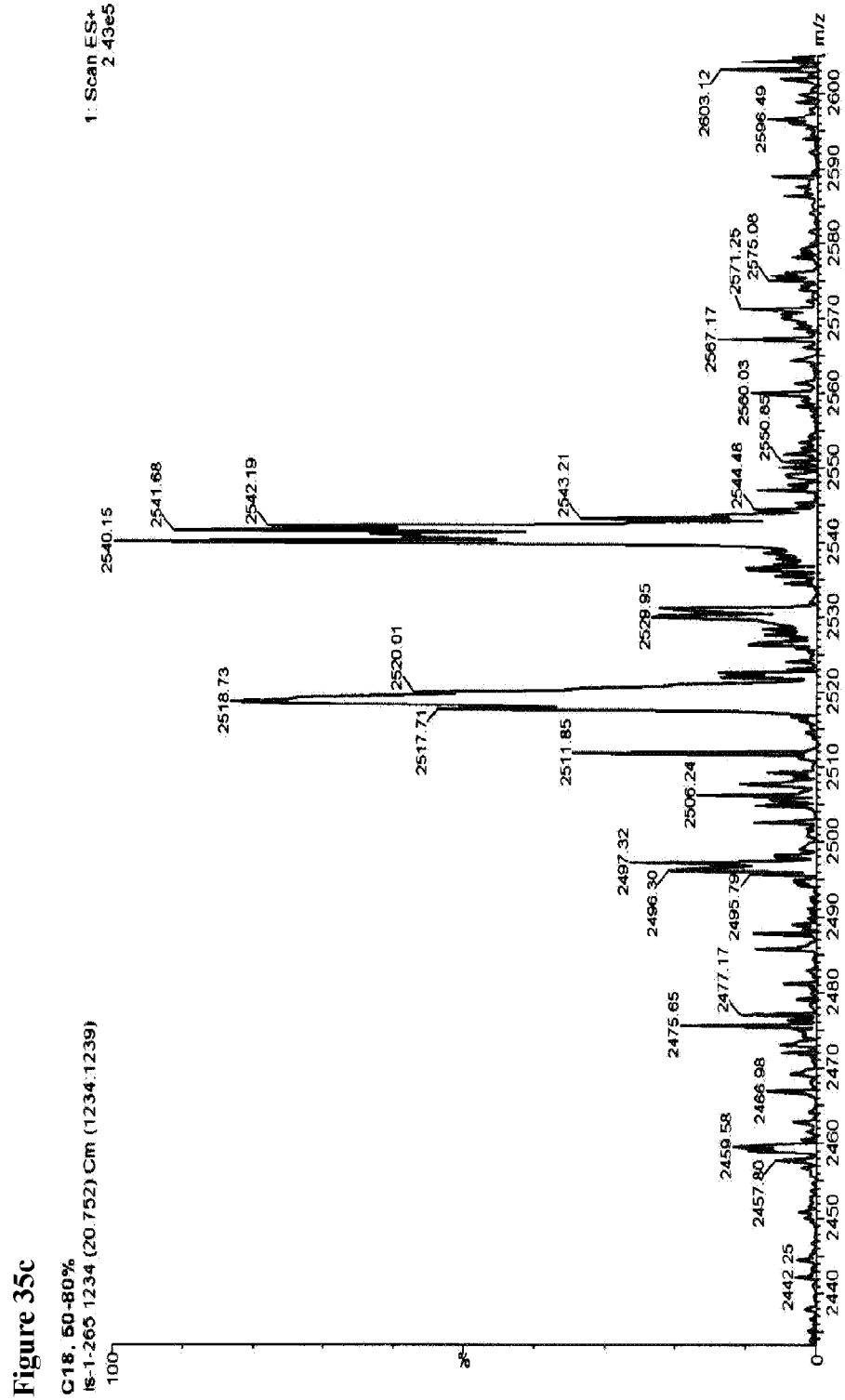
Figure 36A:
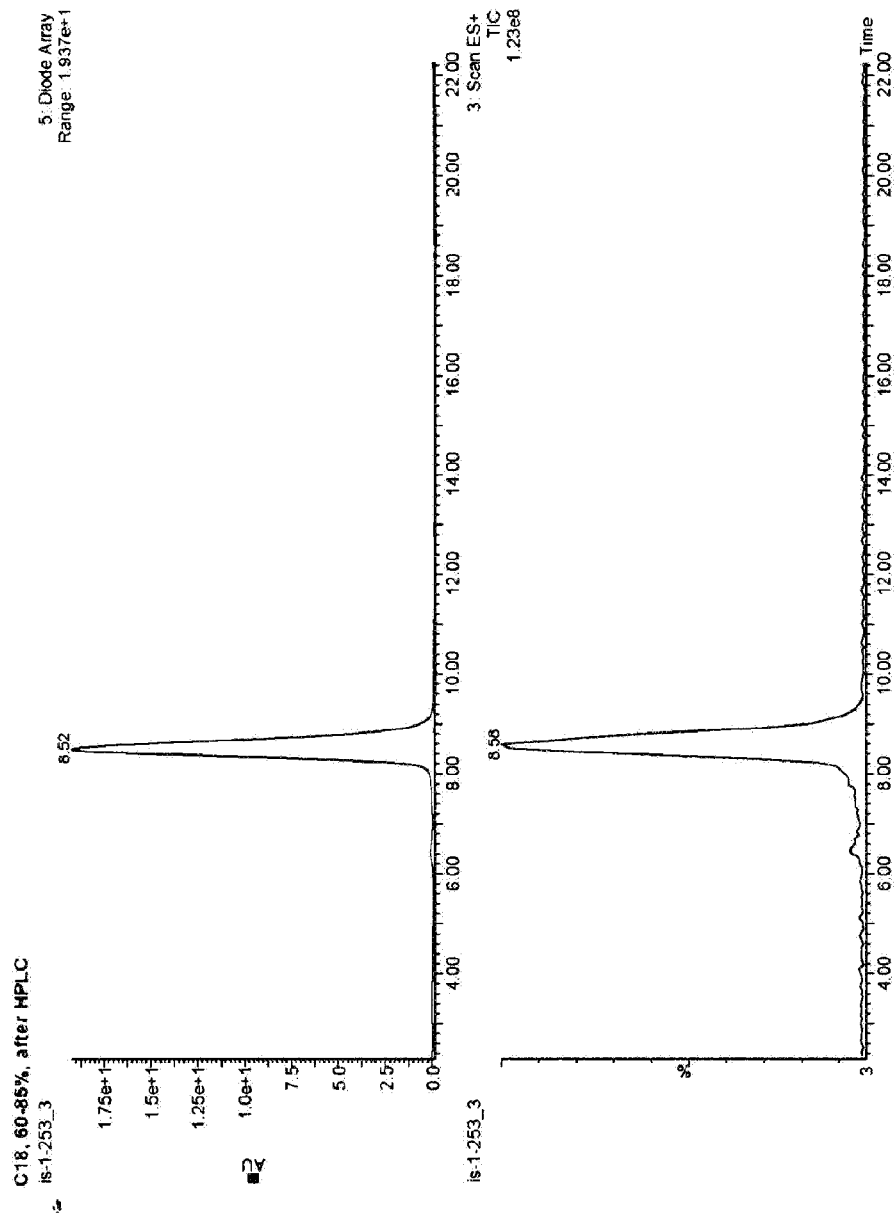
FIGS. 36*a-c* depict LCMS characterization data for purified glycopeptide 5-15.
Figure 36B:
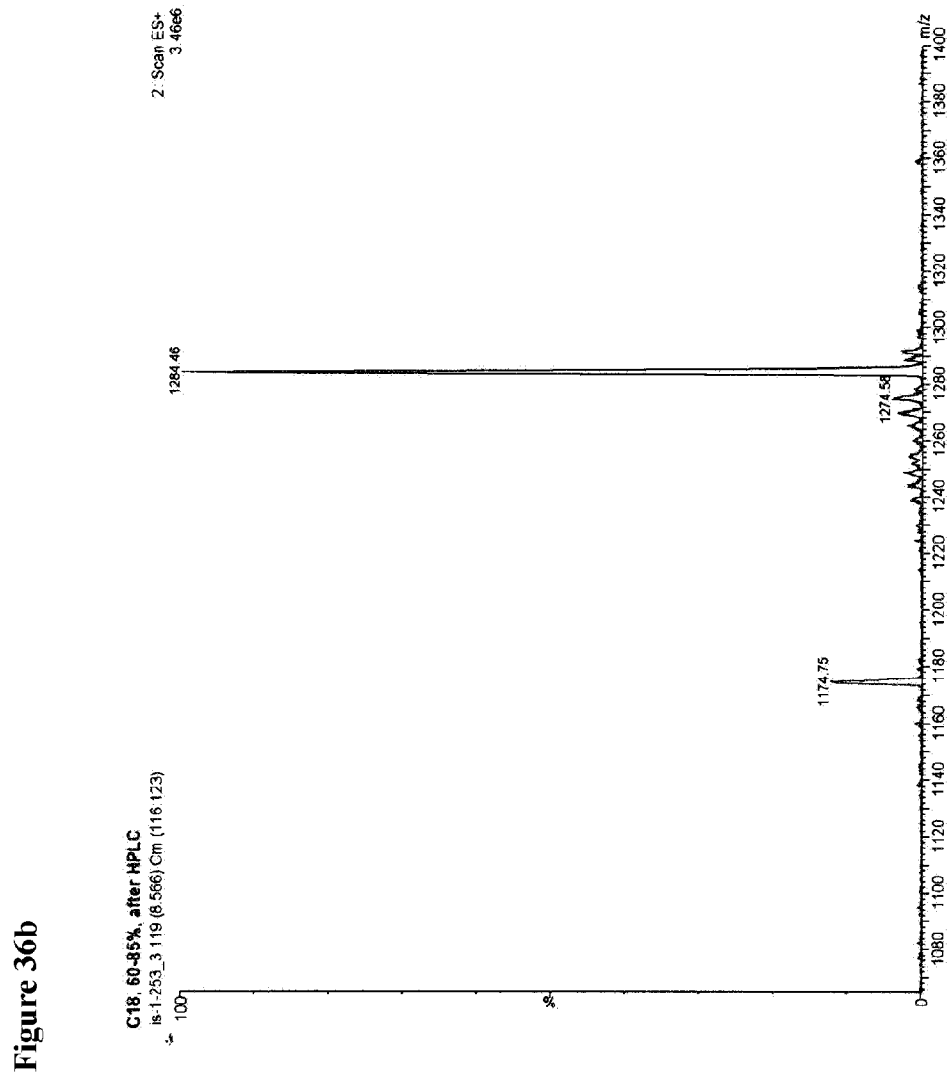
Figure 36C:
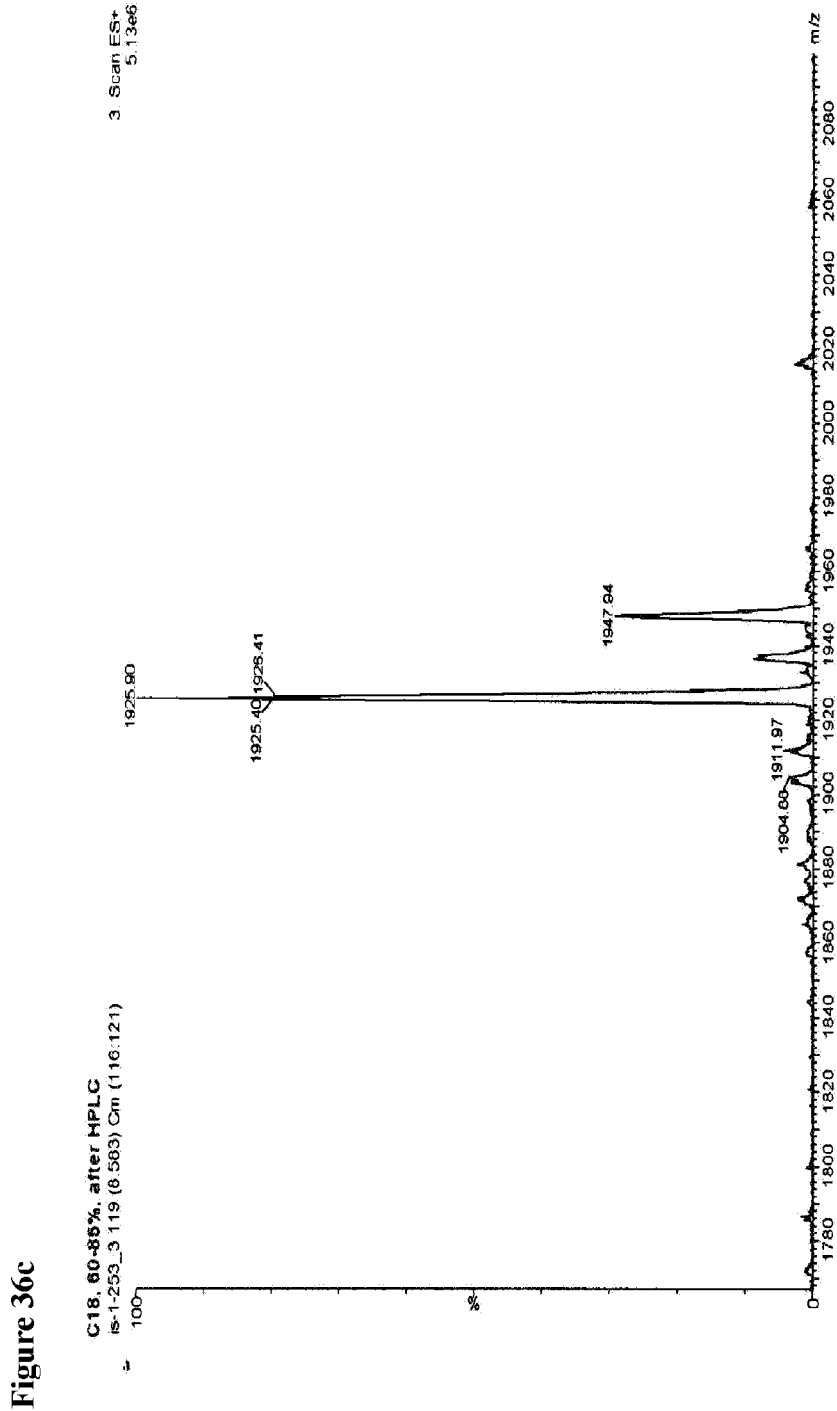
Figure 37A:
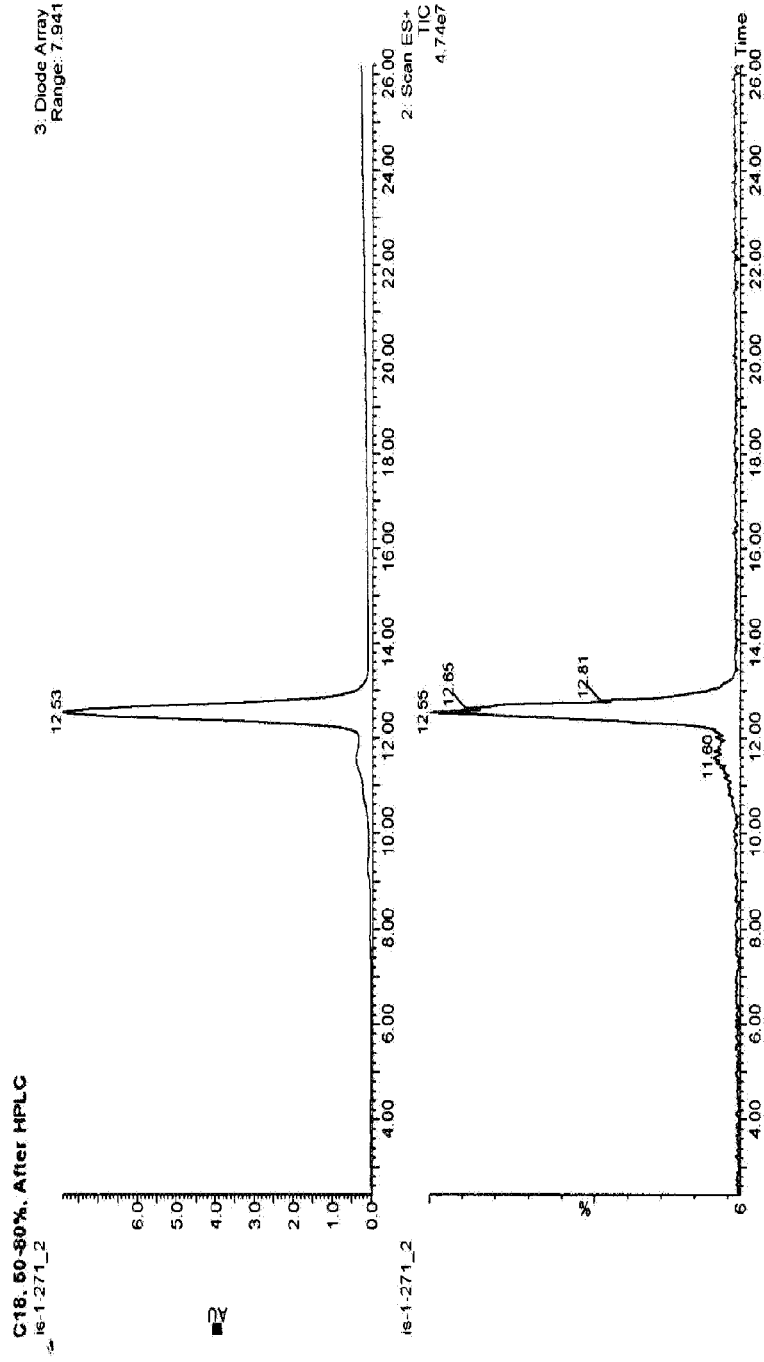
FIGS. 37*a-c* depict LCMS characterization data for purified glycopeptide 5-16.
Figure 37B:
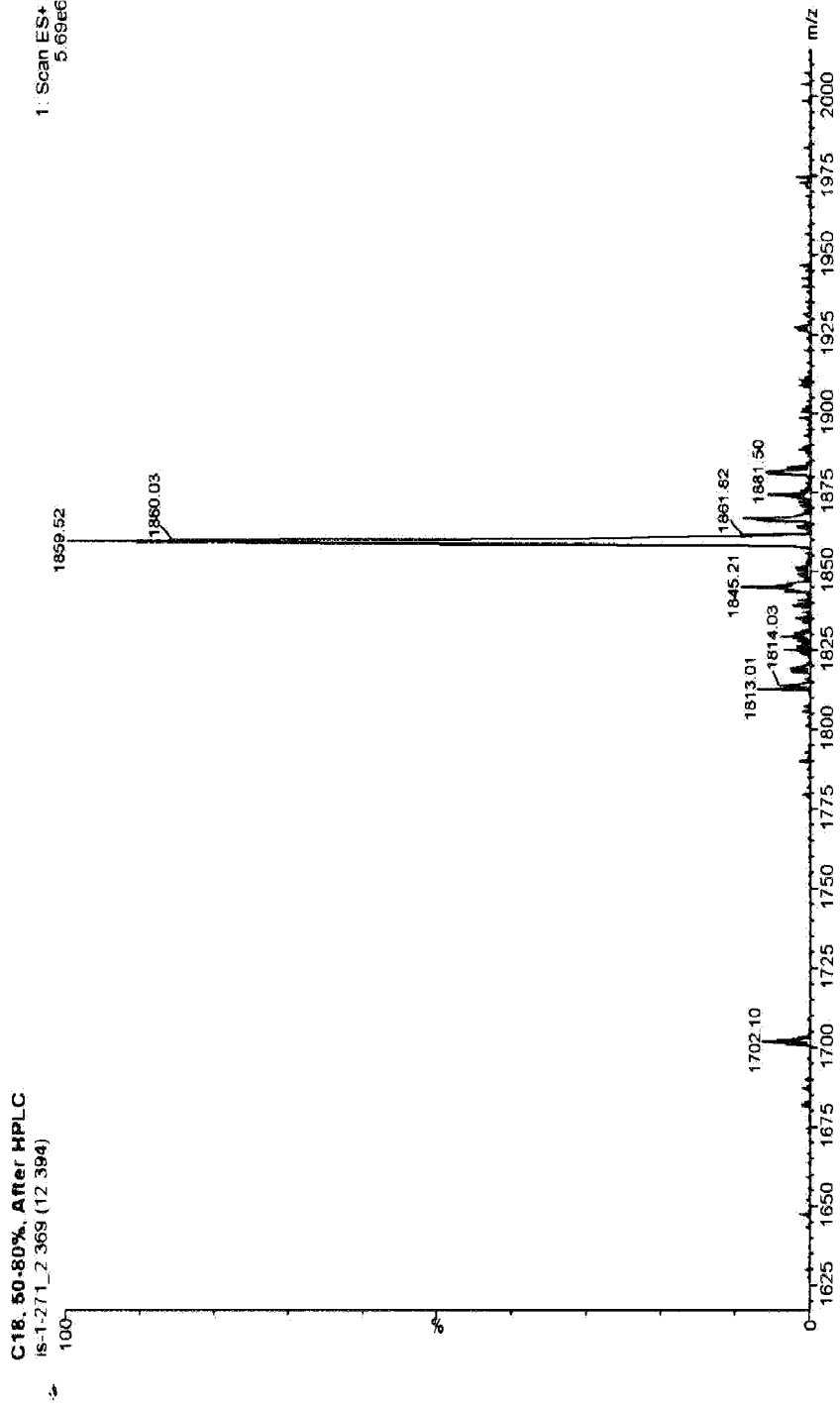
Figure 37C:
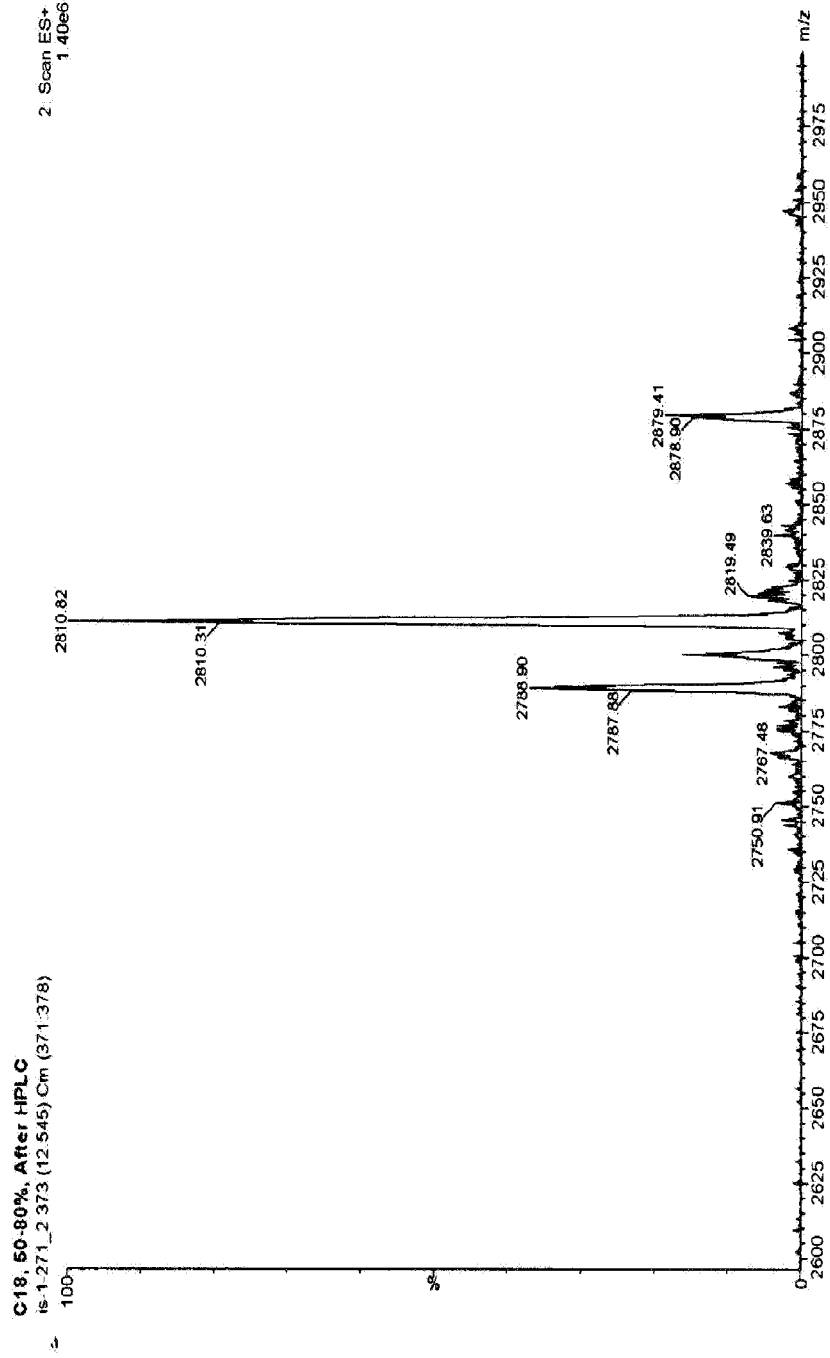
Figure 38A:
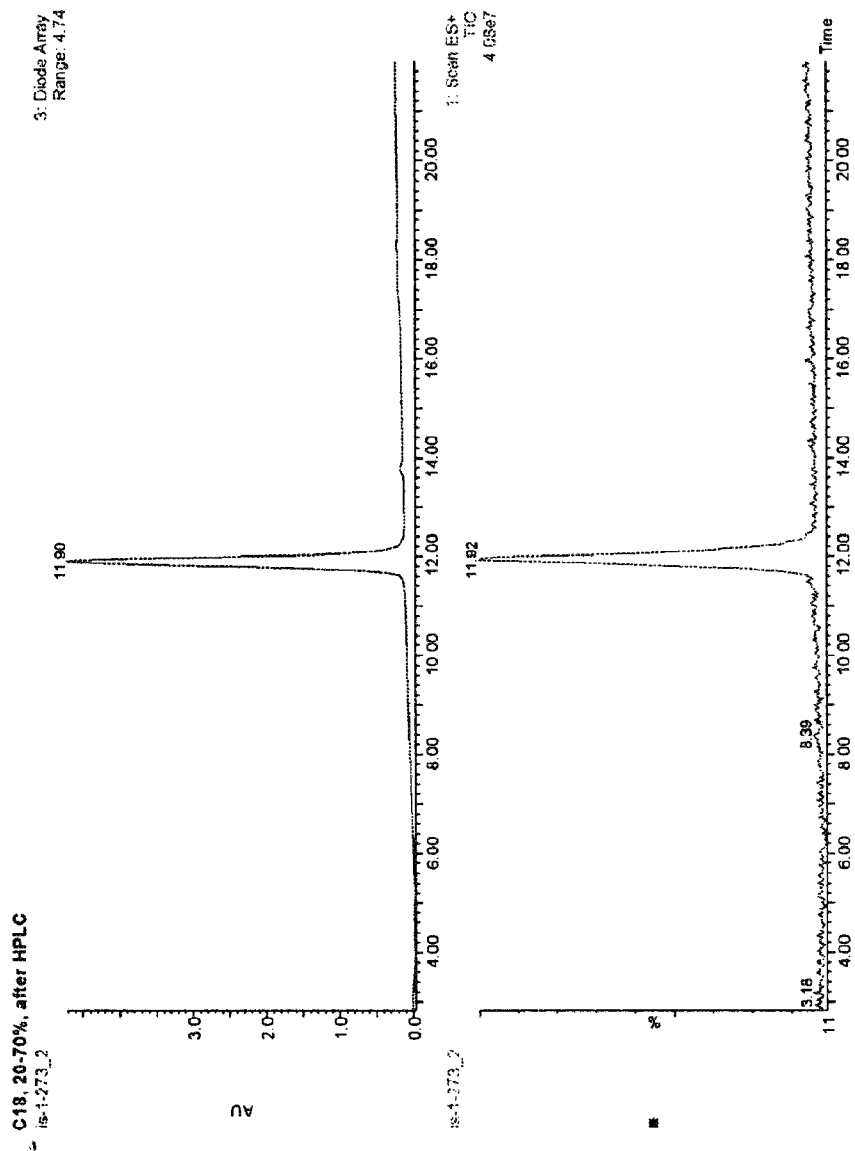
FIGS. 38*a-b* depict LCMS characterization data for purified glycopeptide 5-4.
Figure 38B:
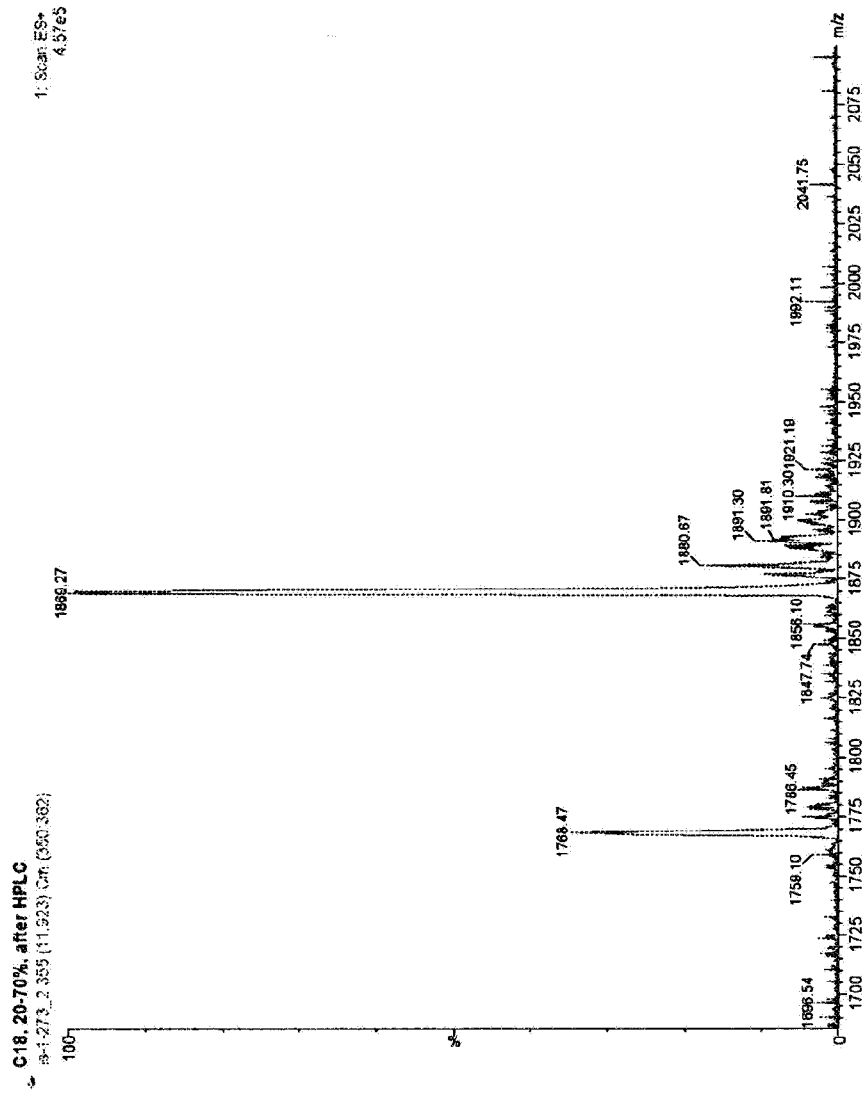
Figure 39A:
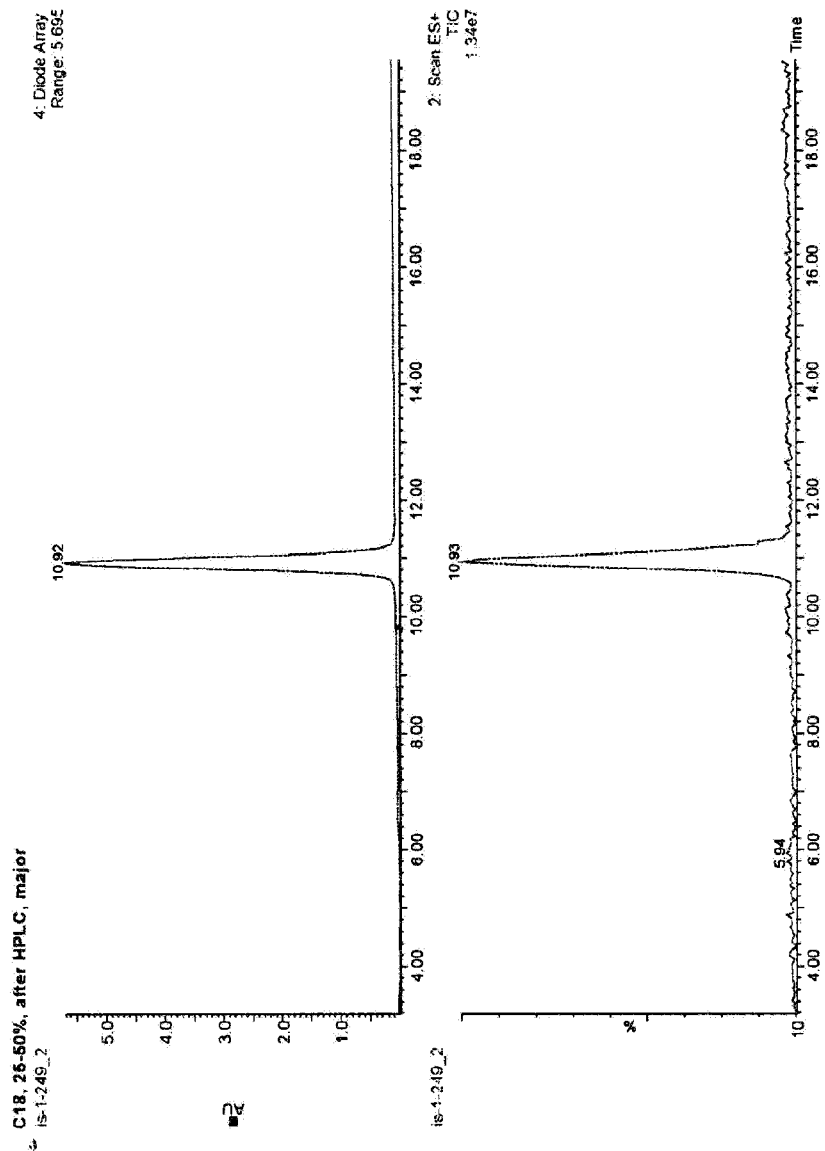
FIGS. 39*a-b* depict LCMS characterization data for purified glycopeptide 5-5.
Figure 39B:
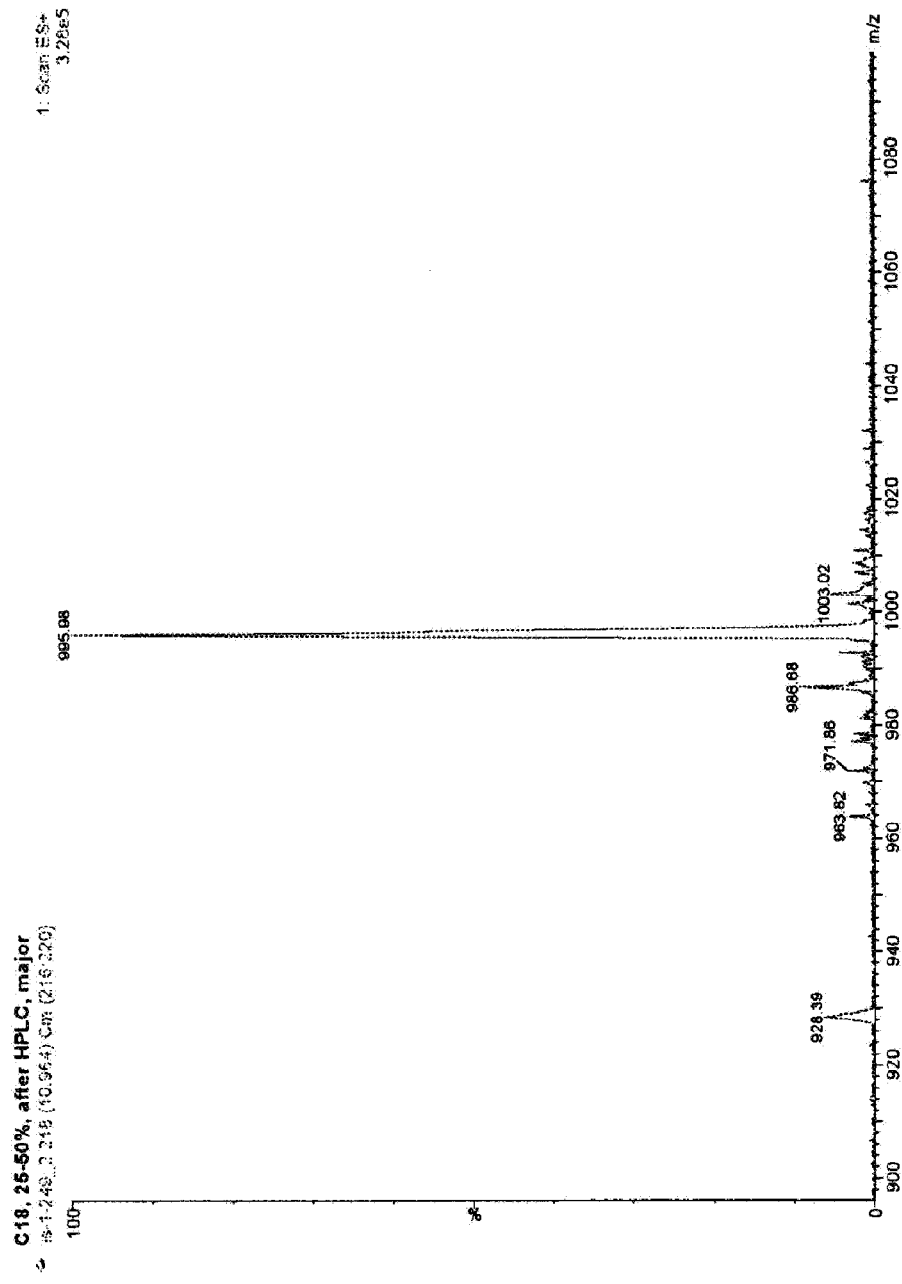
Figure 40A:
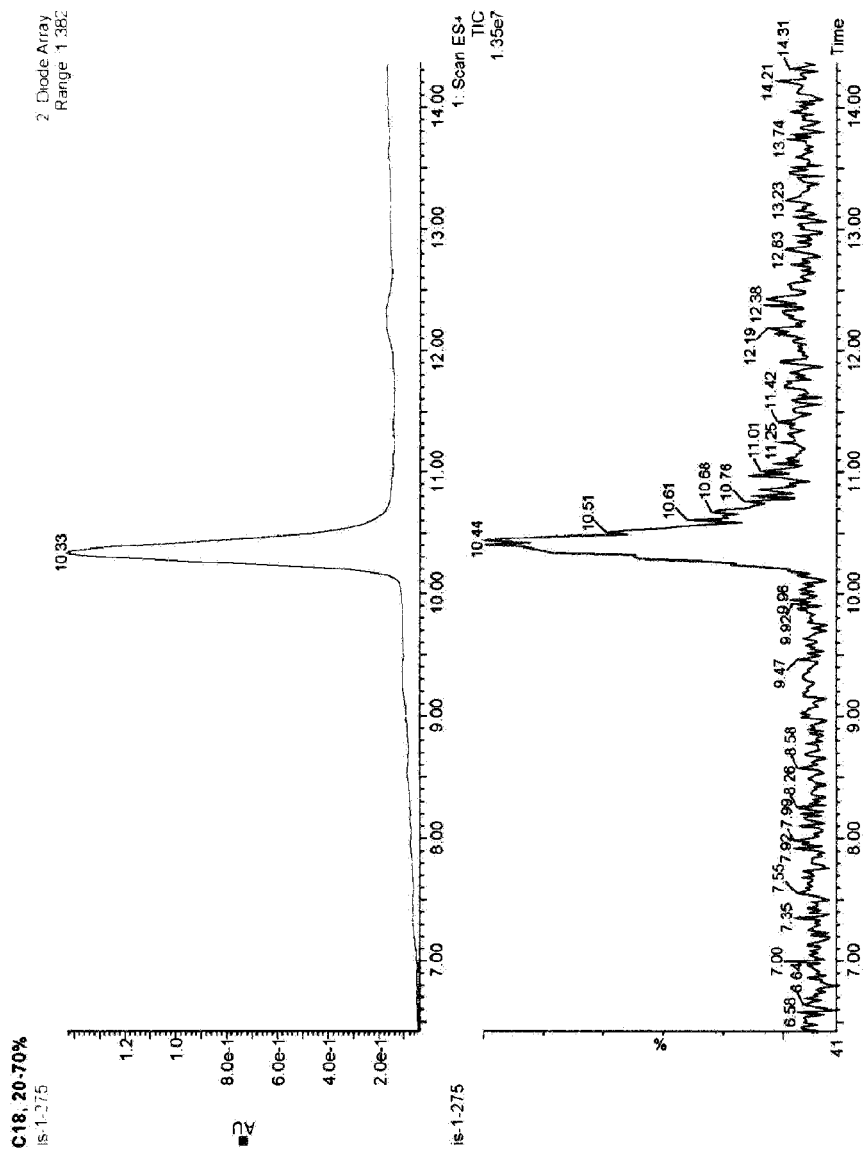
FIGS. 40*a-b* depict LCMS characterization data for purified glycopeptide 5-6.
Figure 40B:
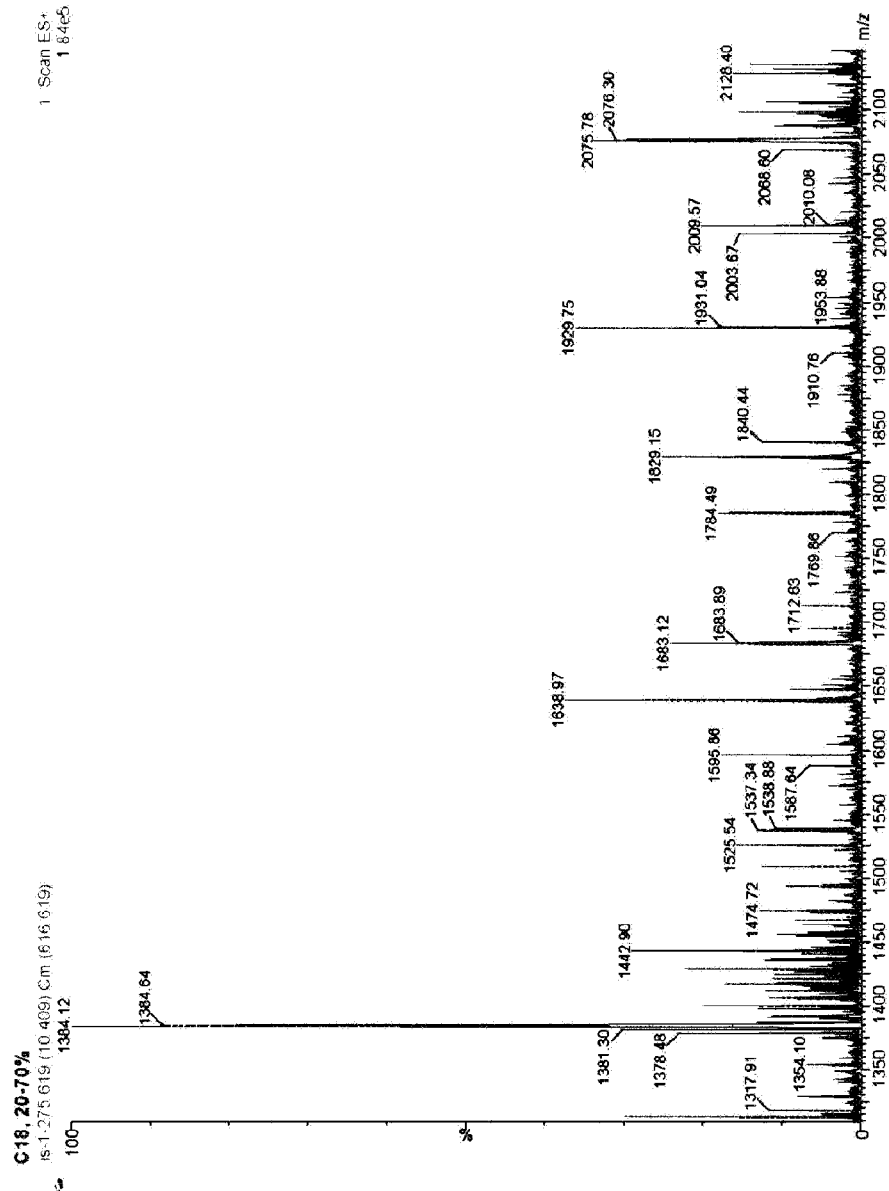
Figure 41A:
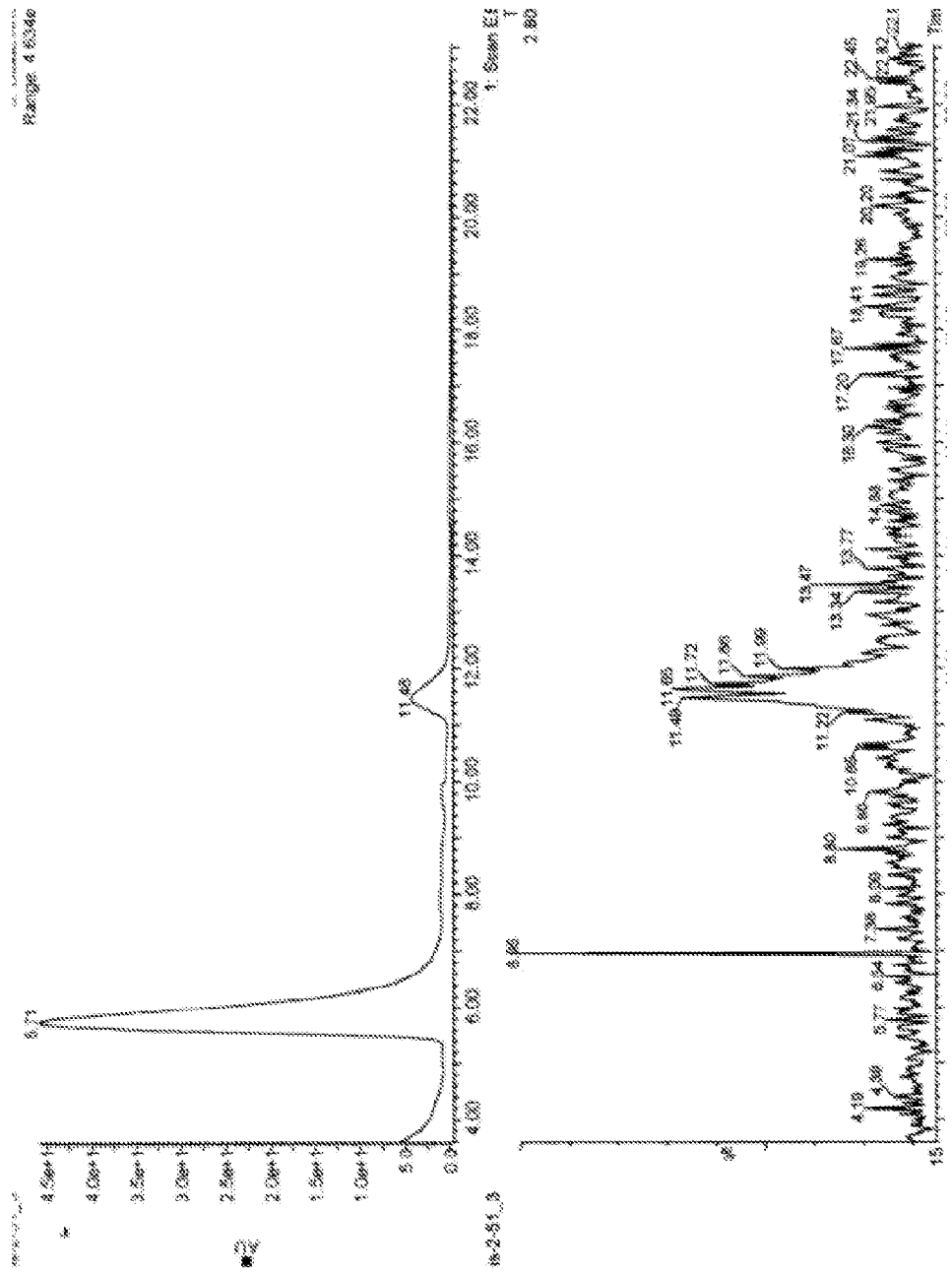
FIGS. 41*a-c* depict LCMS characterization data for purified glycopeptide 5-19.
Figure 41B:
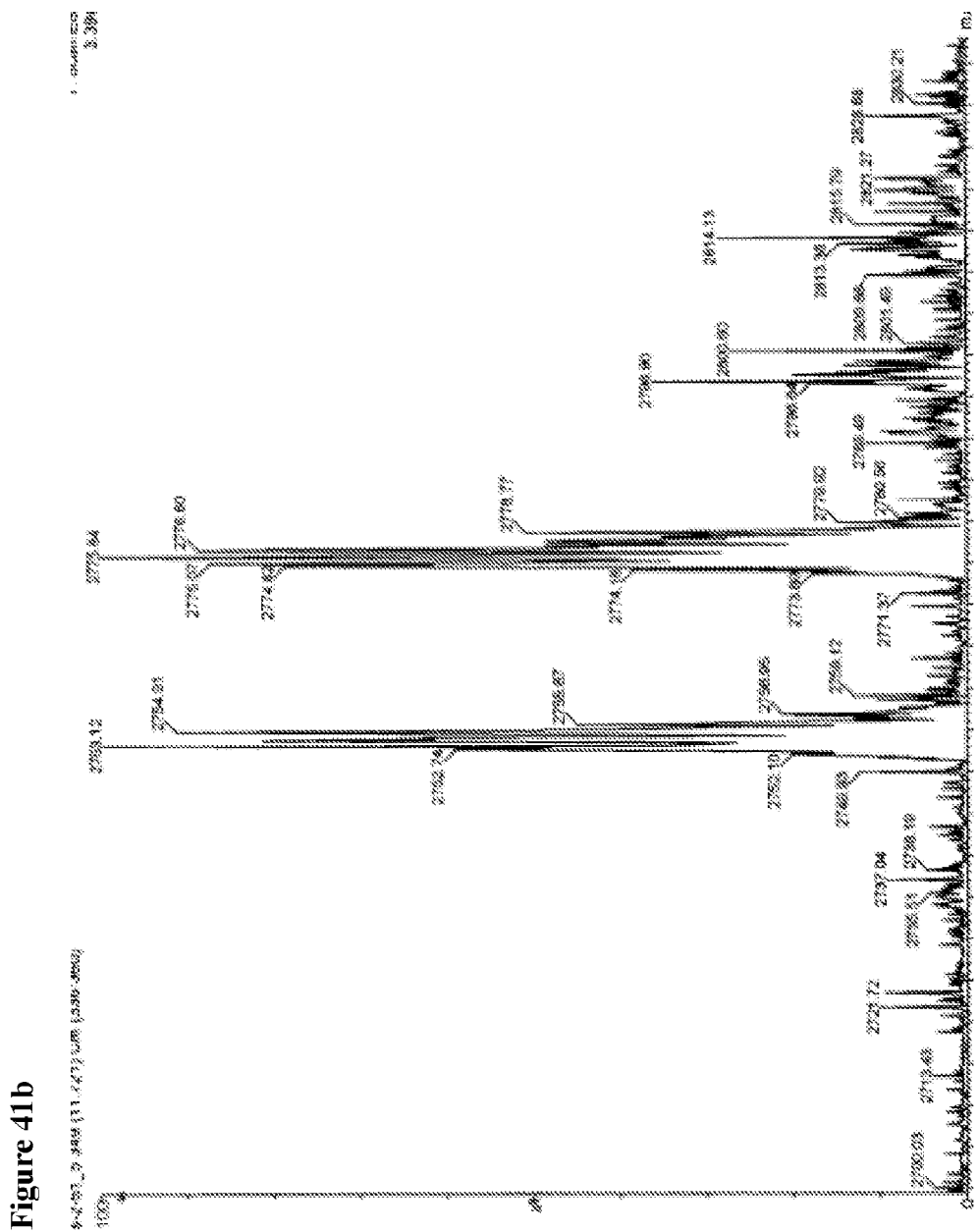
Figure 41C:
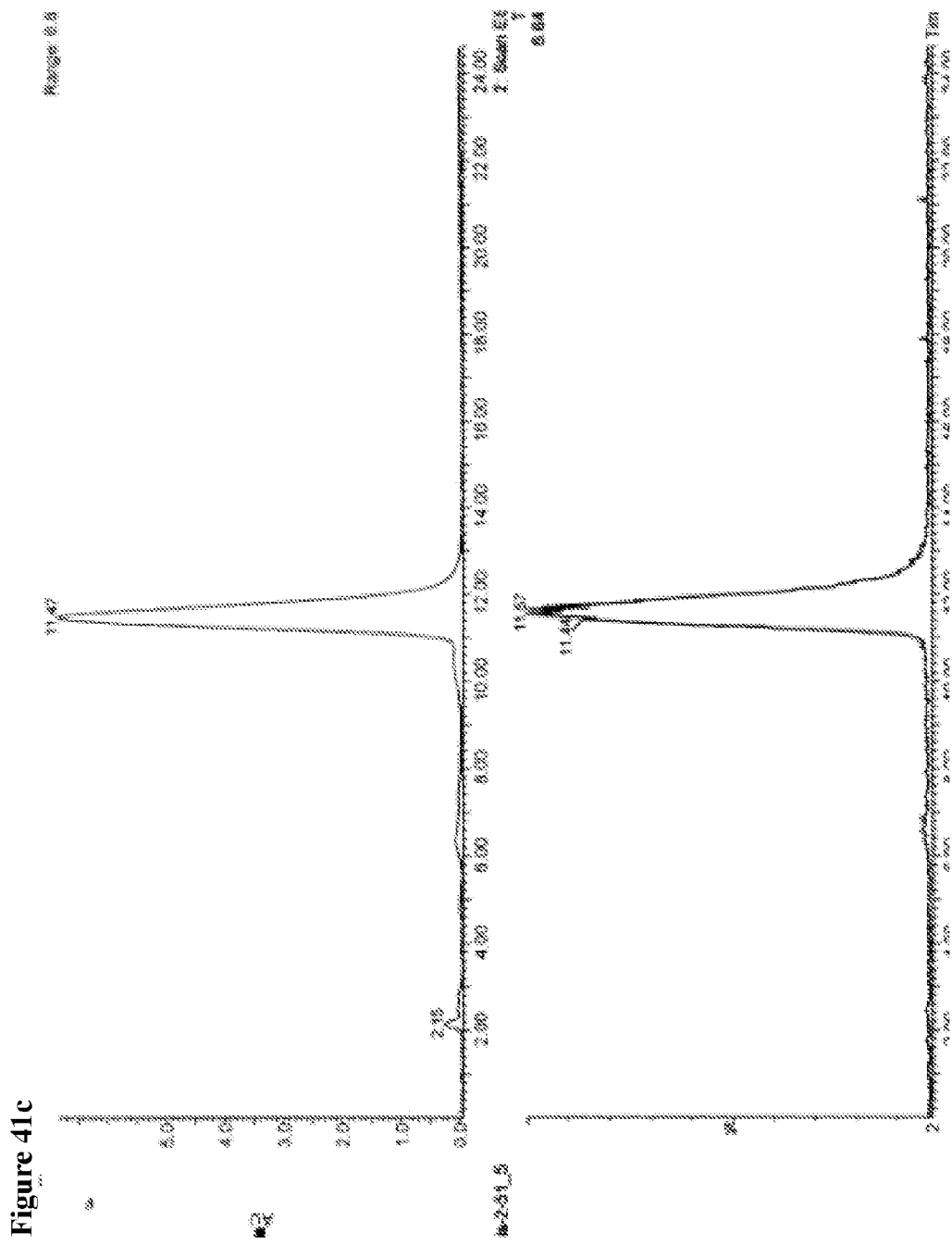
Figure 42A:
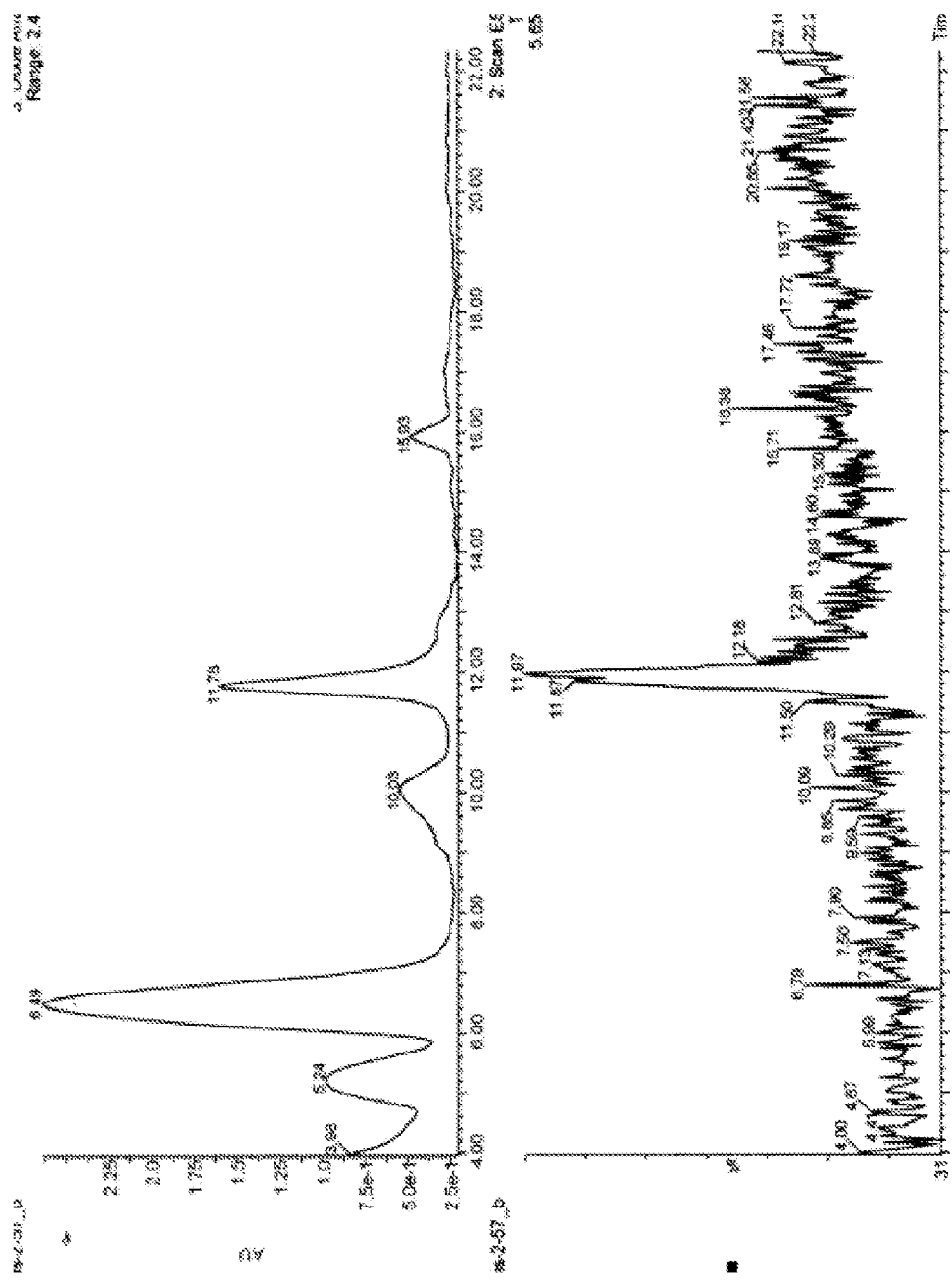
FIGS. 42*a-c* depict LCMS characterization data for purified glycopeptide 5-7.
Figure 42B:
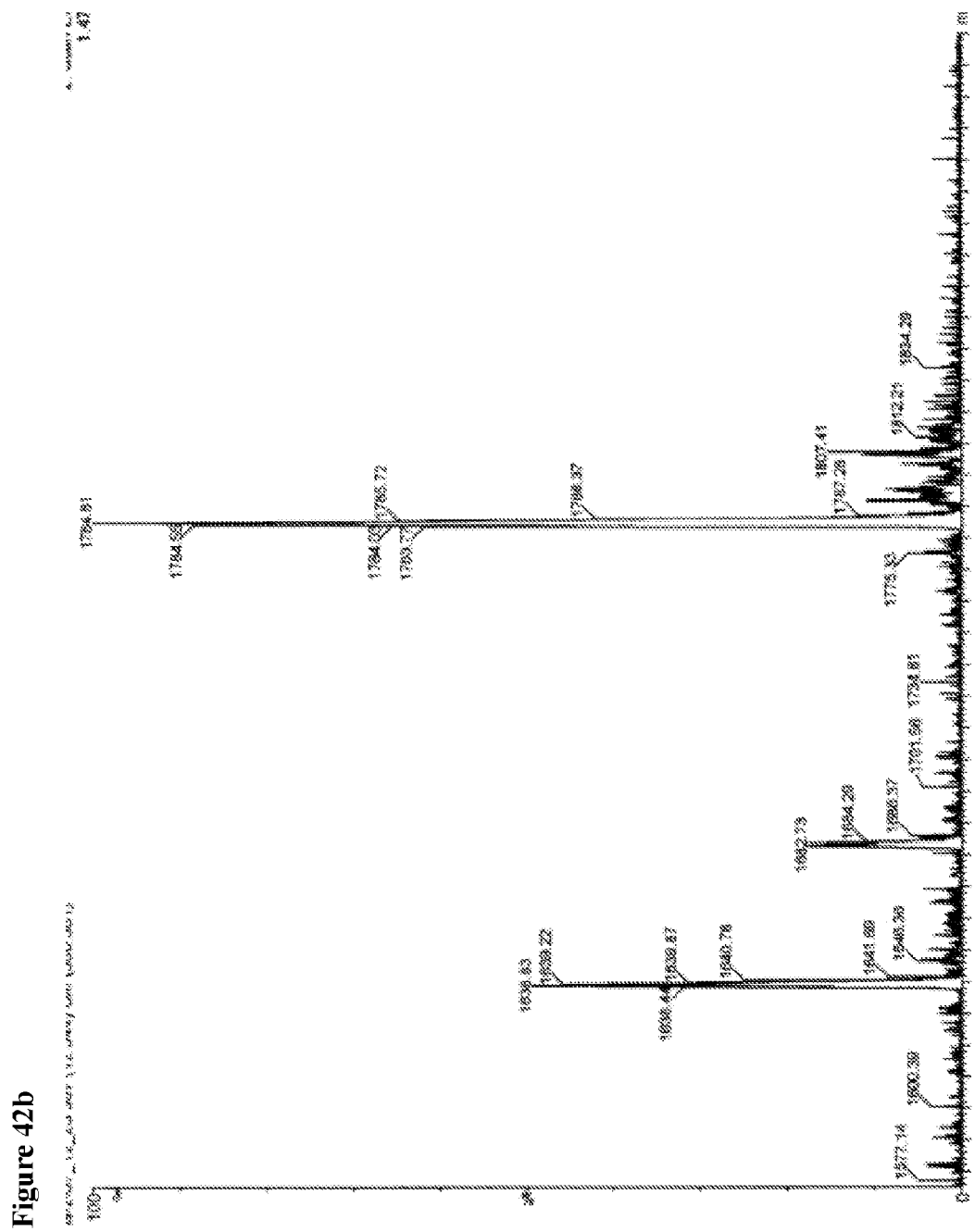
Figure 42C:
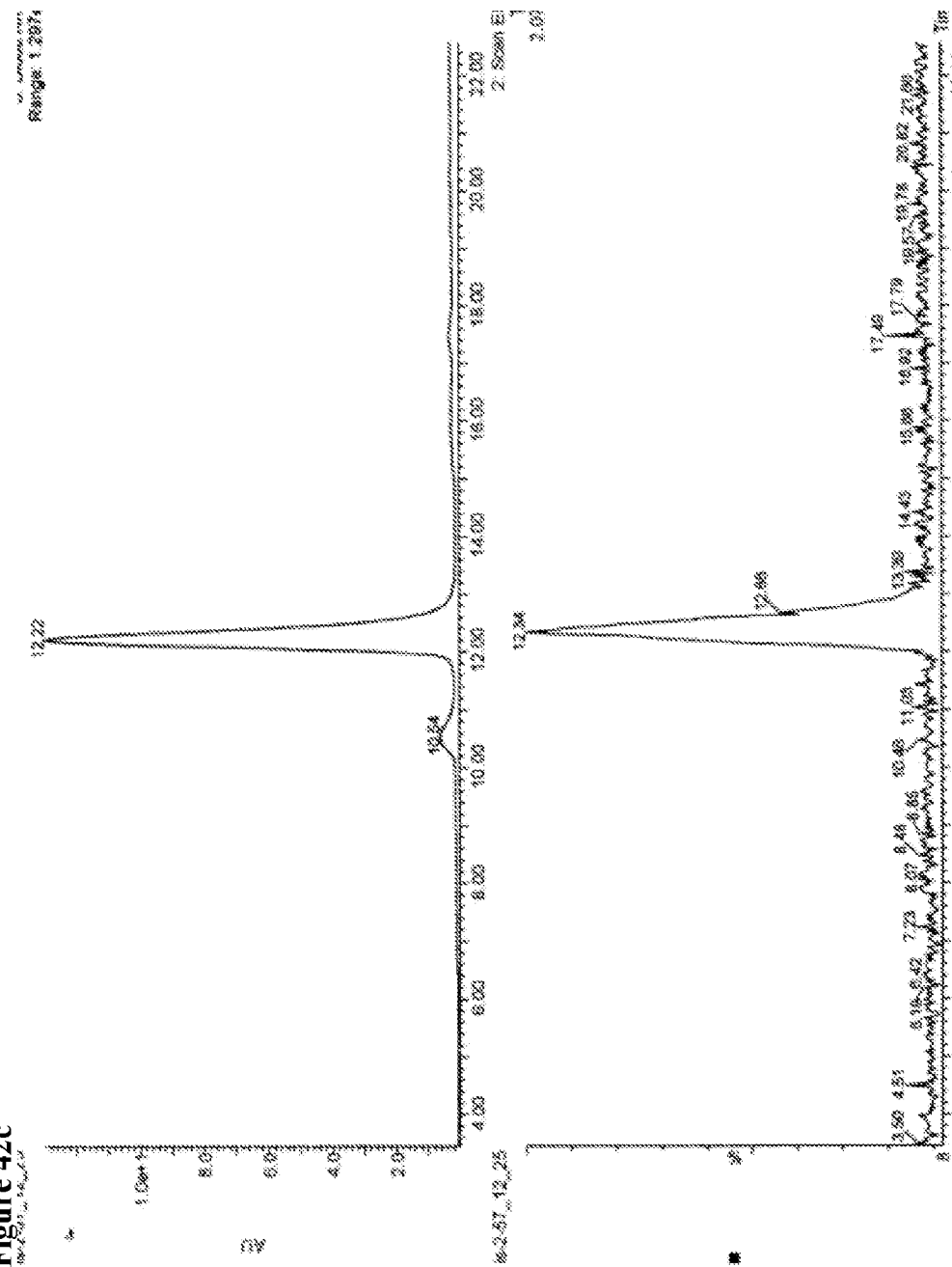

Following selective tert-butyl deprotection of 5-18 under the conditions described in FIG. 28, intermediate 5-13 was in hand. We then commenced the sequential attachment of the Tn and STn carbohydrate antigens. In the event, coupling of Tn 5-2 with peptide 5-13 proceeded efficiently to produce Tn glycopeptide construct (FIGS. 31a-b). The liberation of additional reaction sites by palladium-mediated allyl deprotection (Kunz, H.; Waldmann, H. *Angew. Chem., Int. Ed.* 1984, 23, 71-72) resulted in a high yield of divalent product 5-20. Addition of STn 5-3 to activated 5-20 and subsequent global deacetylation completed the synthesis of tetravalent antigen 5-7 in good overall yield.

In summary, this Example demonstrates the synthesis of cyclic multivalent glycopeptide constructs comprising carbohydrate determinants.

General Experimental Information:

Analytical Equipment: $^1$H-NMR spectra were recorded on a Bruker AVII+-600 spectrometer in $d_6$-DMSO or $D_2O$. Low resolution mass spectra (electrospray ionization) were acquired on a ZQ Micromass spectrometer. Samples were introduced by direct infusion. In the case of LC/MS, analysis was performed with a Waters Alliance analytical LC system in tandem with the Micromass ZQ. All HPLC was run with TFA (trifluoroacetic acid)-buffered eluents: A=0.05% v/v TFA/Water, B=0.04% v/v TFA/Acetonitrile. DMSO was purchased from Aldrich (Anhydrous grade) and used without further purification. DIEA (iPr$_2$NEt) was freshly distilled from CaH$_2$. DBU (Diazabicycloundecene) and Piperidine were purchased from Aldrich and used without further purification. HATU (O-(7-azabenzotriazol-1-yl)-N,N,N',N'-tetramethyluronium hexafluorophosphate) was purchased from GenScript and used without further purification. Peptide synthesis resins and Fmoc-amino acids were purchased from NovaBiochem.

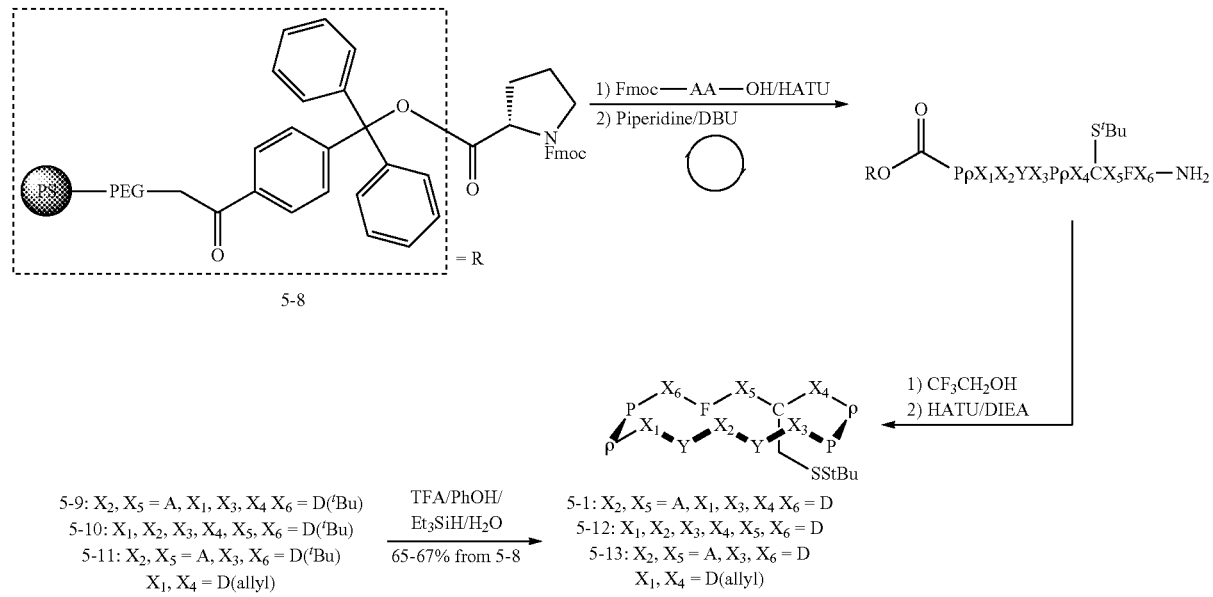

(Image discloses the linear 'PρX$_1$YX$_2$YX$_3$PρX$_4$CX$_5$FX$_6$' sequence as SEQ ID NO: 52 and constructs 5-9, 5-10, 5-11, 5-1, 5-12 and 5-13 as SEQ ID NOS 53-58, respectively.

Cyclic Peptide 5-1:

Fmoc-Pro-NovaSyn TGT resin (5-8) (0.5 g, 0.2 mmol/g, purchased from NovaBiochem) was subjected continuous flow automated peptide synthesis. For coupling steps, resin was treated with a 3-fold excess of HATU and Fmoc amino acids in DIEA/DMF, and for deblocking, a solution of 2% Piperidine/2% DBU in DMF was used. The amino acids used were, in order of synthesis, Fmoc-D-Pro-OH, Fmoc-Asp($^t$Bu)-OH, Fmoc-Tyr($^t$Bu)-OH, Fmoc-Ala-OH, Fmoc-Tyr($^t$Bu)-OH, Fmoc-Asp($^t$Bu)-OH, Fmoc-Pro-OH, Fmoc-D-Pro-OH, Fmoc-Asp($^t$Bu)-OH, Fmoc-Cys(S$^t$Bu)-OH, Fmoc-Ala-OH, Fmoc-Phe-OH, Fmoc-Asp($^t$Bu)-OH. The resin was then transferred to a manual peptide synthesis vessel and treated with a cleavage solution of 5 mL of 20% trifluoroethanol in dichloromethane for 2 hours. The beads were filtered, rinsed with another 5 mL cleavage solution, filtered again, and then treated for another 2 hours with 5 mL of cleavage solution. This process was repeated for a total of three 2-hour cleavage cycles, and the combined filtrate was concentrated in vacuo to afford ~160 mg crude linear protected peptide as a colorless glass. This material was redissolved in 50 mL of 1% v/v DIEA in DMF. HOAt (32.5 mg, 0.239 mmol, 3 equiv.) was added, followed by HATU (91 mg, 0.239 mmol, 3 equiv.). After 1 hour, the solvent was removed in vacuo (using a rotary evaporator, ~1 mm Hg, 30° C.), affording the crude cyclic protected peptide contaminated with HATU/HOAt-derived byproducts. (ESI MS analysis showed predominantly the desired product peak, 1992.1 (M+H)). This material was then redissolved in 10 mL of 87.5% TFA/5% water/5% phenol/2.5% triethylsilane (v/v/m/v) solution and stirred for 30 minutes. Solvent was removed in vacuo then the residue was triturated with 25 mL diethyl ether 4 times to afford crude peptide 5-1. This was purified in eight batches by preparative reverse-phase HPLC (on a 21.4×250 mm Varian Microsorb C18 Dynamax column, 100 Å pore size, 5 µM particle size column) using a gradient of 20-60% B buffer (see General Info) over 30 min, flow rate 16 mL/min, 235 nm UV detection. The peak with retention time of 19.2 minutes was collected. LC/MS analysis (20-60% B over 30 min, same solvent system as above, Microsorb C18, 300-5, 2×150 mm, 0.2 mL/min) showed the peptide 5-1 at 17 min and MS spectrum with base peaks of 1656.0 (M+H, [1655.6 calc]). Lyophilization of these fractions yielded 108 mg of 5-1 (65% yield based on proline-loaded resin 5-8).

Cyclic Peptide 5-12:

Cyclic peptide 5-12 was synthesized under the same condition as above. The crude mixture was purified in eight batches by preparative reverse-phase HPLC (on a 21.4×250 mm Varian Microsorb C18 Dynamax column, 100 Å pore size, 5 µM particle size column) using a gradient of 25-60% B buffer (see General Info) over 30 min, flow rate 16 mL/min, 235 nm UV detection. The peak with retention time of 16.6 minutes was collected. LC/MS analysis (20-60% B over 30 min, same solvent system as above, Microsorb C18, 300-5, 2×150 mm, 0.2 mL/min) showed the peptide 5-12 at 18 min and MS spectrum with base peaks of 1743.7 (M+H, [1743.6 calc]). Lyophilization of these fractions yielded 117 mg of 5-12 (67% yield based on proline-loaded resin 5-8).

Cyclic Peptide 5-13:

Cyclic peptide 5-13 was synthesized under the same condition as above. The crude mixture was purified in eight batches by preparative reverse-phase HPLC (on a 21.4×250 mm Varian Microsorb C18 Dynamax column, 100 Å pore size, 5 µM particle size column) using a gradient of 25-60% B buffer (see General Info) over 30 min, flow rate 16 mL/min, 235 nm UV detection. The peak with retention time of 16.6 minutes was collected. LC/MS analysis (30-70% B over 30 min, same solvent system as above, Microsorb C18, 300-5, 2×150 mm, 0.2 mL/min) showed the peptide 5-13 at 16 min and MS spectrum with base peaks of 1736.1 (M+H, [1735.7 calc]). Lyophilization of these fractions yielded 113 mg of 5-13 (65% yield based on proline-loaded resin 5-7).

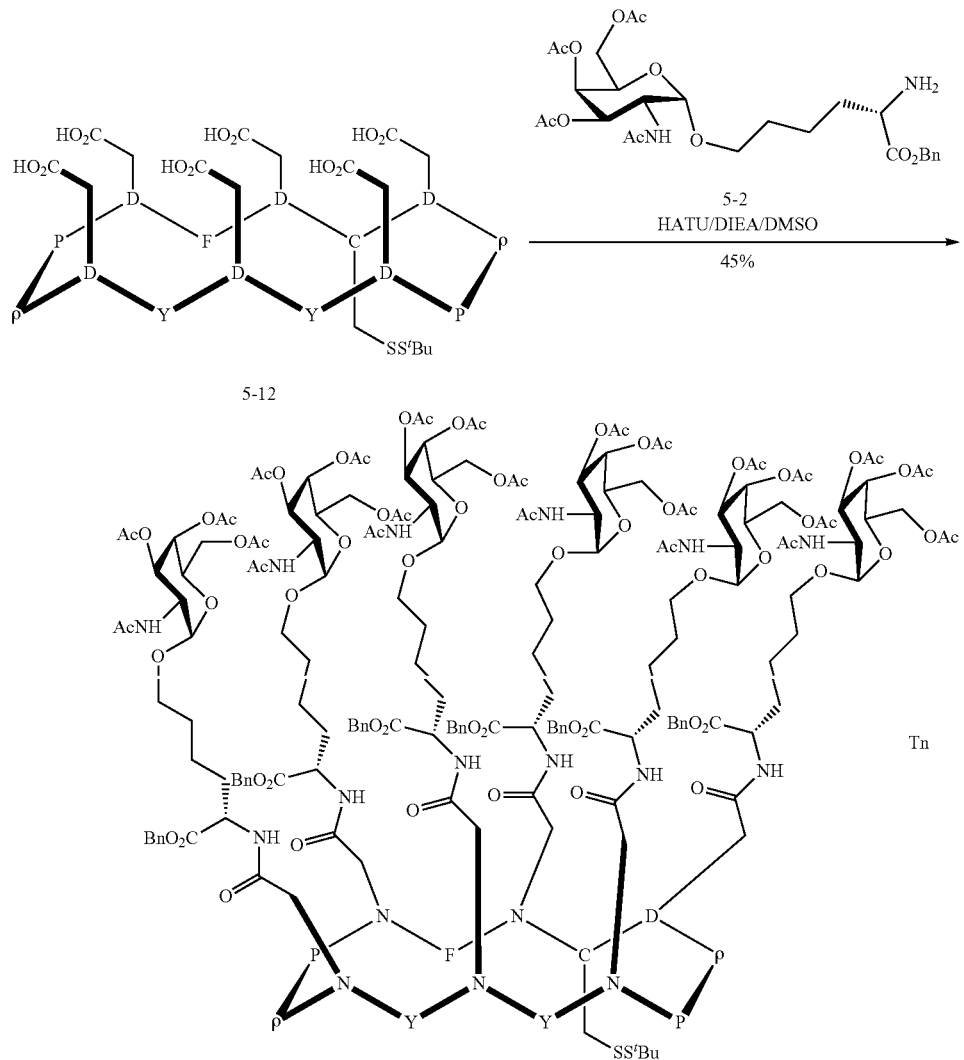

(Image Discloses '5-12' as SEQ ID NO: 57 and '5-14' as SEQ ID NO: 59)

Protected Hexavalent Glycopeptide 5-14:

Solutions of each reaction participant were prepared with a stirring bar in flame-dried vials under argon as follows: Peptide 5-12 (2 mg, 1.15 µmol), Tn 5-2 (4.88 mg, 8.62 µmol), were dissolved in 1 mL DMSO. To this mixture, HATU (2.9 mg, 7.6 µmol in 100 µL DMSO) was added, followed by dry iPr$_2$NEt (4.5 µL, 25.74 µmol), producing a strong yellow color. After 4 hours, the crude reaction mixture was diluted with ~500 µL of 50% B HPLC buffer and, this was purified in two batches by preparative reverse-phase HPLC using a gradient of 55-80% B over 30 minutes, flow rate 16 mL/min, 235 nm UV detection. The column used was a 21.4×250 mm Varian Microsorb C18 Dynamax column, 100 Å pore size, 5 µM particle size. Retention time for protected hexavalent glycopeptide 5-14 was 19 minutes. LC/MS analysis of the crude reaction mixture (50-80% B over 30 min, same solvent system as above, Microsorb C18, 300-5, 2×150 mm, 0.2 mL/min) showed the protected hexavalent glycopeptide 5-14 at 21 min and MS spectrum with base peaks of 2517.7 (M+2H, [2517.0 calc]) and 1679.7 (M+3H [1678.4 calc]). Lyophilization of these fractions yielded 2.6 mg (45%) of 5-14.

(Image Discloses '5-1' as SEQ ID NO: 56 and '5-15' as SEQ ID NO: 60)

Protected Tetravalent Glycopeptide 5-15:

Solutions of each reaction participant were prepared with a stir bar in flame-dried vials under argon as follows: Peptide 5-1 (2 mg, 1.21 µmol), Tn 5-2 (3.43 mg, 6.04 µmol), were dissolved in 0.5 mL DMSO. To this mixture, HATU (2.3 mg, 6.04 µmol in 100 µL DMSO) was added, followed by dry iPr$_2$NEt (5.1 µL, 29 µmol), producing a strong yellow color. After 4 hours, the crude reaction mixture was diluted with 500 µL of 50% B HPLC buffer and, this was purified in two batches by preparative reverse-phase HPLC using a gradient of 50-80% B over 30 minutes, flow rate 16 mL/min, 235 nm UV detection. The column used was a 21.4×250 mm Varian Microsorb C18 Dynamax column, 100 Å pore size, 5 µM particle size. Retention time for protected hexavalent glycopeptide 5-12 was 9 minutes. LC/MS analysis (60-85% B over 30 min, same solvent system as above, Microsorb C18, 300-5, 2×150 mm, 0.2 mL/min) showed the protected tetravalent glycopeptide 5-15 at 8.5 min and MS spectrum with base peaks of 1925.4 (M+2H, [1924.8 calc]) and 1284.5 (M+3H [1283.5 calc]). Lyophilization of these fractions yielded 2.7 mg (57%) of 5-15.

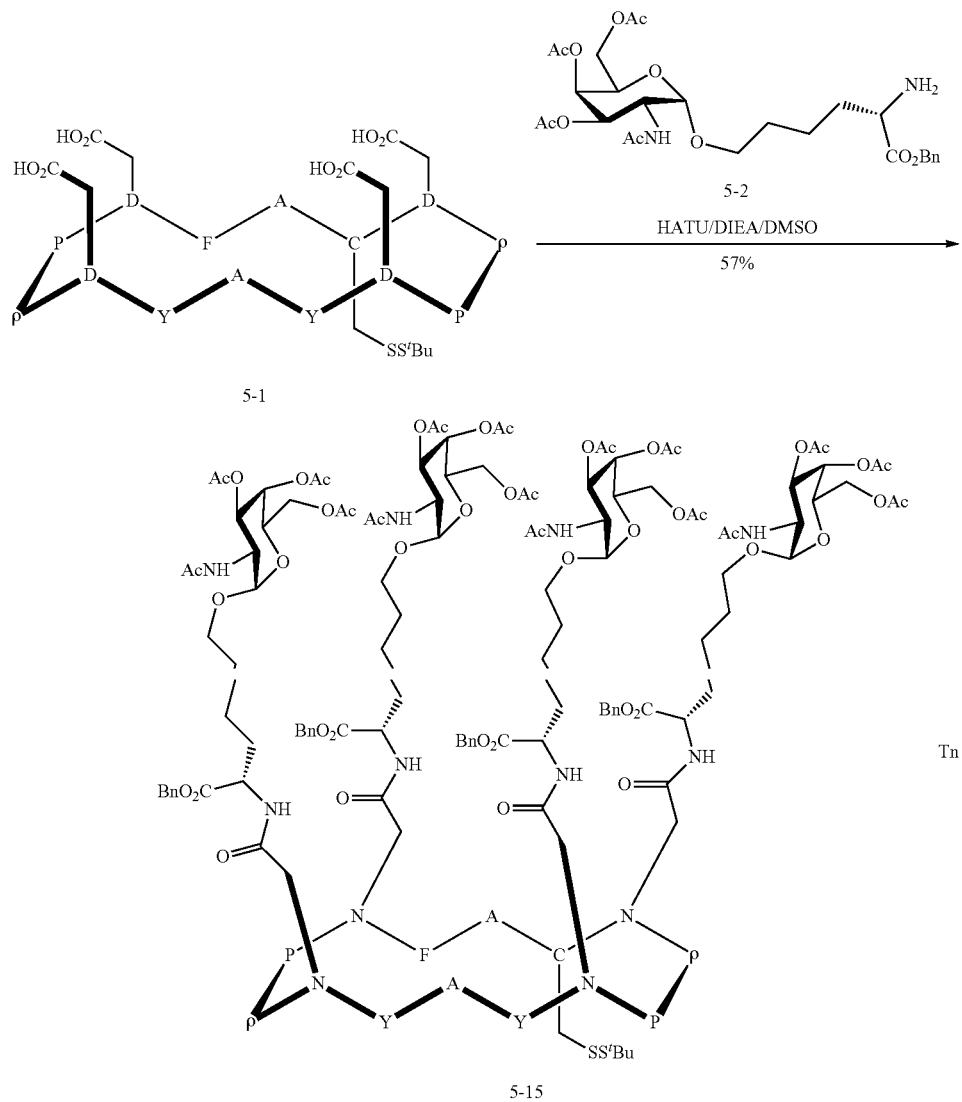

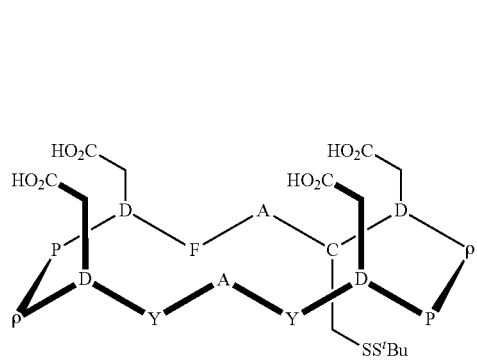

5-1

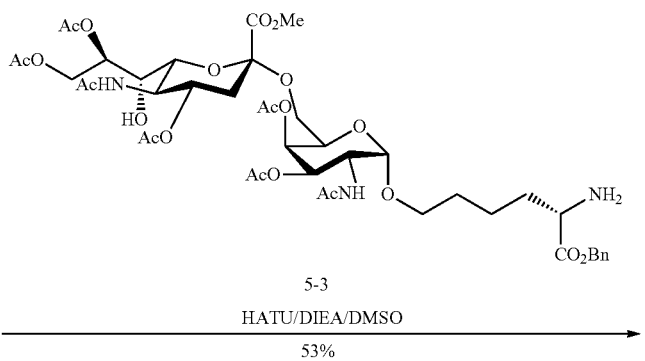

5-3

HATU/DIEA/DMSO
────────────────→
53%

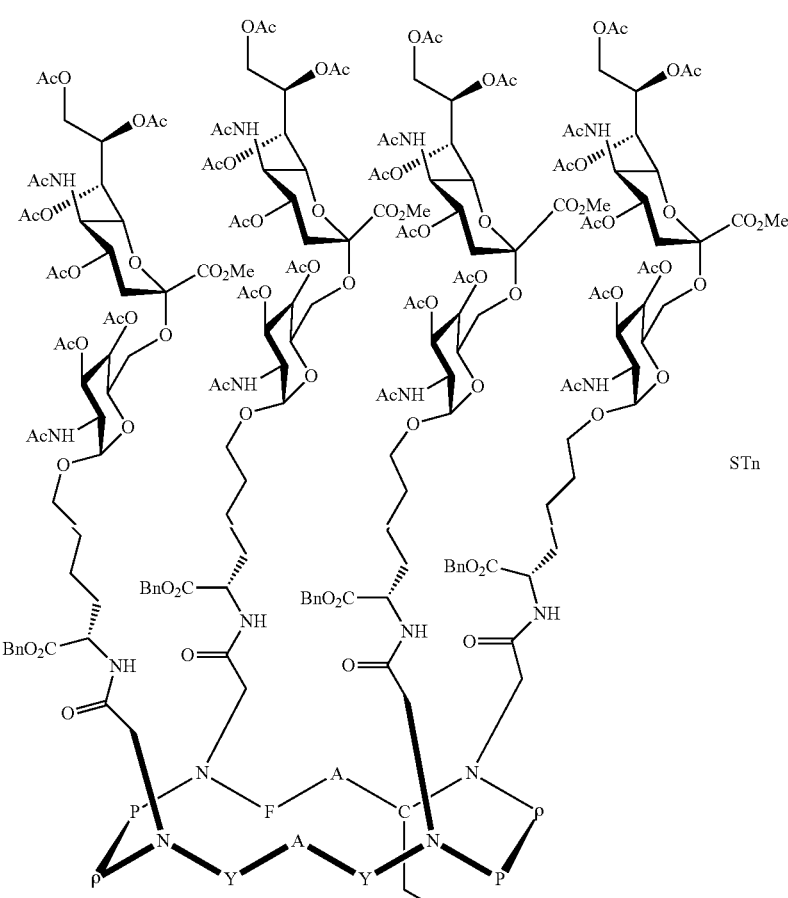

5-16

(Image Discloses '5-1' as SEQ ID NO: 56 and '5-16' as SEQ ID NO: 61)

Protected Tetravalent Glycopeptide 5-16:

Solutions of each reaction participant were prepared with a stir bar in flame-dried vials under argon as follows: Peptide 5-1 (2.3 mg, 1.41 μmol), STn 5-3 (11.3 mg, 11.31 μmol), were dissolved in 0.9 mL DMSO. To this mixture, HATU (2.7 mg, 7.07 μmol in 100 μL DMSO) was added, followed by dry iPr$_2$NEt (3.7 μL, 21 μmol), producing a strong yellow color. After 4 hours, the crude reaction mixture was diluted with ~500 μL of 50% B HPLC buffer and, this was purified in two batches by preparative reverse-phase HPLC using a gradient of 50-80% B over 30 minutes, flow rate 16 mL/min, 235 nm UV detection. The column used was a 21.4×250 mm Varian Microsorb C18 Dynamax column, 100 Å pore size, 5 μM particle size. Retention time for protected tetravalent glycopeptide 5-16 was 14 minutes. LC/MS analysis of the crude reaction mixture (50-80% B over 30 min, same solvent system as above, Microsorb C18, 300-5, 2×150 mm, 0.2 mL/min) showed the protected tetravalent glycopeptide 5-16 at 13 minutes and MS spectrum with base peaks of 2787.9 (M+2H, [2787.1 calc]) and 1859.5 (M+3H, [1858.4 calc]). Lyophilization of these fractions yielded 4.2 mg (53%) of 5-16.

General Procedure for Global Deprotections of 5-14, 5-15, and 5-16:
The protected glycopeptide was treated with 1 N aq. NaOH (500 μL) and MeOH (750 μL). The resulting mixture was stirred for 14 hours, which was then acidified with 10% aq. HCl (500 μL). This was purified by preparative reverse-phase HPLC (21.4×250 mm Varian Microsorb C18 Dynamax column, 100 Å pore size, 5 μM particle size).
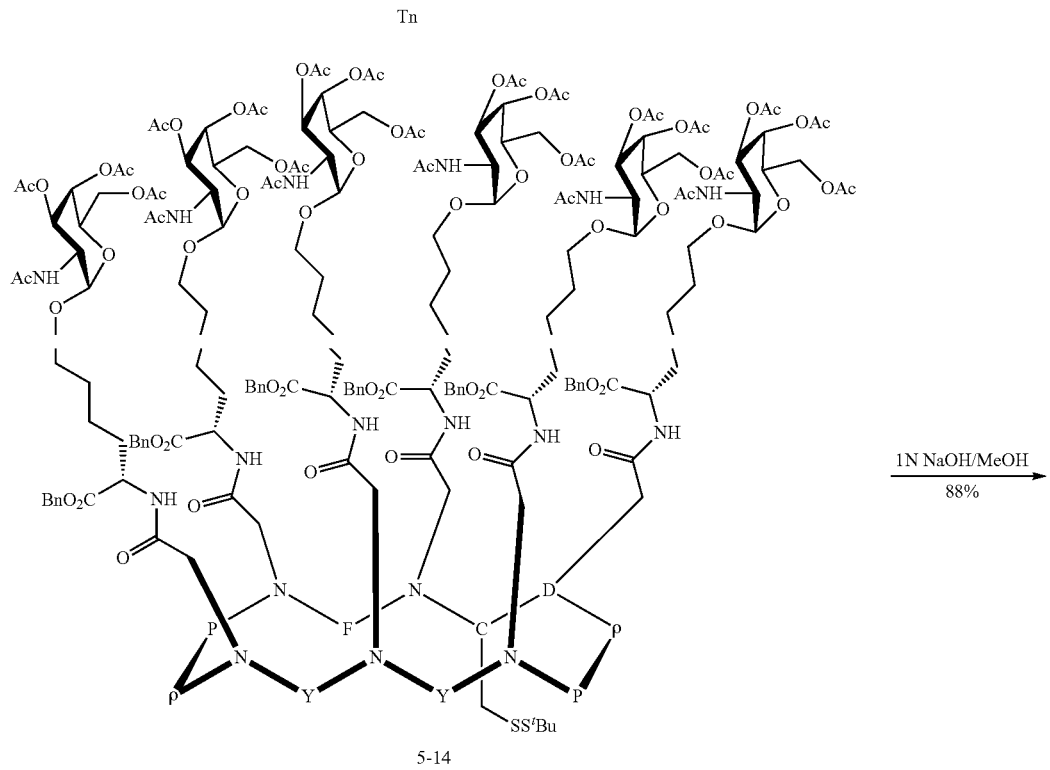
5-14
1N NaOH/MeOH
88%
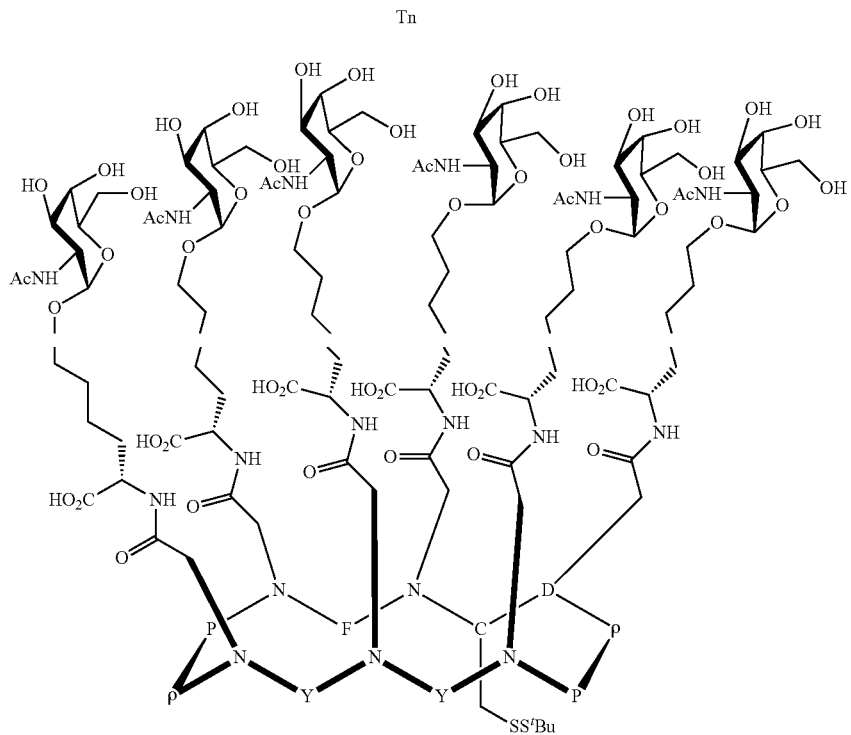
5-4

(Image Discloses '5-14' as SEQ ID NO: 59 and '5-4' as SEQ ID NO: 62)

Hexavalent Glycopeptide 5-4:

2.3 mg of the protected hexavalent glycopeptide 5-14 was used. Hexavalent glycopeptide 5-4 was purified in two batches by preparative reverse-phase HPLC using a gradient of 20-70% B over 30 minutes, flow rate 16 mL/min, 235 nm UV detection. Retention time for hexavalent Glycopeptide 5-4 was 13 minutes. LC/MS analysis (20-70% B over 30 min, same solvent system as above, Microsorb C18, 300-5, 2×150 mm, 0.2 mL/min) showed the hexavalent glycopeptide 5-4 at 12 minutes and MS spectrum with base peaks of 1869.3 (M+2H, [1868.8 cal]). Lyophilization of these fractions yielded 1.5 mg (88%) of 5-4.

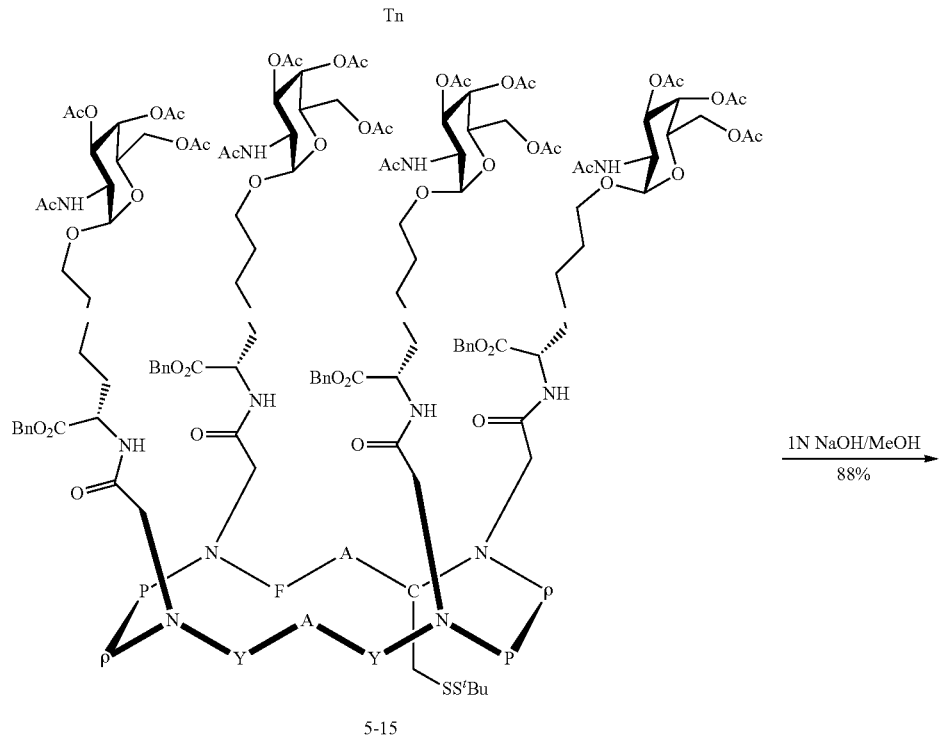

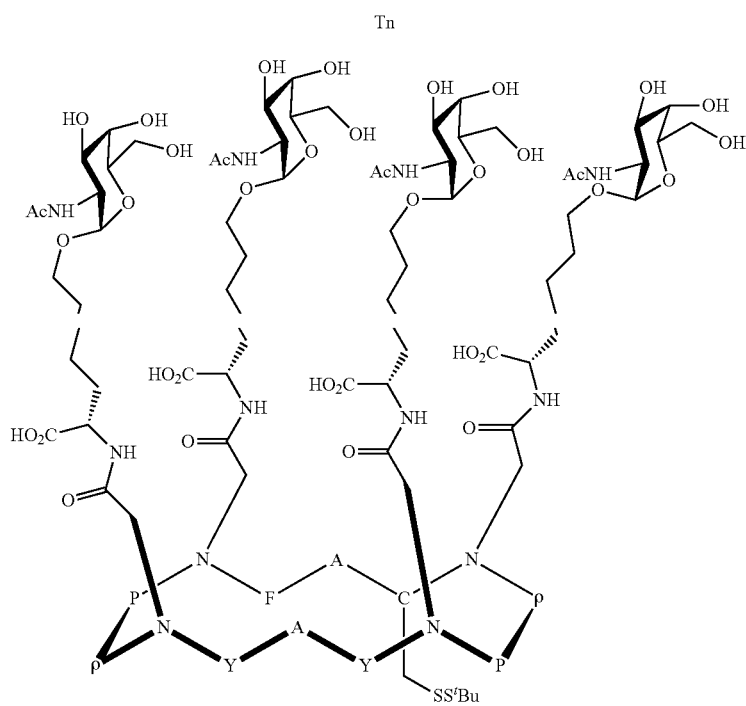

(Image Discloses '5-15' as SEQ ID NO: 60 and '5-5' as SEQ ID NO: 63)

Tetravalent Glycopeptide 5-5:

5.9 mg of the protected tetravalent glycopeptide 5-15 was used. Tetravalent glycopeptide 5-5 was purified in two batches by preparative reverse-phase HPLC using a gradient of 25-50% B over 30 minutes, flow rate 16 mL/min, 235 nm UV detection. Retention time for tetravalent glycopeptide 5-5 was 13 minutes. LC/MS analysis (25-50% B over 30 min, same solvent system as above, Microsorb C18, 300-5, 2×150 mm, 0.2 mL/min) showed the tetravalent glycopeptide 5-5 at 11 minutes and MS spectrum with base peaks of 1492.7 (M+2H, [1492.6 calc]) and 996.0 (M+3H, [995.4 calc]). Lyophilization of these fractions yielded 4 mg (88%) of 5-5.

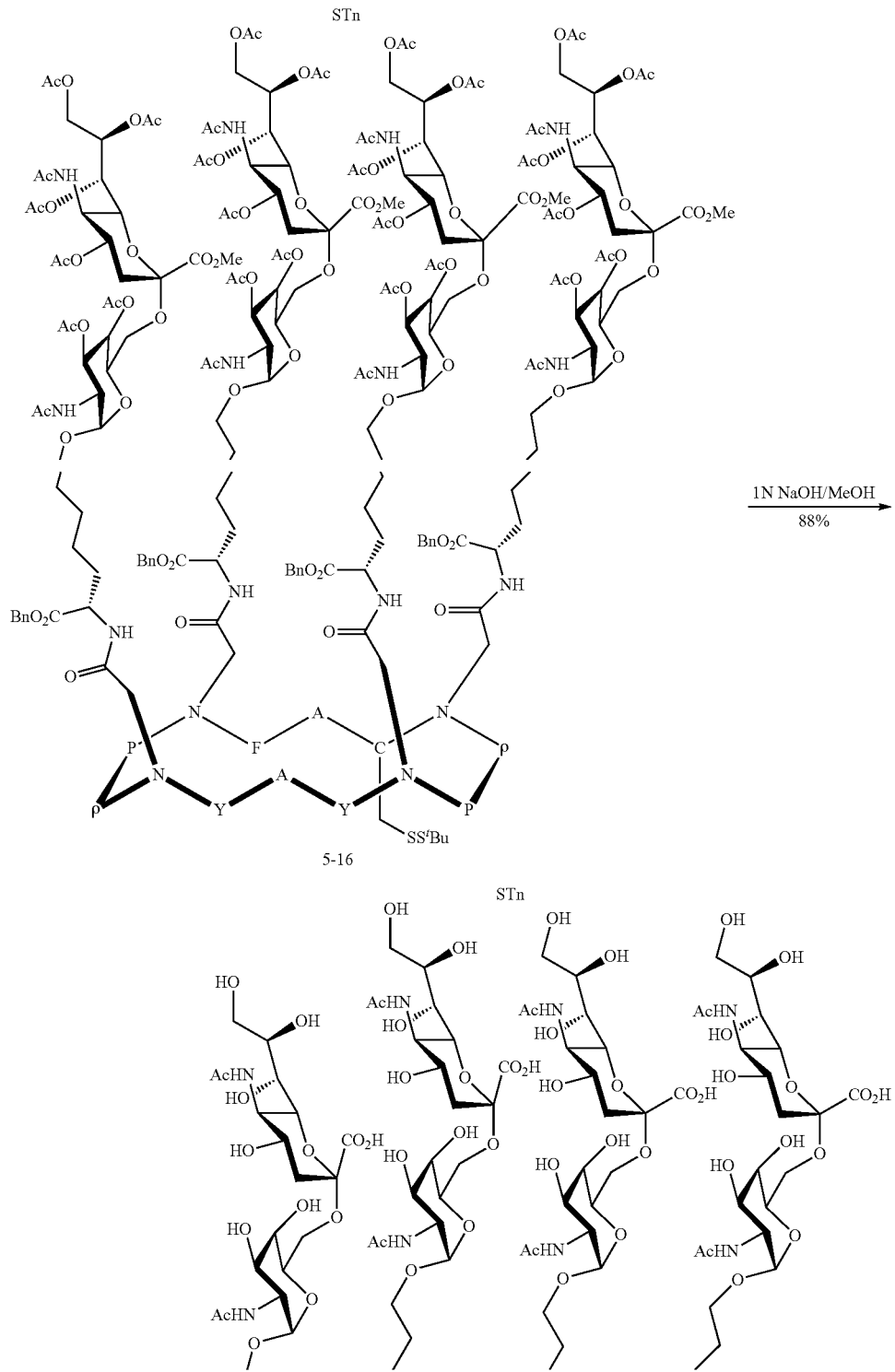

-continued

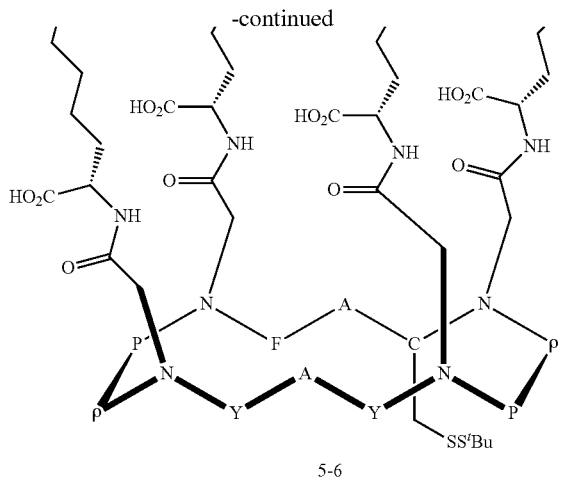

5-6

(Image Discloses '5-16' as SEQ ID NO: 61 and '5-6' as SEQ ID NO: 64)

Tetravalent Glycopeptide 5-6:

2.5 mg of the protected tetravalent glycopeptide 5-16 was used. Tetravalent glycopeptide 5-6 was purified in two batches by preparative reverse-phase HPLC using a gradient of 20-70% B over 30 minutes, flow rate 16 mL/min, 235 nm UV detection. Retention time for tetravalent glycopeptide 5-6 was 11 minutes. LC/MS analysis (20-70% B over 30 min, same solvent system as above, Microsorb C18, 300-5, 2×150 mm, 0.2 mL/min) showed the tetravalent glycopeptide 5-6 at 10 minutes and MS spectrum with base peaks of 2075.8 (M+2H, [2074.8 calc]) and 1384.1 (M+3H, [1383.6 calc]). Lyophilization of these fractions yielded 2.5 mg (84%) of 5-6.

Protected Divalent Glycopeptide 5-19:

Solutions of each reaction participant were prepared with a stir bar in flame-dried vials under argon as follows: Peptide 5-13 (8.8 mg, 5.07 µmol), Tn 5-2 (8.6 mg, 15.21 µmol), were dissolved in 1.0 mL DMSO. To this mixture, HATU (5.8 mg, 15.21 µmol in 100 µL DMSO) was added, followed by dry iPr$_2$NEt (8 µL, 45.6 µmol), producing a strong yellow color. After 2 hours, the crude reaction mixture was diluted with ~500 µL of 50% B HPLC buffer and, this was purified in two batches by preparative reverse-phase HPLC using a gradient of 5-55% B over 3 minutes then 55-90% B over 30 minutes, flow rate 16 mL/min, 235 nm UV detection. The column used was a 21.4×250 mm Varian Microsorb C18 Dynamax column, 100 Å pore size, 5 µM particle size. Retention time for diallyl divalent glycopeptide was 14 minutes. LC/MS analysis of the crude reaction mixture (55-75% B over 30 min, same solvent system as above, Microsorb C18, 300-5, 2×150 mm, 0.2 mL/min) showed the diallyl divalent glycopeptide at 9.5 minutes and MS spectrum with base peaks of 2833.14 (M+H, [2832.18 calc]) and 2855.23 (M+Na, [2854.15 calc]). Lyophilization of these fractions yielded 9.5 mg (66%) of diallyl divalent glycopeptide. This construct was then treated with 4-methylmorpholine (2.7 µL, 24 µmol) and tetrakis(triphenylphosphine)palladium (8.1 mg, 7 µmol) in 1 mL DMF. After 2 hours, this was purified in two batches by preparative reverse-phase HPLC using a gradient of 45-70% B over 30 minutes, flow rate 16 mL/min, 235 nm UV detection. The column used was a 21.4×250 mm Varian Microsorb C18 Dynamax column, 100 Å pore size, 5 µM particle size. Retention time for protected divalent glycopeptides 5-19 was 14 minutes. LC/MS analysis of the crude reaction mixture (45-70% B over 30 min, same solvent system as above, Microsorb C18, 300-5, 2×150 mm, 0.2 mL/min) showed the protected divalent glycopeptides 5-19 at 11.5 minutes and MS spectrum with base peaks of 2752.74 (M+H, [2752.11 calc]) and 1376.74 (M+2H, [1376.56 calc]). Lyophilization of these fractions yielded 8.4 mg (91%) of 5-19.

Tetravalent Glycopeptide 5-7:

Solutions of each reaction participant were prepared with a stir bar in flame-dried vials under argon as follows: Glycopeptide 5-19 (2.1 mg, 0.76 µmol), STn 5-3 (2.3 mg, 2.3 µmol), were dissolved in 1.0 mL DMSO. To this mixture, HATU (0.87 mg, 2.3 µmol in 100 µL DMSO) was added, followed by dry iPr$_2$NEt (1.6 µL, 9.2 µmol), producing a strong yellow color. After 3 hours, LC/MS analysis of the crude reaction mixture (50-80% B over 30 min, same solvent system as above, Microsorb C18, 300-5, 2×150 mm, 0.2 mL/min) showed the protected tetravalent glycopeptide at 15 minutes and MS spectrum with base peaks of 2356.75 (M+2H, [2355.94 calc]) and 1571.99 (M+3H, [1570.96 calc]). After the removal of solvent by vigorous stream of air, this was subjected to global deprotection under the condition described above. This was then purified by preparative reverse-phase HPLC using a gradient of 20-70% B over 30 minutes, flow rate 16 mL/min, 235 nm UV detection. The column used was a 21.4×250 mm Varian Microsorb C18 Dynamax column, 100 Å pore size, 5 µM particle size. Retention time for tetravalent glycopeptides 5-7 was 12 minutes. LC/MS analysis of the crude reaction mixture (20-70% B over 30 min, same solvent system as above, Microsorb C18, 300-5, 2×150 mm, 0.2 mL/min) showed the tetravalent glycopeptides 5-7 at 12 minutes and MS spectrum with base peaks of 1784.55 (M+2H, [1783.74 calc]). Lyophilization of these fractions yielded 1.9 mg (70%) of 5-7.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A multi-antigenic construct having the structure (SEQ ID NO: 24)

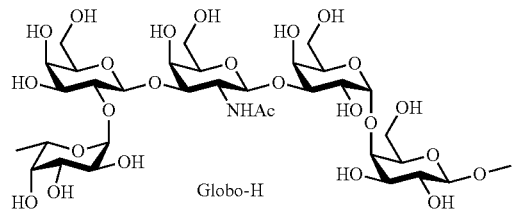

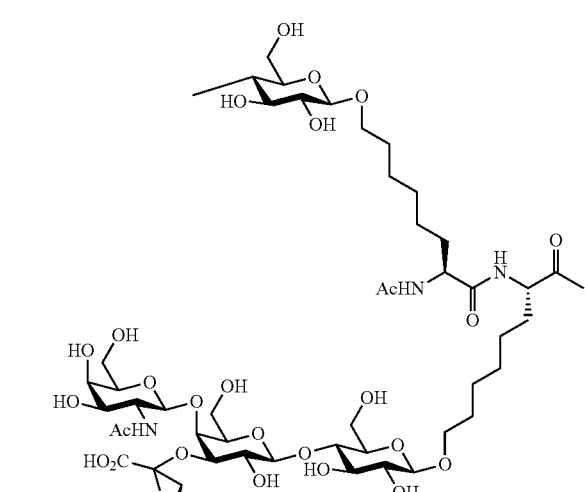

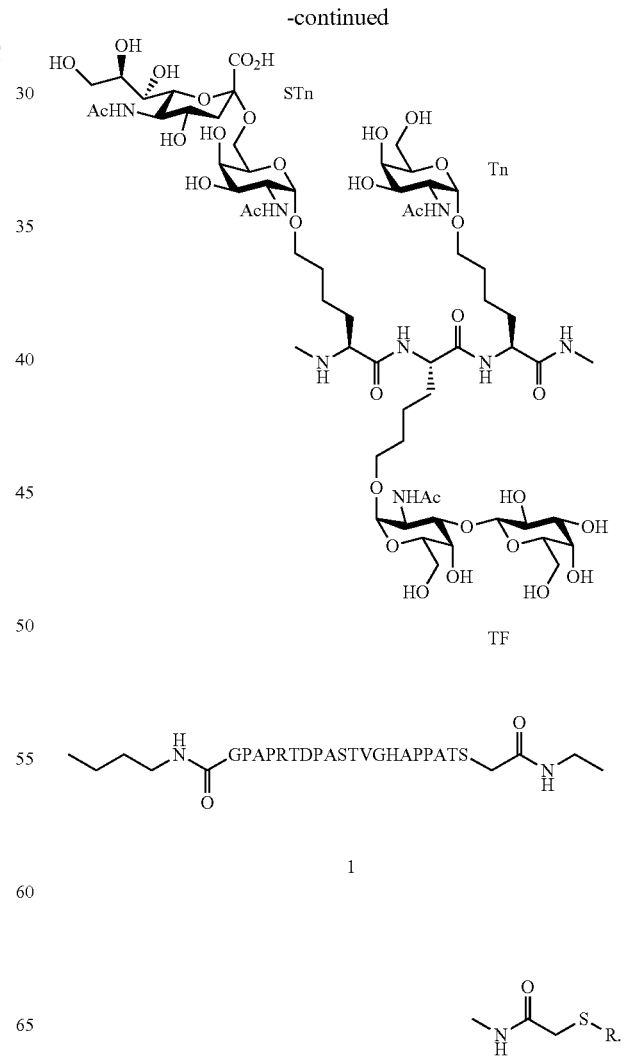

-continued

R = 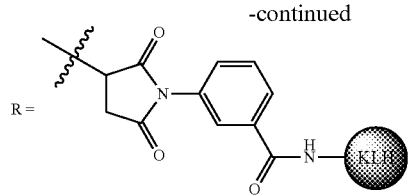

5

2. A pharmaceutical composition comprising a therapeutically effective amount of a construct of claim 1 and at least one pharmaceutically acceptable carrier or excipient.

3. A construct having the structure of:

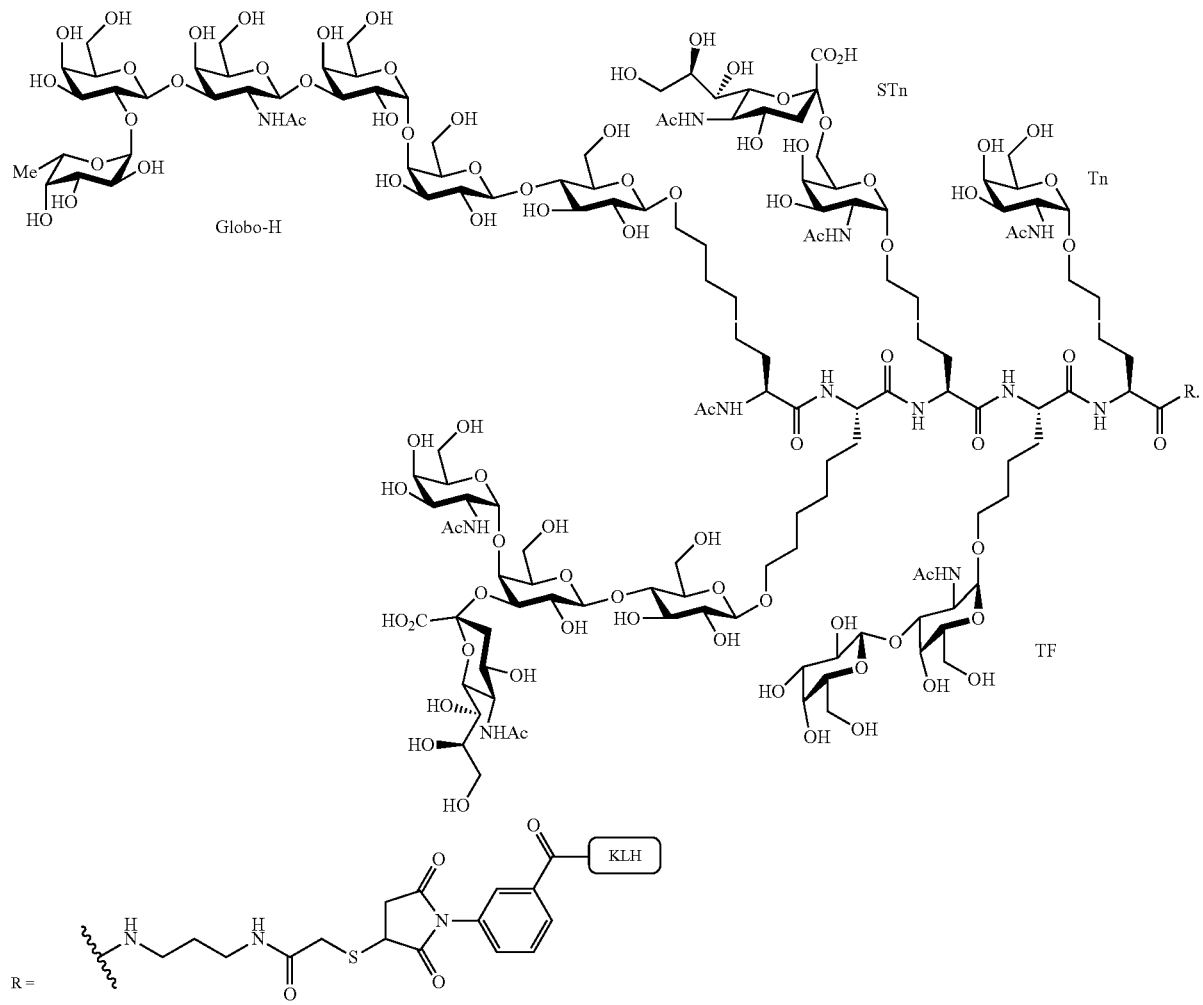

4. A pharmaceutical composition comprising a therapeutically effective amount of a construct of claim 3 and at least one pharmaceutically acceptable carrier.

* * * * *